US009617309B2

(12) United States Patent
Verdine et al.

(10) Patent No.: US 9,617,309 B2
(45) Date of Patent: Apr. 11, 2017

(54) PROLINE-LOCKED STAPLED PEPTIDES AND USES THEREOF

(71) Applicant: President and Fellows of Harvard College, Cambridge, MA (US)

(72) Inventors: Gregory L. Verdine, Boston, MA (US); Kazuhiro Hayashi, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/431,280

(22) PCT Filed: Sep. 26, 2013

(86) PCT No.: PCT/US2013/062004
§ 371 (c)(1),
(2) Date: Mar. 25, 2015

(87) PCT Pub. No.: WO2014/052647
PCT Pub. Date: Apr. 3, 2014

(65) Prior Publication Data
US 2015/0239937 A1 Aug. 27, 2015

Related U.S. Application Data

(60) Provisional application No. 61/705,950, filed on Sep. 26, 2012, provisional application No. 61/789,157, filed on Mar. 15, 2013.

(51) Int. Cl.
C07K 7/56 (2006.01)
C07K 1/113 (2006.01)
C07D 207/16 (2006.01)

(52) U.S. Cl.
CPC ............. C07K 7/56 (2013.01); C07D 207/16 (2013.01); C07K 1/113 (2013.01)

(58) Field of Classification Search
CPC ...................................... C07K 7/56
USPC ...................................... 530/317
See application file for complete search history.

(56) References Cited

U.S. PATENT DOCUMENTS

| 4,270,537 A | 6/1981 | Romaine |
| 4,596,556 A | 6/1986 | Morrow et al. |
| 4,730,006 A | 3/1988 | Bohme et al. |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,120,859 A | 6/1992 | Webb |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,364,851 A | 11/1994 | Joran |
| 5,383,851 A | 1/1995 | McKinnon et al. |
| 5,417,662 A | 5/1995 | Hjertman et al. |
| 5,446,128 A | 8/1995 | Kahn |
| 5,466,220 A | 11/1995 | Brenneman |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,599,302 A | 2/1997 | Lilley et al. |
| 5,622,852 A | 4/1997 | Korsmeyer |
| 5,649,912 A | 7/1997 | Peterson |
| 5,663,316 A | 9/1997 | Xudong |
| 5,704,911 A | 1/1998 | Parsons |
| 5,708,136 A | 1/1998 | Burrell et al. |
| 5,750,767 A | 5/1998 | Carpino et al. |
| 5,811,515 A | 9/1998 | Grubbs et al. |
| 5,824,483 A | 10/1998 | Houston, Jr. et al. |
| 5,834,209 A | 11/1998 | Korsmeyer |
| 5,856,445 A | 1/1999 | Korsmeyer |
| 5,874,529 A | 2/1999 | Gilon et al. |
| 5,893,397 A | 4/1999 | Peterson et al. |
| 5,922,863 A | 7/1999 | Grubbs et al. |
| 5,955,593 A | 9/1999 | Korsmeyer |

(Continued)

FOREIGN PATENT DOCUMENTS

| WO | WO 96/02642 A1 | 2/1996 |
| WO | WO 96/20951 A1 | 7/1996 |

(Continued)

OTHER PUBLICATIONS

U.S. Appl. No. 14/880,080, filed Oct. 9, 2015, Verdine et al.
U.S. Appl. No. 14/775,315, filed Sep. 11, 2015, Verdine et al.
U.S. Appl. No. 14/898,222, filed Dec. 14, 2015, Verdine et al.
U.S. Appl. No. 14/896,132, filed Dec. 4, 2015, Palchaudhuri et al.
International Search Report and Written Opinion for PCT/US2014/042329, mailed Nov. 24, 2014.

(Continued)

*Primary Examiner* — David Lukton
(74) *Attorney, Agent, or Firm* — Clark & Elbing LLP

(57) ABSTRACT

The present invention provides a new type of alpha-helix nucleating cross-link ("staple") formed by olefin metathesis of a proline derivative with an alkenyl side chain and another amino acid derivative with an alkenyl side chain. The proline derivatives as described herein have been found to be strong nucleators of alpha-helix formation. The invention also provides moieties for shielding the free amide N—H's at the N-terminus of an alpha-helix, thereby further stabilizing the helix. The proline derivatives, precursors prior to cross-linking, and the cross-linked peptides are provided as well as methods of using and preparing these compounds and peptides.

27 Claims, 37 Drawing Sheets

(56) References Cited

U.S. PATENT DOCUMENTS

| | | |
|---|---|---|
| 5,965,703 A | 10/1999 | Horne et al. |
| 5,993,412 A | 11/1999 | Deily et al. |
| 5,998,583 A | 12/1999 | Korsmeyer |
| 6,051,554 A | 4/2000 | Hornik et al. |
| 6,153,391 A | 11/2000 | Picksley et al. |
| 6,184,344 B1 | 2/2001 | Kent et al. |
| 6,271,198 B1 | 8/2001 | Braisted et al. |
| 6,326,354 B1 | 12/2001 | Gross et al. |
| 6,348,558 B1 | 2/2002 | Harris et al. |
| 6,444,425 B1 | 9/2002 | Reed et al. |
| 6,610,657 B1 | 8/2003 | Goueli |
| 6,613,874 B1 | 9/2003 | Mazur et al. |
| 6,703,382 B2 | 3/2004 | Wang et al. |
| 6,713,280 B1 | 3/2004 | Huang et al. |
| 6,849,428 B1 | 2/2005 | Evans et al. |
| 6,875,594 B2 | 4/2005 | Muir et al. |
| 7,064,193 B1 | 6/2006 | Cory et al. |
| 7,083,983 B2 | 8/2006 | Lane et al. |
| 7,084,244 B2 | 8/2006 | Gilon et al. |
| 7,183,059 B2 | 2/2007 | Verdine et al. |
| 7,192,713 B1 | 3/2007 | Verdine et al. |
| 7,202,332 B2 | 4/2007 | Arora et al. |
| 7,247,700 B2 | 7/2007 | Korsmeyer et al. |
| 7,538,190 B2 | 5/2009 | Robinson et al. |
| 7,705,118 B2 | 4/2010 | Arora et al. |
| 7,723,469 B2 | 5/2010 | Walensky et al. |
| 7,745,573 B2 | 6/2010 | Robinson et al. |
| 7,786,072 B2 | 8/2010 | Verdine et al. |
| 8,324,428 B2 | 12/2012 | Verdine et al. |
| 8,592,377 B2 | 11/2013 | Verdine et al. |
| 8,895,699 B2 | 11/2014 | Verdine et al. |
| 8,957,026 B2 | 2/2015 | Verdine et al. |
| 9,163,330 B2 | 10/2015 | Verdine et al. |
| 2004/0023887 A1 | 2/2004 | Pillutla et al. |
| 2004/0038901 A1 | 2/2004 | Basler et al. |
| 2004/0067503 A1 | 4/2004 | Tan et al. |
| 2004/0171809 A1 | 9/2004 | Korsmeyer et al. |
| 2005/0250680 A1 | 11/2005 | Walensky et al. |
| 2006/0008848 A1 | 1/2006 | Verdine et al. |
| 2006/0014675 A1 | 1/2006 | Arora et al. |
| 2006/0148715 A1 | 7/2006 | Tweardy |
| 2008/0262200 A1 | 10/2008 | Nash |
| 2009/0047711 A1 | 2/2009 | Nash |
| 2009/0088553 A1 | 4/2009 | Nash |
| 2009/0149630 A1 | 6/2009 | Walensky et al. |
| 2009/0176964 A1 | 7/2009 | Walensky et al. |
| 2009/0326192 A1 | 12/2009 | Nash et al. |
| 2010/0081611 A1 | 4/2010 | Bradner et al. |
| 2010/0168388 A1 | 7/2010 | Bernal et al. |
| 2010/0184628 A1 | 7/2010 | Nash |
| 2010/0184645 A1 | 7/2010 | Verdine et al. |
| 2010/0216688 A1 | 8/2010 | Nash et al. |
| 2010/0234563 A1 | 9/2010 | Arora et al. |
| 2010/0298201 A1 | 11/2010 | Nash et al. |
| 2011/0028753 A1 | 2/2011 | Verdine et al. |
| 2011/0144303 A1 | 6/2011 | Nash et al. |
| 2011/0144306 A1 | 6/2011 | Verdine et al. |
| 2011/0223149 A1 | 9/2011 | Nash et al. |
| 2011/0263815 A1 | 10/2011 | Nash |
| 2012/0082636 A1 | 4/2012 | Walensky et al. |
| 2012/0172311 A1 | 7/2012 | Nash et al. |
| 2012/0190818 A1 | 7/2012 | Nash |
| 2012/0270800 A1 | 10/2012 | Verdine et al. |
| 2013/0005943 A1 | 1/2013 | Arora et al. |
| 2013/0023646 A1 | 1/2013 | Nash et al. |
| 2013/0177979 A1 | 7/2013 | Turkson |
| 2013/0211046 A1 | 8/2013 | Verdine et al. |
| 2014/0005118 A1 | 1/2014 | Verdine et al. |
| 2014/0011979 A1 | 1/2014 | Verdine et al. |
| 2014/0162339 A1 | 6/2014 | Verdine et al. |
| 2014/0235549 A1 | 8/2014 | Moellering et al. |
| 2014/0256912 A1 | 9/2014 | Moellering et al. |
| 2014/0323701 A1 | 10/2014 | Nash et al. |
| 2015/0225471 A1 | 8/2015 | Liang |
| 2015/0284437 A1 | 10/2015 | Verdine et al. |
| 2015/0376227 A1 | 12/2015 | Verdine et al. |
| 2016/0024153 A1 | 1/2016 | Verdine et al. |

FOREIGN PATENT DOCUMENTS

| | | |
|---|---|---|
| WO | WO 96/34878 A1 | 11/1996 |
| WO | WO 97/13537 A1 | 4/1997 |
| WO | WO 97/37705 A1 | 10/1997 |
| WO | WO 99/14259 A1 | 3/1999 |
| WO | WO 99/34833 A1 | 7/1999 |
| WO | WO 99/34850 A1 | 7/1999 |
| WO | WO 00/06187 A2 | 2/2000 |
| WO | WO 02/064790 A2 | 8/2002 |
| WO | WO 03/106491 A2 | 12/2003 |
| WO | WO 03/106491 A3 | 12/2003 |
| WO | WO 2004/041275 A1 | 5/2004 |
| WO | WO 2004/058804 A1 | 7/2004 |
| WO | WO 2005/040202 A2 | 5/2005 |
| WO | WO 2005/040202 A3 | 5/2005 |
| WO | WO 2005/044839 A2 | 5/2005 |
| WO | WO 2005/044839 A3 | 5/2005 |
| WO | WO 2005/085457 A2 | 9/2005 |
| WO | WO 2005/090388 A1 | 9/2005 |
| WO | WO 2005/118620 A2 | 12/2005 |
| WO | WO 2005/118620 A3 | 12/2005 |
| WO | WO 2005/118634 A2 | 12/2005 |
| WO | WO 2005/118634 A3 | 12/2005 |
| WO | WO 2006/103666 A2 | 10/2006 |
| WO | WO 2007/141533 A2 | 12/2007 |
| WO | WO 2008/061192 A2 | 5/2008 |
| WO | WO 2008/095063 A1 | 8/2008 |
| WO | WO 2008/121767 A2 | 10/2008 |
| WO | WO 2009/042237 A2 | 4/2009 |
| WO | WO 2009/126292 A2 | 10/2009 |
| WO | WO 2010/011313 A2 | 1/2010 |
| WO | WO 2010/034029 A1 | 3/2010 |
| WO | WO 2010/068684 A2 | 6/2010 |
| WO | WO 2011/008260 A2 | 1/2011 |
| WO | WO 2012/040459 A2 | 3/2012 |
| WO | WO 2012/174423 A1 | 12/2012 |
| WO | WO 2014/052647 A2 | 4/2014 |
| WO | WO 2014/055564 A1 | 4/2014 |

OTHER PUBLICATIONS

International Preliminary Report on Patentability for PCT/US2014/042329, mailed Dec. 23, 2015.
International Search Report and Written Opinion for PCT/US2014/041338, mailed Nov. 10, 2014.
International Preliminary Report on Patentability for PCT/US2014/041338, mailed Dec. 17, 2015.
[No Author Listed] Brain Tumors. Merck Manuals. Aug. 21, 2014. merckmanuals.com/home/brain_spinal_cord_and_nerve_disorders/tumors_of_the_nervous_system/brain_tumors.html. 9 pages.
[No Author Listed] Overview of Leukemia. Merck Manuals. Aug. 20, 2014. merckmanuals.com/home/blood_disorders/leukemias/overview_of_leukemia.html?qt=Leukemia&alt=sh. 2 pages.
[No Author Listed] Colorectal Cancer. Merck Manuals. Aug. 21, 2014. merckmanuals.com/home/digestive_disorders/tumors_of_the_digestive_system/colorectal_cancer.html. 5 pages.
[No Author Listed] Prostate Cancer. Merck Manuals. Aug. 21, 2014. merckmanuals.com/home/kidney_and_urinary_tract_disorders/cancers_of_the_kidney_and_genitourinary_tract/prostate_cancer.html?qt=prostatecancer&alt=sh. 8 pages.
[No Author Listed] Breast Cancer. Merck Manuals. Aug. 21, 2014. merckmanuals.com/home/womens_health_issues/breast_disorders/breast_cancer.html. 20 pages.
[No Author Listed] Bladder Cancer. Merck Manuals. Aug. 21, 2014. merckmanuals.com/home/kidney_and_urinary_tract_disorders/cancers_of_the_kidney_and_genitourinary_tract/bladder_cancer.html. 2 pages.
Friedman-Einat et al., Target gene identification: target specific transcriptional activation by three murine homeodomain/VP16 14/hybrid proteins in *Saccharomyces cerevisiae*. J Exp Zool. Feb. 15, 1996;274(3):145-56.

(56) References Cited

OTHER PUBLICATIONS

Lindsay et al., Rab coupling protein (RCP), a novel Rab4 and Rab11 effector protein. J Biol Chem. Apr. 5, 2002;277(14):12190-9. Epub Jan. 10, 2002.
Lomar et al., Synthese symmetrischerf ketone unter verwendung von 2-Phenyl-2-oxazolin-5-on. Chemische Berichte. 1980;113(12):3706-15.
Lu et al., Both Pbx1 and E2A-Pbx1 bind the DNA motif ATCAATCAA cooperatively with the products of multiple murine Hox genes, some of which are themselves oncogenes. Mol Cell Biol. Jul. 1995;15(7):3786-95.
Lu et al., Structural determinants within Pbx1 that mediate cooperative DNA binding with pentapeptide-containing Hox proteins: proposal for a model of a Pbx1-Hox-DNA complex. Mol Cell Biol. Apr. 1996;16(4):1632-40.
Palchaudhuri et al., Differentiation induction in acute myeloid leukemia using site-specific DNA-targeting. 55th ASH Annual Meeting and Exposition. Dec. 9, 2013. Accessed at https://ash.confex.com/ash/2013/webprogram/Paper60843.html. 1 page.
U.S. Appl. No. 13/383,881, filed Jan. 13, 2012, Verdine et al.
U.S. Appl. No. 13/055,279, filed Jan. 21, 2011, Verdine et al.
U.S. Appl. No. 14/748,287, filed Jun. 24, 2015, Verdine et al.
U.S. Appl. No. 12/593,384, filed Mar. 5, 2010, Verdine et al.
U.S. Appl. No. 14/027,064, filed Sep. 13, 2013, Verdine et al.
U.S. Appl. No. 13/825,709, filed Mar. 22, 2013, Verdine et al.
U.S. Appl. No. 14/615,235, filed Feb. 5, 2015, Verdine et al.
U.S. Appl. No. 14/126,642, filed Dec. 16, 2013, Moellering et al.
U.S. Appl. No. 14/432,804, filed Apr. 1, 2015, Liang et al.
U.S. Appl. No. 14/127,039, filed Dec. 17, 2013, Moellering et al.
U.S. Appl. No. 09/574,086, filed May 18, 2000, Verdine et al.
U.S. Appl. No. 11/148,976, filed Jun. 9, 2005, Verdine et al.
U.S. Appl. No. 12/796,212, filed Jun. 8, 2010, Verdine et al.
U.S. Appl. No. 13/680,905, filed Nov. 19, 2012, Verdine et al.
U.S. Appl. No. 14/068,844, filed Oct. 31, 2013, Verdine et al.
U.S. Appl. No. 12/420,816, filed Apr. 8, 2009, Nash et al.
U.S. Appl. No. 13/570,146, filed Aug. 8, 2012, Nash et al.
U.S. Appl. No. 14/156,350, filed Jan. 15, 2014, Nash et al.
Extended European Search Report for EP 10800148.8, mailed Oct. 16, 2013.
Invitation to Pay Additional Fees for PCT/US2010/001952, mailed Oct. 29, 2010.
International Search Report and Written Opinion for PCT/US2010/001952, mailed Feb. 2, 2011.
International Preliminary Report on Patentability for PCT/US2010/001952, mailed Jan. 26, 2012.
Extended European Search Report for EP 09800675.2, mailed Dec. 6, 2012.
Invitation to Pay Additional Fees for PCT/US2009/004260, mailed Mar. 19, 2010.
International Search Report and Written Opinion for PCT/US2009/004260, mailed Oct. 15, 2010.
International Preliminary Report on Patentability for PCT/US2009/004260, mailed Feb. 3, 2011.
Extended European Search Report for EP 12159110.1, mailed Jul. 20, 2012.
Extended European Search Report for EP 12159110 1, mailed Sep. 27, 2012.
International Search Report and Written Opinion for PCT/US2008/058575, mailed Nov. 17, 2008.
International Preliminary Report on Patentability for PCT/US2008/058575, mailed Oct. 8, 2009.
Invitation to Pay Additional Fees for PCT/US2011/052755, mailed Feb. 16, 2012.
International Search Report and Written Opinion for PCT/US2011/052755, mailed Apr. 25, 2012.
International Preliminary Report on Patentability for PCT/US2011/052755, mailed Apr. 4, 2013.
International Search Report and Written Opinion for PCT/US2012/042738, mailed Oct. 18, 2012.
International Preliminary Report on Patentability for PCT/US2012/042738, mailed Jan. 3, 2014.
Invitation to Pay Additional Fees for PCT/US2013/062004, mailed Jan. 2, 2014.
International Search Report and Written Opinion for PCT/US2013/062004, mailed Apr. 23, 2014.
International Preliminary Report on Patentability for PCT/US2013/062004, mailed Apr. 9, 2015.
International Search Report and Written Opinion for PCT/US2013/062929, mailed Jan. 30, 2014.
International Preliminary Report on Patentability for PCT/US2013/062929, mailed Apr. 16, 2015.
International Search Report and Written Opinion for PCT/US2014/025544, mailed Sep. 10, 2014.
Invitation to Pay Additional Fees for PCT/US2014/025544, mailed Jul. 22, 2014.
International Search Report and Written Opinion for PCT/US2014/058680, mailed Apr. 23, 2015.
Extended European Search Report for EP 12800679.8, mailed Oct. 2, 2014.
International Search Report and Written Opinion for PCT/US2012/042719, mailed Nov. 1, 2012.
International Preliminary Report on Patentability for PCT/US2012/042719, mailed Jan. 3, 2014.
International Search Report and Written Opinion for PCT/US2008/052580, mailed May 16, 2008.
[No Author Listed] Designing Custom Peptide. from SIGMA Genosys, p. 1. Accessed Jul. 27, 2012.
Adhikary et al., Transcriptional regulation and transformation by Myc proteins. Nat Rev Mol Cell Biol. Aug. 2005;6(8):635-45.
Agola et al., Rab GTPases as regulators of endocytosis, targets of disease and therapeutic opportunities. Clin Genet. Oct. 2011; 80(4):305-318.
Altschul et al., Basic local alignment search tool. J Mol Biol. Oct. 5, 1990;215(3):403-10.
Aman et al., cDNA cloning and characterization of the human interleukin 13 receptor alpha chain. J Biol Chem. Nov. 15, 1996;271(46):29265-70.
Andrews et al., Forming Stable Helical Peptides Using Natural and Artificial Amino Acids. Tetrahedron. 1999;55:11711-43.
Andrews et al., Kinetic analysis of the interleukin-13 receptor complex. J Biol Chem. Nov. 29, 2002;277(48):46073-8. Epub Sep. 26, 2002.
Armstrong et al., X=Y-ZH Systems as potential 1,3-dipoles. 5. Intramolecular cycloadditions of imines of a-amino acid esters. Tetrahedron. 1985;41(17):3547-58.
Artavanis-Tsakonas et al., Notch signaling: cell fate control and signal integration in development. Science. Apr. 30, 1999;284(5415):770-6.
Attisano et al., TGFbeta and Wnt pathway cross-talk. Cancer Metastasis Rev. Jan.-Jun. 2004;23(1-2):53-61.
Babcock, Proteins, radicals, isotopes, and mutants in photosynthetic oxygen evolution. Proc Natl Acad Sci U S A. Dec. 1, 1993;90(23):10893-5.
Babine et al., Molecular Recognition of Proteinminus signLigand Complexes: Applications to Drug Design. Chem Rev. Aug. 5, 1997;97(5):1359-1472.
Banerjee et al., Structure of a DNA glycosylase searching for lesions. Science. Feb. 24, 2006;311(5764):1153-7.
Banerjee et al., Structure of a repair enzyme interrogating undamaged DNA elucidates recognition of damaged DNA. Nature. Mar. 31, 2005;434(7033):612-8.
Bang et al., Total chemical synthesis of crambin. J Am Chem Soc. Feb. 11, 2004;126(5):1377-83.
Barandon et al., Reduction of infarct size and prevention of cardiac rupture in transgenic mice overexpressing FrzA. Circulation. Nov. 4, 2003;108(18):2282-9. Epub Oct. 27, 2003.
Barker et al., Mining the Wnt pathway for cancer therapeutics. Nat Rev Drug Discov. Dec. 2006;5(12):997-1014.
Beloken et al., Chiral Complexes of Ni(II), Cu(II) and Cu(I) as Reagents, Catalysts and Receptors for Asymmetric Synthesis and Chiral Recognition of Amino Acids. Pure & Appl Chem. 1992;64(12):1917-24.

(56) References Cited

OTHER PUBLICATIONS

Belokon et al., Improved procedures for the synthesis of (S)-2-[N-(N'-benzyl-prolyl)amino]benzophenone (BPB) and Ni(II) complexes of Schiff's bases derived from BPB and amino acids. Tetrahedron: Asymmetry. 1998;9:4249-52.

Bennett et al., Regulation of osteoblastogenesis and bone mass by Wnt10b. Proc Natl Acad Sci U S A. Mar. 1, 2005;102(9):3324-9. Epub Feb. 22, 2005.

Berendsen et al., A glimpse of the Holy Grail? Science. Oct. 23, 1998;282(5389):642-3.

Berge et al., Pharmaceutical salts. J Pharm Sci. Jan. 1977;66(1):1-19.

Bernal et al., Reactivation of the p53 tumor suppressor pathway by a stapled p53 peptide. J Am Chem Soc. Mar. 7, 2007;129(9):2456-7. Epub Feb. 7, 2007.

Biagini et al., Cross-metathesis of Unsaturated α-amino Acid Derivatives. J Chem Soc Perkin Trans. 1998;1:2485-99.

Bierzynski et al., A salt bridge stabilizes the helix formed by isolated C-peptide of Rnase A. Proc Natl Acad Sci U S A. Apr. 1982;79(8):2470-4.

Blackwell et al., Highly Efficient Synthesis of Covalently Cross-Linked Peptide Helices by Ring-Closing Metathesis. Angew Chem Int Ed. 1998;37(23):3281-84.

Blackwell et al., Ring-closing metathesis of olefinic peptides: design, synthesis, and structural characterization of macrocyclic helical peptides. J Org Chem. Aug. 10, 2001;66(16):5291-302.

Blundell et al., Atomic positions in rhombohedral 2-zinc insulin crystals. Nature. Jun. 25, 1971;231(5304):506-11.

Bode et al., Chemoselective amide ligations by decarboxylative condensations of N-alkylhydroxylamines and alpha-ketoacids. Angew Chem Int Ed Engl. Feb. 13, 2006;45(8):1248-52.

Boyden et al., High bone density due to a mutation in LDL-receptor-related protein 5. N Engl J Med. May 16, 2002;346(20):1513-21.

Bracken et al., Synthesis and Nuclear Magnetic Resonance Structure Determination of an α-Helical, Bicyclic, Lactam-Bridged Hexapeptide. J Am Chem Soc. 1994;116:6431-32.

Bradley et al., Limits of cooperativity in a structurally modular protein: response of the Notch ankyrin domain to analogous alanine substitutions in each repeat. J Mol Biol. Nov. 22, 2002;324(2):373-86.

Brandt et al., Dimeric fragment of the insulin receptor alpha-subunit binds insulin with full holoreceptor affinity. J Biol Chem. Apr. 13, 2001;276(15):12378-84. Epub Jan. 12, 2001.

Bray, Notch signalling: a simple pathway becomes complex. Nat Rev Mol Cell Biol. Sep. 2006;7(9):678-89.

Brou et al., A novel proteolytic cleavage involved in Notch signaling: the role of the disintegrin-metalloprotease TACE. Mol Cell. Feb. 2000;5(2):207-16.

Brubaker et al., Solution structure of the interacting domains of the Mad-Sin3 complex: implications for recruitment of a chromatin-modifying complex. Cell. Nov. 10, 2000;103(4):655-65.

Brusselle et al., Allergen-induced airway inflammation and bronchial responsiveness in wild-type and interleukin-4-deficient mice. Am J Respir Cell Mol Biol. Mar. 1995;12(3):254-9.

Burger et al., Synthesis of a-(trifluoromethyl)-substituted a-amino acids. Part 7. An efficient synthesis for a-trifluoromethyl-substituted w-carboxy a-amino acids. Chemiker-Zeitung. 1990;114(3):101-04. German.

Caricasole et al., The Wnt pathway, cell-cycle activation and beta-amyloid: novel therapeutic strategies in Alzheimer's disease? Trends Pharmacol Sci. May 2003;24(5):233-8.

Carillo et al., The Multiple Sequence Alignment Problem in Biology. SIAM J Applied Math. 1988;48:1073-82.

Carlson et al., Specificity landscapes of DNA binding molecules elucidate biological function. Proc Natl Acad Sci U S A. Mar. 9, 2010;107(10):4544-9. doi: 10.1073/pnas.0914023107. Epub Feb. 22, 2010.

Chen et al., Determination of the helix and beta form of proteins in aqueous solution by circular dichroism. Biochemistry. Jul. 30, 1974;13(16):3350-9.

Chen et al., Small molecule-mediated disruption of Wnt-dependent signaling in tissue regeneration and cancer. Nat Chem Biol. Feb. 2009;5(2):100-7. Epub Jan. 4, 2009.

Cheng et al., Emerging role of RAB GTPases in cancer and human disease. Cancer Res. Apr. 1, 2005;65(7):2516-9.

Cheng et al., The RAB25 small GTPase determines aggressiveness of ovarian and breast cancers. Nat Med. Nov. 2004;10(11):1251-6. Epub Oct. 24, 2004.

Cheon et al., beta-Catenin stabilization dysregulates mesenchymal cell proliferation, motility, and invasiveness and causes aggressive fibromatosis and hyperplastic cutaneous wounds. Proc Natl Acad Sci U S A. May 14, 2002;99(10):6973-8. Epub Apr. 30, 2002.

Chia et al., Emerging roles for Rab family GTPases in human cancer. Biochim Biophys Acta. Apr. 2009;1795(2):110-6.

Chiaramonte et al., Studies of murine schistosomiasis reveal interleukin-13 blockade as a treatment for established and progressive liver fibrosis. Hepatology. Aug. 2001;34(2):273-82.

Christodoulides et al., WNT10B mutations in human obesity. Diabetologia. Apr. 2006;49(4):678-84. Epub Feb. 14, 2006.

Clark et al., Supramolecular Design by Covalent Capture. Design of a Peptide Cylinder via Hydrogen-Bond-Promoted Intermolecular Olefin Metathesis. J Am Chem Soc. 1995;117:12364-65.

Clevers, Wnt/beta-catenin signaling in development and disease. Cell. Nov. 3, 2006;127(3):469-80.

Cohn et al., Cutting Edge: IL-4-independent induction of airway hyperresponsiveness by Th2, but not Th1, cells. J Immunol. Oct. 15, 1998;161(8):3813-6.

Colaluca et al., NUMB controls p53 tumour suppressor activity. Nature. Jan. 3, 2008;451(7174):76-80. doi: 10.1038/nature06412.

Cole et al., Transcription-independent functions of MYC: regulation of translation and DNA replication. Nat Rev Mol Cell Biol. Oct. 2008;9(10):810-5. Epub Aug. 13, 2008.

Cong et al., A protein knockdown strategy to study the function of beta-catenin in tumorigenesis. BMC Mol Biol. Sep. 29, 2003;4:10.

Cossu et al., Wnt signaling and the activation of myogenesis in mammals. EMBO J. Dec. 15, 1999;18(24):6867-72.

Cox et al., Insulin receptor expression by human prostate cancers. Prostate. Jan. 1, 2009;69(1):33-40. doi: 10.1002/pros.20852.

Cusack et al., 2,4,6-Tri-isopropylbenzenesulphonyl Hydrazide: A Convenient Source of Di-imide. Tetrahedron. 1976;32:2157-62.

Danial et al., Dual role of proapoptotic BAD in insulin secretion and beta cell survival. Nat Med. Feb. 2008;14(2):144-53. doi: 10.1038/nm1717. Epub Jan. 27, 2008.

Darnell, Transcription factors as targets for cancer therapy. Nat Rev Cancer. Oct. 2002;2(10):740-9.

David et al., Expressed protein ligation. Method and applications. Eur J Biochem. Feb. 2004;271(4):663-77.

Dawson et al., Synthesis of proteins by native chemical ligation. Science. Nov. 4, 1994;266(5186):776-9.

De Guzman et al., Structural basis for cooperative transcription factor binding to the CBP coactivator. J Mol Biol. Feb. 3, 2006;355(5):1005-13. Epub Oct. 5, 2005.

De La O et al., Notch and Kras reprogram pancreatic acinar cells to ductal intraepithelial neoplasia. Proc Natl Acad Sci U S A. Dec. 2, 2008;105(48):18907-12. doi: 10.1073/pnas.0810111105. Epub Nov. 21, 2008.

De Meyts et al., Insulin interactions with its receptors: experimental evidence for negative cooperativity. Biochem Biophys Res Commun. Nov. 1, 1973;55(1):154-61.

De Meyts, The structural basis of insulin and insulin-like growth factor-I receptor binding and negative co-operativity, and its relevance to mitogenic versus metabolic signalling. Diabetologia. Sep. 1994;37 Suppl 2:S135-48.

De Strooper et al., A presenilin-1-dependent gamma-secretase-like protease mediates release of Notch intracellular domain. Nature. Apr. 8, 1999;398(6727):518-22.

Debinski et al., Retargeting interleukin 13 for radioimmunodetection and radioimmunotherapy of human high-grade gliomas. Clin Cancer Res. Oct. 1999;5(10 Suppl):3143s-3147s.

Del Bianco et al., Mutational and energetic studies of Notch 1 transcription complexes. J Mol Biol. Feb. 8, 2008;376(1):131-40. Epub Nov. 28, 2007.

(56) References Cited

OTHER PUBLICATIONS

Denmark et al., Cyclopropanation with Diazomethane and Bis(oxazoline)palladium(II) Complexes. J Org Chem. May 16, 1997;62(10):3375-3389.
Devereux et al., A comprehensive set of sequence analysis programs for the VAX. Nucleic Acids Res. Jan. 11, 1984;12(1 Pt 1):387-95.
Dombroski et al., Isolation of an active human transposable element. Science. Dec. 20, 1991;254(5039):1805-8.
Doron et al., Probiotics: their role in the treatment and prevention of disease. Expert Rev Anti Infect Ther. 2006;4:261-75.
Dovey et al., Functional gamma-secretase inhibitors reduce beta-amyloid peptide levels in brain. J Neurochem. Jan. 2001;76(1):173-81.
Duronio, Insulin receptor is phosphorylated in response to treatment of HepG2 cells with insulin-like growth factor I. Biochem J. Aug. 15, 1990;270(1):27-32.
Eglen et al., The use of AlphaScreen technology in HTS: current status. Curr Chem Genomics. Feb. 25, 2008;1:2-10. doi: 10.2174/1875397300801010002.
Eisenmesser et al., Solution structure of interleukin-13 and insights into receptor engagement. J Mol Biol. Jun. 29, 2001;310(1):231-41.
Ellis et al., Design, synthesis, and evaluation of a new generation of modular nucleophilic glycine equivalents for the efficient synthesis of sterically constrained alpha-amino acids. J Org Chem. Oct. 27, 2006;71(22):8572-8.
Ellisen et al., TAN-1, the human homolog of the *Drosophila* notch gene, is broken by chromosomal translocations in T lymphoblastic neoplasms. Cell. Aug. 23, 1991;66(4):649-61.
Erlanson et al., The leucine zipper domain controls the orientation of AP-1 in the NFAT.AP-1.DNA complex. Chem Biol. Dec. 1996;3(12):981-91.
Evans et al., The Rise of Azide-Alkyne 1,3-Dipolar 'Click' Cycloaddition and its Application to Polymer Science and Surface Modification. Australian Journal of Chemistry. 2007;60:384-95.
Favrin et al., Two-state folding over a weak free-energy barrier. Biophys J. Sep. 2003;85(3):1457-65.
Fischbach et al., Specific biochemical inactivation of oncogenic Ras proteins by nucleoside diphosphate kinase. Cancer Res. Jul. 15, 2003;63(14):4089-94.
Fischer et al., The HIV-1 Rev activation domain is a nuclear export signal that accesses an export pathway used by specific cellular RNAs. Cell. Aug. 11, 1995;82(3):475-83.
Fisher et al., Myc/Max and other helix-loop-helix/leucine zipper proteins bend DNA toward the minor groove. Proc Natl Acad Sci U S A. Dec. 15, 1992;89(24):11779-83.
Formaggio et al., Inversion of 3(10)-helix screw sense in a (D-alpha Me)Leu homo-tetrapeptide induced by a guest D-(alpha Me)Val residue. J Pept Sci. Nov.-Dec. 1995;1(6):396-402.
Friedmann et al., RAM-induced allostery facilitates assembly of a notch pathway active transcription complex. J Biol Chem. May 23, 2008;283(21):14781-91. doi: 10.1074/jbc.M709501200. Epub Apr. 1, 2008.
Fromme et al., Structural basis for removal of adenine mispaired with 8-oxoguanine by MutY adenine DNA glycosylase. Nature. Feb. 12, 2004;427(6975):652-6.
Fryer et al., Mastermind mediates chromatin-specific transcription and turnover of the Notch enhancer complex. Genes Dev. Jun. 1, 2002;16(11):1397-411.
Fuchs et al., Socializing with the neighbors: stem cells and their niche. Cell. Mar. 19, 2004;116(6):769-78.
Fung et al., Delta-like 4 induces notch signaling in macrophages: implications for inflammation. Circulation. Jun. 12, 2007;115(23):2948-56. Epub May 28, 2007.
Furstner et al., Alkyne Metathesis: Development of a Novel Molybdenum-Based Catalyst System and Its Application to the Total Synthesis of Epothilone A and C. Chem Euro J. 2001;7(24):5299-5317.
Furstner et al., Mo[N(t-Bu)(AR)]3 Complexes As Catalyst Precursors: In Situ Activation and Application to Metathesis Reactions of Alkynes and Diynes. J Am Chem Soc. 1999;121:9453-54.
Furstner et al., Nozaki-Hiyama-Kishi Reactions Catalytic in Chromium. J Am Chem Soc. 1996:118:12349-57.
Fustero et al., Asymmetric synthesis of new beta,beta-difluorinated cyclic quaternary alpha-amino acid derivatives. Org Lett. Aug. 31, 2006;8(18):4129-32.
Gallivan et al., A neutral, water-soluble olefin metathesis catalyst based on an N-heterocyclic carbene ligand. Tetrahedron Letters. 2005;46:2577-80.
Gante, Peptidomimetics—Tailored Enzyme Inhibitors. J Angew Chem Int Ed Engl. 1994;33:1699-1720.
Garg et al., Mutations in NOTCH1 cause aortic valve disease. Nature. Sep. 8, 2005;437(7056):270-4. Epub Jul. 17, 2005.
Gat et al., De Novo hair follicle morphogenesis and hair tumors in mice expressing a truncated beta-catenin in skin. Cell. Nov. 25, 1998;95(5):605-14.
Gavathiotis et al., BAX activation is initiated at a novel interaction site. Nature. Oct. 23, 2008;455(7216):1076-81.
Gentle et al., Direct production of proteins with N-terminal cysteine for site-specific conjugation. Bioconjug Chem. May-Jun. 2004;15(3):658-63.
Gerber-Lemaire et al., Glycosylation pathways as drug targets for cancer: glycosidase inhibitors. Mini Rev Med Chem. Sep. 2006;6(9):1043-52.
Giannis et al., Peptidomimetics for Receptor Ligands—Discovery, Development, and Medical Perspectives. Angew Chem Int Ed Engl. 1993;32:1244-67.
Gong et al., LDL receptor-related protein 5 (LRP5) affects bone accrual and eye development. Cell. Nov. 16, 2001;107(4):513-23.
Goodson et al., Potential Growth Antagonists. I. Hydantoins and Disubstituted Glycines. J Org Chem. 1960;25:1920-24.
Görlich et al., Transport between the cell nucleus and the cytoplasm. Annu Rev Cell Dev Biol. 1999;15:607-60.
Goun et al., Molecular transporters: synthesis of oligoguanidinium transporters and their application to drug delivery and real-time imaging. Chembiochem. Oct. 2006;7(10):1497-515.
Greenfield et al., Computed circular dichroism spectra for the evaluation of protein conformation. Biochemistry. Oct. 1969;8(10):4108-16.
Greenlee et al., A General Synthesis of α-vinyl-α-amino acids. Tetrahedron Letters. 1978;42:3999-4002.
Grossmann et al., Inhibition of oncogenic Wnt signaling through direct targeting of β-catenin. Proc Natl Acad Sci U S A. Oct. 30, 2012;109(44):17942-7. doi: 10.1073/pnas.1208396109. Epub Oct. 15, 2012.
Grubbs et al., Ring-Closing Metathesis and Related Processes in Organic Synthesis. Acc Chem Res. 1995;28:446-52.
Grünig et al., Requirement for IL-13 independently of IL-4 in experimental asthma. Science. Dec. 18, 1998;282(5397):2261-3.
Guinn et al., Synthesis and characterization of polyamides containing unnatural amino acids. Biopolymers. May 1995;35(5):503-12.
Guo et al., Probing the alpha-helical structural stability of stapled p53 peptides: molecular dynamics simulations and analysis. Chem Biol Drug Des. Apr. 2010;75(4):348-59. doi: 10.1111/j.1747-0285.2010.00951.x.
Gupta et al., Long-term effects of tumor necrosis factor-alpha treatment on insulin signaling pathway in HepG2 cells and HepG2 cells overexpressing constitutively active Akt/PKB. J Cell Biochem. Feb. 15, 2007;100(3):593-607.
Harper et al., Efficacy of a bivalent L1 virus-like particle vaccine in prevention of infection with human papillomavirus types 16 and 18 in young women: a randomized controlled trial. Lancet. Nov. 13-19, 2004;364(9447):1757-65.
Harris et al., Synthesis of proline-modified analogues of the neuroprotective agent glycyl-l-prolyl-glutamic acid (GPE). Tetrahedron. 2005;61:10018-35.
Hartmann et al., Dual roles of Wnt signaling during chondrogenesis in the chicken limb. Development. Jul. 2000;127(14):3141-59.
Hartmann, A Wnt canon orchestrating osteoblastogenesis. Trends Cell Biol. Mar. 2006;16(3):151-8. Epub Feb. 7, 2006.
Hellman et al., Electrophoretic mobility shift assay (EMSA) for detecting protein-nucleic acid interactions. Nat Protoc. 2007;2(8):1849-61.

(56) References Cited

OTHER PUBLICATIONS

Henchey et al., Contemporary strategies for the stabilization of peptides in the α-helical conformation. Curr Opin Chem Biol. 2008;12:692-97.
Hilton et al., Notch signaling maintains bone marrow mesenchymal progenitors by suppressing osteoblast differentiation. Nat Med. Mar. 2008;14(3):306-14. doi: 10.1038/nm1716. Epub Feb. 24, 2008.
Hipfner et al., Connecting proliferation and apoptosis in development and disease. Nat Rev Mol Cell Biol. Oct. 2004;5(10):805-15.
Hoang et al., Dickkopf 3 inhibits invasion and motility of Saos-2 osteosarcoma cells by modulating the Wnt-beta-catenin pathway. Cancer Res. Apr. 15, 2004;64(8):2734-9.
Holford et al., Adding 'splice' to protein engineering. Structure. Aug. 15, 1998;6(8):951-6.
Huang et al., How insulin binds: the B-chain alpha-helix contacts the L1 beta-helix of the insulin receptor. J Mol Biol. Aug. 6, 2004;341(2):529-50.
Huang et al., Tankyrase inhibition stabilizes axin and antagonizes Wnt signalling. Nature. Oct. 1, 2009;461(7264):614-20. Epub Sep. 16, 2009.
Jackson et al., General Approach to the Synthesis of Short α-Helical Peptides. J Am Chem Soc. 1991;113:9391-92.
Jamieson et al., Granulocyte-macrophage progenitors as candidate leukemic stem cells in blast-crisis CML. N Engl J Med. Aug. 12, 2004;351(7):657-67.
Jensen et al., Activation of the insulin receptor (IR) by insulin and a synthetic peptide has different effects on gene expression in IR-transfected L6 myoblasts. Biochem J. Jun. 15, 2008;412(3):435-45. doi: 10.1042/BJ20080279.
Jordan et al., Wnt4 overexpression disrupts normal testicular vasculature and inhibits testosterone synthesis by repressing steroidogenic factor 1/beta-catenin synergy. Proc Natl Acad Sci U S A. Sep. 16, 2003;100(19):10866-71. Epub Aug. 29, 2003.
Joutel et al., Notch3 mutations in CADASIL, a hereditary adult-onset condition causing stroke and dementia. Nature. Oct. 24, 1996;383(6602):707-10.
Junutula et al., Molecular characterization of Rab11 interactions with members of the family of Rab11-interacting proteins. J Biol Chem. Aug. 6, 2004;279(32):33430-7. Epub Jun. 1, 2004.
Karle et al., Structural characteristics of alpha-helical peptide molecules containing Aib residues. Biochemistry. Jul. 24, 1990;29(29):6747-56.
Karwoski et al., Lysinonorleucine cross-link formation in alpha amino heptenoic acid-substituted peptide derivatives. Biopolymers. 1978;17(5):1119-27.
Katoh et al., Cross-talk of WNT and FGF signaling pathways at GSK3beta to regulate beta-catenin and SNAIL signaling cascades. Cancer Biol Ther. Sep. 2006;5(9):1059-64. Epub Sep. 4, 2006.
Katsu et al., The human frizzled-3 (FZD3) gene on chromosome 8p21, a receptor gene for Wnt ligands, is associated with the susceptibility to schizophrenia. Neurosci Lett. Dec. 15, 2003;353(1):53-6.
Kaul et al., Stereochemical control of peptide folding. Bioorg Med Chem. Jan. 1999;7(1):105-17.
Kawamoto, Targeting the BCL9/B9L binding interaction with beta-catenin as a potential anticancer strategy. PhD Thesis. Jun. 3, 2010. Available at http://deepblue.lib.umich.edu/handle/2027.42/75846 last accessed Apr. 9, 2012. Abstract only. 2 pages.
Kazmaier, Sythesis of Quaternary Amino Acids Containing β, γ- as well as γ,δ-Unsaturated Side Chains via Chelate-Enolate Claisen Rearrangement. Tetrahedron Letters. 1996;37(30):5351-4.
Kelly-Welch et al., Interleukin-4 and Interleukin-13 Signaling Connections Maps. Science. 2003;300:1527-28.
Khalil et al., An efficient and high yield method for the N-tert-butoxycarbonyl protection of sterically hindered amino acids. Tetrahedron Lett. 1996;37(20):3441-44.
Kim et al., Introduction of all-hydrocarbon i,i+3 staples into alpha-helices via ring-closing olefin metathesis. Org Lett. Jul. 2, 2010;12(13):3046-9. doi: 10.1021/ol1010449.
Kim et al., Stereochemical effects of all-hydrocarbon tethers in i,i+4 stapled peptides. Bioorg Med Chem Lett. May 1, 2009;19(9):2533-6. Epub Mar. 13, 2009.
Kim et al., Synthesis of all-hydrocarbon stapled α-helical peptides by ring-closing olefin metathesis. Nat Protoc. Jun. 2011;6(6):761-71. doi: 10.1038/nprot.2011.324. Epub May 12, 2011.
Kimmerlin et al., '100 years of peptide synthesis': ligation methods for peptide and protein synthesis with applications to beta-peptide assemblies. J Pept Res. Feb. 2005;65(2):229-60.
Kinzler et al., Identification of FAP locus genes from chromosome 5q21. Science. Aug. 9, 1991;253(5020):661-5.
Kinzler et al., Lessons from hereditary colorectal cancer. Cell. Oct. 18, 1996;87(2):159-70.
Knackmuss et al., Specific inhibition of interleukin-13 activity by a recombinant human single-chain immunoglobulin domain directed against the IL-13 receptor alpha1 chain. Biol Chem. Mar. 2007;388(3):325-30.
Kohler et al., DNA specificity enhanced by sequential binding of protein monomers. Proc Natl Acad Sci U S A. Oct. 12, 1999;96(21):11735-9.
Kolb et al., Click Chemistry: Diverse Chemical Function from a Few Good Reactions. Angew Chem Int Ed Engl. Jun. 1, 2001;40(11):2004-2021.
Kondo et al., Frizzled 4 gene (FZD4) mutations in patients with familial exudative vitreoretinopathy with variable expressivity. Br J Ophthalmol. Oct. 2003;87(10):1291-5.
Konishi et al, Gamma-secretase inhibitor prevents Notch3 activation and reduces proliferation in human lung cancers. Cancer Res. Sep. 1, 2007;67(17):8051-7.
Korcsmáros et al., Uniformly curated signaling pathways reveal tissue-specific cross-talks and support drug target discovery. Bioinformatics. Aug. 15, 2010;26(16):2042-50. Epub Jun. 11, 2010.
Korinek et al., Depletion of epithelial stem-cell compartments in the small intestine of mice lacking Tcf-4. Nat Genet. Aug. 1998;19(4):379-83.
Kotha et al., Modification of constrained peptides by ring-closing metathesis reaction. Bioorg Med Chem Lett. Jun. 4, 2001;11(11):1421-3.
Kouzarides, Acetylation: a regulatory modification to rival phosphorylation? EMBO J. Mar. 15, 2000;19(6):1176-9.
Kovall et al., Crystal structure of the nuclear effector of Notch signaling, CSL, bound to DNA. EMBO J. Sep. 1, 2004;23(17):3441-51. Epub Aug. 5, 2004.
Kozlovsky et al., GSK-3 and the neurodevelopmental hypothesis of schizophrenia. Eur Neuropsychopharmacol. Feb. 2002;12(1):13-25.
Kristensen et al., Expression and characterization of a 70-kDa fragment of the insulin receptor that binds insulin. Minimizing ligand binding domain of the insulin receptor. J Biol Chem. Jul. 10, 1998;273(28):17780-6.
Kristensen et al., Functional reconstitution of insulin receptor binding site from non-binding receptor fragments. J Biol Chem. May 24, 2002;277(21):18340-5. Epub Mar. 18, 2002.
Kurose et al., Cross-linking of a B25 azidophenylalanine insulin derivative to the carboxyl-terminal region of the alpha-subunit of the insulin receptor. Identification of a new insulin-binding domain in the insulin receptor. J Biol Chem. Nov. 18, 1994;269(46):29190-7.
Kussie et al., Structure of the MDM2 oncoprotein bound to the p53 tumor suppressor transactivation domain. Science. Nov. 8, 1996;274(5289):948-53.
Kutchukian et al., All-atom model for stabilization of alpha-helical structure in peptides by hydrocarbon staples. J Am Chem Soc. Apr. 8, 2009;131(13):4622-7.
Lacombe et al., Reduction of Olefins on Solid Support Using Diimide. Tetrahderon Lett. 1998;39:6785-86.
Lammi et al., Mutations in AXIN2 cause familial tooth agenesis and predispose to colorectal cancer. Am J Hum Genet. May 2004;74(5):1043-50. Epub Mar. 23, 2004.
Laporte et al., Molecular and structural basis of cytokine receptor pleiotropy in the interleukin-4/13 system. Cell. Jan. 25, 2008;132(2):259-72.

(56) References Cited

OTHER PUBLICATIONS

Le Geuzennec et al., Molecular characterization of Sin3 PAH-domain interactor specificity and identification of PAH partners. Nucleic Acids Res. 2006;34(14):3929-37. Epub Aug. 12, 2006.

Le Geuzennec et al., Molecular determinants of the interaction of Mad with the PAH2 domain of mSin3. J Biol Chem. Jun. 11, 2004;279(24):25823-9. Epub Mar. 26, 2004.

Leduc et al., Helix-stabilized cyclic peptides as selective inhibitors of steroid receptor-coactivator interactions. Proc Natl Acad Sci USA. 2003;100(20):11273-78.

Lewis et al., Apoptosis in T cell acute lymphoblastic leukemia cells after cell cycle arrest induced by pharmacological inhibition of notch signaling. Chem Biol. Feb. 2007;14(2):209-19.

Li et al., Alagille syndrome is caused by mutations in human Jagged1, which encodes a ligand for Notch1. Nat Genet. Jul. 1997;16(3):243-51.

Li et al., Modulation of Notch signaling by antibodies specific for the extracellular negative regulatory region of NOTCH3. J Biol Chem. Mar. 21, 2008;283(12):8046-54. doi: 10.1074/jbc.M800170200. Epub Jan. 8, 2008.

Li et al., Notch3 signaling promotes the development of pulmonary arterial hypertension. Nat Med. Nov. 2009;15(11):1289-97. doi: 10.1038/nm.2021. Epub Oct. 25, 2009.

Liang et al., Wnt5a inhibits B cell proliferation and functions as a tumor suppressor in hematopoietic tissue. Cancer Cell. Nov. 2003;4(5):349-60.

Liskamp, Conformationally restricted amino acids and dipeptides, (non)peptidomimetics and secondary structure mimetics. Red Travl Chim Pays-Bas. 1994;113:1-19.

Little et al., A Mutation in the LDL Receptor-Related Protein 5 Gene Results in the Autosomal Dominant High-Bone-Mass Trait. Am J Hum Genet. 2002;70:11-19.

Liu et al., Chemical Ligation Approach to Form a Peptide Bond between Unprotected Peptide Segments. Concept and Model Study. J Am Chem Soc. 1994;116(10):4149-53.

Liu et al., Targeted degradation of beta-catenin by chimeric F-box fusion proteins. Biochem Biophys Res Commun. Jan. 23, 2004;313(4):1023-9.

Lo et al., Phosphorylation by the beta-catenin/MAPK complex promotes 14-3-3-mediated nuclear export of TCF/POP-1 in signal-responsive cells in C. elegans. Cell. Apr. 2, 2004;117(1):95-106.

Logan et al., The Wnt signaling pathway in development and disease. Annu Rev Cell Dev Biol. 2004;20:781-810.

Losey et al., Crystal structure of *Staphylococcus aureus* tRNA adenosine deaminase TadA in complex with RNA. Nat Struct Mol Biol. Feb. 2006;13(2):153-9. Epub Jan. 15, 2006.

Lou et al., The first three domains of the insulin receptor differ structurally from the insulin-like growth factor 1 receptor in the regions governing ligand specificity. Proc Natl Acad Sci U S A. Aug. 15, 2006;103(33):12429-34. Epub Aug. 7, 2006.

Loughlin et al., Functional variants within the secreted frizzled-related protein 3 gene are associated with hip osteoarthritis in females. Proc Natl Acad Sci U S A. Jun. 29, 2004;101(26):9757-62. Epub Jun. 21, 2004.

Lubman et al., Quantitative dissection of the Notch:CSL interaction: insights into the Notch-mediated transcriptional switch. J Mol Biol. Jan. 19, 2007;365(3):577-89. Epub Oct. 3, 2006.

Luo et al., Wnt signaling and human diseases: what are the therapeutic implications? Lab Invest. Feb. 2007;87(2):97-103. Epub Jan. 8, 2007.

Luscher et al., The basic region/helix-loop-helix/leucine zipper domain of Myc proto-oncoproteins: function and regulation. Oncogene. May 13, 1999;18(19):2955-66.

Luu et al, Wnt/beta-catenin signaling pathway as a novel cancer drug target. Curr Cancer Drug Targets. Dec. 2004;4(8):653-71.

Macmillan, Evolving strategies for protein synthesis converge on native chemical ligation. Angew Chem Int Ed Engl. Nov. 27, 2006;45(46):7668-72.

Marshall et al., Back to the future: ribonuclease A. Biopolymers. 2008;90(3):259-77.

McKern et al., Structure of the insulin receptor ectodomain reveals a folded-over conformation. Nature. Sep. 14, 2006;443(7108):218-21. Epub Sep. 6, 2006.

McNamara et al., Peptides constrained by an aliphatic linkage between two C(alpha) sites: design, synthesis, and unexpected conformational properties of an i,(i+4)-linked peptide. J Org Chem. Jun. 29, 2001;66(13):4585-94.

Menting et al., A thermodynamic study of ligand binding to the first three domains of the human insulin receptor: relationship between the receptor alpha-chain C-terminal peptide and the site 1 insulin mimetic peptides. Biochemistry. Jun. 16, 2009;48(23):5492-500. doi: 10.1021/bi900261q.

Meyers et al., Formation of mutually exclusive Rab11 complexes with members of the family of Rab11-interacting proteins regulates Rab11 endocytic targeting and function. J Biol Chem. Dec. 13, 2002;277(50):49003-10. Epub Oct. 9, 2002.

Miller et al., Application of Ring-Closing Metathesis to the Synthesis of Rigidified Amino Acids and Peptides. J Am Chem Soc. 1996;118(40):9606-9614.

Miller et al., Synthesis of Conformationally Restricted Amino Acids and Peptides Employing Olefin Metathesis. J Am Chem Soc. 1995;117(21):5855-5856.

Miloux et al., Cloning of the human IL-13R alpha1 chain and reconstitution with the IL4R alpha of a functional IL-4/IL-13 receptor complex. FEBS Lett. Jan. 20, 1997;401(2-3):163-6.

Miyaoka et al., Increased expression of Wnt-1 in schizophrenic brains. Schizophr Res. Jul. 27, 1999;38(1):1-6.

Moellering et al., Computational modeling and molecular optimization of stabilized alpha-helical peptides targeting NOTCH-CSL transcriptional complexes. European Journal of Cancer Supplements Nov. 2010; 8(7):30. DOI: 10.1016/S1359-6349(10)71774-2. Abstract 69.

Moellering et al., Direct inhibition of the NOTCH transcription factor complex. Nature. Nov. 12, 2009;462(7270):182-8.

Moon et al., WNT and beta-catenin signalling: diseases and therapies. Nat Rev Genet. Sep. 2004;5(9):689-99.

Morin, beta-catenin signaling and cancer. Bioessays. Dec. 1999;21(12):1021-30.

Moy et al., Solution structure of human IL-13 and implication for receptor binding. J Mol Biol. Jun. 29, 2001;310(1):219-30.

Mudher et al., Alzheimer's disease—do tauists and baptists finally shake hands? Trends Neurosci. Jan. 2002;25(1):22-6.

Muir et al., Expressed protein ligation: a general method for protein engineering. Proc Natl Acad Sci U S A. Jun. 9, 1998;95(12):6705-10.

Muir, Semisynthesis of proteins by expressed protein ligation. Annu Rev Biochem. 2003;72:249-89. Epub Feb. 27, 2003.

Muppidi et al., Conjugation of spermine enhances cellular uptake of the stapled peptide-based inhibitors of p53-Mdm2 interaction. Bioorg Med Chem Lett. Dec. 15, 2011;21(24):7412-5. doi: 10.1016/j.bmcl.2011.10.009. Epub Oct. 12, 2011.

Mynarcik et al., Alanine-scanning mutagenesis of a C-terminal ligand binding domain of the insulin receptor alpha subunit. J Biol Chem. Feb. 2, 1996;271(5):2439-42.

Mynarcik et al., Identification of common ligand binding determinants of the insulin and insulin-like growth factor 1 receptors. Insights into mechanisms of ligand binding. J Biol Chem. Jul. 25, 1997;272(30):18650-5.

Myung et al., the ubiquitin-proteasome pathway and proteasome inhibitors. Med Res Rev. Jul. 2001;21(4):245-73.

Nair et al., X-ray structures of Myc-Max and Mad-Max recognizing DNA. Molecular bases of regulation by proto-oncogenic transcription factors. Cell. Jan. 24, 2003;112(2):193-205.

Nakashima et al., Cross-talk between Wnt and bone morphogenetic protein 2 (BMP-2) signaling in differentiation pathway of C2C12 myoblasts. J Biol Chem. Nov. 11, 2005;280(45):37660-8. Epub Sep. 2, 2005.

Nam et al., Structural basis for cooperativity in recruitment of MAML coactivators to Notch transcription complexes. Cell. Mar. 10, 2006;124(5):973-83.

(56) References Cited

OTHER PUBLICATIONS

Nam et al., Structural requirements for assembly of the CSL. intracellular Notch1.Mastermind-like 1 transcriptional activation complex. J Biol Chem. Jun. 6, 2003;278(23):21232-9. Epub Mar. 18, 2003.
Nefedova et al., Involvement of Notch-1 signaling in bone marrow stroma-mediated de novo drug resistance of myeloma and other malignant lymphoid cell lines. Blood. May 1, 2004;103(9):3503-10. Epub Dec. 11, 2003.
Ngo et al., Computational complexity, protein structure prediction, and the levinthal paradox. In: The Protein Folding Problem and Tertiary Structure Prediction. K. Mem, Jr., et al. Eds. 1994:433-506.
Niemann et al., Homozygous WNT3 mutation causes tetra-amelia in a large consanguineous family. Am J Hum Genet. Mar. 2004;74(3):558-63. Epub Feb. 5, 2004.
Nilsson et al., Staudinger ligation: a peptide from a thioester and azide. Org Lett. Jun. 29, 2000;2(13):1939-41.
Niranjan et al., The Notch pathway in podocytes plays a role in the development of glomerular disease. Nat Med. Mar. 2008;14(3):290-8. doi: 10.1038/nm1731. Epub Mar. 2, 2008.
Nishisho et al., Mutations of chromosome 5q21 genes in FAP and colorectal cancer patients. Science. Aug. 9, 1991;253(5020):665-9.
Node et al., Hard Acid and Soft Nucleophile Systems. 3. Dealkylation of Esters with Aluminum Halide-Thiol and Aluminum Halide-Sulfide Stustems. J Org Chem. 1981;46:1991-93.
Noguera-Troise et al., Blockade of Dll4 inhibits tumour growth by promoting non-productive angiogenesis. Nature. Dec. 21, 2006;444(7122):1032-7.
Okamura et al., Redundant regulation of T cell differentiation and TCRalpha gene expression by the transcription factors LEF-1 and TCF-1. Immunity. Jan. 1998;8(1):11-20.
Olson et al., Sizing up the heart: development redux in disease. Genes Dev. Aug. 15, 2003;17(16):1937-56. Epub Jul. 31, 2003.
O'Neil et al., FBW7 mutations in leukemic cells mediate NOTCH pathway activation and resistance to gamma-secretase inhibitors. J Exp Med. Aug. 6, 2007;204(8):1813-24. Epub Jul. 23, 2007.
Oswald et al., RBP-Jkappa/SHARP recruits CtIP/CtBP corepressors to silence Notch target genes. Mol Cell Biol. Dec. 2005;25(23):10379-90.
Pakotiprapha et al., Crystal structure of Bacillus stearothermophilus UvrA provides insight into ATP-modulated dimerization, UvrB interaction, and DNA binding. Mol Cell. Jan. 18, 2008;29(1):122-33. Epub Dec. 27, 2007.
Palomero et al., Mutational loss of PTEN induces resistance to NOTCH1 inhibition in T-cell leukemia. Nat Med. Oct. 2007;13(10):1203-10. Epub Sep. 16, 2007.
Park et al., Notch3 gene amplification in ovarian cancer. Cancer Res. Jun. 15, 2006;66(12):6312-8.
Pellois et al., Semisynthetic proteins in mechanistic studies: using chemistry to go where nature can't. Curr Opin Chem Biol. Oct. 2006;10(5):487-91. Epub Aug. 28, 2006.
Perantoni, Renal development: perspectives on a Wnt-dependent process. Semin Cell Dev Biol. Aug. 2003;14(4):201-8.
Phelan et al., A General Method for Constraining Short Peptides to an α-Helical Conformation. J Am Chem Soc. 1997;119(3):455-60.
Picksley et al., Immunochemical analysis of the interaction of p53 with MDM2;—fine mapping of the MDM2 binding site on p53 using synthetic peptides. Oncogene. Sep. 1994;9(9):2523-9.
Pillutla et al., Peptides identify the critical hotspots involved in the biological activation of the insulin receptor. J Biol Chem. Jun. 21, 2002;277(25):22590-4. Epub Apr. 18, 2002.
Pinnix et al., Active Notch1 confers a transformed phenotype to primary human melanocytes. Cancer Res. Jul. 1, 2009;69(13):5312-20. doi: 10.1158/0008-5472.CAN-08-3767. Epub Jun. 23, 2009.
Polakis, The oncogenic activation of beta-catenin. Curr Opin Genet Dev. Feb. 1999;9(1):15-21.
Qiu et al., Convenient, Large-Scale Asymmetric Synthesis of Enantiomerically Pure trans-Cinnamylglycine and -α-Alaniene. Tetrahedron. 2000;56:2577-82.

Rao et al, Inhibition of NOTCH signaling by gamma secretase inhibitor engages the RB pathway and elicits cell cycle exit in T-cell acute lymphoblastic leukemia cells. Cancer Res. Apr. 1, 2009;69(7):3060-8. doi: 10.1158/0008-5472.CAN-08-4295. Epub Mar. 24, 2009.
Rawlinson et al., CRM1-mediated nuclear export of dengue virus RNA polymerase NS5 modulates interleukin-8 induction and virus production. J Biol Chem. Jun. 5, 2009;284(23):15589-97. Epub Mar. 18, 2009.
Reya et al., Wnt signalling in stem cells and cancer. Nature. Apr. 14, 2005;434(7035):843-50.
Rich et al., Synthesis of the cytostatic cyclic tetrapeptide, chlamydocin. Tetranderon Letts. 1983;24(48):5305-08.
Ridgway et al., Inhibition of Dll4 signalling inhibits tumour growth by deregulating angiogenesis. Nature. Dec. 21, 2006;444(7122):1083-7.
Robert, A hierarchical "nesting" approach to describe the stability of alpha helices with side-chain interactions. Biopolymers. 1990;30(3-4):335-47.
Robitaille et al., Mutant frizzled-4 disrupts retinal angiogenesis in familial exudative vitreoretinopathy. Nat Genet. Oct. 2002;32(2):326-30. Epub Aug. 12, 2002.
Rodova et al., The polycystic kidney disease-1 promoter is a target of the beta-catenin/T-cell factor pathway. J Biol Chem. Aug. 16, 2002;277(33):29577-83. Epub Jun. 4, 2002.
Roos et al., Synthesis of α-Substituted α-Amino Acids via Cationic Intermediates. J Org Chem. 1993;58:3259-68.
Ross et al., Inhibition of adipogenesis by Wnt signaling. Science. Aug. 11, 2000;289(5481):950-3.
Rudinger, Characteristics of the amino acids as components of a peptide hormone sequence. In: Peptide Hormones. J. A. Parsons, ed. University Park Press. Jun. 1976:1-7.
Sadot et al., Down-regulation of beta-catenin by activated p53. Mol Cell Biol. Oct. 2001;21(20):6768-81.
Sali et al., Stabilization of protein structure by interaction of alpha-helix dipole with a charged side chain. Nature. Oct. 20, 1988;335(6192):740-3.
Sampietro et al., Crystal structure of a beta-catenin/BCL9/Tcf4 complex. Mol Cell. Oct. 20, 2006;24(2):293-300.
Satoh et al., AXIN1 mutations in hepatocellular carcinomas, and growth suppression in cancer cells by virus-mediated transfer of AXIN1. Nat Genet. Mar. 2000;24(3):245-50.
Sattler et al., Structure of Bcl-xL-Bak peptide complex: recognition between regulators of apoptosis. Science. Feb. 14, 1997;275(5302):983-6.
Saxon et al., Cell surface engineering by a modified Staudinger reaction. Science. Mar. 17, 2000;287(5460):2007-10.
Schäffer et al., A novel high-affinity peptide antagonist to the insulin receptor. Biochem Biophys Res Commun. Nov. 14, 2008;376(2):380-3. doi: 10.1016/j.bbrc.2008.08.151. Epub Sep. 7, 2008.
Schäffer et al., Assembly of high-affinity insulin receptor agonists and antagonists from peptide building blocks. Proc Natl Acad Sci U S A. Apr. 15, 2003;100(8):4435-9. Epub Apr. 8, 2003.
Schafmiester et al., An All-Hydrocarbon Cross-Linking System for Enhancing the Helicity and Metabolic Stability of Peptides. J Am Chem Soc. 2000;122:5891-92.
Scheffzek et al., The Ras-RasGAP complex: structural basis for GTPase activation and its loss in oncogenic Ras mutants. Science. Jul. 18, 1997;277(5324):333-8.
Schinzel et al., The phosphate recognition site of *Escherichia coli* maltodextrin phosphorylase. FEBS Lett. Jul. 29, 1991;286(1-2):125-8.
Schmiedeberg et al., Reversible backbone protection enables combinatorial solid-phase ring-closing metathesis reaction (RCM) in peptides. Org Lett. Jan. 10, 2002;4(1):59-62.
Scholtz et al., The mechanism of alpha-helix formation by peptides. Annu Rev Biophys Biomol Struct. 1992;21:95-118.
Schrock et al., Tungsten(VI) Neopentylidyne Complexes. Organometallics. 1982;1:1645-51.
Schwarzer et al., Protein semisynthesis and expressed protein ligation: chasing a protein's tail. Curr Opin Chem Biol. Dec. 2005;9(6):561-9. Epub Oct. 13, 2005.

(56) References Cited

OTHER PUBLICATIONS

Scott et al., Evidence of insulin-stimulated phosphorylation and activation of the mammalian target of rapamycin mediated by a protein kinase B signaling pathway. Proc Natl Acad Sci U S A. Jun. 23, 1998;95(13):7772-7.

Seabra et al., Rab GTPases, intracellular traffic and disease. Trends Mol Med. Jan. 2002;8(1):23-30.

Seiffert et al., Presenilin-1 and -2 are molecular targets for gamma-secretase inhibitors. J Biol Chem. Nov. 3, 2000;275(44):34086-91.

Shair, A closer view of an oncoprotein-tumor suppressor interaction. Chem Biol. Nov. 1997;4(11):791-4.

Shiba et al., Structural basis for Rab11-dependent membrane recruitment of a family of Rab11-interacting protein 3 (FIP3)/Arfophilin-1. Proc Natl Acad Sci U S A. Oct. 17, 2006;103(42):15416-21. Epub Oct. 9, 2006.

Si et al., CCN1/Cyr61 is regulated by the canonical Wnt signal and plays an important role in Wnt3A-induced osteoblast differentiation of mesenchymal stem cells. Mol Cell Biol. Apr. 2006;26(8):2955-64.

Siddle et al., Specificity in ligand binding and intracellular signalling by insulin and insulin-like growth factor receptors. Biochem Soc Trans. Aug. 2001;29(Pt 4):513-25.

Skinner et al., Basic helix-loop-helix transcription factor gene family phylogenetics and nomenclature. Differentiation. Jul. 2010;80(1):1-8. doi: 10.1016/j.diff.2010.02.003. Epub Mar. 10, 2010.

Smith et al., Structural resolution of a tandem hormone-binding element in the insulin receptor and its implications for design of peptide agonists. Proc Natl Acad Sci U S A. Apr. 13, 2010;107(15):6771-6. doi: 10.1073/pnas.1001813107. Epub Mar. 26, 2010.

Soucek et al., Modelling Myc inhibition as a cancer therapy. Nature. Oct. 2, 2008;455(7213):679-83. Epub Aug. 17, 2008.

Sparey et al., Cyclic sulfamide gamma-secretase inhibitors. Bioorg Med Chem Lett. Oct. 1, 2005;15(19):4212-6.

Stein et al., Rab proteins and endocytic trafficking: potential targets for therapeutic intervention. Adv Drug Deliv Rev. Nov. 14, 2003;55(11):1421-37.

Stenmark et al., The Rab GTPase family. Genome Biol. 2001;2(5):3007.1-3007.7.

Still et al., Semianalytical Treatment of Solvation for Molecular Mechanics and Dynamics. J Am Chem Soc. 1990;112:6127-29.

Struhl et al., Presenilin is required for activity and nuclear access of Notch in *Drosophila*. Nature. Apr. 8, 1999;398(6727):522-5.

Stueanaes et al., Beta-adrenoceptor stimulation potentiates insulin-stimulated PKB phosphorylation in rat cardiomyocytes via cAMP and PKA. Br J Pharmacol. May 2010;160(1):116-29. doi: 10.1111/j.1476-5381.2010.00677.x.

Su et al., Eradication of pathogenic beta-catenin by Skp1/Cullin/F box ubiquitination machinery. Proc Natl Acad Sci U S A. Oct. 28, 2003;100(22):12729-34. Epub Oct. 16, 2003.

Surinya et al., Role of insulin receptor dimerization domains in ligand binding, cooperativity, and modulation by anti-receptor antibodies. J Biol Chem. May 10, 2002;277(19):16718-25. Epub Mar. 1, 2002.

Takeda et al., Human sebaceous tumors harbor inactivating mutations in LEF1. Nat Med. Apr. 2006;12(4):395-7. Epub Mar. 26, 2006.

Tanaka, Design and synthesis of non-proteinogenic amino acids and secondary structures of their peptides. Yakugaku Zasshi. Oct. 2006;126(10):931-44. Japanese.

Thompson et al., Mutants of interleukin 13 with altered reactivity toward interleukin 13 receptors. J Biol Chem. Oct. 15, 1999;274(42):29944-50.

Tian et al., Linear non-competitive inhibition of solubilized human gamma-secretase by pepstatin A methylester, L685458, sulfonamides, and benzodiazepines. J Biol Chem. Aug. 30, 2002;277(35):31499-505. Epub Jun. 18, 2002.

Tian et al., The role of the Wnt-signaling antagonist DKK1 in the development of osteolytic lesions in multiple myeloma. N Engl J Med. Dec. 25, 2003;349(26):2483-94.

Tolbert et al., New methods for proteomic research: preparation of proteins with N-terminal cysteines for labeling and conjugation. Angew Chem Int Ed Engl. Jun. 17, 2002;41(12):2171-4.

Toniolo, Conformationally restricted peptides through short-range cyclizations. Int J Pept Protein Res. Apr. 1990;35(4):287-300.

Toomes et al., Mutations in LRP5 or FZD4 underlie the common familial exudative vitreoretinopathy locus on chromosome 11q. Am J Hum Genet. Apr. 2004;74(4):721-30. Epub Mar. 11, 2004.

Tornøe et al., Peptidotriazoles on solid phase: [1,2,3]-triazoles by regiospecific copper(i)-catalyzed 1,3-dipolar cycloadditions of terminal alkynes to azides. J Org Chem. May 3, 2002;67(9):3057-64.

Torrance et al., Combinatorial chemoprevention of intestinal neoplasia. Nat Med. Sep. 2000;6(9):1024-8.

Tsuji et al., Antiproliferative activity of REIC/Dkk-3 and its significant down-regulation in non-small-cell lung carcinomas. Biochem Biophys Res Commun. Nov. 23, 2001;289(1):257-63.

Tsuruzoe et al., Insulin receptor substrate 3 (IRS-3) and IRS-4 impair IRS-1- and IRS-2-mediated signaling. Mol Cell Biol. Jan. 2001;21(1):26-38.

Ueki et al., Increased insulin sensitivity in mice lacking p85beta subunit of phosphoinositide 3-kinase. Proc Natl Acad Sci U S A. Jan. 8, 2002;99(1):419-24. Epub Dec. 18, 2001.

Ueki et al., Positive and negative regulation of phosphoinositide 3-kinase-dependent signaling pathways by three different gene products of the p85alpha regulatory subunit. Mol Cell Biol. Nov. 2000;20(21):8035-46.

Uesugi et al., The alpha-helical FXXPhiPhi motif in p53: TAF interaction and discrimination by MDM2. Proc Natl Acad Sci U S A. Dec. 21, 1999;96(26):14801-6.

Ullman et al., Luminescent oxygen channeling immunoassay: measurement of particle binding kinetics by chemiluminescence. Proc Natl Acad Sci U S A. Jun. 7, 1994;91(12):5426-30.

Vaickus et al., Immune markers in hematologic malignancies. Crit Rev Oncol Hematol. Dec. 1991;11(4):267-97.

Van Genderen et al., Development of several organs that require inductive epithelial-mesenchymal interactions is impaired in LEF-1-deficient mice. Genes Dev. Nov. 15, 1994;8(22):2691-703.

Van Gijn et al., The wnt-frizzled cascade in cardiovascular disease. Cardiovasc Res. Jul. 2002;55(1):16-24.

Varallo et al., Beta-catenin expression in Dupuytren's disease: potential role for cell-matrix interactions in modulating beta-catenin levels in vivo and in vitro. Oncogene. Jun. 12, 2003;22(24):3680-4.

Vartak et al., Allosteric Modulation of the Dopamine Receptor by Conformationally Constrained Type VI β-Turn Peptidomimetics of Pro-Leu-Gly-$NH_2$. J Med Chem. 2007;50(26):6725-6729.

Venancio et al., Reconstructing the ubiquitin network: cross-talk with other systems and identification of novel functions. Genome Biol. 2009;10(3):R33. Epub Mar. 30, 2009.

Verdine et al., Stapled peptides for intracellular drug targets. Methods Enzymol. 2012;503:3-33. doi: 10.1016/B978-0-12-396962-0.00001-X.

Verdine et al., The challenge of drugging undruggable targets in cancer: lessons learned from targeting BCL-2 family members. Clin Cancer Res. Dec. 15, 2007;13(24):7264-70.

Verma et al., Small interfering RNAs directed against beta-catenin inhibit the in vitro and in vivo growth of colon cancer cells. Clin Cancer Res. Apr. 2003;9(4):1291-300.

Voet et al., Biochemistry. Second Edition. John Wiley & Sons, Inc. 1995:235-241.

Walensky et al., A stapled BID BH3 helix directly binds and activates BAX. Mol Cell. Oct. 20, 2006;24(2):199-210.

Walensky et al., Activation of apoptosis in vivo by a hydrocarbon-stapled BH3 helix. Science. Sep. 3, 2004;305(5689):1466-70.

Walter et al., Critical role for IL-13 in the development of allergen-induced airway hyperreactivity. J Immunol. Oct. 15, 2001;167(8):4668-75.

Wang et al., Inhibition of p53 degradation by Mdm2 acetylation. FEBS Lett. Mar. 12, 2004;561(1-3):195-201.

(56) References Cited

OTHER PUBLICATIONS

Wang, 4-Alkyl-2-trichloromethyloxazolidin-5-ones: Valuable Precursors to Enantiomerically Pure C- and N-Protected α-Alkyl Prolines. Synlett. 1999;1:33-36.
Wei et al., Disorder and structure in the Rab11 binding domain of Rab11 family interacting protein 2. Biochemistry. Jan. 27, 2009;48(3):549-57. doi: 10.1021/bi8020197.
Weng et al., Activating mutations of NOTCH1 in human T cell acute lymphoblastic leukemia. Science. Oct. 8, 2004;306(5694):269-71.
Weng et al., Growth suppression of pre-T acute lymphoblastic leukemia cells by inhibition of notch signaling. Mol Cell Biol. Jan. 2003;23(2):655-64.
Westhoff et al., Alterations of the Notch pathway in lung cancer. Proc Natl Acad Sci U S A. Dec. 29, 2009;106(52):22293-8. doi: 10.1073/pnas.0907781106. Epub Dec. 10, 2009.
Wilen et al., Strategies in Optical Resolution. Tetrahedron. 1977;33:2725-36.
Wilen, Tables of Resolving Agents and Optical Resolutions. E.L. Eliel, ed. Universtify of Notre Dame Press, Notre Dame, IN. 1972:268-98.
Williams et al., Asymmetric synthesis of 2,6-diamino-6-(hydroxymethyl)pimelic acid: assignment of stereochemistry. J Am Chem Soc. 1991;113(18):6976-6981.
Williams et al., Asymmetric Synthesis of Monosubstituted and α,α-Disubstituted α-Amino Acids via Diastereoselective Glycine Enolate Alkylations. J Am Chem Soc. 1991;113:9276-86.
Wills-Karp et al., Interleukin-13: central mediator of allergic asthma. Science. Dec. 18, 1998;282(5397):2258-61.
Wills-Karp, Interleukin-13 in asthma pathogenesis. Immunol Rev. Dec. 2004;202:175-90.
Wills-Karp, The gene encoding interleukin-13: a susceptibility locus for asthma and related traits. Respir Res. 2000;1(1):19-23. Epub Jul. 17, 2000.
Wilson et al., Crystal structure of the CSL-Notch-Mastermind ternary complex bound to DNA. Cell. Mar. 10, 2006;124(5):985-96.
Wilson et al., The FIP3-Rab11 protein complex regulates recycling endosome targeting to the cleavage furrow during late cytokinesis. Mol Biol Cell. Feb. 2005;16(2):849-60. Epub Dec. 15, 2004.
Woon et al., Linking of 2-oxoglutarate and substrate binding sites enables potent and highly selective inhibition of JmjC histone demethylases. Angew Chem Int Ed Engl. Feb. 13, 2012;51(7):1631-4. doi: 10.1002/anie.201107833. Epub Jan. 12, 2012.
Wu et al., MAML1, a human homologue of *Drosophila* mastermind, is a transcriptional co-activator for NOTCH receptors. Nat Genet. Dec. 2000;26(4):484-9.
Wu et al., Therapeutic antibody targeting of individual Notch receptors. Nature. Apr. 15, 2010;464(7291):1052-7. doi: 10.1038/nature08878.
Xi et al., Use of DNA and peptide nucleic acid molecular beacons for detection and quantification of rRNA in solution and in whole cells. Appl Environ Microbiol. Sep. 2003;69(9):5673-8.
Xing et al., Crystal structure of a beta-catenin/axin complex suggests a mechanism for the beta-catenin destruction complex. Genes Dev. Nov. 15, 2003;17(22):2753-64. Epub Nov. 4, 2003.
Yang et al., Synthesis and helical structure of lactam bridged BH3 peptides derived from pro-apoptotic Bcl-2 family proteins. Bioorg Med Chem Lett. 2004;14:1403-06.
Yang et al., Therapeutic dosing with anti-interleukin-13 monoclonal antibody inhibits asthma progression in mice. J Pharmacol Exp Ther. Apr. 2005;313(1):8-15. Epub Jan. 11, 2005.
Ye et al., Neurogenic phenotypes and altered Notch processing in *Drosophila* Presenilin mutants. Nature. Apr. 8, 1999;398(6727):525-9.
Yu et al., The role of Axin2 in calvarial morphogenesis and craniosynostosis. Development. Apr. 2005;132(8):1995-2005.
Zhang et al., A cell-penetrating helical peptide as a potential HIV-1 inhibitor. J Mol Biol. May 2, 2008;378(3):565-80. doi: 10.1016/j.jmb.2008.02.066. Epub Mar. 6, 2008.
Zhou et al., Identification of Ubiquitin Target Proteins Using Cell-Based Arrays. J Proteome Res. 2007;6:4397-4406.
Zhou et al., Lymphoid enhancer factor 1 directs hair follicle patterning and epithelial cell fate. Genes Dev. Mar. 15, 1995;9(6):700-13.
Zhou et al., Tyrosine kinase inhibitor STI-571/Gleevec down-regulates the beta-catenin signaling activity. Cancer Lett. Apr. 25, 2003;193(2):161-70.
Zimm et al., Theory of the Phase Transition between Helix and Random Coil in Polypeptide Chains. J Chem Phys. 1959;31:526-35.
Zor et al., Solution structure of the KIX domain of CBP bound to the transactivation domain of c-Myb. J Mol Biol. Mar. 26, 2004;337(3):521-34.
International Preliminary Report on Patentability for PCT/US2014/025544, mailed Sep. 24, 2015.

NMR measurements of Pro-locked Stapled Peptide 4
~ $P_{R3}AAS_3KRARNTEAAW$ (Total Yield = 34%)

1 ~ P   A A L K R A R N T E A A W
2 ~ P$_{R3}$ A A S$_3$ K R A R N T E A A W

1 = SEQ ID NO:1
2 = SEQ ID NO:2

Fig. 2

GCN4– DNA complex
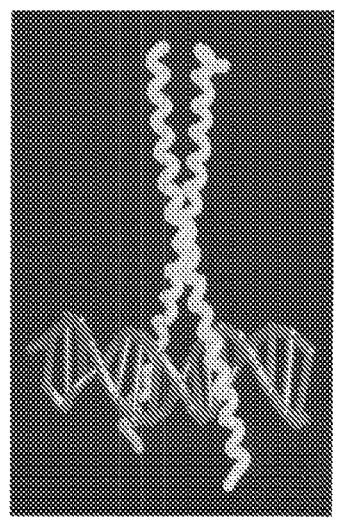
Coiled-coil region
Basic region
X-ray structure (2.9 Å resolution)
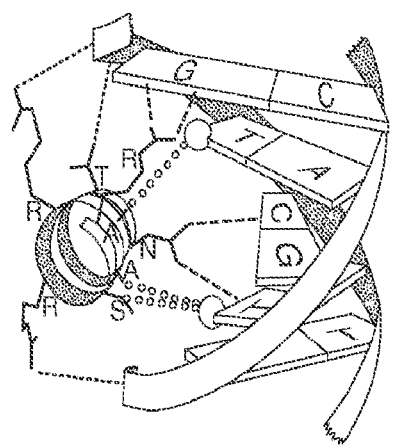
Interaction of GCN4 with DNA
Basic region (SEQ ID NO:3)
NH$_2$ – M(224)KDPAALKRARNTEAARRSRARKLQR(249) – COOH
Coiled-coil region (SEQ ID NO:4)
NH$_2$ – MKQLEDKVEELLSKNYHLENEVARLKKLVGER – COOH
Fig. 9

|    |       |   |   |    |   |   |   |   |   |   |   |   | SEQ ID NO: |
|----|-------|---|---|----|---|---|---|---|---|---|---|---|---|
| 1) | P | A | A | L | K | R | A | R | N | T | E | A | A | W | 1 |
| 2) | P$_{R3}$ | A | A | L | K | R | A | R | N | T | E | A | A | W | 5 |
| 3) | P$_{S3}$ | A | A | L | K | R | A | R | N | T | E | A | A | W | 6 |
| 4) | P$_{R3}$ | A | A | S$_3$ | K | R | A | R | N | T | E | A | A | W | 2 |
| 5) | P$_{R3}$ | A | A | R$_3$ | K | R | A | R | N | T | E | A | A | W | 7 |
| 6) | P$_{S3}$ | A | A | S$_3$ | K | R | A | R | N | T | E | A | A | W | 8 |
| 7) | P$_{S3}$ | A | A | R$_3$ | K | R | A | R | N | T | E | A | A | W | 9 |
| 8) | P$_{SO3}$ | A | A | L | K | R | A | R | N | T | E | A | A | W | 10 |
| 9) | P$_{SO3}$ | A | A | S$_5$ | K | R | A | R | N | T | E | A | A | W | 11 |
| 10) | P$_{SO3}$ | A | A | R$_5$ | K | R | A | R | N | T | E | A | A | W | 12 |
| 19) | P$_{R3}$ | A | A | S$_4$ | K | R | A | R | N | T | E | A | A | W |   |
| 11) | P$_{R3}$ | A | A | S$_5$ | K | R | A | R | N | T | E | A | A | W | 13 |
| 12) | R$_3$ | A | A | S$_3$ | K | R | A | R | N | T | E | A | A | W | 14 |

N terminus ~ NHAc or NAc, C terminus ~ CONH$_2$

Fig. 13

Screening of peptide sequence based on Alanine sequences

13)　　　P　　A　A　A　A　A　A　W　　15
14)　　　$P_{R3}$　A　A　A　A　A　A　W　　16
15)　　　$P_{R3}$　A　A　$S_3$　A　A　A　W　　17
16)　　　$P_{R3}$　A　A　$S_5$　A　A　A　W　　18

N terminus ~ NHAc, C terminus ~ $CONH_2$

Screening of unstapled peptides based on GCN4 basic region

4)　　　$P_{R3}$　A　A　$S_3$　K　R　A　R　N　T　E　A　A　W　　19
11)　　　$P_{R3}$　A　A　$S_5$　K　R　A　R　N　T　E　A　A　W　　20
12)　　　$R_3$　A　A　$S_3$　K　R　A　R　N　T　E　A　A　W　　21

N terminus ~ NHAc, C terminus ~ $CONH_2$

Fig. 14

Olefin metathesis reaction by Grubbs-catalyst 1st generation

4) Single peak in LC/MS (16 h) ⟶ Z–isomer (11 Hz)

5) Multiple peaks in LC/MS (no product)

6) 5 ~ 6 peaks in LC/MS (product: trace)

7) 5 ~ 6 peaks in LC/MS (product: trace)

9) Single peak in LC/MS (4 h)

10) Multiple peaks in LC/MS (no product)

11) Single peak in LC/MS (4 h)

12) 2 isomers in LC/MS (major : minor = 5 : 1) (8 h)

13) Single peak in LC/MS (4 h, 50 °C)

Fig. 15

4) P_{R3}  A  A  S_3  K  R  A  R  N  T  E  A  A  W
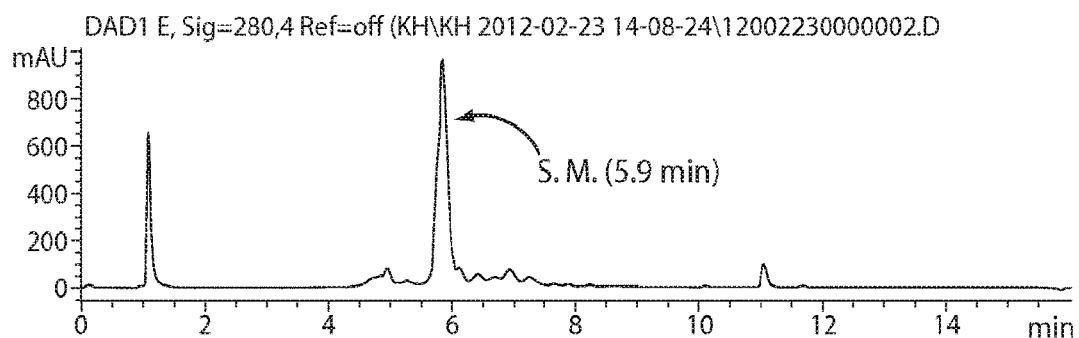
⇩ 2 h x 8 (16h)
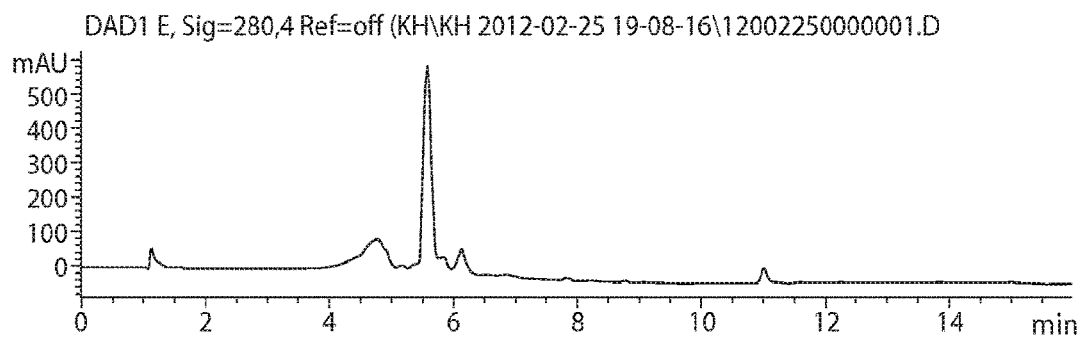
Fig. 16

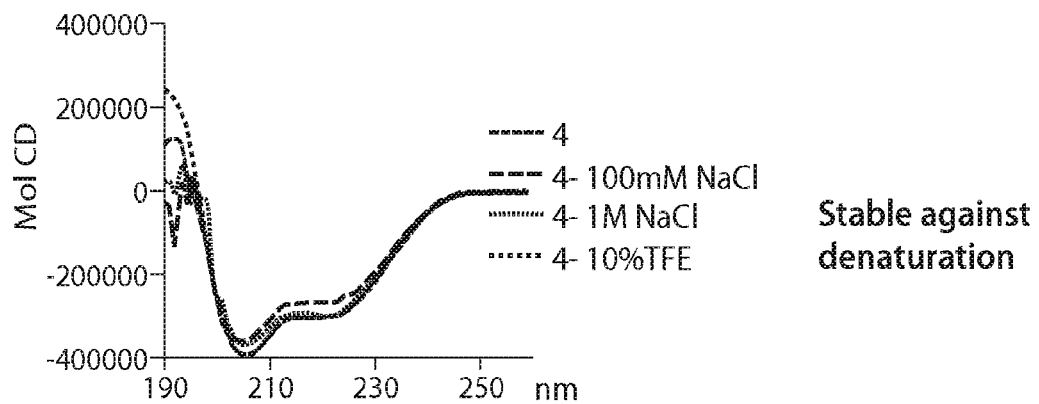
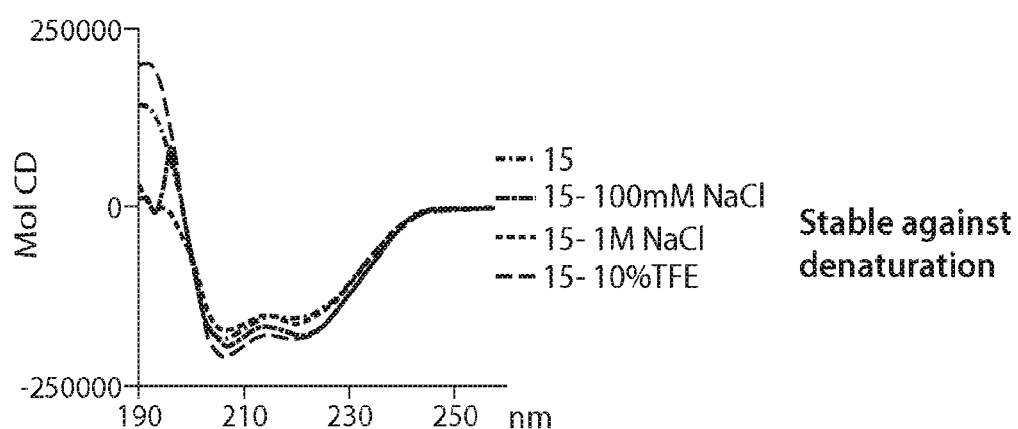
Fig. 19

Pro-locked Stapled peptides based on full-length GCN4 basic region

17) ~ P A A L K R A R N T E A A R
      R S R A R K L Q R W    SEQ ID NO: 22

18) ~ P$_{R3}$ A A S$_3$ K R A R N T E A A R
      R S R A R K L Q R W    SEQ ID NO: 23

20) ~ P$_{R3}$ A A S$_5$ K R A R N T E A A R
      R S R A R K L Q R W

A 40 °C enhancement was observed approximately when the plateau of melting curve of 18 was compared with that of 17.

Cell penetration ability of Pro-locked Stapled Peptide 18
- P$_{R3}$AAS$_3$KRARNTEAARRSRARKLQRW (24 mer)

WT peptide 17 (0.1 μM): left ~ FITC-labeled Peptide 17, right ~ DAPI

 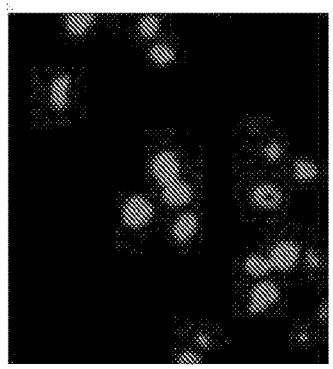

The cell penetration of peptide 17 wasn't observed at all in 0.1 μM concentration.

Stapled peptide 18 (0.1 μM): left ~ FITC-labeled Peptide 18, right ~ DAPI

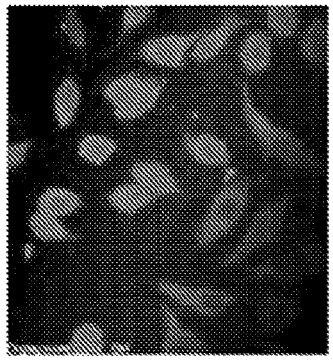 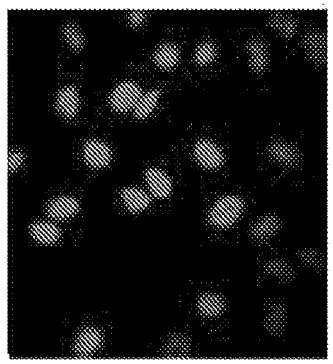

Significant cell penetration of peptide 18 was observed even 0.1 μM concentration.

Fig. 24

Cell penetration abilities of several peptides (HeLa cell)
0.5% DMSO
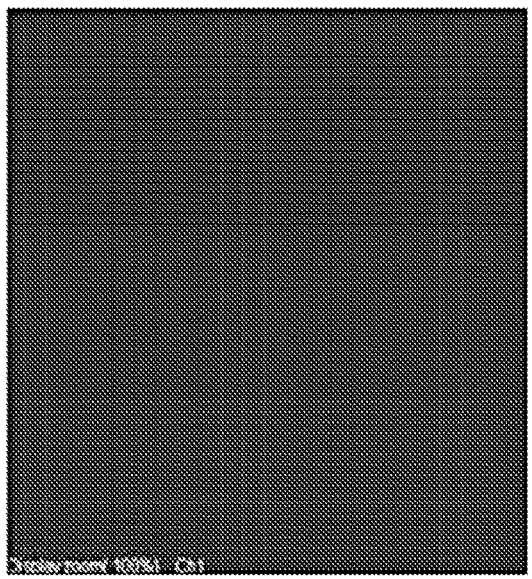
Peptide 17 (1 μM)
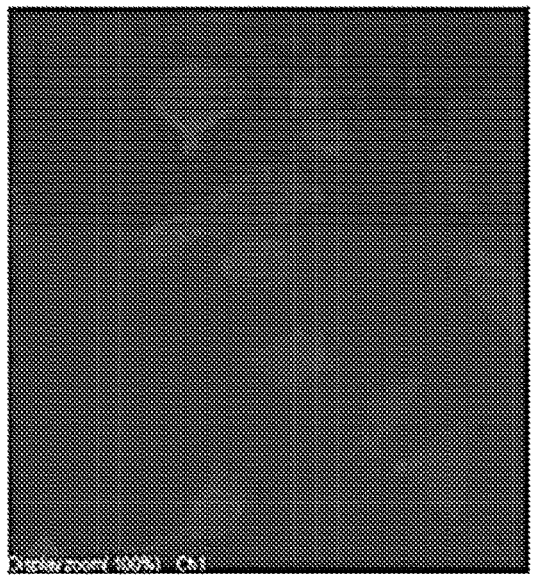
Peptide 18 (1 μM)
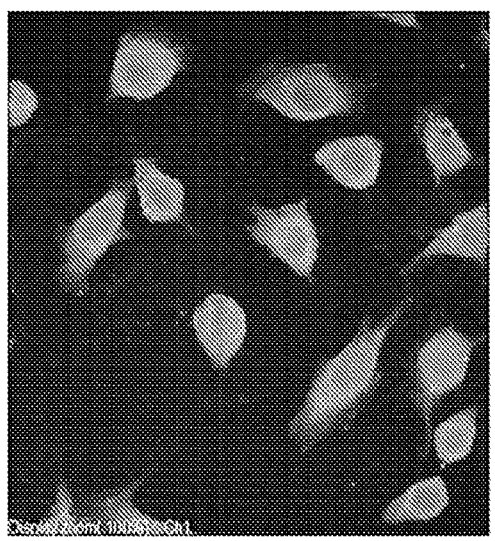
Peptide 18 (DAPI)
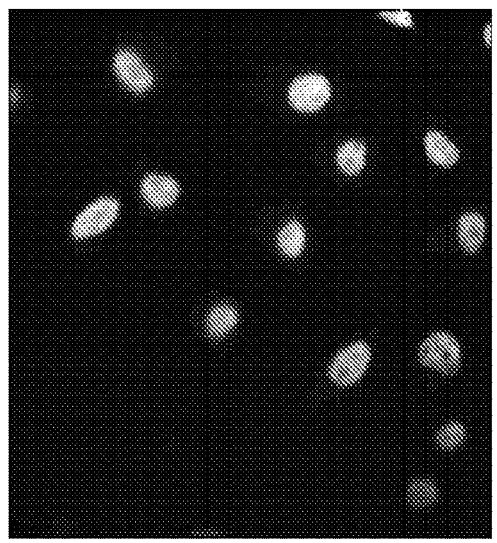
Fig. 25

NMR measurements of Pro-locked Stapled Peptide 4
~ P$_{R3}$AAS$_3$KRARNTEAAW (Total yield = 34%)

1. Coupling constant ~ 11.0 Hz (Z isomer)
2. 49% and 77% NOE were observed between two olefinic protons (Z isomer)
3. 13 crosspeaks which indicate α-helix were observed (NOESY)

| | | | | | | | | | | | | |
|---|---|---|---|---|---|---|---|---|---|---|---|---|
| 1) | P | A | A | L | K | R | A | R | N | T | E | A | A | W |
| 4) | $P_{R3}$ | A | A | $S_3$ | K | R | A | R | N | T | E | A | A | W |
| 19) | $P_{R3}$ | A | A | $S_4$ | K | R | A | R | N | T | E | A | A | W |
| 11) | $P_{R3}$ | A | A | $S_5$ | K | R | A | R | N | T | E | A | A | W |
| 12) | $R_3$ | A | A | $S_3$ | K | R | A | R | N | T | E | A | A | W |
| 25) | $R_5$ | A | A | $S_5$ | K | R | A | R | N | T | E | A | A | W |
| 26) | $S_5$ | A | A | L | $S_5$ | R | A | R | N | T | E | A | A | W |

N terminus ~ NHAc or NAc, C terminus ~ CONH$_2$

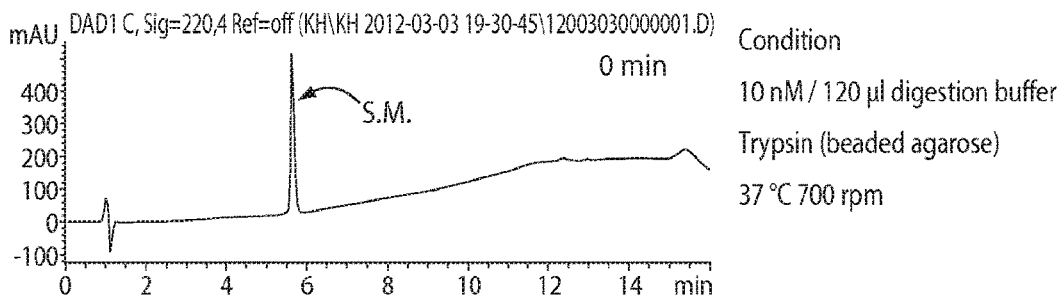
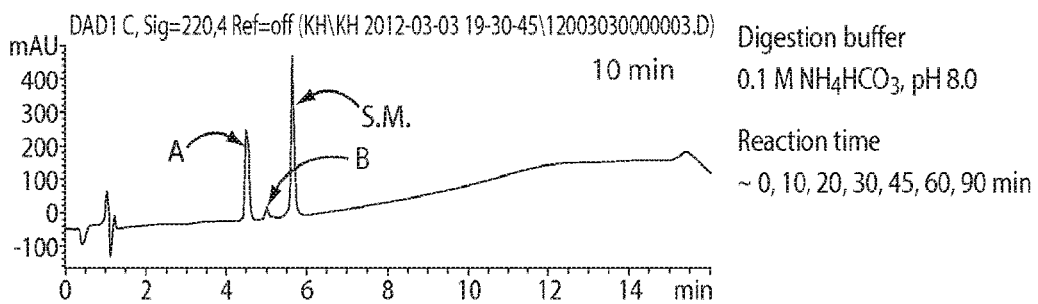
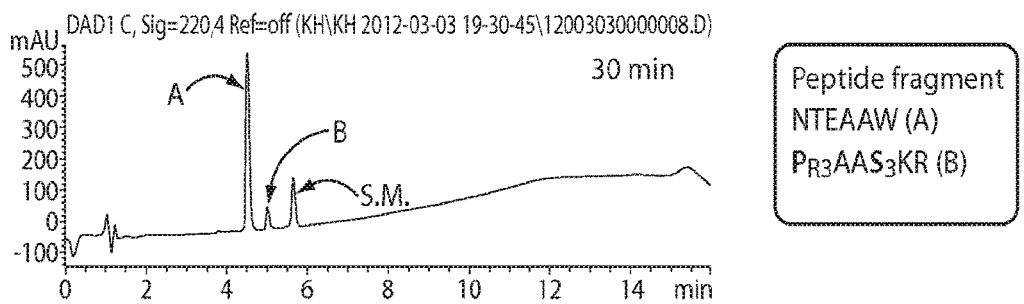
Fig. 31

Stability of proline stapled peptides against trypsin proteolysis

1) P    A    A    L    K    R    A    R    N    T    E    A    A    W
2) P$_{R3}$  A    A    L    K    R    A    R    N    T    E    A    A    W
4) P$_{R3}$  A    A    S$_3$  K    R    A    R    N    T    E    A    A    W

N terminus ~ NHAc or NAc, C terminus ~ CONH$_2$ k (rate constant) (s$^{-1}$)
1 ~ 5.70 x 10$^{-4}$, 2 ~ 5.60 x 10$^{-4}$, 4 ~ 3.99 x 10$^{-4}$ ⇒ 1.4–fold enhancement (1 vs 4)

| | | | | | | | | | | | | |
|---|---|---|---|---|---|---|---|---|---|---|---|---|
| 1) | P | A | A | L | K | R | A | R | N | T | E | A | A | W |
| 4) | $P_{R3}$ | A | A | $S_3$ | K | R | A | R | N | T | E | A | A | W |
| 27) | $P_{S5}$ | A | A | L | K | R | $S_8$ | R | N | T | E | A | A | W |
| 28) | $P_{S5}$ | A | A | L | K | R | $R_8$ | R | N | T | E | A | A | W |
| 29) | $P_{S5}$ | A | A | L | K | R | A | $S_8$ | N | T | E | A | A | W |
| 30) | $P_{S5}$ | A | A | L | K | R | A | $R_8$ | N | T | E | A | A | W |
| 31) | $R_5$ | A | A | L | K | R | A | $S_8$ | N | T | E | A | A | W |

N terminus ~ NHAc or NAc, C terminus ~ CONH$_2$

% helicity:
4 Z isomer = 66%,
29 Stapled = 61%
31 Staples = 48%

| | | | | | | | | | | | | |
|---|---|---|---|---|---|---|---|---|---|---|---|---|
|1)|P|A|A|L|K|R|A|R|N|T|E|A|A|W|
|4)|$P_{R3}$|A|A|$S_3$|K|R|A|R|N|T|E|A|A|W|
|29)|$P_{S5}$|A|A|L|K|R|A|$S_8$|N|T|E|A|A|W|
|32)|$P_{R3}$|A|A|$B_5$|K|R|$S_5$|R|N|T|E|A|A|W|
|33)|$P_{R3}$|A|A|$B_5$|K|R|A|$R_5$|N|T|E|A|A|W|
|34)|$P_{R3}$|A|A|$B_5$|K|R|A|R|N|T|$S_8$|A|A|W|

N terminus ~ NHAc, C terminus ~ $CONH_2$

% helicity:
4 Z isomer = 66%,
29 St = 61%
32 St minor = 74%
32 major St = 79%
33 St = 47%
34 St = 81%

35) Ac P$_{R3}$ A A S$_3$ K R A R N T E R$_3$ A W NH-Allyl
36) Ac P$_{R3}$ A A S$_3$ K R A R N T E R$_4$ A W NH-Allyl
37) Ac P$_{R3}$ A A S$_3$ K R A R N T E R$_5$ A W NH-Allyl
38) Ac P$_{R3}$ A A S$_3$ K R A R N T E R$_3$ A W NH-Butenyl
39) Ac P$_{R3}$ A A S$_3$ K R A R N T E R$_4$ A W NH-Butenyl
40) Ac P$_{R3}$ A A S$_3$ K R A R N T E R$_5$ A W NH-Butenyl
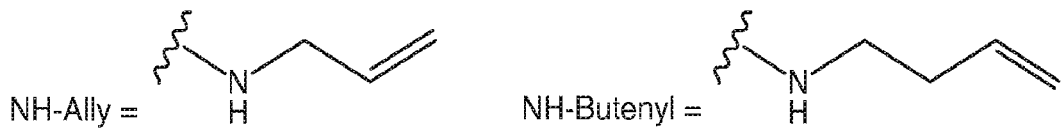
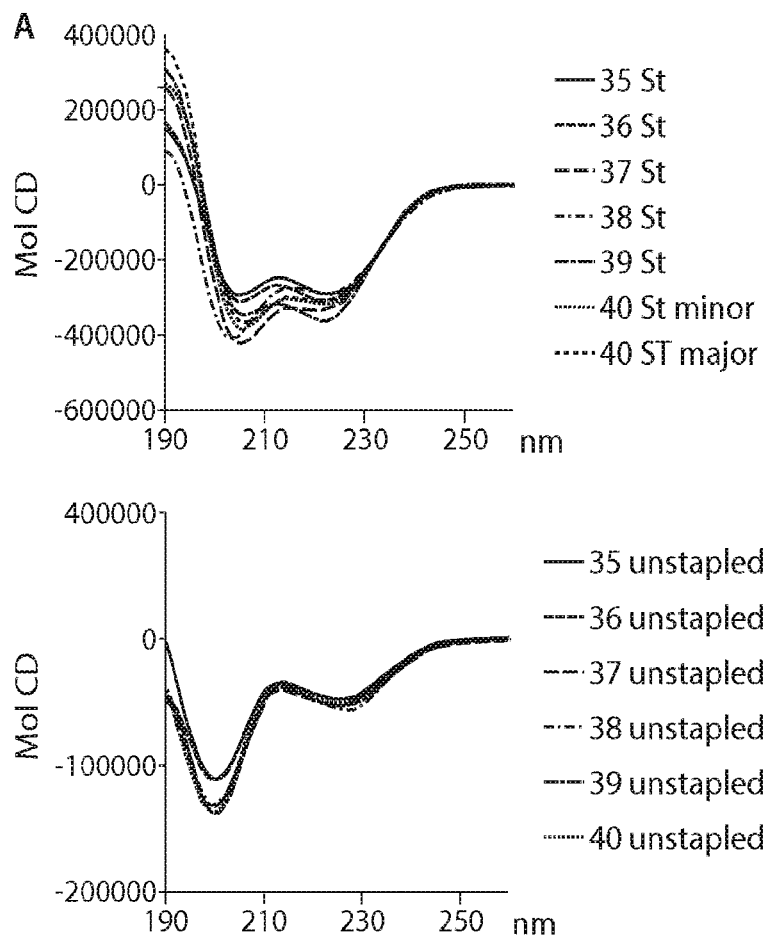
% helicity:
35 St = 64%, 36 St = 69%, 37 St = 73%, 38 St = 64%,
39 St = 80%, 40 minor St = 70%, 40 Major St = 68%
Fig. 37

PROLINE-LOCKED STAPLED PEPTIDES AND USES THEREOF

RELATED APPLICATIONS

The present application is a national stage filing under 35 U.S.C. §371 of international PCT application, PCT/US2013/062004, filed Sep. 26, 2013 which claims priority under 35 U.S.C. §119(e) to U.S. provisional patent applications, U.S. Ser. No. 61/705,950, filed Sep. 26, 2012, and U.S. Ser. No. 61/789,157, filed Mar. 15, 2013, each of which is incorporated herein by reference.

BACKGROUND OF THE INVENTION

The important biological roles that peptides and polypeptides play as hormones, enzyme inhibitors, substrates, neurotransmitters, and neuromediators has led to the widespread use of peptides and peptide mimetics in medicinal chemistry as therapeutic agents. The peptide's bioactive conformation, combining structural elements such as alpha-helices, beta-sheets, turns, and/or loops, is important as it allows for selective biological recognition of receptors or enzymes, thereby influencing cell-cell communication and/or controlling vital cell functions, such as metabolism, immune defense, and reproduction (Babine et al., *Chem. Rev.* (1997) 97:1359). The alpha-helix is one of the major structural components of peptides. However, alpha-helical peptides have a propensity for unraveling and forming random coils, which are, in most cases, biologically less active, or even inactive, and are highly susceptible to proteolytic degradation.

Many research groups have developed strategies for the design and synthesis of more robust peptides as therapeutics. For example, one strategy has been to incorporate more robust functionalities into the peptide chain while still maintaining the peptide's unique conformation and secondary structure (see, for example, Gante et al., *Angew. Chem. Int. Ed. Engl.* (1994) 33:1699-1720; Liskamp et al., *Recl. Trav. Chim. Pays-Bas* (1994) 113:1; Giannis et al., *Angew. Chem. Int. Ed. Engl.* (1993) 32:1244; P. D. Bailey, *Peptide Chemistry*, Wiley, New York, 1990, p. 182; and references cited therein). Another approach has been to stabilize the peptide via covalent crosslinks (see, for example, Phelan et al., *J. Am. Chem. Soc.* (1997) 119:455; Leuc et al., *Proc. Nat'l. Acad. Sci. USA* (2003) 100:11273; Bracken et al., *J. Am. Chem. Soc.* (1994) 116:6432; and Yan et al., *Bioorg. Med. Chem.* (2004) 14:1403). Crosslinking a polypeptide predisposed to have an alpha-helical secondary structure can constrain the polypeptide to its native alpha-helical conformation. The constrained secondary structure may, for example, increase the peptide's resistance to proteolytic cleavage, may increase the peptide's hydrophobicity, may allow for better penetration of the peptide into the target cell (e.g., through an energy-dependent transport mechanism such as pinocytosis), and/or may lead to an improvement in the peptide's biological activity relative to the corresponding uncrosslinked peptide. Therefore, there remains a need and interest in developing new crosslinked alpha-helical polypeptides as therapeutic agents as well as research tools.

SUMMARY OF THE INVENTION

The present invention provides a new type of alpha-helix nucleating staple formed using an N-terminal proline derivative with an alkenyl or alkynyl side chain (e.g., alpha-allylproline). Although proline is commonly considered to be an alpha-helix disrupting amino acid, it frequently occurs at the N-terminus of alpha-helices. Therefore, proline can be considered to be a helix-nucleating residue. Such a staple using a proline derivative may be formed with any other amino acid with an alkenyl or alkynyl side chain using an olefin metathesis reaction. Proline and the residue preceding it (such as serine, aspartate, and glutamate) have also been found to be good at cloaking the amide N—H's at the beginning of an alpha-helix through the formation of hydrogen bonds and have led to the design of other capping moieties for alpha-helical peptides as described herein. The proline derivative for stapling has been found to be a strong nucleator of alpha-helix formation, and peptides with such a staple may be of use in targeting various extracellular and intracellular targets as well as conferring oral bioavailability on peptides.

In one aspect, the disclosure provides stabilized peptides (e.g., staples and stitched) and methods for increasing the stability of peptides. In some embodiments, the disclosure provides peptides with improved biological properties and methods for improving the biological properties of peptides. The disclosure provides peptides with improved capacity to penetrate cell membranes and/or otherwise get into cells. The disclosure therefore also provides peptides as therapeutic agents and as deliver aids to deliver peptide-drug conjugates intracellularly.

In one aspect, the disclosure provides peptides that are stabilized by stapling the peptide at the N-terminus of an alpha-helix through the introduction of a proline-locked staple. It was surprisingly found that proline could be used to stabilize peptides. The finding was surprising at least because proline is commonly considered an α-helix-disrupting amino acid. In some embodiments, the proline-locked stapled peptide includes a proline at position i that is covalently linked to the alpha-carbon of a second amino acid at position i+3. While alpha-helical peptides are relatively stable once formed, initiation of alpha helix formation is challenging because the attendant conformational ordering is entropically expensive (*J. Chem. Phys*, 1959, 31, 526-535). As provided herein, introducing a helix staple, such as a proline-locked staple at the N-terminus of an alpha-helical peptide helps with the formation of, and further stabilizes, an alpha-helix. Once a single turn of the α-helix is formed, its downstream propagation can occur spontaneously, provided that helix-disrupting sequences are not present.

In one aspect, the disclosure provides peptides with improved ability to cross cell membranes. An increased ability of peptides to cross the cell membrane is correlated with an increase in the capacity of the peptide to acts as a therapeutic. Peptides often have difficulty crossing (cell) membranes because of the availability of unpaired hydrogen bonds in the peptide (e.g., in the peptide backbone). The disclosure provides methods for minimizing the availability of unpaired hydrogen bonds in a peptide by binding N-terminal amide protons tightly into hydrogen-bonding interactions. As disclosed herein, locating an amino acid with a side chain that can interact with amide protons at the N-terminal side of an alpha helix minimizes the availability of free amide protons. The undesired free N-terminal amides are "masked" thereby minimizing any undesired interactions with other agents (e.g., the cell membrane or components thereof). In some embodiments, the amino acid before the proline is an amino acid with a side chain that can interact with the free amide protons at the beginning of the helix. For instance, the disclosure provides a modified arginine with increased ability to mask N-terminal amide protons by providing additional hydrogen bond acceptor.

In one aspect, the disclosure provides stabilized peptides that nucleate α-helix formation through a proline-locked staple while also binding N-terminal amide protons tightly through hydrogen-bonding interactions. As provided herein, the stabilized peptides with amide proton hydrogen bond acceptors may have a proline at position i that is covalently coupled to an amino acid at position i+3, and a modified arginine residue at position i−1 (as described herein) which interacts with the amide protons of the peptide backbone of the amino acids at position i+1 and i+2. In certain other embodiments, the i−1 position is occupied by a natural amino acid such as serine, aspartate, or glutatmate.

The proline-locked stapled peptides provided herein are strong nucleators of α-helix formation, as shown by the high helicity of peptides bearing the proline-lock feature. In addition, the peptides provided herein, through masking the N-terminal amide protons, further enhance the ability of the peptides to cross cell membranes. Thus, the Pro-locked stapled peptides provided herein may be used in targeting previously "undruggable" intracellular therapeutic targets.

The details of one or more embodiments of the invention are set forth in the Detailed Description of Certain Embodiments, as described below. Other features, objects, and advantages of the invention will be apparent from the Definitions, Examples, Figures, and Claims.

BRIEF DESCRIPTION OF THE DRAWINGS

FIG. 2 shows two peptides with partial basic region of GCN4.

FIG. 9 shows a GCN4-DNA complex and the basic and coiled-coil regions of GCN4.

FIG. 13 shows examples of proline-locked stapled peptides.

FIG. 14 shows examples of proline-locked stapled and unstapled peptides.

FIG. 15 shows an example of olefin-metathesis by Grubbs-catalysis.

FIG. 16 shows a LC/MS chromatogram of the olefin-metathesis reaction by Grubbs-catalysis of peptide "4" (SEQ ID NO:2).

FIG. 19 shows CD spectra of selected proline-locked stapled peptides in various solutions.

FIG. 24 shows the ability of proline-locked stapled peptides 17 and 18 to penetrate cells at the concentration of 0.1 M.

FIG. 25 shows the ability of proline-locked stapled peptides 17 and 18 to penetrate cells at the concentration of 1 M.

FIG. 31 shows proline stapled peptides against trypsin proteolysis.

FIG. 37 shows CD spectra of exemplified stapled peptides.

DEFINITIONS

Figure 1:
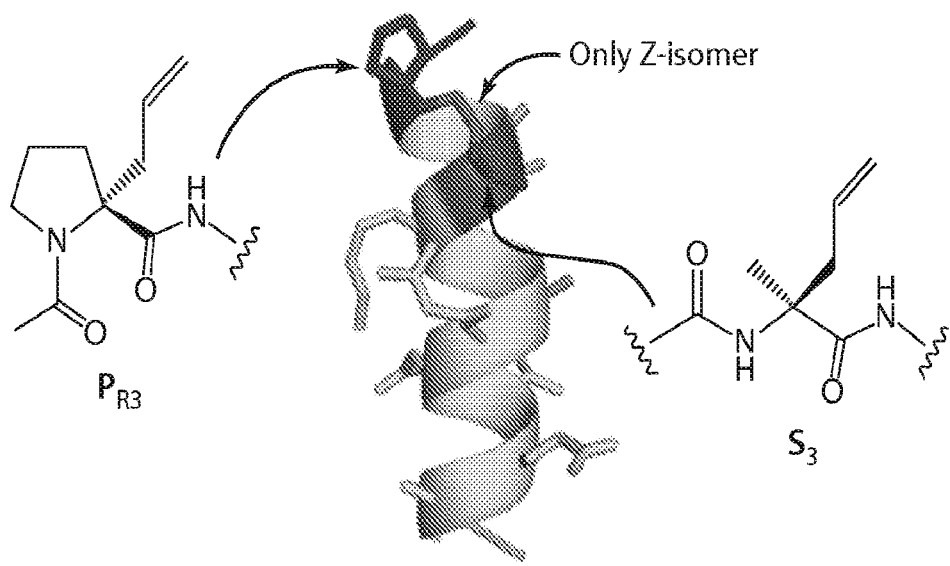
FIG. 1 provides an example of a proline-locked stapled peptide 4.

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds and polypeptides described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds and polypeptides described herein as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, substituent names which end in the suffix "-ene" refer to a biradical derived from the removal of an additional hydrogen atom from monoradical group as defined herein. Thus, for example, the monoradical alkyl, as defined herein, is the biradical alkylene upon removal of an additional hydrogen atom. Likewise, alkenyl is alkenylene; alkynyl is alkynylene; heteroalkyl is heteroalkylene; heteroalkenyl is heteroalkenylene; heteroalkynyl is heteroalkynylene; carbocyclyl is carbocyclylene; heterocyclyl is heterocyclylene; aryl is arylene; and heteroaryl is heteroarylene.

The term "aliphatic," as used herein, refers to alkyl, alkenyl, alkynyl, and carbocyclic groups. Likewise, the term "heteroaliphatic" as used herein, refers to heteroalkyl, heteroalkenyl, heteroalkynyl, and heterocyclic groups.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1, 2, 3, or 4 heteroatoms within the parent chain ("hetero$C_{1-10}$ alkyl"). In some embodiments, a heteroalkyl group is a saturated group having 1 to 9 carbon atoms and 1, 2, 3, or 4 heteroatoms within the parent chain ("hetero$C_{1-9}$ alkyl"). In some embodiments, a heteroalkyl group is a saturated group having 1 to 8 carbon atoms and 1, 2, 3, or 4 heteroatoms within the parent chain ("hetero$C_{1-8}$ alkyl"). In some embodiments, a heteroalkyl group is a saturated group having 1 to 7 carbon atoms and 1, 2, 3, or 4 heteroatoms within the parent chain ("hetero$C_{1-7}$ alkyl"). In some embodiments, a heteroalkyl group is a saturated group having 1 to 6 carbon atoms and 1, 2, or 3 heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

As used herein, "alkenyl" refers to a radical of a straight-chain or branched hydrocarbon group having from 2 to 10 carbon atoms and one or more double bonds (e.g., 1, 2, 3, or 4 double bonds) and no triple bonds. In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1, 2, 3, or 4 heteroatoms within the parent chain ("heteroC$_{2-10}$ alkenyl"). In some embodiments, a heteroalkenyl group has 2 to 9 carbon atoms at least one double bond, and 1, 2, 3, or 4 heteroatoms within the parent chain ("heteroC$_{2-9}$ alkenyl"). In some embodiments, a heteroalkenyl group has 2 to 8 carbon atoms, at least one double bond, and 1, 2, 3, or 4 heteroatoms within the parent chain ("heteroC$_{2-8}$ alkenyl"). In some embodiments, a heteroalkenyl group has 2 to 7 carbon atoms, at least one double bond, and 1, 2, 3, or 4 heteroatoms within the parent chain ("heteroC$_{2-7}$ alkenyl"). In some embodiments, a heteroalkenyl group has 2 to 6 carbon atoms, at least one double bond, and 1, 2, or 3 heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

As used herein, "alkynyl" refers to a radical of a straight-chain or branched hydrocarbon group having from 2 to 10 carbon atoms and one or more triple bonds (e.g., 1, 2, 3, or 4 triple bonds) and optionally one or more double bonds (e.g., 1, 2, 3, or 4 double bonds) ("C$_{2-10}$ alkynyl"). An alkynyl group that has one or more triple bonds and one or more double bonds is also referred to as an "ene-yene" group. In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1, 2, 3, or 4 heteroatoms within the parent chain ("heteroC$_{2-10}$ alkynyl"). In some embodiments, a heteroalkynyl group has 2 to 9 carbon atoms, at least one triple bond, and 1, 2, 3, or 4 heteroatoms within the parent chain ("heteroC$_{2-9}$ alkynyl"). In some embodiments, a heteroalkynyl group has 2 to 8 carbon atoms, at least one triple bond, and 1, 2, 3, or 4 heteroatoms within the parent chain ("heteroC$_{2-8}$ alkynyl"). In some embodiments, a heteroalkynyl group has 2 to 7 carbon atoms, at least one triple bond, and 1, 2, 3, or 4 heteroatoms within the parent chain ("heteroC$_{2-7}$ alkynyl"). In some embodiments, a heteroalkynyl group has 2 to 6 carbon atoms, at least one triple bond, and 1, 2, or 3 heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-10}$ carbocyclyl. In certain embodiments, the carbocyclyl group is a substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-10}$ cycloalkyl. In certain embodiments, the cycloalkyl group is a substituted C$_{3-10}$ cycloalkyl.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 it electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as defined herein, substituted by an aryl group, as defined herein, wherein the point of attachment is on the alkyl moiety.

As used herein, "heteroaryl" refers to a radical of a 5-14 membered monocyclic or polycyclic (e.g., bicyclic or tricyclic) 4n+2 aromatic ring system (e.g., having 6, 10, or 14 it electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a group that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a group that does not contain a double or triple bond, i.e., contains all single bonds.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-14}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

As used herein, the term "hydroxyl" or "hydroxy" refers to the group —OH. The term "substituted hydroxyl" or "substituted hydroxyl," by extension, refers to a hydroxy group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

As used herein, the term, "amino" refers to the group —NH$_2$. The term "substituted amino," by extension, refers to a monosubstituted amino, a disubstituted amino, or a trisubstituted amino, as defined herein.

As used herein, the term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$, and R$^{cc}$ are as defined herein, and wherein R$^{bb}$ of the group —NH(R$^{bb}$) is not hydrogen.

As used herein, the term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

As used herein, the term "trisubstituted amino" or a "quaternary amino salt" or a "quaternary salt" refers to a nitrogen atom covalently attached to four groups such that the nitrogen is cationic, wherein the cationic nitrogen atom is further complexed with an anionic counterion, e.g., such as groups of the Formula —N(R$^{bb}$)$_3$$^+$X$^-$ and —N(R$^{bb}$)$_2$—$^+$X$^-$, wherein R$^{bb}$ and X$^-$ are as defined herein.

As used herein, a "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methanesulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

As used herein, the term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

As used herein, the term "sulfinyl" refers to the group —S(=O)R$^{aa}$, wherein R$^{aa}$ is as defined herein.

As used herein, the term "acyl" refers a group wherein the carbon directly attached to the parent molecule is sp$^2$ hybridized, and is substituted with an oxygen, nitrogen or sulfur atom, e.g., a group selected from ketones (—C(=O)

$R^{aa}$), carboxylic acids (—CO$_2$H), aldehydes (—CHO), esters (—CO$_2R^{aa}$), thioesters (—C(=O)SR$^{aa}$, —C(=S)SR$^{aa}$), amides (—C(=O)N(R$^{bb}$)$_2$, —C(=O)NR$^{bb}$SO$_2R^{aa}$) thioamides (—C(=S)N(R$^{bb}$)$_2$), and imines (—C(=NR$^{bb}$)R$^{aa}$, —C(=NR$^{bb}$)OR$^{aa}$, —C(=NR$^{bb}$)N(R$^{bb}$)$_2$), wherein $R^{aa}$ and $R^{bb}$ are as defined herein.

As used herein, the term "azido" refers to a group of the formula —N$_3$.

As used herein, the term "cyano" refers to a group of the formula —CN.

As used herein, the term "isocyano" refers to a group of the formula —NC.

As used herein, the term "nitro" refers to a group of the formula —NO$_2$.

As used herein, the term "halo" or "halogen" refers to fluorine (fluoro, —F), chlorine (chloro, —Cl), bromine (bromo, —Br), or iodine (iodo, —I).

As used herein, the term "oxo" refers to a group of the formula =O.

As used herein, the term "thiooxo" refers to a group of the formula =S.

As used herein, the term "imino" refers to a group of the formula =N(R$^b$).

As used herein, the term "silyl" refers to the group —Si(R$^{aa}$)$_3$, wherein $R^{aa}$ is as defined herein.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2R^{aa}$, —SO$_2R^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2R^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2R^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an amino protecting group (also referred to herein as a "nitrogen protecting group"). Amino protecting groups include, but are not limited to, —OH, —OR$^{aa}$, —N(R$^{cc}$)$_2$, —C(=O)R$^{aa}$, —C(=O)N(R$^{cc}$)$_2$, —CO$_2R^{aa}$, —SO$_2R^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2R^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Amino protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, amino protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Amino protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Amino protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), J3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other amino protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is a hydroxyl protecting group (also referred to herein as an "oxygen protecting group"). Hydroxyl protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Hydroxyl protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary hydroxyl protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxide, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1, 3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

A "thiol protecting group" is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of protected thiol groups further include, but are not limited to, thioesters, carbonates, sulfonates allyl thioethers, thioethers, silyl thioethers, alkyl thioethers, arylalkyl thioethers, and alkyloxyalkyl thioethers. Examples of ester groups include formates, acetates, proprionates, pentanoates, crotonates, and benzoates. Specific examples of ester groups include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxycrotonate, benzoate, p-benylbenzoate, 2,4,6-trimethylbenzoate. Examples of carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of silyl groups include trimethylsilyl, triethylsilyl, t-butyldimethylsilyl, t-butyldiphenylsilyl, triisopropylsilyl ether, and other trialkylsilyl ethers. Examples of alkyl groups include methyl, benzyl, p-methoxybenzyl, 3,4-dimethoxybenzyl, trityl, t-butyl, and allyl ether, or derivatives thereof. Examples of arylalkyl groups include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

The term "amino acid" refers to a molecule containing both an amino group and a carboxyl group. Amino acids include alpha-amino acids and beta-amino acids, the structures of which are depicted below. In certain embodiments, the amino acid is an alpha amino acid. In certain embodiments, the amino acid is an unnatural amino acid. In certain embodiments, the amino acid is a natural amino acid. In certain embodiments, the amino acid is an unnatural amino acid.

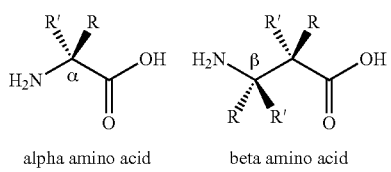

alpha amino acid     beta amino acid

Exemplary amino acids include, without limitation, natural alpha amino acids such as D- and L-isomers of the 20 common naturally occurring alpha amino acids found in peptides, u peptides (e.g., A, R, N, C, D, Q, E, G, H, I, L, K, M, F, P, S, T, W, Y, V, as provided in Table 1 depicted below), unnatural alpha-amino acids (as depicted in Tables 2 and 3 below), natural beta-amino acids (e.g., beta-alanine), and unnnatural beta-amino acids.

Amino acids used in the construction of peptides of the present invention may be prepared by organic synthesis, or obtained by other routes, such as, for example, degradation of or isolation from a natural source. In certain embodiments of the present invention, the formula —[$X_{AA}$]— or -[G]- corresponds to the natural and/or unnatural amino acids having the following formulae:

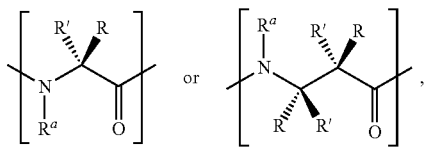

wherein R and R' correspond a suitable amino acid side chain, as defined below and herein, and R$^a$ is as defined below and herein.

TABLE 1

| Exemplary natural alpha-amino acids | Amino acid side chains | |
|---|---|---|
| | R | R' |
| L-Alanine (A) | —CH$_3$ | —H |
| L-Arginine (R) | —CH$_2$CH$_2$CH$_2$—NHC(=NH)NH$_2$ | —H |
| L-Asparagine (N) | —CH$_2$C(=O)NH$_2$ | —H |
| L-Aspartic acid (D) | —CH$_2$CO$_2$H | —H |
| L-Cysteine (C) | —CH$_2$SH | —H |
| L-Glutamic acid (E) | —CH$_2$CH$_2$CO$_2$H | —H |
| L-Glutamine (Q) | —CH$_2$CH$_2$C(=O)NH$_2$ | —H |
| Glycine (G) | —H | —H |
| L-Histidine (H) | —CH$_2$-2-(1H-imidazole) | —H |
| L-Isoleucine (I) | -sec-butyl | —H |
| L-Leucine (L) | -iso-butyl | —H |
| L-Lysine (K) | —CH$_2$CH$_2$CH$_2$CH$_2$NH$_2$ | —H |
| L-Methionine (M) | —CH$_2$CH$_2$SCH$_3$ | —H |
| L-Phenylalanine (F) | —CH$_2$Ph | —H |
| L-Proline (P) | -2-(pyrrolidine) | —H |
| L-Serine (S) | —CH$_2$OH | —H |
| L-Threonine (T) | —CH$_2$CH(OH)(CH$_3$) | —H |
| L-Tryptophan (W) | —CH$_2$-3-(1H-indole) | —H |
| L-Tyrosine (Y) | —CH$_2$-(p-hydroxyphenyl) | —H |
| L-Valine (V) | -isopropyl | —H |

TABLE 2

| Exemplary unnatural alpha-amino acids | Amino acid side chains | |
|---|---|---|
| | R | R' |
| D-Alanine | —H | —CH$_3$ |
| D-Arginine | —H | —CH$_2$CH$_2$CH$_2$—NHC(=NH)NH$_2$ |
| D-Asparagine | —H | —CH$_2$C(=O)NH$_2$ |
| D-Aspartic acid | —H | —CH$_2$CO$_2$H |
| D-Cysteine | —H | —CH$_2$SH |
| D-Glutamic acid | —H | —CH$_2$CH$_2$CO$_2$H |
| D-Glutamine | —H | —CH$_2$CH$_2$C(=O)NH$_2$ |
| D-Histidine | —H | —CH$_2$-2-(1H-imidazole) |
| D-Isoleucine | —H | -sec-butyl |
| D-Leucine | —H | -iso-butyl |
| D-Lysine | —H | —CH$_2$CH$_2$CH$_2$CH$_2$NH$_2$ |
| D-Methionine | —H | —CH$_2$CH$_2$SCH$_3$ |
| D-Phenylalanine | —H | —CH$_2$Ph |
| D-Proline | —H | -2-(pyrrolidine) |
| D-Serine | —H | —CH$_2$OH |
| D-Threonine | —H | —CH$_2$CH(OH)(CH$_3$) |
| D-Tryptophan | —H | —CH$_2$-3-(1H-indole) |
| D-Tyrosine | —H | —CH$_2$-(p-hydroxyphenyl) |
| D-Valine | —H | -isopropyl |
| Di-vinyl | —CH=CH$_2$ | —CH=CH$_2$ |
| | R and R' are equal to: | |
| α-methyl-Alanine (Aib) | —CH$_3$ | —CH$_3$ |
| α-methyl-Arginine | —CH$_3$ | —CH$_2$CH$_2$CH$_2$—NHC(=NH)NH$_2$ |
| α-methyl-Asparagine | —CH$_3$ | —CH$_2$C(=O)NH$_2$ |

TABLE 2-continued

| Exemplary unnatural alpha-amino acids | Amino acid side chains | |
|---|---|---|
| | R | R' |
| α-methyl-Aspartic acid | —CH₃ | —CH₂CO₂H |
| α-methyl-Cysteine | —CH₃ | —CH₂SH |
| α-methyl-Glutamic acid | —CH₃ | —CH₂CH₂CO₂H |
| α-methyl-Glutamine | —CH₃ | —CH₂CH₂C(=O)NH₂ |
| α-methyl-Histidine | —CH₃ | —CH₂-2-(1H-imidazole) |
| α-methyl-Isoleucine | —CH₃ | -sec-butyl |
| α-methyl-Leucine | —CH₃ | -iso-butyl |
| α-methyl-Lysine | —CH₃ | —CH₂CH₂CH₂CH₂NH₂ |
| α-methyl-Methionine | —CH₃ | —CH₂CH₂SCH₃ |
| α-methyl-Phenyl-alanine | —CH₃ | —CH₂Ph |
| α-methyl-Proline | —CH₃ | -2-(pyrrolidine) |
| α-methyl-Serine | —CH₃ | —CH₂OH |
| α-methyl-Threonine | —CH₃ | —CH₂CH(OH)(CH₃) |
| α-methyl-Tryptophan | —CH₃ | —CH₂-3-(1H-indole) |
| α-methyl-Tyrosine | —CH₃ | —CH₂-(p-hydroxyphenyl) |
| α-methyl-Valine | —CH₃ | -isopropyl |
| Di-vinyl | —CH=CH₂ | —CH=CH₂ |
| Norleucine | —H | —CH₂CH₂CH₂CH₃ |

TABLE 3

| Exemplary unnatural alpha-amino acids | Amino acid side chains R and R' is equal to hydrogen or —CH₃, and: |
|---|---|
| Terminally unsaturated alpha-amino acids and bis alpha-amino acids(e.g., modified cysteine, modified lysine, modified tryptophan, modified serine, modified threonine, modified proline, modified histidine, modified alanine, and the like). | —(CH₂)$_g$—S—(CH₂)$_g$CH=CH₂, <br> —(CH₂)$_g$—O—(CH₂)$_g$CH=CH₂, <br> —(CH₂)$_g$—NH—(CH₂)$_g$CH=CH₂, <br> —(CH₂)$_g$—(C=O)—S—(CH₂)$_g$CH=CH₂, <br> —(CH₂)$_g$—(C=O)—O—(CH₂)$_g$CH=CH₂, <br> —(CH₂)$_g$—(C=O)—NH—(CH₂)$_g$CH=CH₂, <br> —CH₂CH₂CH₂CH₂—NH—(CH₂)$_g$CH=CH₂, <br> —(C₆H₅)—p-O—(CH₂)$_g$CH=CH₂, <br> —CH(CH₃)—O—(CH₂)$_g$CH=CH₂, <br> —CH₂CH(—O—CH=CH₂)(CH₃), <br> -histidine-N((CH₂)$_g$CH=CH₂), <br> -tryptophan-N((CH₂)$_g$CH=CH₂), and <br> —(CH₂)$_{g+1}$(CH=CH₂), <br> wherein: <br> each instance of g is, independently, 0 to 10. |

| Exemplary unnatural alpha-amino acids |
|---|

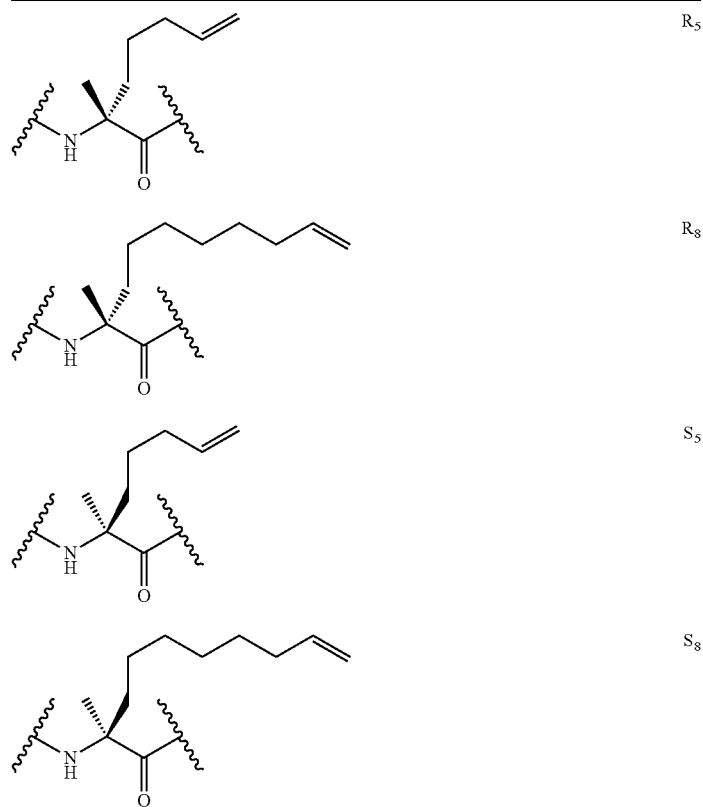

R₅

R₈

S₅

S₈

TABLE 3-continued
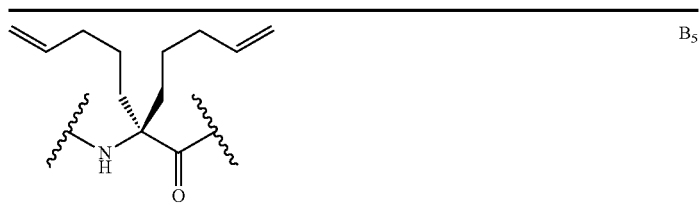 B5
 R3
 S3
 S4
 P$_{R3}$
 P$_{S5}$
 P$_{S3}$
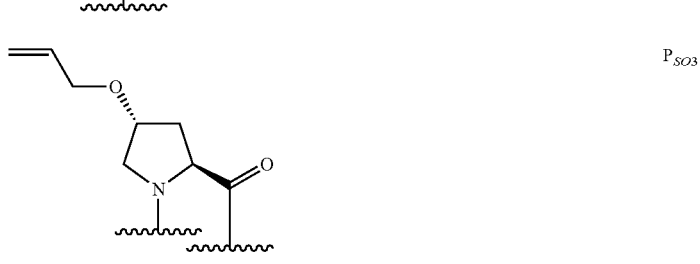 P$_{SO3}$ There are many known unnatural amino acids any of which may be included in the peptides of the present invention. See for example, S. Hunt, *The Non-Protein Amino Acids: In Chemistry and Biochemistry of the Amino Acids*, edited by G. C. Barrett, Chapman and Hall, 1985. Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with —C(=O)C$_6$H$_5$; —CF$_3$; —CN; -halo; —NO$_2$; CH$_3$), disubstituted phenylalanines, substituted tyrosines (e.g., further substituted with —C(=O)C$_6$H$_5$; —CF$_3$; —CN; -halo; —NO$_2$; CH$_3$), and statine. Additionally, the amino acids suitable for use in the present invention may be derivatized to include amino acid residues that are hydroxylated, phosphorylated, sulfonated, acylated, and glycosylated, to name a few.

The term "amino acid side chain" refers to a group attached to the alpha- or beta-carbon of an amino acid. A "suitable amino acid side chain" includes, but is not limited to, any of the suitable amino acid side chains as defined above, and as provided in Tables 1 to 3.

For example, suitable amino acid side chains include methyl (as the alpha-amino acid side chain for alanine is methyl), 4-hydroxyphenylmethyl (as the alpha-amino acid side chain for tyrosine is 4-hydroxyphenylmethyl) and thiomethyl (as the alpha-amino acid side chain for cysteine is thiomethyl), etc. A "terminally unsaturated amino acid side chain" refers to an amino acid side chain bearing a terminal unsaturated moiety, such as a substituted or unsubstituted, double bond (e.g., olefinic) or a triple bond (e.g., acetylenic), that participates in crosslinking reaction with other terminal unsaturated moieties in the polypeptide chain. In certain embodiments, a "terminally unsaturated amino acid side chain" is a terminal olefinic amino acid side chain. In certain embodiments, a "terminally unsaturated amino acid side chain" is a terminal acetylenic amino acid side chain. In certain embodiments, the terminal moiety of a "terminally unsaturated amino acid side chain" is not further substituted. Terminally unsaturated amino acid side chains include, but are not limited to, side chains as depicted in Table 3.

A "peptide" or "polypeptide" comprises a polymer of amino acid residues linked together by peptide (amide) bonds. The term(s), as used herein, refers to proteins, polypeptides, and peptide of any size, structure, or function. Typically, a peptide or polypeptide will be at least three amino acids long. A peptide or polypeptide may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. One or more of the amino acids in a peptide or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification. A peptide or polypeptide may also be a single molecule or may be a multi-molecular complex, such as a protein. A peptide or polypeptide may be just a fragment of a naturally occurring protein or peptide. A peptide or polypeptide may be naturally occurring, recombinant, or synthetic, or any combination thereof.

As used herein "dipeptide" refers to two covalently linked amino acids.

As used herein, the term "salt" or "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, quaternary salts, e.g., cationic trisubstituted amino groups, e.g., as defined herein.

The following definitions are more general terms used throughout the present application.

The term "subject," as used herein, refers to any animal. In certain embodiments, the subject is a mammal. In certain embodiments, the term "subject", as used herein, refers to a human (e.g., a man, a woman, or a child).

The terms "administer," "administering," or "administration," as used herein refers to implanting, absorbing, ingesting, injecting, or inhaling, the inventive polypeptide or compound.

The terms "treat" or "treating," as used herein, refers to partially or completely alleviating, inhibiting, ameliorating, and/or relieving the disease or condition from which the subject is suffering.

The terms "effective amount" and "therapeutically effective amount," as used herein, refer to the amount or concentration of a biologically active agent conjugated to a stitched or stapled polypeptide as described herein, or amount or concentration of a stitched or stapled polypeptide as described herein, that, when administered to a subject, is effective to at least partially treat a condition from which the subject is suffering.

As used herein, when two entities are "conjugated" to one another they are linked by a direct or indirect covalent or non-covalent interaction. In certain embodiments, the association is covalent. In other embodiments, the association is non-covalent. Non-covalent interactions include hydrogen bonding, van der Waals interactions, hydrophobic interactions, magnetic interactions, and electrostatic interactions. An indirect covalent interaction is when two entities are covalently connected, optionally through a linker group.

As used herein, a "biologically active agent" or "therapeutically active agent" refers to any substance used as a medicine for treatment, prevention, delay, reduction or amelioration of a disease, condition, or disorder, and refers to a substance that is useful for therapy, including prophylactic and therapeutic treatment. A biologically active agent also includes a compound that increases the effect or effectiveness of another compound, for example, by enhancing potency or reducing adverse effects of the other compound.

In certain embodiments, a biologically active agent is an anti-cancer agent, antibiotic, anti-viral agent, anti-HIV agent, anti-parasite agent, anti-protozoal agent, anesthetic, anticoagulant, inhibitor of an enzyme, steroidal agent, steroidal or non-steroidal anti-inflammatory agent, antihistamine, immunosuppressant agent, anti-neoplastic agent, antigen, vaccine, antibody, decongestant, sedative, opioid, analgesic, anti-pyretic, birth control agent, hormone, prostaglandin, progestational agent, anti-glaucoma agent, ophthalmic agent, anti-cholinergic, analgesic, anti-depressant, anti-psychotic, neurotoxin, hypnotic, tranquilizer, anti-convulsant, muscle relaxant, anti-Parkinson agent, anti-spasmodic, muscle contractant, channel blocker, miotic agent, anti-secretory agent, anti-thrombotic agent, anticoagulant, anti-cholinergic, β-adrenergic blocking agent, diuretic, cardiovascular active agent, vasoactive agent, vasodilating agent, anti-hypertensive agent, angiogenic agent, modulators of cell-extracellular matrix interactions (e.g. cell growth inhibitors and anti-adhesion molecules), or inhibitors/intercalators of DNA, RNA, protein-protein interactions, protein-receptor interactions, etc.

Exemplary biologically active agents include, but are not limited to, small organic molecules such as drug compounds, peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the biologically active agent is a cell. Exemplary cells include immune system cells (e.g., mast, lymphocyte, plasma cell, macrophage, dendritic cell, neutrophils, eosinophils), connective tissue cells (e.g., blood cells, erythrocytes, leucocytes, megakarocytes, fibroblasts, osteoclasts), stem cells (e.g., embryonic stem cells, adult stem cells), bone cells, glial cells, pancreatic cells, kidney cells, nerve cells, skin cells, liver cells, muscle cells, adipocytes, Schwann cells, Langerhans cells, as well as (micro)-tissues such as the Islets of Langerhans.

In certain embodiments, the biologically active agent is a small organic molecule.

In certain embodiments, a small organic molecule is non-peptidic. In certain embodiments, a small organic molecule is non-oligomeric. In certain embodiments, a small organic molecule is a natural product or a natural product-like compound having a partial structure (e.g., a substructure) based on the full structure of a natural product. Exemplary natural products include steroids, penicillins, prostaglandins, venoms, toxins, morphine, paclitaxel (Taxol), morphine, cocaine, digitalis, quinine, tubocurarine, nicotine, muscarine, artemisinin, cephalosporins, tetracyclines, aminoglycosides, rifamycins, chloramphenicol, asperlicin, lovastatin, ciclosporin, curacin A, eleutherobin, discodermolide, bryostatins, dolostatins, cephalostatins, antibiotic peptides, epibatidine, α-bungarotoxin, tetrodotoxin, teprotide, and neurotoxins from *Clostridium botulinum*. In certain embodiments, a small organic molecule is a drug approved by the Food and Drugs Administration as provided in the Code of Federal Regulations (CFR).

As used herein, a "label" refers to a moiety that has at least one element, isotope, or functional group incorporated into the moiety which enables detection of the inventive polypeptide to which the label is attached. Labels can be directly attached (ie, via a bond) or can be attached by a linker (e.g., such as, for example, a cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene, or any combination thereof, which can make up a linker). It will be appreciated that the label may be attached to the inventive polypeptide at any position that does not interfere with the biological activity or characteristic of the inventive polypeptide that is being detected.

In general, a label can fall into any one (or more) of five classes: a) a label which contains isotopic moieties, which may be radioactive or heavy isotopes, including, but not limited to, $^{2}H$, $^{3}H$, $^{13}C$, $^{14}C$, $^{15}N$, $^{31}P$, $^{32}P$, $^{35}S$, $^{67}Ga$, $^{99m}Tc$ (Tc-99m), $^{111}In$, $^{123}I$, $^{125}I$, $^{169}Yb$, and $^{186}Re$; b) a label which contains an immune moiety, which may be antibodies or antigens, which may be bound to enzymes (e.g., such as horseradish peroxidase); c) a label which is a colored, luminescent, phosphorescent, or fluorescent moieties (e.g., such as the fluorescent label FITC); d) a label which has one or more photoaffinity moieties; and e) a label which has a ligand moiety with one or more known binding partners (such as biotin-streptavidin, FK506-FKBP, etc.). Any of these type of labels as described above may also be referred to as "diagnostic agents" as defined herein.

In certain embodiments, such as in the identification of a biological target, label comprises a radioactive isotope, preferably an isotope which emits detectable particles, such as 0 particles. In certain embodiments, the label comprises one or more photoaffinity moieties for the direct elucidation of intermolecular interactions in biological systems. A variety of known photophores can be employed, most relying on photoconversion of diazo compounds, azides, or diazirines to nitrenes or carbenes (see, Bayley, H., Photogenerated Reagents in Biochemistry and Molecular Biology (1983), Elsevier, Amsterdam, the entire contents of which are incorporated herein by reference). In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

In certain embodiments, the label comprises one or more fluorescent moieties. In certain embodiments, the label is the fluorescent label FITC. In certain embodiments, the label comprises a ligand moiety with one or more known binding partners. In certain embodiments, the label comprises the ligand moiety biotin.

As used herein, a "diagnostic agent" refers to imaging agents. Exemplary imaging agents include, but are not limited to, those used in positron emissions tomography (PET), computer assisted tomography (CAT), single photon emission computerized tomography, x-ray, fluoroscopy, and magnetic resonance imaging (MRI); anti-emetics; and contrast agents. Exemplary diagnostic agents include but are not limited to, fluorescent moieties, luminescent moieties, magnetic moieties; gadolinium chelates (e.g., gadolinium chelates with DTPA, DTPA-BMA, DOTA and HP-DO3A), iron chelates, magnesium chelates, manganese chelates, copper chelates, chromium chelates, iodine-based materials useful for CAT and x-ray imaging, and radionuclides. Suitable radionuclides include, but are not limited to, $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101}$mRh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99}$mTc, $^{14}$C, $^{13}$N, $^{15}$O, $^{32}$P, $^{33}$P, and $^{18}$F. Fluorescent and luminescent moieties include, but are not limited to, a variety of different organic or inorganic small molecules commonly referred to as "dyes," "labels," or "indicators." Examples include, but are not limited to, fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g., U.S. Patent Publication 2004/0067503; Valeur, B., "Molecular Fluorescence: Principles and Applications," John Wiley and Sons, 2002; and *Handbook of Fluorescent Probes and Research Products, Molecular Probes*, 9$^{th}$ edition, 2002).

DETAILED DESCRIPTION OF CERTAIN EMBODIMENTS OF THE INVENTION

In one aspect, the disclosure provides stabilized stapled peptides with a proline derivative for stapling at the N-terminus of the helix and methods for increasing the stability of peptides using a proline-derivative for stapling. In some embodiments, the disclosure provides peptides with increased alpha-helicity and methods for increasing the alpha-helicity of peptides. In some embodiments, the disclosure provides stapled peptides with a proline derivative at the N-terminus of the alpha-helix and methods for providing such stapled peptides. In some embodiments, the disclosure provides proline-locked stapled peptides and methods for providing proline-locked stapled peptides.

In one aspect, the disclosure provides peptides that are stabilized by stapling the peptide at the N-terminus of an alpha-helix through the introduction of a proline-containing staple or a proline-locked staple. It was surprisingly found that proline could be used to stabilize peptides. The finding was surprising at least because proline is commonly considered an α-helix-disrupting amino acid. In some embodiments, the proline-locked stapled peptide includes a proline at position i that is covalently connected with the alpha-carbon of a second amino acid at position i+3. While alpha-helical peptides are relatively stable once formed, initiation of alpha helix formation is challenging because the attendant conformational ordering is entropically expensive (*J. Chem. Phys*, 1959, 31, 526-535). As provided herein, introducing a helix staple, such as a proline staple or a proline-locked staple at the N-terminus of an alpha helical peptide helps with the formation of, and further stabilizes, an alpha-helix. Once a single turn of the α-helix is formed, its downstream propagation can occur spontaneously, provided that helix-disruption sequences are not present.

In one aspect, the disclosure provides a peptide stapling system having helix-nucleating ability. In some embodiments, the peptide stapling system is a peptide with a proline-derivative at the N-terminus of the staple. In some embodiments, the peptide stapling system is a proline-locked stapled peptide or "Pro-lock". It should be appreciated that the peptide stabilized by a proline-lock may be a peptide that is mostly in alpha-helical conformation, or the peptide may be part of a larger protein that includes one or more alpha-helical regions. In some embodiments, the Pro-locked staple is located in the N-terminal region of a peptide. In some embodiments, the proline of the Pro-locked staple is located at the N-terminal position of the helix. In some embodiments, the Pro-locked staple comprises a covalent bind between a proline at position i and a second amino acid at position i+3 in a peptide. It should be appreciated that homo-proline and other unnatural cyclic amino acids, as described further herein, can be used instead of proline in the proline locks. To facilitate to covalent bond of the proline-lock, the proline comprises an additional functional group that can undergo a reaction to for a covalent bond. In some embodiments, the functional group is a double bond (e.g., a vinyl group). In some embodiments, the functional group is located at the alpha-carbon on the proline. In some embodiments, the functional group is located on any position on the proline ring.

In some embodiments, the amino acid at position i+3 is serine, alanine, glycine, aspartic acid or glutamic acid. To facilitate the formation of the covalent bond of the proline-lock the amino acid at position i+3 may include an additional functional group that can undergo a reaction to form a covalent bond. In some embodiments, the additional functional group that can undergo a reaction to form a covalent bond is located at the alpha carbon of the second amino acid. In some embodiments, the group that can undergo a reaction to form a covalent bond is part of the natural side chain of the amino acid.

In some embodiments, the proline locked staple includes a covalent binding between a proline at position i and an amino acid located at position i+3. In some embodiments, the helix-nucleating "staple" is formed between an N-terminal α-allylproline (e.g., P$_{R3}$) and an α-methyl,α-allylglycine (S$_3$) at positions i and i+3 in a peptide. In some embodiments, the helix-nucleating "staple" is formed between (R)—N-(Acetyl)-2-(2'-propenyl)proline ("P$_{R3}$") or (R)—N-[(9H-Fluoren-9-ylmethoxy)carbonyl]-2-(2'-propenyl)proline and (S)—N-[(9H-Fluoren-9-ylmethoxy)carbonyl]-2-(2'-propylenyl)alanine at positions i and i+3 in a peptide.

The unnatural amino acids of the proline-lock can be introduced into the peptide through peptide synthesis techniques as described herein. In some embodiments, the amino acid sequence including the proline lock is synthesized or prepared separately and the amino acid sequence is coupled to a peptide to be stabilized. Thus, in some embodiments, the disclosure provides a method of increasing the stability and/or helicity of peptide that include a step of coupling the peptide to an amino acid sequence comprising a proline-locked staple.

The proline-locked peptides comprising the covalent bond may be synthesized according to any of the methods disclosed herein. In some embodiments, a crosslink between the proline with the functional group and the amino acid at position i+3 is formed by Grubb's catalyst. In some embodiments, a crosslink between the proline with the functional group and the amino acid at position i+3 is formed by ruthenium-mediated olefin metathesis. In some embodiment, the Pro-locked stapled peptides are synthesized using (R)—N-(Acetyl)-2-(2'-propenyl)proline and (S)—N-[(9H-Fluoren-9-ylmethoxy)carbonyl]-2-(2'-propylenyl)alanine as amino acid building blocks at position i and i+3, respectively, allowing for the generation of a proline-locked stapled peptide. In some embodiments, the peptides are subjected to ruthenium-mediated olefin metathesis, resulting in formation of an exclusively cis olefinic crosslink.

In some embodiments, the peptides provided herein comprise stabilizing elements in addition to the proline-locked staple. In some embodiments, the peptides comprise multiple pro-locked staples. In some embodiments, the peptides comprise a Pro-locked staples and a staple other than a Pro-locked staple. Peptide staples other than Pro-locked staples are provided for instance in WO2008/121767. In general, it has been shown that the pharmacologic properties of α-helical peptides can be greatly improved through the use of a hydrocarbon "staple" that enforces the α-helical conformation of peptides (See e.g., *Science*, 2004, 305, 1466-1470). In some embodiments, the proline-locked staple and a second staple connect at amino acid i+3 or overlap in amino acid sequence. Thus, for instance, in addition to a proline-locked amino staple between i and i+3, a peptide may have a second staple that starts at position i+3 (e.g., between i+3 and i+7), or a second staple that starts at position i+1 or i+2, and thus "overlaps" with the proline-locked staple. Compared to stapled peptides disclosed previously, the Pro-locked stapled peptides disclosed herein have the extra advantage that they can be used even when a crosslink cannot be introduced into any position of an α-helix other than at its N-terminus.

In some embodiments, the peptides comprising the proline-locked staples may have additional stabilizing elements. In some embodiments, the peptides have an amino acid composition allowing for helix stabilizing salt bridges. In some embodiments, the peptides have been modified to covalently connect the salt bridges. In some embodiments, the peptides have functional groups that stabilize the helix dipole.

In one aspect, the disclosure provides peptides with an improved ability to cross cell membranes. An increased ability of peptides to cross the cell membrane is correlated with an increase in the capacity of the peptide to acts as a therapeutic. Peptides often have difficulty crossing (cell) membranes because of the availability of unpaired hydrogen bonds in the peptide (e.g., in the peptide backbone). The disclosure provides methods for minimizing the availability of unpaired hydrogen bonds in a peptide by binding N-terminal amide protons tightly into hydrogen-bonding interactions. As disclosed herein, locating an amino acid with a side chain that can interact with amide protons at the N-terminal side of an alpha helix minimizes the availability of unwanted amide protons. The undesired free N-terminal amide proteins are "masked" thereby minimizing any undesired interactions with other agents (e.g., the cell membrane or components thereof). In some embodiments, the amino acid with the side chain that can interact with amide protons is modified to increase the available hydrogen binders. For instance, the disclosure provides a modified arginine with increased ability to mask N-terminal amide protons by providing additional hydrogen-bonding interaction partners.

In one aspect, the disclosure provides methods and compositions for improving pharmacological properties of peptides. In some embodiments, the disclosure provides peptides with improved capacity for passive cell penetration (e.g., by improved capacity for passive cell membrane traversal). In some embodiments, the disclosure provides methods for improving the passive cell penetration of peptides. In some embodiments, the disclosure provides peptides with minimized unwanted N-terminal amide N—H proton interactions. In some embodiments, the disclosure provides methods for generating peptides with minimized unwanted amide N—H proton interactions. Decreasing the availability of freely available hydrogen bonds in N—H protons will minimize the interactions the peptide will have with third parties (e.g., a membrane or membrane components) allowing for better traversal of the membrane. In some embodiments, the disclosure provides peptides with improved passive cell penetration and minimized amide N—H proton interactions. In some embodiments, the disclosure provides methods for improving the passive cell penetration of peptides by minimizing amide N—H proton interactions. In some embodiments, the peptides with improved passive cell penetration are proline-locked staple peptides. In some embodiments, the peptides with improved passive cell penetration have minimized amide N—H bond interactions by "cloaking" or "masking" the amide N—H's. In some embodiments, the peptides with minimized amide N—H interactions have minimized the interactions of amide N—H's located at the N-terminus of the peptide. In some embodiments, the peptides with improved passive cell penetration are proline-locked staple peptides with minimized amide N—H bond interactions. In some embodiments, the amide N—H interactions are minimized by introducing an amino acid with a negatively charged side chain and/or electron donor on its side chain on the N-terminal side of the polypeptide. In some embodiments, the amide N—H interactions are minimized by introducing an amino acid with a negatively charged side chain and/or electron donor on its side chain on the N-terminal side of a helix within the polypeptide. In some embodiments, the amino acid allowing for the minimization of N—H proton interactions is serine, threonine, aspartic acid, glutamic acid or asparagine. In some embodiments, the amino acid is has been modified to increase the number of electron donating groups on the side chain. In some embodiments, the amino acid is a modified asparagine as disclosed herein (also called "asparagine surrogate").

In one aspect, the disclosure provides stabilized peptides that nucleate α-helix formation through a proline-locked staple while also binding N-terminal amide protons tightly through hydrogen-bonding interactions. As provided herein, the stabilized peptides with amide proton binding can have a proline at position i that is covalently coupled to an amino acid at position i+3, and a modified arginine at position i−1 which interacts with the amide protons of the peptide backbone of the amino acids at position i+1 and i+2

Promotion of α-helix stability and masking of N-terminal N—H's improve the biophysical and pharmacological properties of a peptide, including oral bioavailability, binding affinity for a receptor, resistance to proteolytic degradation, cell-penetration, and reduction in the rate of renal clearance. The proline-locked stapled peptides provided herein are strong nucleators of α-helix formation, as shown by the exceptionally high helicity of peptides bearing the proline-lock. In addition, the peptides provided herein, through masking the N-terminal amide protons, further enhance the ability of the peptides to cross cell membranes. Thus, the Pro-locked stapled peptides provided herein can be used in targeting previously "undruggable" intracellular therapeutic targets.

Polypeptides and Precursors

Various stapled and stitched polypeptides are described herein which include proline-locked staple. "Peptide stapling" is a term coined from a synthetic methodology wherein two olefin-containing sidechains present in a polypeptide chain are covalently joined (e.g., "stapled together") using a ring-closing metathesis (RCM) reaction to form a cross-linked ring (see, the cover art for *J. Org. Chem.* (2001) vol. 66, issue 16 describing metathesis-based crosslinking of alpha-helical peptides; Blackwell et al.; *Angew Chem. Int. Ed.* (1994) 37:3281). However, the term "peptide stapling," as used herein, encompasses the joining of two double bond-containing sidechains, two triple bond-containing sidechains, or one double bond-containing and one triple bond-containing side chain, which may be present in a polypeptide chain, using any number of reaction conditions and/or catalysts to facilitate such a reaction, to provide a singly "stapled" polypeptide. Additionally, the term "peptide stitching," as used herein, refers to multiple and tandem "stapling" events in a single polypeptide chain to provide a "stitched" (or multiply stapled) polypeptide.

The stapling or stitching contemplated herein involves contact of a precursor "unstapled" or "unstitched" polypeptide with a ring closing metathesis (RCM) catalyst to provide a stapled or stitched polypeptide. One of ordinary skill in the art will realize that a variety of RCM catalysts can be utilized. In certain embodiments, the RCM catalyst is a tungsten (W), molybdenum (Mo), or ruthenium (Ru) catalyst. In certain embodiments, the RCM catalyst is a ruthenium catalyst. Exemplary RCM catalysts employable by the above synthetic method may be described in Grubbs et al., *Acc. Chem. Res.* 1995, 28, 446-452; U.S. Pat. No. 5,811,515; Schrock et al., *Organometallics* (1982) 1 1645; Gallivan et al., *Tetrahedron Letters* (2005) 46:2577-2580; Furstner et al., *J. Am. Chem. Soc.* (1999) 121:9453; and *Chem. Eur. J.* (2001) 7:5299; the entire contents of each of which are incorporated herein by reference.

Thus, in one aspect, provided is a precursor polypeptide of Formula (P-I):

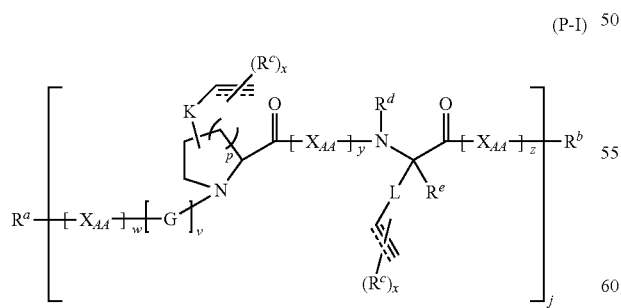

or a salt or stereoisomer thereof;
wherein:
each instance of K and L, is, independently, a bond or a group consisting of one or more combinations of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclene, substituted or unsubstituted carbocyclene, substituted or unsubstituted arylene; substituted or unsubstituted heteroarylene;

$R^a$ is hydrogen; substituted or unsubstituted aliphatic; substituted or unsubstituted heteroaliphatic; substituted or unsubstituted aryl; substituted or unsubstituted heteroaryl; substituted or unsubstituted acyl; a resin; an amino protecting group; a label optionally joined by a linker, wherein the linker is a group consisting of one or more combinations of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted carbocyclene; substituted or unsubstituted heterocyclene; substituted or unsubstituted arylene; or substituted or unsubstituted heteroarylene;

$R^b$ is, $-R^B$, $-OR^B$, $-N(R^B)_2$, or $-SR^B$, wherein each instance of $R^B$ is, independently, hydrogen, substituted or unsubstituted aliphatic; substituted or unsubstituted heteroaliphatic; substituted or unsubstituted aryl; substituted or unsubstituted heteroaryl; substituted or unsubstituted acyl; a resin; a suitable hydroxyl, amino or thiol protecting group; or two $R^B$ groups together form a substituted or unsubstituted 5- to 6-membered heterocyclic or heteroaromatic ring;

each instance of $R^c$, is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; cyano; isocyano; halo; or nitro;

each instance of $R^d$ is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; or an amino protecting group;

each instance of $R^e$ is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; cyano; isocyano; halo; or nitro;

each instance of G is, independently, a natural or unnatural amino acid or a group of the formula:

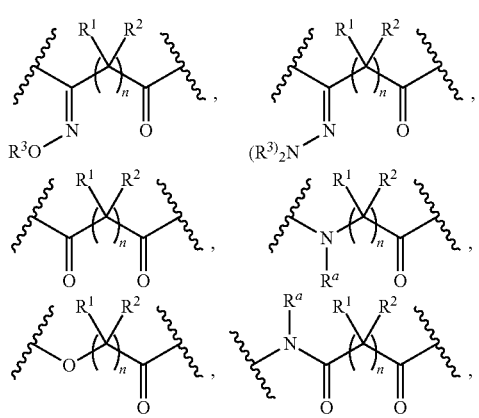

-continued

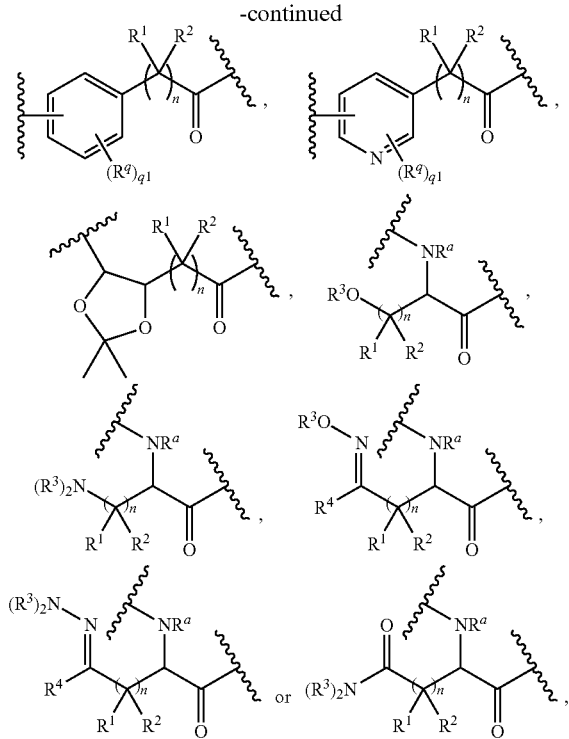

wherein:
n is 1, 2, or 3; and
each instance of $R^1$ and $R^2$ is independently hydrogen; substituted or unsubstituted aliphatic; substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; or halo, or $R^1$ and $R^2$ are joined to form a carbocyclic or heterocyclic ring;
each instance of $R^3$ and $R^4$ is, independently, hydrogen; substituted or unsubstituted aliphatic; substituted or unsubstituted heteroaliphatic; a hydroxyl protecting group when attached to an oxygen atom, or an amino protecting group when attached to a nitrogen atom, or two $R^3$ groups when attached to a nitrogen atom are joined to form a heterocyclic ring;
each instance of $R^q$ is independently halogen, —CN, —$NO_2$, —$N_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, an optionally substituted amino group, or optionally substituted acyl;
q1 is 0, 1, 2, 3, or 4;
each instance of $X_{AA}$ is, independently, a natural or unnatural amino acid;
j is, independently, an integer between 1 to 10, inclusive;
each instance of p is, independently, 1 or 2;
each instance of v is, independently, 0 or 1;
each instance of w and z is, independently, an integer between 0 and 100, inclusive;
each instance of x is, independently, 0, 1, 2, or 3;
y is, independently, an integer of 1 to 8, inclusive; and
═══ corresponds to a double or triple bond.
In certain embodiments, the ═══ corresponds to a double bond. In certain embodiments, the ═══ corresponds to a triple bond.

In certain embodiments, the polypeptide of Formula (P-I) is of the formula:

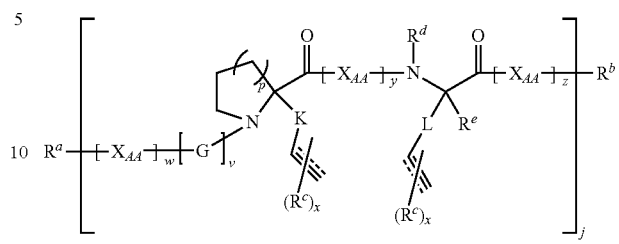

or a salt or stereoisomer thereof.

In certain embodiments, the polypeptide of Formula (P-I) is any one of the formula:

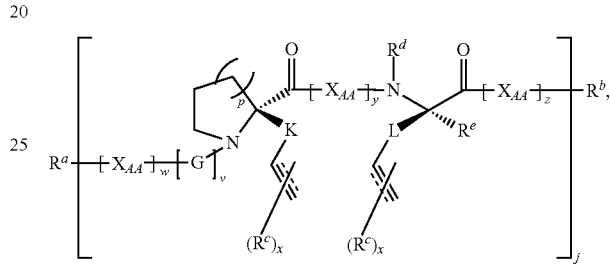

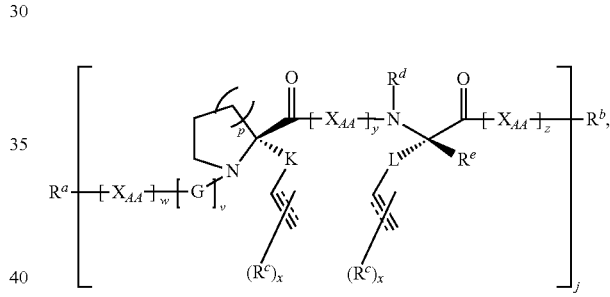

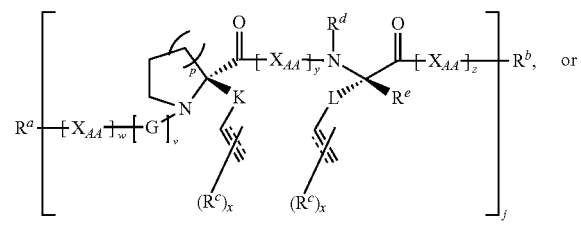

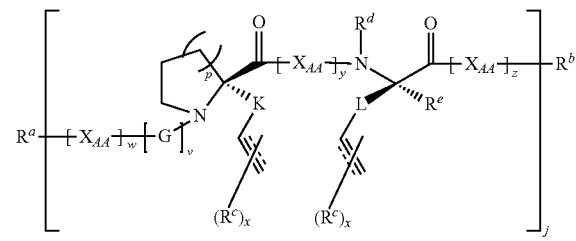

or a salt or stereoisomer thereof.

In certain embodiments, the polypeptide of Formula (P-I) is any one of the formula:
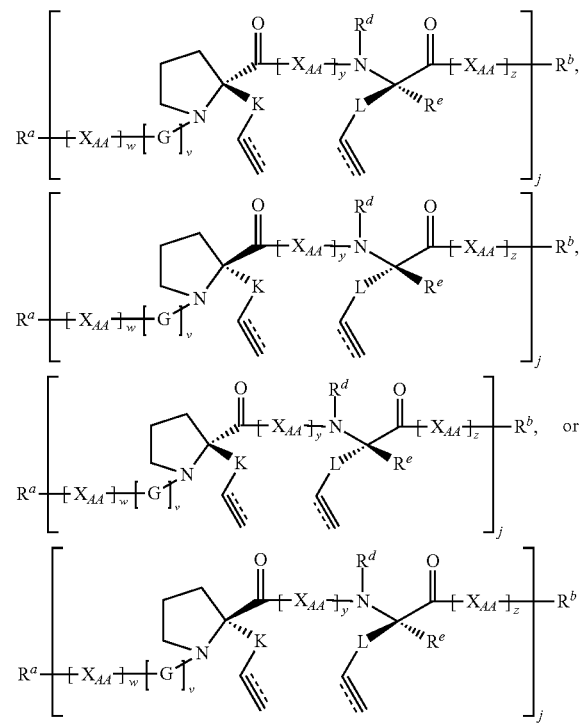
or a salt or stereoisomer thereof.
In certain embodiments, the polypeptide of Formula (P-I) is of the formula:
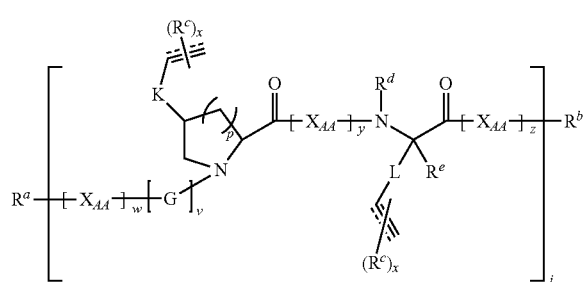
or a salt or stereoisomer thereof.
In certain embodiments, the polypeptide of Formula (P-I) is any one of the formulae:
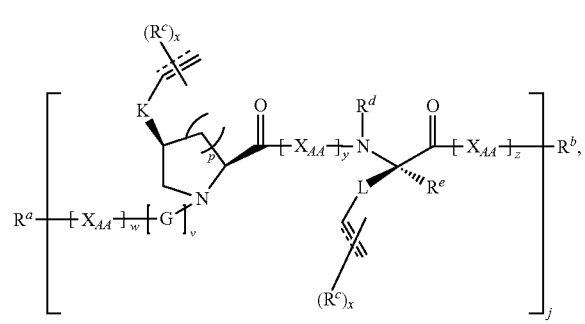
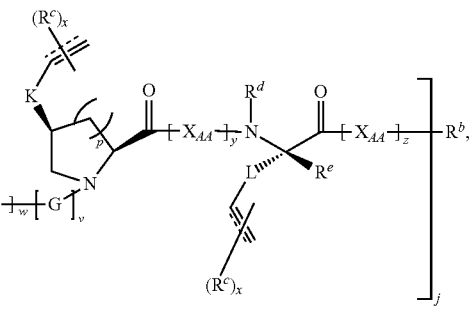
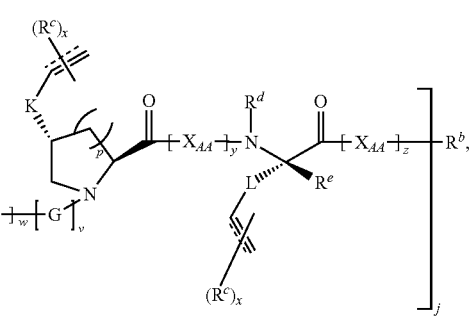

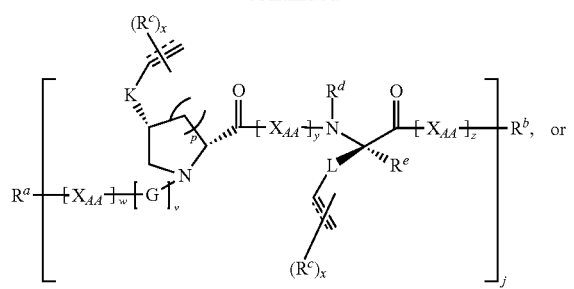

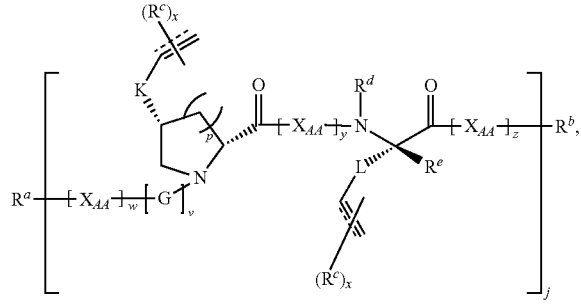

or a salt or stereoisomer thereof.

In certain embodiments, the polypeptide of Formula (P-I) is any one of the formulae:

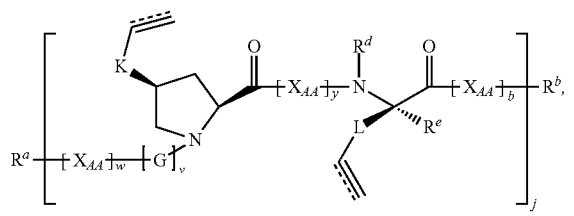

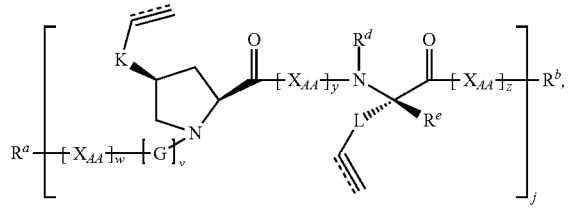

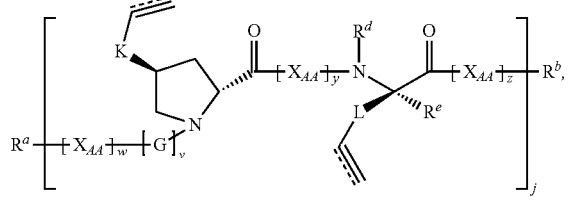

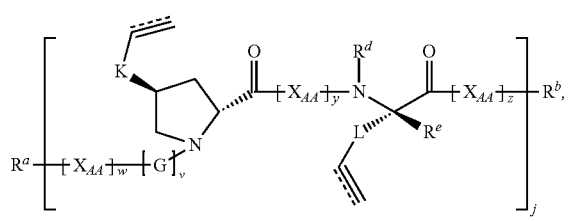

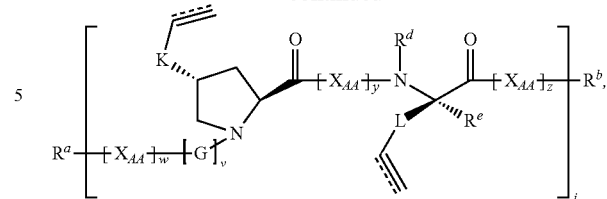

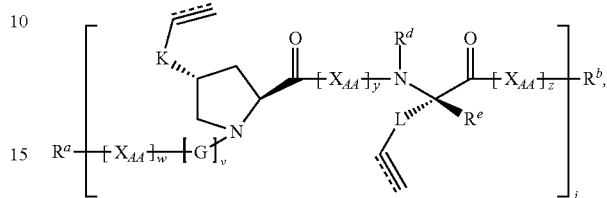

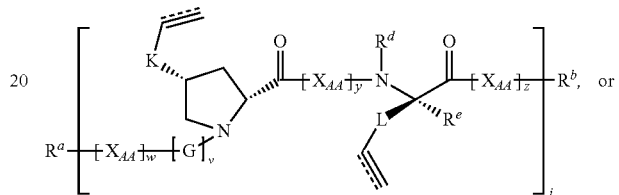

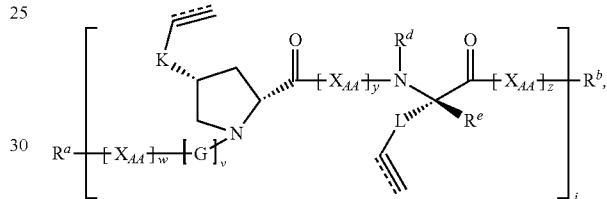

or a salt or stereoisomer thereof.

In certain embodiments, the precursor polypeptide of Formula (P-I), upon contact with a ring closing metathesis catalyst, generates a stapled polypeptide of Formula (I):

(I)

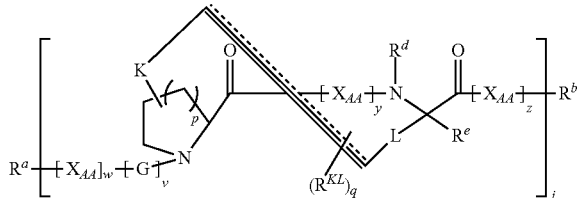

or a salt or stereoisomer thereof;
wherein:

each instance of K and L, is, independently, a bond or a group consisting of one or more combinations of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclene, substituted or unsubstituted carbocyclene, substituted or unsubstituted arylene; substituted or unsubstituted heteroarylene;

$R^a$ is hydrogen; substituted or unsubstituted aliphatic; substituted or unsubstituted heteroaliphatic; substituted or unsubstituted aryl; substituted or unsubstituted heteroaryl; substituted or unsubstituted acyl; a resin; an amino protecting group; a label optionally joined by a linker, wherein the linker is a group consisting of one or more combinations of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted carbocyclene; substituted or unsubstituted heterocyclene; substituted or unsubstituted arylene; or substituted or unsubstituted heteroarylene;

$R^b$ is, $-R^B$, $-OR^B$, $-N(R^B)_2$, or $-SR^B$, wherein each instance of $R^B$ is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; a resin; a suitable hydroxyl, amino or thiol protecting group; or two $R^B$ groups together form a substituted or unsubstituted 5- to 6-membered heterocyclic or heteroaromatic ring;

each instance of $R^{KL}$ is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; azido; cyano; isocyano; halo; or nitro;

each instance of $R^d$ is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; or $R^d$ is an amino protecting group;

each instance of $R^e$ is, independently, a suitable amino acid side chain; hydrogen; substituted or unsubstituted aliphatic; substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; cyano; isocyano; halo; or nitro;

each instance of G is, independently, a natural or unnatural amino acid or a group of the formula:

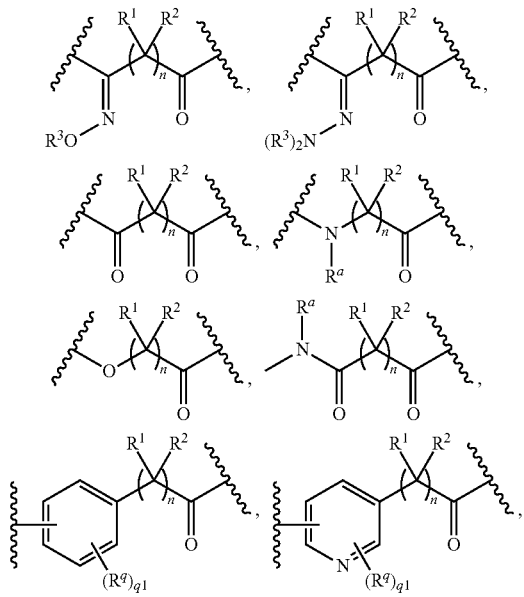

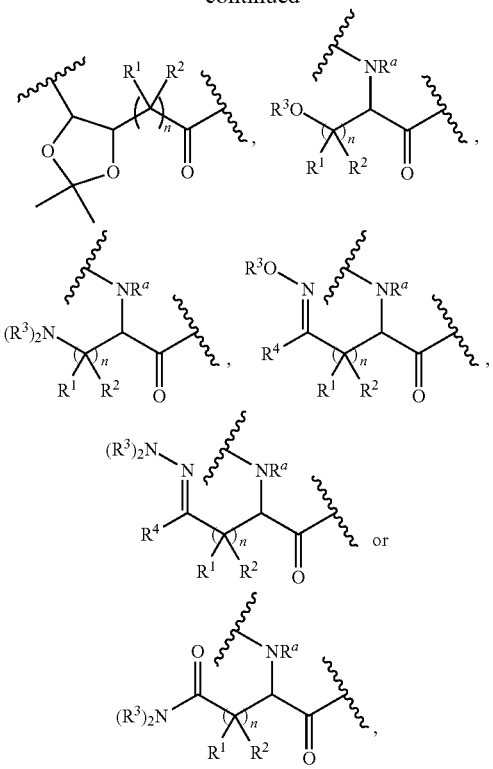

wherein:
n is 1, 2, or 3; and
each instance of $R^1$ and $R^2$ is independently hydrogen; substituted or unsubstituted aliphatic; substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; or halo, or $R^1$ and $R^2$ are joined to form a carbocyclic or heterocyclic ring;
each instance of $R^3$ and $R^4$ is, independently, hydrogen; substituted or unsubstituted aliphatic; substituted or unsubstituted heteroaliphatic; a hydroxyl protecting group when attached to an oxygen atom, or an amino protecting group when attached to a nitrogen atom, or two $R^3$ groups when attached to a nitrogen atom are joined to form a heterocyclic ring;
each instance of $R^q$ is independently halogen, $-CN$, $-NO_2$, $-N_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, an optionally substituted amino group, or optionally substituted acyl;
q1 is 0, 1, 2, 3, or 4;
each instance of $X_{AA}$ is, independently, a natural or unnatural amino acid;
j is, independently, an integer between 1 to 10, inclusive;
p is, independently, 1 or 2;
each instance of q is independently, 0, 1, or 2;
v is, independently, 0 or 1;
each instance of w and z is, independently, an integer between 0 and 100;
y is, independently, an integer of 1 to 8, inclusive; and
===== corresponds to a single, double or triple bond.

In certain embodiments, the ═══ corresponds to a double bond. In certain embodiments, the ═══ corresponds to a triple bond.

In certain embodiments the polypeptide of Formula (I) is of the formula:

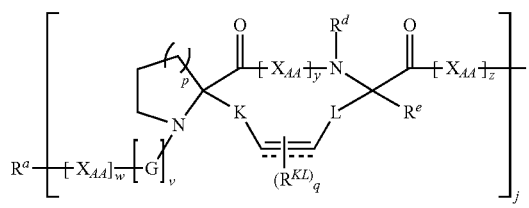

or a salt or stereoisomer thereof.

In certain embodiments, the polypeptide of Formula (I) is any one of the formulae:

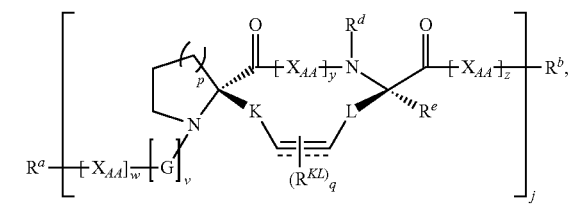

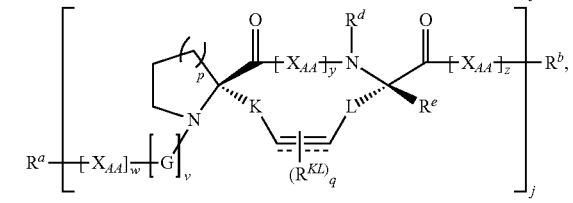

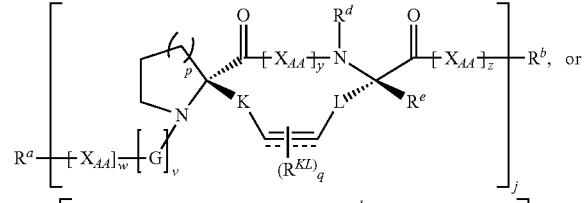

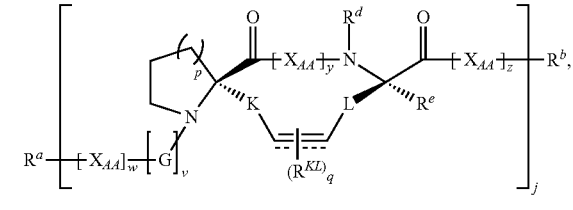

or a salt thereof.

In certain embodiments, the polypeptide of Formula (I) is any one of the formulae:

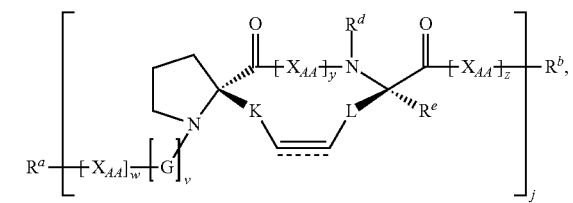

-continued

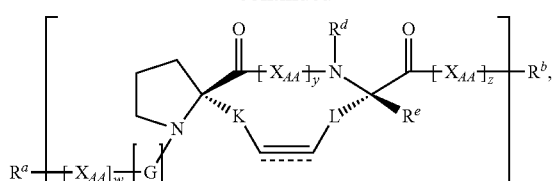

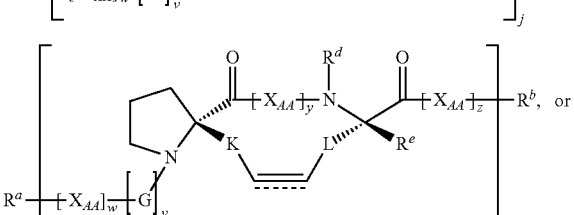

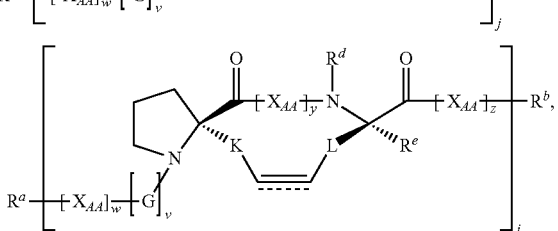

or a salt thereof.

In certain embodiments, the polypeptide of Formula (I) is of the formulae:

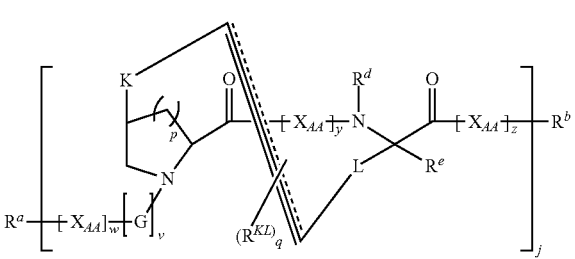

or a salt or stereoisomer thereof.

In certain embodiments, the polypeptide of Formula (I) is any one of the formula:

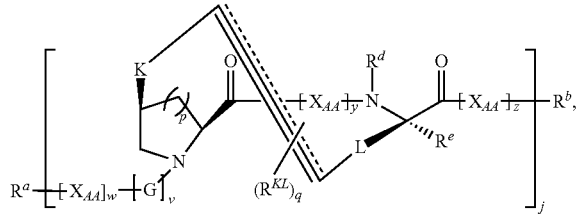

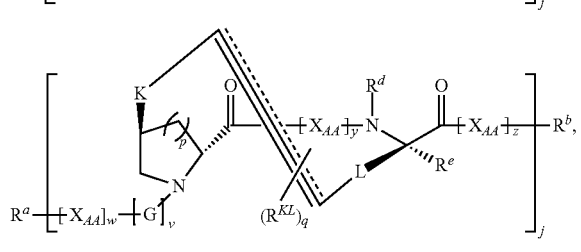

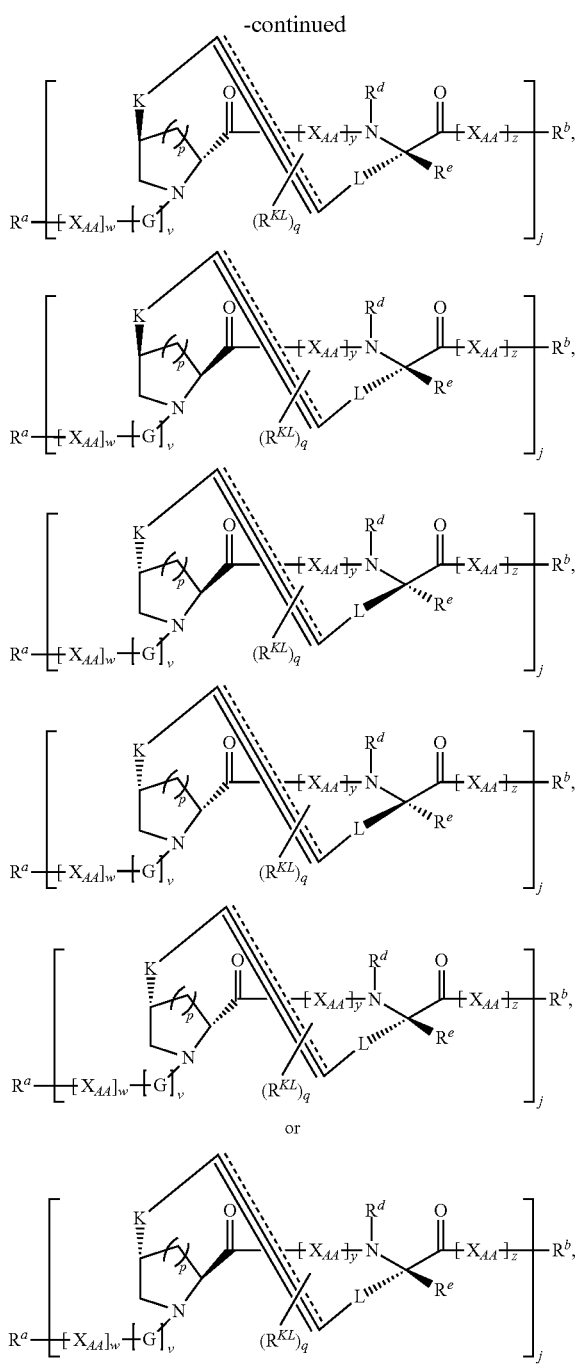
or a salt thereof.
In certain embodiments, the polypeptide of Formula (I) is any one of the formula:
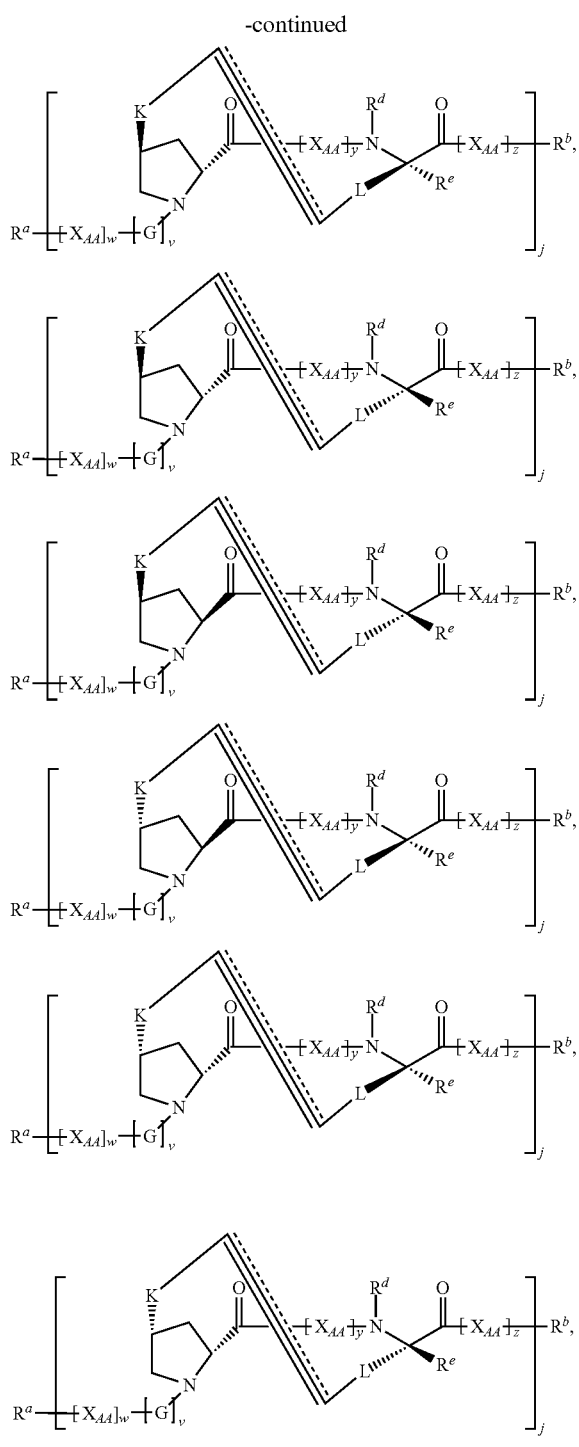
or a salt thereof.

In another aspect, provided is a precursor polypeptide of Formula (P-II):

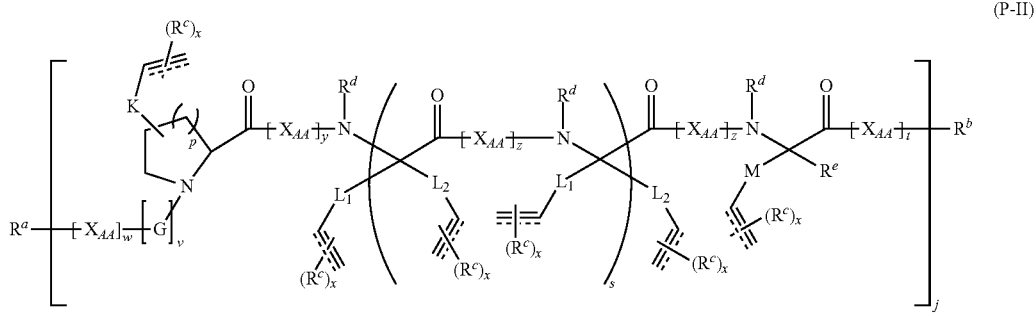

(P-II)

or a salt or stereoisomer thereof;
wherein:
each instance of K, $L_1$, $L_2$, and M, is, independently, a bond or a group consisting of one or more combinations of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclene, substituted or unsubstituted carbocyclene; substituted or unsubstituted arylene; and substituted or unsubstituted heteroarylene;

$R^a$ is hydrogen, substituted or unsubstituted aliphatic; substituted or unsubstituted heteroaliphatic; substituted or unsubstituted aryl; substituted or unsubstituted heteroaryl; substituted or unsubstituted acyl; a resin; an amino protecting group; a label optionally joined by a linker, wherein the linker is a group consisting of one or more combinations of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted carbocyclene; substituted or unsubstituted heterocyclene; substituted or unsubstituted arylene; or substituted or unsubstituted heteroarylene;

$R^b$ is, $-R^B$, $-OR^B$, $-N(R^B)_2$, or $-SR^B$, wherein each instance of $R^B$ is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; a resin; a suitable hydroxyl, amino or thiol protecting group; or two $R^B$ groups together form a substituted or unsubstituted 5- to 6-membered heterocyclic or heteroaromatic ring;

each instance of $R^c$, is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; cyano; isocyano; halo; or nitro;

each instance of $R^d$ is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; or $R^d$ is an amino protecting group;

each instance of $R^e$ is, independently, a suitable amino acid side chain; hydrogen; substituted or unsubstituted aliphatic; substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; cyano; isocyano; halo; or nitro;

each instance of G is, independently, a natural or unnatural amino acid or a group of the formula:

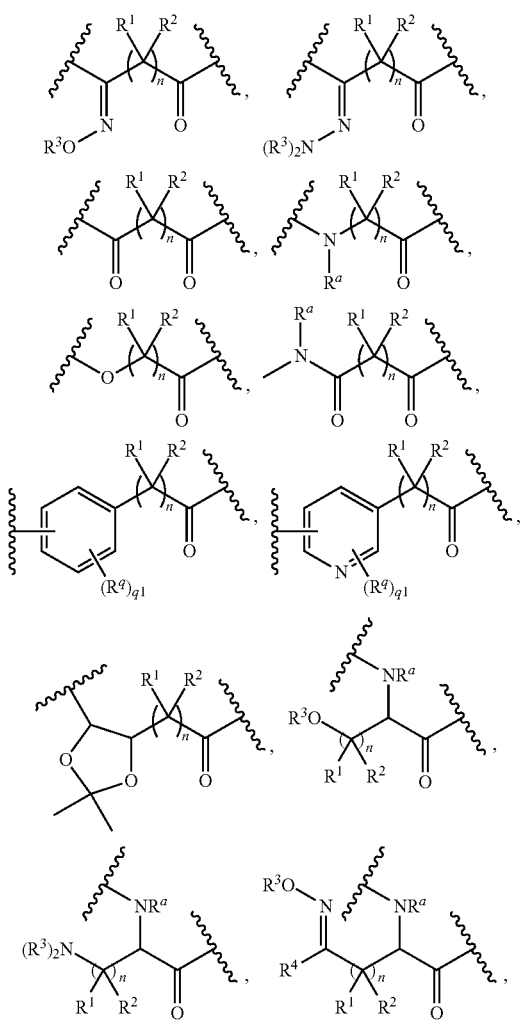

-continued

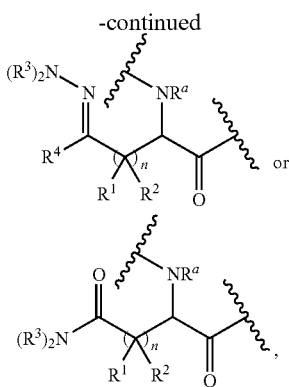

wherein:

n is 1, 2, or 3; and each instance of $R^1$ and $R^2$ is independently hydrogen; substituted or unsubstituted aliphatic; substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; or halo, or $R^1$ and $R^2$ are joined to form a carbocyclic or heterocyclic ring;

each instance of $R^3$ and $R^4$ is, independently, hydrogen; substituted or unsubstituted aliphatic; substituted or unsubstituted heteroaliphatic; a hydroxyl protecting group when attached to an oxygen atom, or an amino protecting group when attached to a nitrogen atom, or two $R^3$ groups when attached to a nitrogen atom are joined to form a heterocyclic ring;

each instance of $R^q$ is independently halogen, —CN, —NO$_2$, —N$_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, an optionally substituted amino group, or optionally substituted acyl;

q1 is 0, 1, 2, 3, or 4;

each instance of $X_{AA}$ is, independently, a natural or unnatural amino acid;

j is, independently, an integer between 1 to 10, inclusive;

p is, independently, 1 or 2;

v is, independently, 0 or 1;

s is 0, 1, or 2;

each instance of t, w and z is, independently, an integer between 0 and 100, inclusive; each instance of x is, independently, 0, 1, 2, or 3;

y is, independently, 1, 2, 3, or 4; and

═══ corresponds to a double or triple bond.

In certain embodiments, the ═══ corresponds to a double bond. In certain embodiments, the ═══ corresponds to a triple bond.

In certain embodiments, the polypeptide of Formula (P-II) is of the formula:

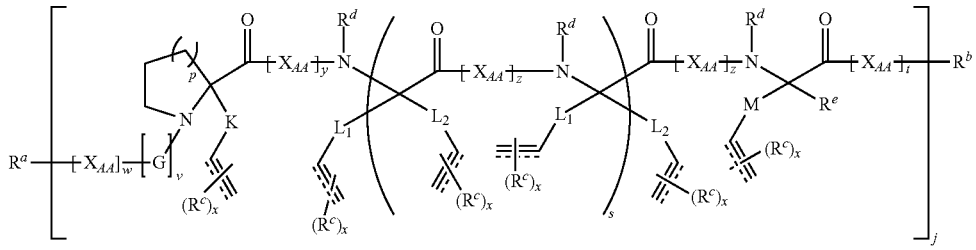

or a salt or stereoisomer thereof.

In certain embodiments, the polypeptide of Formula (P-II) is any one of the formula:

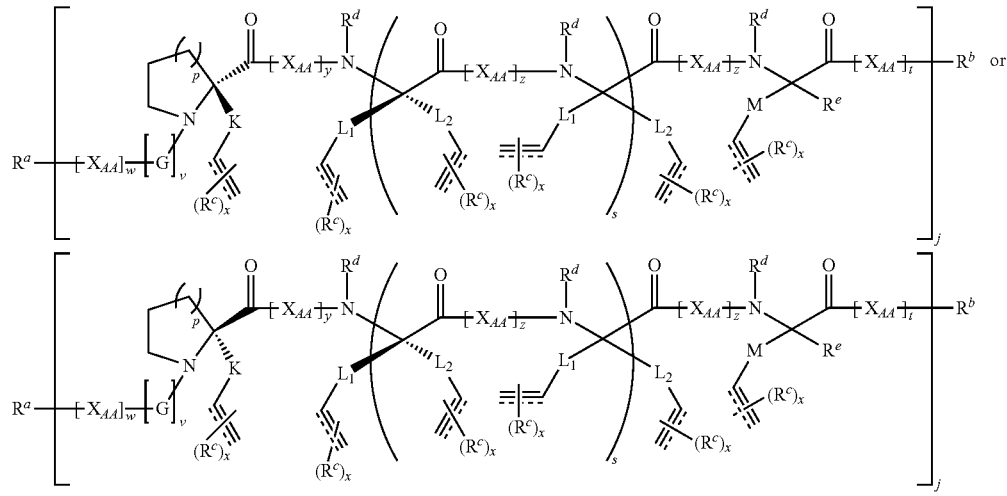

or salt or stereoisomer thereof.

In certain embodiments, the polypeptide of Formula (P-II) is any one of the formula:
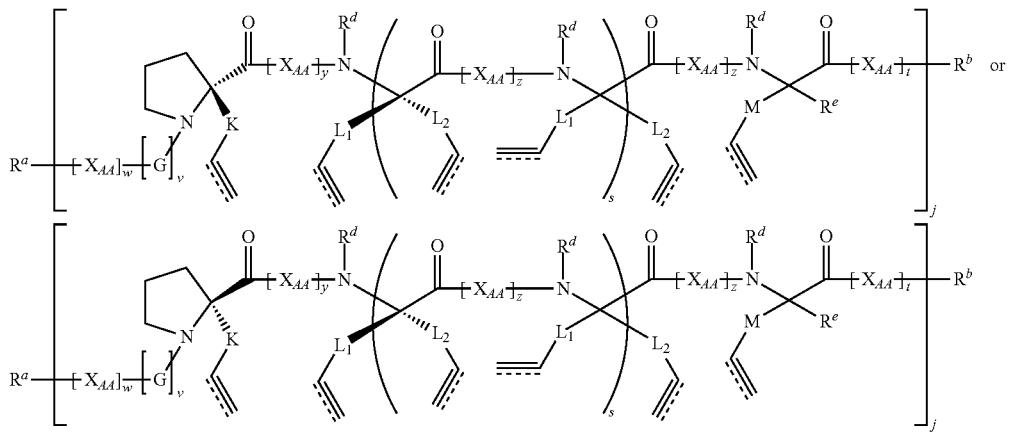
or salt or stereoisomer thereof.
In certain embodiments, the polypeptide of Formula (P-II) is of the formula:
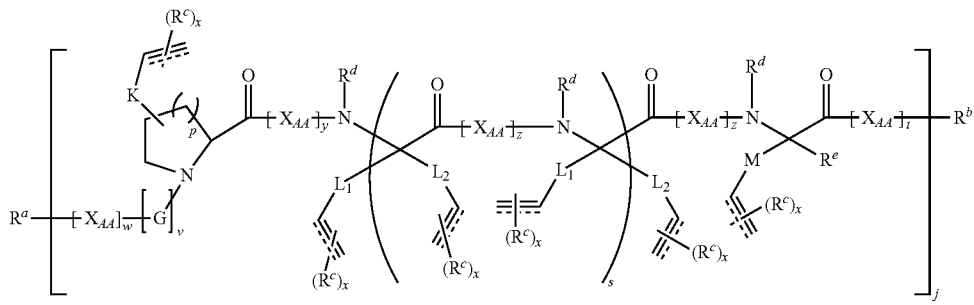
or a salt or stereoisomer thereof.
In certain embodiments, the polypeptide of Formula (II) is any one of the formula:
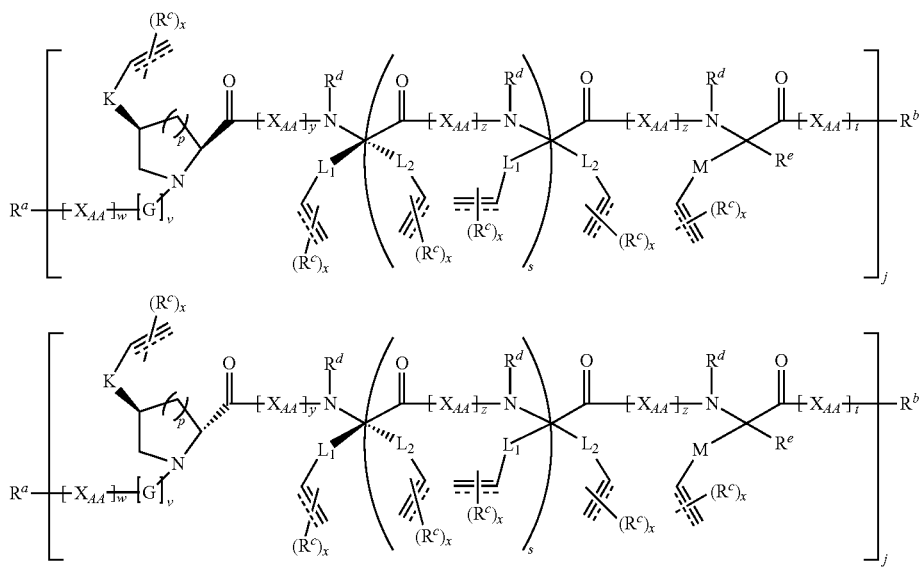

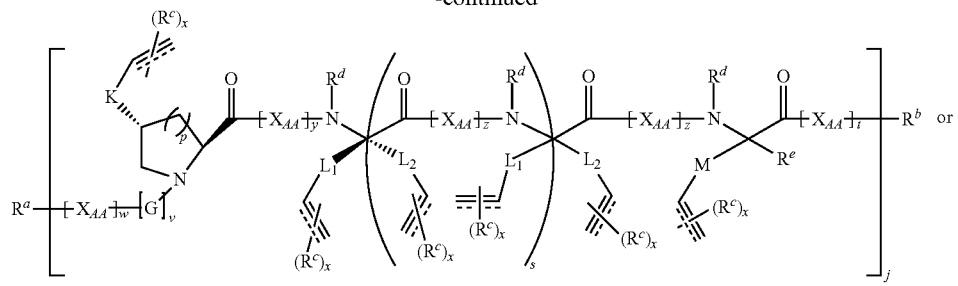
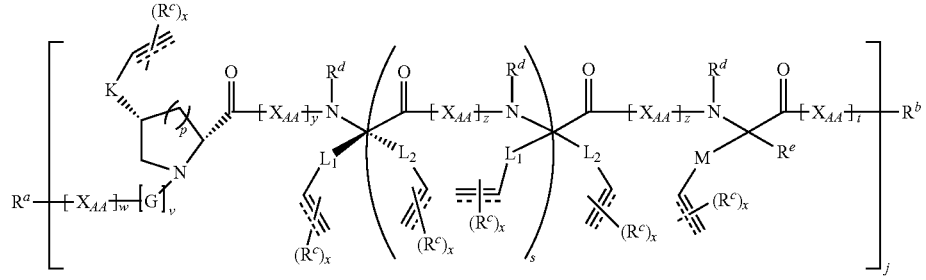
or a salt or stereoisomer thereof.
In certain embodiments, the polypeptide of Formula (II) is any one of the formula:
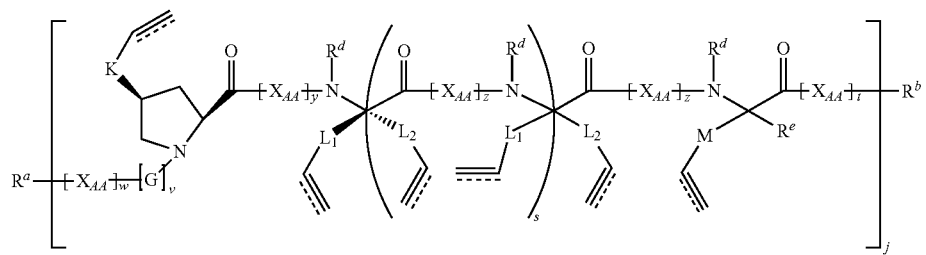
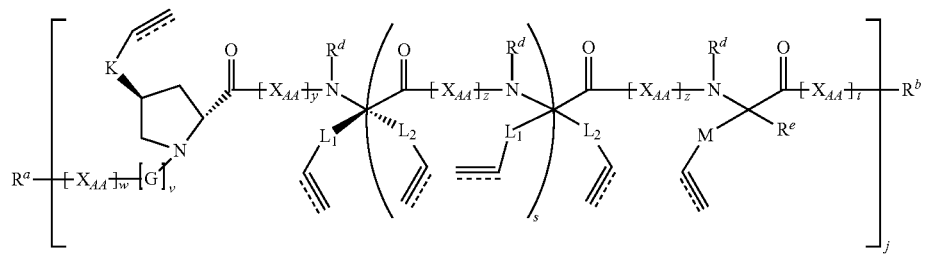
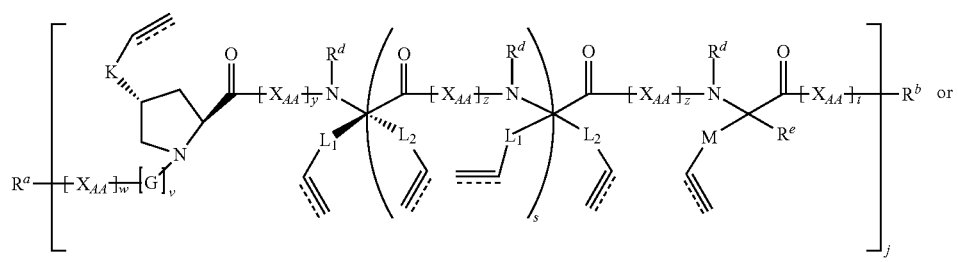

-continued

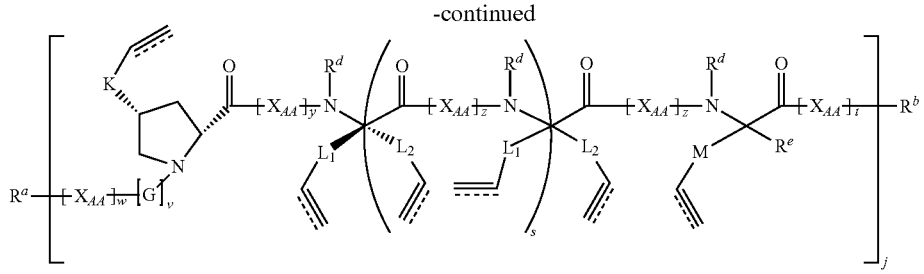

or a salt or stereoisomer thereof.

Furthermore, in certain embodiments, the precursor polypeptide of Formula (P-II), upon contact with a ring closing methathesis catalyst, generates a stitched polypeptide of Formula (II):

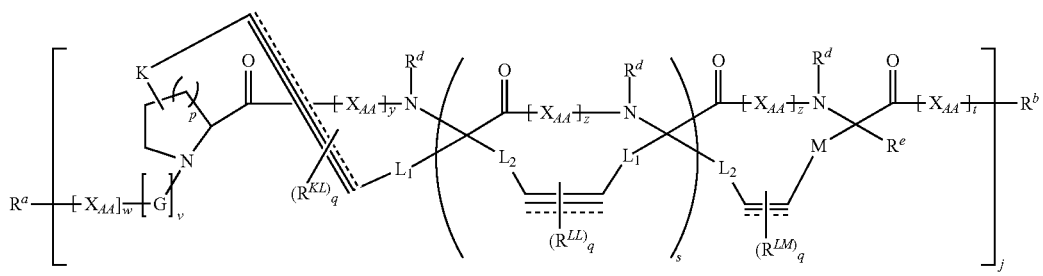

or a salt or stereoisomer thereof,
wherein:

each instance of K, M, $L_1$, and $L_2$, is independently, a bond or a group consisting of one or more combinations of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclene, substituted or unsubstituted carbocyclene, substituted or unsubstituted arylene; substituted or unsubstituted heteroarylene;

$R^a$ is hydrogen; substituted or unsubstituted aliphatic; substituted or unsubstituted heteroaliphatic; substituted or unsubstituted aryl; substituted or unsubstituted heteroaryl; substituted or unsubstituted acyl; a resin; an amino protecting group; a label optionally joined by a linker, wherein the linker is a group consisting of one or more combinations of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted carbocyclene; substituted or unsubstituted heterocyclene; substituted or unsubstituted arylene; or substituted or unsubstituted heteroarylene;

$R^b$ is, $-R^B$, $-OR^B$, $-N(R^B)_2$, or $-SR^B$, wherein each instance of $R^B$ is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; a resin; a suitable hydroxyl, amino or thiol protecting group; or two $R^B$ groups together form a substituted or unsubstituted 5- to 6-membered heterocyclic or heteroaromatic ring;

each instance of $R^c$, is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; cyano; isocyano; halo; or nitro;

each instance of $R^d$ is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; or $R^d$ is an amino protecting group;

each instance of $R^e$ is, independently, a suitable amino acid side chain; hydrogen; substituted or unsubstituted aliphatic; substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; cyano; isocyano; halo; or nitro;

each instance of $R^{KL}$, $R^{LL}$, and $R^{LM}$, is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; azido; cyano; isocyano; halo; nitro;

each instance of G is, independently, a natural or unnatural amino acid or a group of the formula:

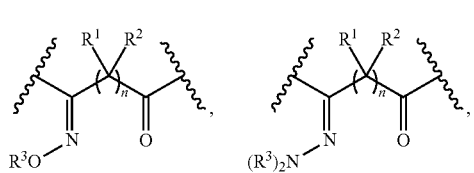

-continued wherein:

n is 1, 2, or 3; and each instance of $R^1$ and $R^2$ is independently hydrogen; substituted or unsubstituted aliphatic; substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; or halo, or $R^1$ and $R^2$ are joined to form a carbocyclic or heterocyclic ring;

each instance of $R^3$ and $R^4$ is, independently, hydrogen; substituted or unsubstituted aliphatic; substituted or unsubstituted heteroaliphatic; a hydroxyl protecting group when attached to an oxygen atom, or an amino protecting group when attached to a nitrogen atom, or two $R^3$ groups when attached to a nitrogen atom are joined to form a heterocyclic ring;

each instance of $R^q$ is independently halogen, —CN, —$NO_2$, —$N_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, an optionally substituted amino group, or optionally substituted acyl;

q1 is 0, 1, 2, 3, or 4;

each instance of $X_{AA}$ is, independently, a natural or unnatural amino acid;

j is, independently, an integer between 1 to 10, inclusive;

p is, independently, 1 or 2;

each instance of q is independently, 0, 1 or 2;

v is, independently, an integer between 0 to 1;

s is 0, 1, or 2;

each instance of t, w and z is, independently, an integer between 0 and 100;

y is, independently, an integer of 1 to 8, inclusive; and

═══ corresponds to a single, double or triple bond.

In certain embodiments, the ═══ corresponds to a double bond. In certain embodiments, the ═══ corresponds to a triple bond.

In certain embodiments, the polypeptide of Formula (II) is of the formula:

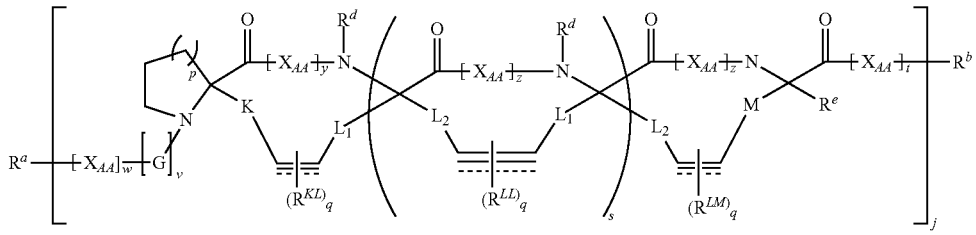

or a salt or stereoisomer thereof.

In certain embodiments, the polypeptide of Formula (II) is any one of the formula:

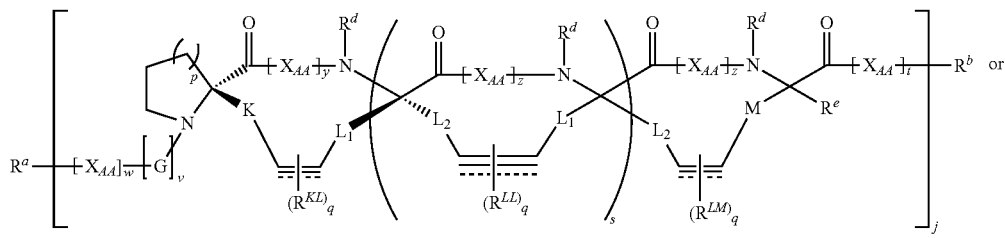

-continued
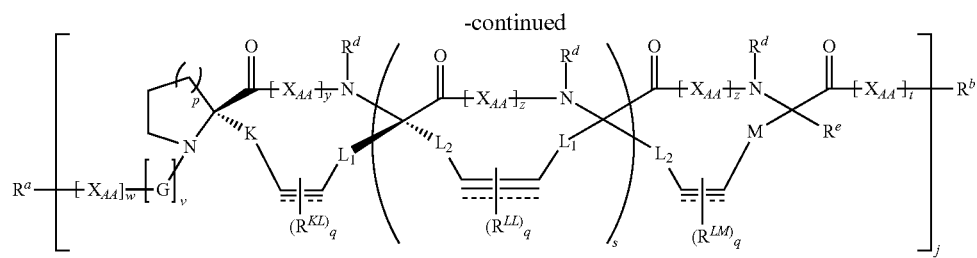
or a salt or stereoisomer thereof.
In certain embodiments, the polypeptide of Formula (II) is any one of the formula:
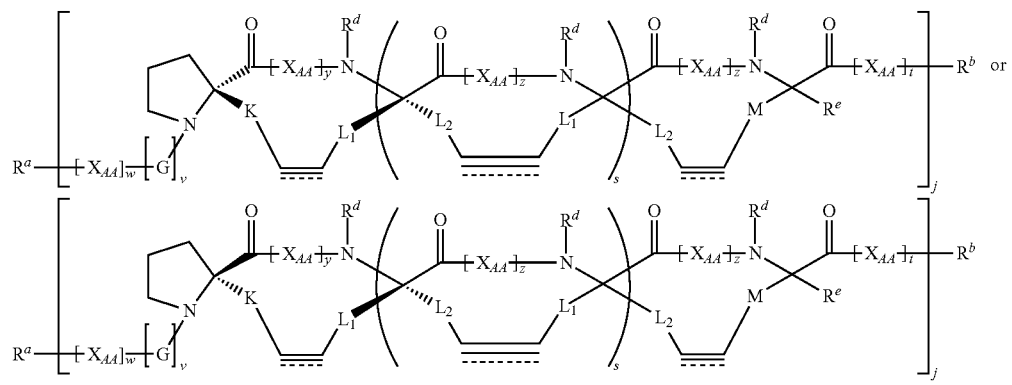
or a salt or stereoisomer thereof.
In certain embodiments, the polypeptide of Formula (II) is of the formula:
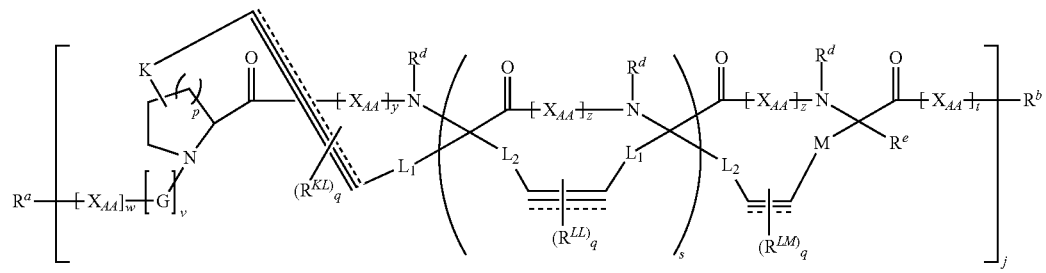
or a salt or stereoisomer thereof.
In certain embodiments, the polypeptide of Formula (II) is any one of the formula:
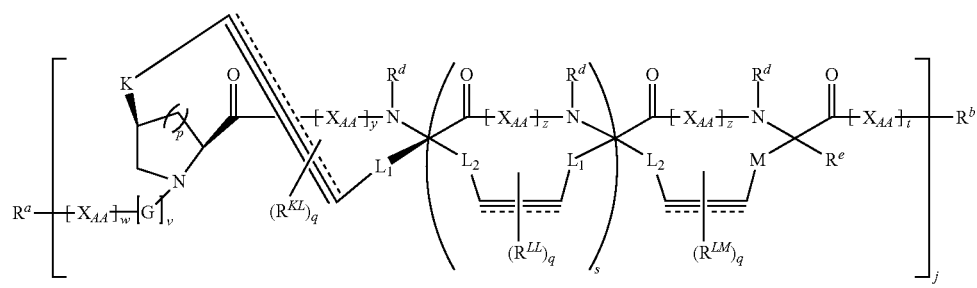

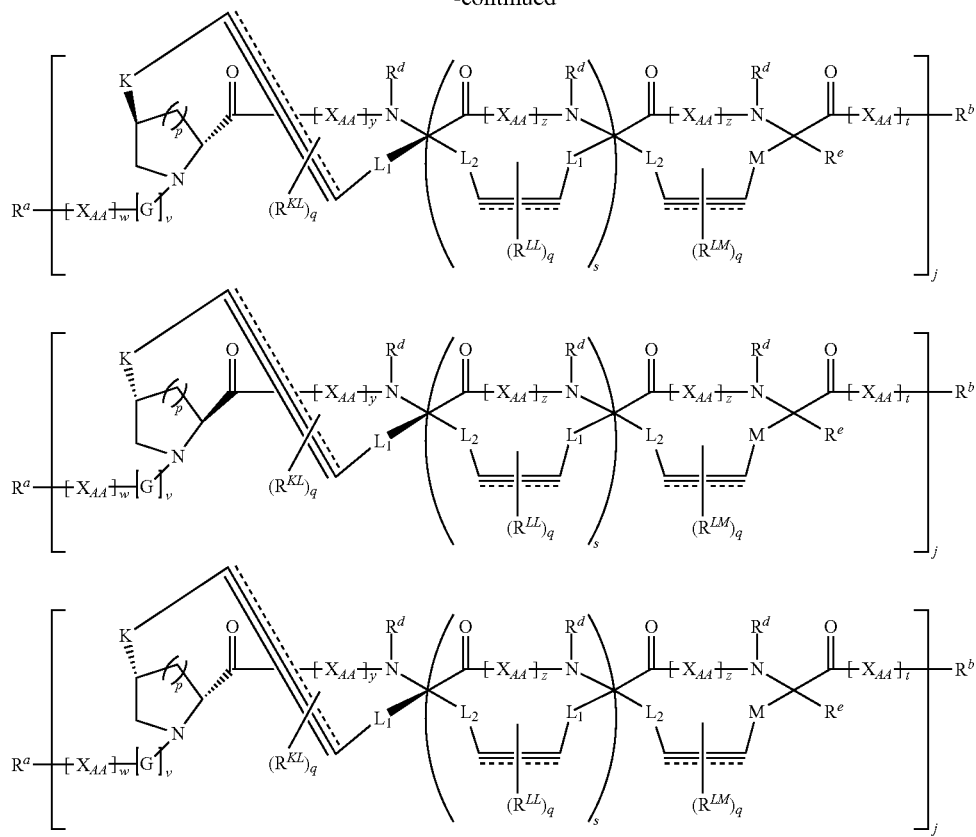
or a salt or stereoisomer thereof.
In certain embodiments, the polypeptide of Formula (II) is any one of the formula
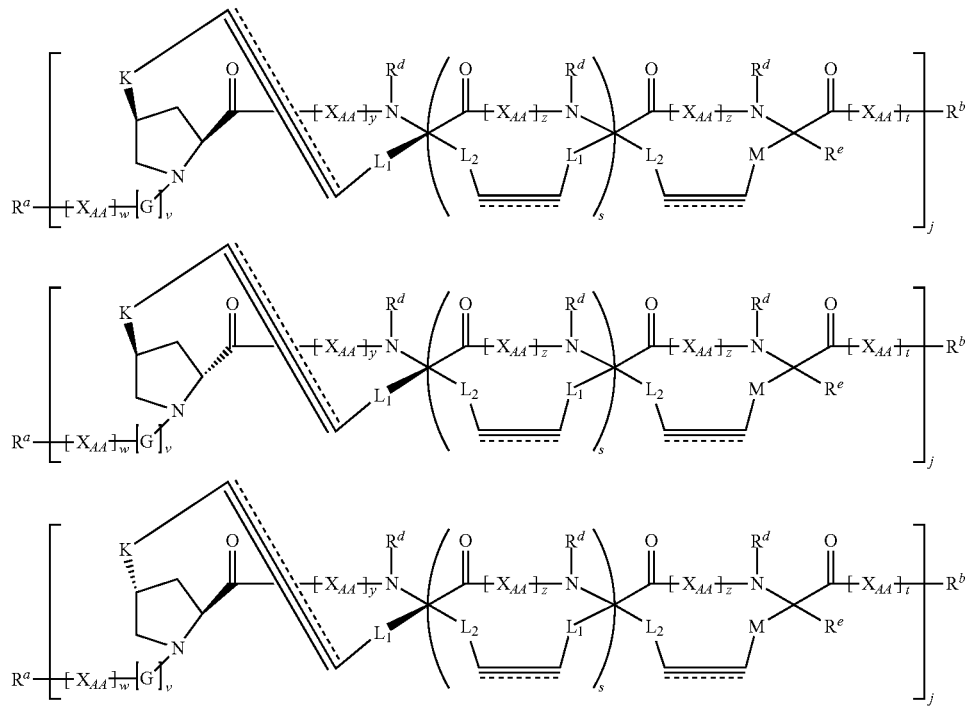

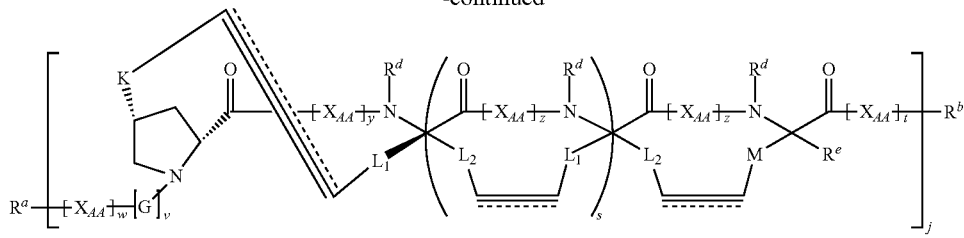

or a salt or stereoisomer thereof.

In yet another aspect, provided are compounds useful in the preparation of the precursor polypeptides which include, but are not limited to, compounds of Formula (III):

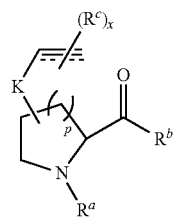
(III)

or salts or stereoisomers thereof; wherein:

p is 1 or 2;

K is a bond or a group consisting of one or more combinations of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclene, substituted or unsubstituted carbocyclene, substituted or unsubstituted arylene; substituted or unsubstituted heteroarylene;

$R^a$ is hydrogen, substituted or unsubstituted aliphatic; substituted or unsubstituted heteroaliphatic; substituted or unsubstituted aryl; substituted or unsubstituted heteroaryl; substituted or unsubstituted acyl; a resin; an amino protecting group; or a label optionally joined by a linker, wherein the linker is a group consisting of one or more combinations of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted carbocyclene; substituted or unsubstituted heterocyclene; substituted or unsubstituted arylene; or substituted or unsubstituted heteroarylene;

$R^b$ is, $—R^B$, $—OR^B$, $—N(R^B)_2$, or $—SR^B$, wherein each instance of $R^B$ is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; a resin; a suitable hydroxyl, amino or thiol protecting group; or two $R^B$ groups together form a substituted or unsubstituted 5- to 6-membered heterocyclic or heteroaromatic ring;

each instance of $R^c$, is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; cyano; isocyano; halo; or nitro;

x is 0, 1, 2, or 3; and

═══ corresponds to a single, double or triple bond.

In certain embodiments, the ═══ corresponds to a double bond. In certain embodiments, the ═══ corresponds to a triple bond.

In certain embodiments, the compound of Formula (III) is of the formula:

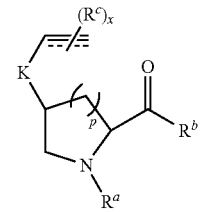

or salt or stereoisomer thereof.

In certain embodiments, the compound of Formula (III) is any one of the formula:

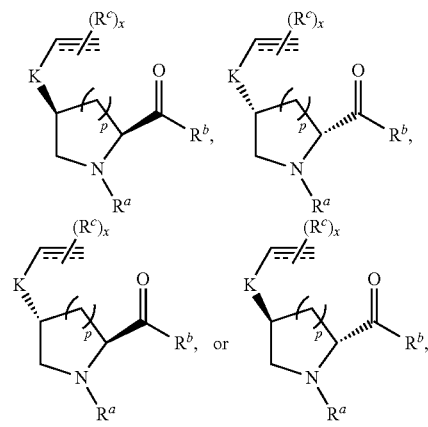

or salt thereof.

In certain embodiments, the compound of Formula (III) is any one of the formula:

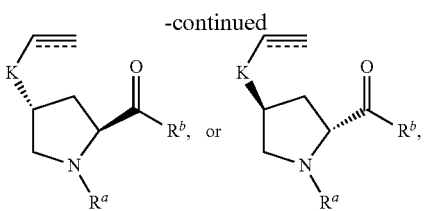

or salt thereof.

In certain embodiments, the compound of Formula (III) is of the formula:

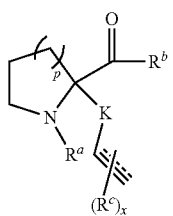

or salt or stereoisomer thereof.

In certain embodiments, the compound of Formula (III) is any one of the formula:

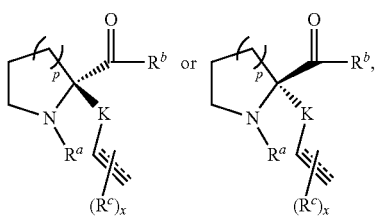

or salt thereof.

In certain embodiments, the compound of Formula (III) is any one of the formula:

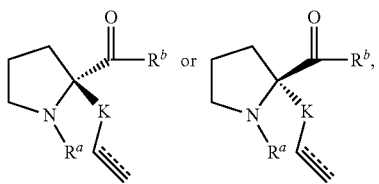

or salt thereof.

Groups K, L, $L_1$, $L_2$, and M

As generally defined above, each instance of K, L, $L_1$, $L_2$, and M is, independently, a bond or a group consisting of one or more combinations of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclene, substituted or unsubstituted carbocyclene, substituted or unsubstituted arylene; substituted or unsubstituted heteroarylene.

As used herein, reference to a group consisting of "one or more combinations" refers to a group comparing 1, 2, 3, 4 or more combinations of the recited divinyl moieties. For example, the group may consist of an alkylene attached to a heteroalkylene, which may be further optionally attached to another alkylene. As used herein "at least one instance" refers to 1, 2, 3, or 4 instances of the recited moiety.

In certain embodiments, K is a bond.

In certain embodiments, K is a group consisting of one or more combinations of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclene, substituted or unsubstituted carbocyclene, substituted or unsubstituted arylene; substituted or unsubstituted heteroarylene.

In certain embodiments, K is a group which comprises at least one instance of substituted or unsubstituted alkylene, e.g., substituted or unsubstituted $C_{1-6}$alkylene, substituted or unsubstituted $C_{1-2}$alkylene, substituted or unsubstituted $C_{2-3}$alkylene, substituted or unsubstituted $C_{3-6}$alkylene, substituted or unsubstituted $C_{4-5}$alkylene, or substituted or unsubstituted $C_{5-6}$alkylene. Exemplary alkylene groups include unsubstituted alkylene groups such as methylene —$CH_2$—, ethylene —$(CH_2)_2$—, n-propylene —$(CH_2)_3$—, n-butylene —$(CH_2)_4$—, n-pentylene —$(CH_2)_5$—, and n-hexylene —$(CH_2)_6$—. In certain embodiments, K is —$CH_2$—. In certain embodiments, K is —$(CH_2)_2$—. In certain embodiments, K is —$(CH_2)_3$—.

In certain embodiments, K is a group which comprises at least one instance of substituted or unsubstituted alkenylene, e.g., substituted or unsubstituted $C_{2-6}$alkenylene, substituted or unsubstituted $C_{2-3}$alkenylene, substituted or unsubstituted $C_{3-4}$alkenylene, substituted or unsubstituted $C_{4-5}$alkenylene, or substituted or unsubstituted $C_{5-6}$alkenylene.

In certain embodiments, K is a group which comprises at least one instance of substituted or unsubstituted alkynylene, e.g., substituted or unsubstituted $C_{2-6}$alkynylene, substituted or unsubstituted $C_{2-3}$alkynylene, substituted or unsubstituted $C_{3-4}$alkynylene, substituted or unsubstituted $C_{4-5}$alkynylene, or substituted or unsubstituted $C_{5-6}$alkynylene.

In certain embodiments, K is a group which comprises at least one instance of substituted or unsubstituted heteroalkylene, e.g., substituted or unsubstituted hetero$C_{1-6}$alkylene, substituted or unsubstituted hetero$C_{1-2}$alkylene, substituted or unsubstituted hetero$C_{2-3}$alkylene, substituted or unsubstituted hetero$C_{3-4}$alkylene, substituted or unsubstituted hetero$C_{4-5}$alkylene, or substituted or unsubstituted hetero$C_{5-6}$alkylene. Exemplary heteroalkylene groups include unsubstituted alkylene groups such as —$(CH_2)_2$—O$(CH_2)_2$—, —$OCH_2$—, —$O(CH_2)_2$—, —$O(CH_2)_3$—, —$O(CH_2)_4$—, —$O(CH_2)_5$—, and —$O(CH_2)_6$—. In certain embodiments, K is —$CH_2O$—, wherein O is linked to the heterocyclyl with nitrogen and $CH_2$ is linked to ≡. In certain embodiments, K is —$(CH_2)_2O$—, wherein O is linked to the heterocyclyl with nitrogen and $CH_2$ is linked to "≡." In certain embodiments, K is —$(CH_2)_3O$—, wherein O is linked to the heterocyclyl with nitrogen and $CH_2$ is linked to "≡".

In certain embodiments, K is a group which comprises at least one instance of substituted or unsubstituted heteroalkenylene, e.g., substituted or unsubstituted hetero$C_{2-6}$alkenylene, substituted or unsubstituted hetero$C_{2-3}$alkenylene, substituted or unsubstituted hetero$C_{3-4}$alkenylene, substituted or unsubstituted hetero$C_{4-5}$alkenylene, or substituted or unsubstituted hetero$C_{5-6}$alkenylene.

In certain embodiments, K is a group which comprises at least one instance of substituted or unsubstituted heteroalkynylene, e.g., substituted or unsubstituted hetero$C_{2-6}$alkynylene, substituted or unsubstituted heteroC$_{2-3}$alkynylene, substituted or unsubstituted heteroC$_{3-4}$alkynylene, substituted or unsubstituted heteroC$_{4-5}$alkynylene, or substituted or unsubstituted heteroC$_{5-6}$alkynylene.

In certain embodiments, K is a group which comprises at least one instance of substituted or unsubstituted carbocyclylene, e.g., substituted or unsubstituted C$_{3-6}$carbocyclylene, substituted or unsubstituted C$_{3-4}$carbocyclylene, substituted or unsubstituted C$_{4-5}$ carbocyclylene, or substituted or unsubstituted C$_{5-6}$ carbocyclylene.

In certain embodiments, K is a group which comprises at least one instance of substituted or unsubstituted heterocyclylene, e.g., substituted or unsubstituted C$_{3-6}$ heterocyclylene, substituted or unsubstituted C$_{3-4}$ heterocyclylene, substituted or unsubstituted C$_{4-5}$ heterocyclylene, or substituted or unsubstituted C$_{5-6}$ heterocyclylene.

In certain embodiments, K is a group which comprises at least one instance of substituted or unsubstituted arylene, e.g., substituted or unsubstituted phenylene.

In certain embodiments, K is a group which comprises at least one instance of substituted or unsubstituted heteroarylene, e.g., substituted or unsubstituted 5- to 6-membered heteroarylene.

In certain embodiments, L is a bond.

In certain embodiments, L is a group consisting of one or more combinations of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclene, substituted or unsubstituted carbocyclene, substituted or unsubstituted arylene; substituted or unsubstituted heteroarylene.

In certain embodiments, L is a group which comprises at least one instance of substituted or unsubstituted alkylene, e.g., substituted or unsubstituted C$_{1-6}$alkylene, substituted or unsubstituted C$_{1-2}$alkylene, substituted or unsubstituted C$_{2-3}$alkylene, substituted or unsubstituted C$_{3-4}$alkylene, substituted or unsubstituted C$_{4-5}$alkylene, or substituted or unsubstituted C$_{5-6}$alkylene. Exemplary alkylene groups include unsubstituted alkylene groups such as methylene —CH$_2$—, ethylene —(CH$_2$)$_2$—, n-propylene —(CH$_2$)$_3$—, n-butylene —(CH$_2$)$_4$—, n-pentylene —(CH$_2$)$_5$—, and n-hexylene —(CH$_2$)$_6$—. In certain embodiments, L is —CH$_2$—. In certain embodiments, L is —(CH$_2$)$_2$—. In certain embodiments, L is —(CH$_2$)$_3$—. In certain embodiments, L is —(CH$_2$)$_4$—. In certain embodiments, L is —(CH$_2$)$_5$—. In certain embodiments, L is —(CH$_2$)$_6$—.

In certain embodiments, L is a group which comprises at least one instance of substituted or unsubstituted alkenylene, e.g., substituted or unsubstituted C$_{2-6}$alkenylene, substituted or unsubstituted C$_{2-3}$alkenylene, substituted or unsubstituted C$_{3-4}$alkenylene, substituted or unsubstituted C$_{4-5}$alkenylene, or substituted or unsubstituted C$_{5-6}$alkenylene.

In certain embodiments, L is a group which comprises at least one instance of substituted or unsubstituted alkynylene, e.g., substituted or unsubstituted C$_{2-6}$alkynylene, substituted or unsubstituted C$_{2-3}$alkynylene, substituted or unsubstituted C$_{3-4}$alkynylene, substituted or unsubstituted C$_{4-5}$alkynylene, or substituted or unsubstituted C$_{5-6}$alkynylene.

In certain embodiments, L is a group which comprises at least one instance of substituted or unsubstituted heteroalkylene, e.g., substituted or unsubstituted heteroC$_{1-6}$alkylene, substituted or unsubstituted heteroC$_{1-2}$alkylene, substituted or unsubstituted heteroC$_{2-3}$alkylene, substituted or unsubstituted heteroC$_{3-4}$alkylene, substituted or unsubstituted heteroC$_{4-5}$alkylene, or substituted or unsubstituted heteroC$_{5-6}$alkylene. Exemplary heteroalkylene groups include unsubstituted alkylene groups such as —(CH$_2$)$_2$—O(CH$_2$)$_2$—, —OCH$_2$—, —O(CH$_2$)$_2$—, —O(CH$_2$)$_3$—, —O(CH$_2$)$_4$—, —O(CH$_2$)$_5$—, and —O(CH$_2$)$_6$—.

In certain embodiments, L is a group which comprises at least one instance of substituted or unsubstituted heteroalkenylene, e.g., substituted or unsubstituted heteroC$_{2-6}$alkenylene, substituted or unsubstituted heteroC$_{2-3}$alkenylene, substituted or unsubstituted heteroC$_{3-4}$alkenylene, substituted or unsubstituted heteroC$_{4-5}$alkenylene, or substituted or unsubstituted heteroC$_{5-6}$alkenylene.

In certain embodiments, L is a group which comprises at least one instance of substituted or unsubstituted heteroalkynylene, e.g., substituted or unsubstituted heteroC$_{2-6}$alkynylene, substituted or unsubstituted heteroC$_{2-3}$alkynylene, substituted or unsubstituted heteroC$_{3-4}$alkynylene, substituted or unsubstituted heteroC$_{4-5}$alkynylene, or substituted or unsubstituted heteroC$_{5-6}$alkynylene.

In certain embodiments, L is a group which comprises at least one instance of substituted or unsubstituted carbocyclylene, e.g., substituted or unsubstituted C$_{3-6}$carbocyclylene, substituted or unsubstituted C$_{3-4}$carbocyclylene, substituted or unsubstituted C$_{4-5}$ carbocyclylene, or substituted or unsubstituted C$_{5-6}$ carbocyclylene.

In certain embodiments, L is a group which comprises at least one instance of substituted or unsubstituted heterocyclylene, e.g., substituted or unsubstituted C$_{3-6}$ heterocyclylene, substituted or unsubstituted C$_{3-4}$ heterocyclylene, substituted or unsubstituted C$_{4-5}$ heterocyclylene, or substituted or unsubstituted C$_{5-6}$ heterocyclylene.

In certain embodiments, L is a group which comprises at least one instance of substituted or unsubstituted arylene, e.g., substituted or unsubstituted phenylene.

In certain embodiments, L is a group which comprises at least one instance of substituted or unsubstituted heteroarylene, e.g., substituted or unsubstituted 5- to 6-membered heteroarylene.

In certain embodiments, L$_1$ is a bond.

In certain embodiments, L$_1$ is a group consisting of one or more combinations of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclene, substituted or unsubstituted carbocyclene, substituted or unsubstituted arylene; substituted or unsubstituted heteroarylene.

In certain embodiments, L$_1$ is a group which comprises at least one instance of substituted or unsubstituted alkylene, e.g., substituted or unsubstituted C$_{1-6}$alkylene, substituted or unsubstituted C$_{1-2}$alkylene, substituted or unsubstituted C$_{2-3}$alkylene, substituted or unsubstituted C$_{3-4}$alkylene, substituted or unsubstituted C$_{4-5}$alkylene, or substituted or unsubstituted C$_{5-6}$alkylene. Exemplary alkylene groups include unsubstituted alkylene groups such as methylene —CH$_2$—, ethylene —(CH$_2$)$_2$—, n-propylene —(CH$_2$)$_3$—, n-butylene —(CH$_2$)$_4$—, n-pentylene —(CH$_2$)$_5$—, and n-hexylene —(CH$_2$)$_6$—. In certain embodiments, L$_1$ is —CH$_2$—. In certain embodiments, L$_1$ is —(CH$_2$)$_2$—. In certain embodiments, L$_1$ is —(CH$_2$)$_3$—. In certain embodiments, L$_1$ is —(CH$_2$)$_4$—. In certain embodiments, L$_1$ is —(CH$_2$)$_5$—. In certain embodiments, L$_1$ is —(CH$_2$)$_6$—.

In certain embodiments, L$_1$ is a group which comprises at least one instance of substituted or unsubstituted alkenylene, e.g., substituted or unsubstituted C$_{2-6}$alkenylene, substituted or unsubstituted C$_{2-3}$alkenylene, substituted or unsubstituted $C_{3-4}$alkenylene, substituted or unsubstituted $C_{4-5}$alkenylene, or substituted or unsubstituted $C_{5-6}$alkenylene.

In certain embodiments, $L_1$ is a group which comprises at least one instance of substituted or unsubstituted alkynylene, e.g., substituted or unsubstituted $C_{2-6}$alkynylene, substituted or unsubstituted $C_{2-3}$alkynylene, substituted or unsubstituted $C_{3-4}$alkynylene, substituted or unsubstituted $C_{4-5}$alkynylene, or substituted or unsubstituted $C_{5-6}$alkynylene.

In certain embodiments, $L_1$ is a group which comprises at least one instance of substituted or unsubstituted heteroalkylene, e.g., substituted or unsubstituted hetero$C_{1-6}$alkylene, substituted or unsubstituted hetero$C_{1-2}$alkylene, substituted or unsubstituted hetero$C_{2-3}$alkylene, substituted or unsubstituted hetero$C_{3-4}$alkylene, substituted or unsubstituted hetero$C_{4-5}$alkylene, or substituted or unsubstituted hetero$C_{5-6}$alkylene. Exemplary heteroalkylene groups include unsubstituted alkylene groups such as —$(CH_2)_2$—$O(CH_2)_2$—, —$OCH_2$—, —$O(CH_2)_2$—, —$O(CH_2)_3$—, —$O(CH_2)_4$—, —$O(CH_2)_5$—, and —$O(CH_2)_6$—.

In certain embodiments, $L_1$ is a group which comprises at least one instance of substituted or unsubstituted heteroalkenylene, e.g., substituted or unsubstituted hetero$C_{2-6}$alkenylene, substituted or unsubstituted hetero$C_{2-3}$alkenylene, substituted or unsubstituted hetero$C_{3-4}$alkenylene, substituted or unsubstituted hetero$C_{4-5}$alkenylene, or substituted or unsubstituted hetero$C_{5-6}$alkenylene.

In certain embodiments, $L_1$ is a group which comprises at least one instance of substituted or unsubstituted heteroalkynylene, e.g., substituted or unsubstituted hetero$C_{2-6}$alkynylene, substituted or unsubstituted hetero$C_{2-3}$alkynylene, substituted or unsubstituted hetero$C_{3-4}$alkynylene, substituted or unsubstituted hetero$C_{4-5}$alkynylene, or substituted or unsubstituted hetero$C_{5-6}$alkynylene.

In certain embodiments, $L_1$ is a group which comprises at least one instance of substituted or unsubstituted carbocyclylene, e.g., substituted or unsubstituted $C_{3-6}$carbocyclylene, substituted or unsubstituted $C_{3-4}$carbocyclylene, substituted or unsubstituted $C_{4-5}$ carbocyclylene, or substituted or unsubstituted $C_{5-6}$ carbocyclylene.

In certain embodiments, $L_1$ is a group which comprises at least one instance of substituted or unsubstituted heterocyclylene, e.g., substituted or unsubstituted $C_{3-6}$ heterocyclylene, substituted or unsubstituted $C_{3-4}$ heterocyclylene, substituted or unsubstituted $C_{4-5}$ heterocyclylene, or substituted or unsubstituted $C_{5-6}$ heterocyclylene.

In certain embodiments, $L_1$ is a group which comprises at least one instance of substituted or unsubstituted arylene, e.g., substituted or unsubstituted phenylene.

In certain embodiments, $L_1$ is a group which comprises at least one instance of substituted or unsubstituted heteroarylene, e.g., substituted or unsubstituted 5- to 6-membered heteroarylene.

In certain embodiments, $L_2$ is a bond.

In certain embodiments, $L_2$ is a group consisting of one or more combinations of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclene, substituted or unsubstituted carbocyclene, substituted or unsubstituted arylene; substituted or unsubstituted heteroarylene.

In certain embodiments, $L_2$ is a group which comprises at least one instance of substituted or unsubstituted alkylene, e.g., substituted or unsubstituted $C_{1-6}$alkylene, substituted or unsubstituted $C_{1-2}$alkylene, substituted or unsubstituted $C_{2-3}$alkylene, substituted or unsubstituted $C_{3-4}$alkylene, substituted or unsubstituted $C_{4-5}$alkylene, or substituted or unsubstituted $C_{5-6}$alkylene. Exemplary alkylene groups include unsubstituted alkylene groups such as methylene —$CH_2$—, ethylene —$(CH_2)_2$—, n-propylene —$(CH_2)_3$—, n-butylene —$(CH_2)_4$—, n-pentylene —$(CH_2)_5$—, and n-hexylene —$(CH_2)_6$—. In certain embodiments, $L_2$ is —$CH_2$—. In certain embodiments, $L_2$ is —$(CH_2)_2$—. In certain embodiments, $L_2$ is —$(CH_2)_3$—. In certain embodiments, $L_2$ is —$(CH_2)_4$—. In certain embodiments, $L_2$ is —$(CH_2)_5$—. In certain embodiments, $L_2$ is —$(CH_2)_6$—.

In certain embodiments, $L_2$ is a group which comprises at least one instance of substituted or unsubstituted alkenylene, e.g., substituted or unsubstituted $C_{2-6}$alkenylene, substituted or unsubstituted $C_{2-3}$alkenylene, substituted or unsubstituted $C_{3-4}$alkenylene, substituted or unsubstituted $C_{4-5}$alkenylene, or substituted or unsubstituted $C_{5-6}$alkenylene.

In certain embodiments, $L_2$ is a group which comprises at least one instance of substituted or unsubstituted alkynylene, e.g., substituted or unsubstituted $C_{2-6}$alkynylene, substituted or unsubstituted $C_{2-3}$alkynylene, substituted or unsubstituted $C_{3-4}$alkynylene, substituted or unsubstituted $C_{4-5}$alkynylene, or substituted or unsubstituted $C_{5-6}$alkynylene.

In certain embodiments, $L_2$ is a group which comprises at least one instance of substituted or unsubstituted heteroalkylene, e.g., substituted or unsubstituted hetero$C_{1-6}$alkylene, substituted or unsubstituted hetero$C_{1-2}$ alkylene, substituted or unsubstituted hetero$C_{2-3}$alkylene, substituted or unsubstituted hetero$C_{3-4}$alkylene, substituted or unsubstituted hetero$C_{4-5}$alkylene, or substituted or unsubstituted hetero$C_{5-6}$ alkylene. Exemplary heteroalkylene groups include unsubstituted alkylene groups such as —$(CH_2)_2$—$O(CH_2)_2$—, —$OCH_2$—, —$O(CH_2)_2$—, —$O(CH_2)_3$—, —$O(CH_2)_4$—, —$O(CH_2)_5$—, and —$O(CH_2)_6$—.

In certain embodiments, $L_2$ is a group which comprises at least one instance of substituted or unsubstituted heteroalkenylene, e.g., substituted or unsubstituted hetero$C_{2-6}$alkenylene, substituted or unsubstituted hetero$C_{2-3}$alkenylene, substituted or unsubstituted hetero$C_{3-4}$alkenylene, substituted or unsubstituted hetero$C_{4-5}$alkenylene, or substituted or unsubstituted hetero$C_{5-6}$alkenylene.

In certain embodiments, $L_2$ is a group which comprises at least one instance of substituted or unsubstituted heteroalkynylene, e.g., substituted or unsubstituted hetero$C_{2-6}$alkynylene, substituted or unsubstituted hetero$C_{2-3}$alkynylene, substituted or unsubstituted hetero$C_{3-4}$alkynylene, substituted or unsubstituted hetero$C_{4-5}$alkynylene, or substituted or unsubstituted hetero$C_{5-6}$alkynylene.

In certain embodiments, $L_2$ is a group which comprises at least one instance of substituted or unsubstituted carbocyclylene, e.g., substituted or unsubstituted $C_{3-6}$carbocyclylene, substituted or unsubstituted $C_{3-4}$carbocyclylene, substituted or unsubstituted $C_{4-5}$ carbocyclylene, or substituted or unsubstituted $C_{5-6}$ carbocyclylene.

In certain embodiments, $L_2$ is a group which comprises at least one instance of substituted or unsubstituted heterocyclylene, e.g., substituted or unsubstituted $C_{3-6}$ heterocyclylene, substituted or unsubstituted $C_{3-4}$ heterocyclylene, substituted or unsubstituted $C_{4-5}$ heterocyclylene, or substituted or unsubstituted $C_{5-6}$ heterocyclylene.

In certain embodiments, $L_2$ is a group which comprises at least one instance of substituted or unsubstituted arylene, e.g., substituted or unsubstituted phenylene.

In certain embodiments, $L_2$ is a group which comprises at least one instance of substituted or unsubstituted heteroarylene, e.g., substituted or unsubstituted 5- to 6-membered heteroarylene.

In certain embodiments, M is a bond.

In certain embodiments, M is a group consisting of one or more combinations of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclene, substituted or unsubstituted carbocyclene, substituted or unsubstituted arylene; substituted or unsubstituted heteroarylene.

In certain embodiments, M is a group which comprises at least one instance of substituted or unsubstituted alkylene, e.g., substituted or unsubstituted $C_{1-6}$alkylene, substituted or unsubstituted $C_{1-2}$alkylene, substituted or unsubstituted $C_{2-3}$alkylene, substituted or unsubstituted $C_{3-4}$alkylene, substituted or unsubstituted $C_{4-5}$alkylene, or substituted or unsubstituted $C_{5-6}$alkylene. Exemplary alkylene groups include unsubstituted alkylene groups such as methylene —$CH_2$—, ethylene —$(CH_2)_2$—, n-propylene —$(CH_2)_3$—, n-butylene —$(CH_2)_4$—, n-pentylene —$(CH_2)_5$—, and n-hexylene —$(CH_2)_6$—. In certain embodiments, M is —$CH_2$—. In certain embodiments, M is —$(CH_2)_2$—. In certain embodiments, M is —$(CH_2)_3$—. In certain embodiments, M is —$(CH_2)_4$—. In certain embodiments, M is —$(CH_2)_5$—. In certain embodiments, M is —$(CH_2)_6$—.

In certain embodiments, M is a group which comprises at least one instance of substituted or unsubstituted alkenylene, e.g., substituted or unsubstituted $C_{2-6}$alkenylene, substituted or unsubstituted $C_{2-3}$alkenylene, substituted or unsubstituted $C_{3-4}$alkenylene, substituted or unsubstituted $C_{4-5}$alkenylene, or substituted or unsubstituted $C_{5-6}$alkenylene.

In certain embodiments, M is a group which comprises at least one instance of substituted or unsubstituted alkynylene, e.g., substituted or unsubstituted $C_{2-6}$alkynylene, substituted or unsubstituted $C_{2-3}$alkynylene, substituted or unsubstituted $C_{3-4}$alkynylene, substituted or unsubstituted $C_{4-5}$alkynylene, or substituted or unsubstituted $C_{5-6}$alkynylene.

In certain embodiments, M is a group which comprises at least one instance of substituted or unsubstituted heteroalkylene, e.g., substituted or unsubstituted hetero$C_{1-6}$alkylene, substituted or unsubstituted hetero$C_{1-2}$alkylene, substituted or unsubstituted hetero$C_{2-3}$ alkylene, substituted or unsubstituted hetero$C_{3-4}$alkylene, substituted or unsubstituted hetero$C_{4-5}$alkylene, or substituted or unsubstituted hetero$C_{5-6}$alkylene. Exemplary heteroalkylene groups include unsubstituted alkylene groups such as —$(CH_2)_2$—$O(CH_2)_2$—, —$OCH_2$—, —$O(CH_2)_2$—, —$O(CH_2)_3$—, —$O(CH_2)_4$—, —$O(CH_2)_5$—, and —$O(CH_2)_6$—.

In certain embodiments, M is a group which comprises at least one instance of substituted or unsubstituted heteroalkenylene, e.g., substituted or unsubstituted hetero$C_{2-6}$alkenylene, substituted or unsubstituted hetero$C_{2-3}$alkenylene, substituted or unsubstituted hetero$C_{3-4}$alkenylene, substituted or unsubstituted hetero$C_{4-5}$alkenylene, or substituted or unsubstituted hetero$C_{5-6}$alkenylene.

In certain embodiments, M is a group which comprises at least one instance of substituted or unsubstituted heteroalkynylene, e.g., substituted or unsubstituted hetero$C_{2-6}$alkynylene, substituted or unsubstituted hetero$C_{2-3}$alkynylene, substituted or unsubstituted hetero$C_{3-4}$alkynylene, substituted or unsubstituted hetero$C_{4-5}$alkynylene, or substituted or unsubstituted hetero$C_{5-6}$alkynylene.

In certain embodiments, M is a group which comprises at least one instance of substituted or unsubstituted carbocyclylene, e.g., substituted or unsubstituted $C_{3-6}$ carbocyclylene, substituted or unsubstituted $C_{3-4}$carbocyclylene, substituted or unsubstituted $C_{4-5}$ carbocyclylene, or substituted or unsubstituted $C_{5-6}$ carbocyclylene.

In certain embodiments, M is a group which comprises at least one instance of substituted or unsubstituted heterocyclylene, e.g., substituted or unsubstituted $C_{3-6}$ heterocyclylene, substituted or unsubstituted $C_{3-4}$ heterocyclylene, substituted or unsubstituted $C_{4-5}$ heterocyclylene, or substituted or unsubstituted $C_{5-6}$ heterocyclylene.

In certain embodiments, M is a group which comprises at least one instance of substituted or unsubstituted arylene, e.g., substituted or unsubstituted phenylene.

In certain embodiments, M is a group which comprises at least one instance of substituted or unsubstituted heteroarylene, e.g., substituted or unsubstituted 5- to 6-membered heteroarylene.

Groups $R^a$ and $R^b$

As generally defined above, $R^a$ is hydrogen; substituted or unsubstituted aliphatic; substituted or unsubstituted heteroaliphatic; substituted or unsubstituted aryl; substituted or unsubstituted heteroaryl; substituted or unsubstituted acyl; a resin; an amino protecting group; a label optionally joined by a linker, wherein the linker is a group consisting of one or more combinations of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted carbocyclene; substituted or unsubstituted heterocyclene; substituted or unsubstituted arylene; or substituted or unsubstituted heteroarylene.

In certain embodiments, $R^a$ is hydrogen.

In certain embodiments, $R^a$ is substituted or unsubstituted aliphatic; i.e., substituted or unsubstituted alkyl, alkenyl, alkynyl, or carbocyclyl.

In certain embodiments, $R^a$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. Exemplary $R^a$ $C_{1-6}$alkyl groups include, but are not limited to, substituted or unsubstituted methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$).

In certain embodiments, $R^a$ is substituted or unsubstituted heteroaliphatic; i.e., substituted or unsubstituted heteroalkyl, heteroalkenyl, heteroalkynyl, or heterocyclyl.

In certain embodiments, $R^a$ is substituted or unsubstituted aryl;

In certain embodiments, $R^a$ is substituted or unsubstituted heteroaryl.

In certain embodiments, $R^a$ is substituted or unsubstituted acyl, e.g., acetyl —C(═O)$CH_3$.

In certain embodiments, $R^a$ is a resin.

In certain embodiments, $R^a$ is an amino protecting group.

In certain embodiments, $R^a$ is a label optionally joined by a linker.

Group $R^b$

As generally defined above, $R^b$ is, —$R^B$, —$OR^B$, —N($R^B$)$_2$, or —$SR^B$, wherein each instance of $R^B$ is, independently, hydrogen, substituted or unsubstituted aliphatic; substituted or unsubstituted heteroaliphatic; substituted or unsubstituted aryl; substituted or unsubstituted heteroaryl; substituted or unsubstituted acyl; a resin; a suitable hydroxyl, amino or thiol protecting group; or two $R^B$ groups together form a substituted or unsubstituted 5- to 6-membered heterocyclic or heteroaromatic ring.

In certain embodiments, $R^b$ is $-R^B$, e.g., $R^b$ is hydrogen, substituted or unsubstituted aliphatic; substituted or unsubstituted heteroaliphatic; substituted or unsubstituted aryl; substituted or unsubstituted heteroaryl. In certain embodiments, $R^b$ is substituted or unsubstituted aliphatic, e.g., substituted or unsubstituted alkyl, alkenyl, alkynyl, or carbocycyl.

In certain embodiments, $R^b$ is $-OR^B$, e.g., $-OH$.

In certain embodiments, $R^b$ is $-N(R^B)_2$, e.g., $-NH(C=O)CH_3$.

In certain embodiments, $R^b$ is $-SR^B$, e.g., $-SH$.

Group $R^c$ and Variable x

As generally defined above, each instance of $R^c$, is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; cyano; isocyano; halo; or nitro, and each instance of x is, independently, 0, 1, 2, or 3.

In certain embodiments, each instance of x is 0 and $R^c$ is thus absent. In certain embodiments at least one instance of x is 1, and thus at least one instance of $R^c$ is a non-hydrogen substituent.

Groups $R^{KL}$, $R^{LL}$, and $R^{LM}$ and Variable q

As generally defined above, each instance of $R^{KL}$, $R^{LL}$, and $R^{LM}$, is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; azido; cyano; isocyano; halo; nitro; and each instance of q is, independently 0, 1, or 2.

In certain embodiments, each instance of q is 0 and $R^{KL}$, $R^{LL}$, and $R^{LM}$, are thus absent. In certain embodiments at least one instance of q is 1, and thus at least one instance of $R^{KL}$, $R^{LL}$, and $R^{LM}$, is a non-hydrogen substituent.

Group $R^d$

As generally defined above, each instance of $R^d$ is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; or an amino protecting group.

In certain embodiments, each instance of $R^d$ is hydrogen or substituted or unsubstituted aliphatic, e.g., substituted or unsubstituted alkyl, alkenyl, alkynyl, or carbocycyl. In certain embodiments, each instance of $R^d$ is hydrogen or substituted or unsubstituted alkyl, e.g., $-CH_3$.

Group $R^e$

As generally defined above, each instance of $R^e$ is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; cyano; isocyano; halo; or nitro.

In certain embodiments, each instance of $R^e$ is hydrogen or substituted or unsubstituted aliphatic, e.g., substituted or unsubstituted alkyl, alkenyl, alkynyl, or carbocycyl. In certain embodiments, each instance of $R^e$ is hydrogen or substituted or unsubstituted, e.g., $-CH_3$, $-CH_2OH$, $-COOH$, or $-CH_2COOH$. In certain embodiments, $R^e$ is $-CH_3$.

Group G and Variable v

As generally defined above, each instance of G is, independently, a natural or unnatural amino acid or a group of the formula:

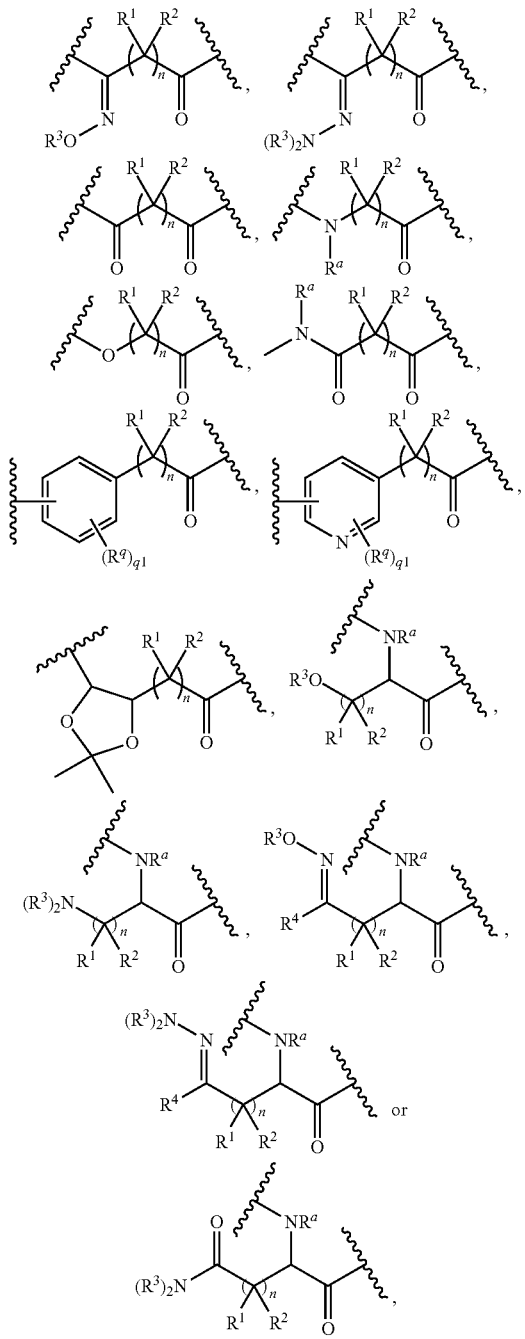

wherein:

n is 1, 2, or 3; and each instance of $R^1$ and $R^2$ is independently hydrogen; substituted or unsubstituted aliphatic; substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; or halo, or $R^1$ and $R^2$ are joined to form a carbocyclic or heterocyclic ring;

each instance of $R^3$ and $R^4$ is, independently, hydrogen; substituted or unsubstituted aliphatic; substituted or unsubstituted heteroaliphatic; a hydroxyl protecting group when attached to an oxygen atom, or an amino protecting group when attached to a nitrogen atom, or two $R^3$ groups when attached to a nitrogen atom are joined to form a heterocyclic ring;

each instance of $R^q$ is independently halogen, —CN, —$NO_2$, —$N_3$, optionally substituted alkyl, optionally substituted alkenyl, optionally substituted alkynyl, optionally substituted carbocyclyl, optionally substituted phenyl, optionally substituted heterocyclyl, optionally substituted heteroaryl, optionally substituted alkoxy, an optionally substituted amino group, or optionally substituted acyl;

q1 is 0, 1, 2, 3, or 4; and each instance of v is, independently, 0 or 1.

In certain embodiments, v is 0 and G in that particular instance is absent.

However, in certain embodiments, v is 1.

In certain embodiments, G is independently, serine, arginine, aspartic acid, or glutamic acid. In certain embodiments, G is serine. In certain embodiments, G is arginine. In certain embodiments, G is aspartic acid. In certain embodiments, G is glutamic acid.

In certain embodiments, G is a group of formula:

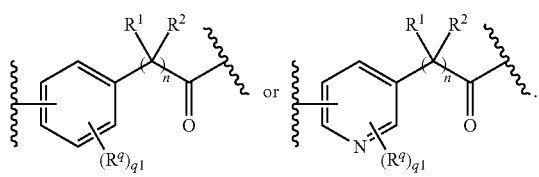

In certain embodiments, G is a group of formula:

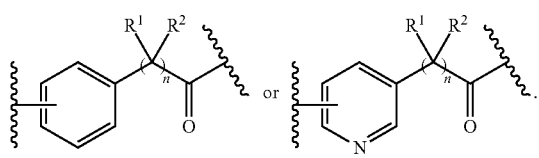

In certain embodiments, G is a group of formula:

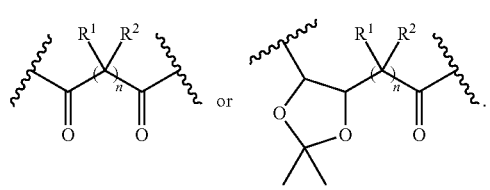

In certain embodiments, G is a group of formula:

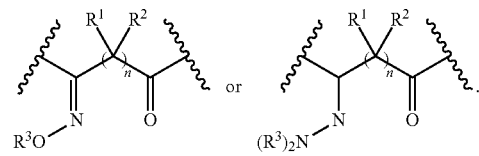

In certain embodiments, G is a group of formula:

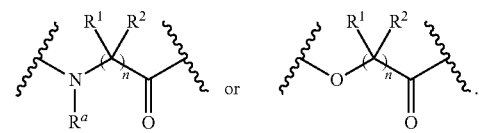

In certain embodiments, G is a group of formula:

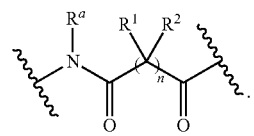

In certain embodiments, G is a group of formula:

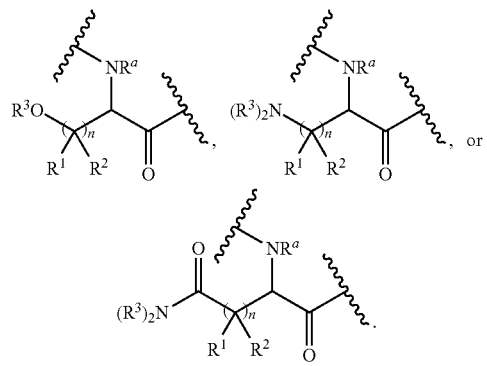

In certain embodiments, G is a group of formula:

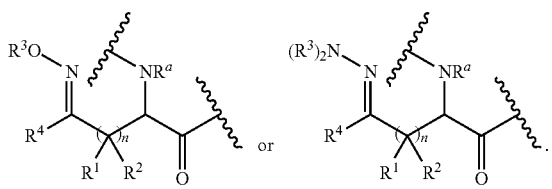

In certain embodiments, n is 1. In certain embodiments, n is 2. In certain embodiments, n is 3.

In certain embodiments, at least one instance of $R^1$ is hydrogen.

In certain embodiments, at least one instance of $R^1$ is substituted or unsubstituted aliphatic, e.g., substituted or unsubstituted alkyl, alkenyl, alkynyl, or carbocyclyl. In certain embodiments, at least one instance of $R^1$ is substituted or unsubstituted alkyl, e.g., —$CH_3$.

In certain embodiments, at least one instance of $R^2$ is hydrogen.

In certain embodiments, at least one instance of $R^2$ is substituted or unsubstituted aliphatic, e.g., substituted or unsubstituted alkyl, alkenyl, alkynyl, or carbocyclyl. In certain embodiments, at least one instance of $R^2$ is substituted or unsubstituted alkyl, e.g., $-CH_3$.

In certain embodiments, at least one instance of $R^1$ is hydrogen and at least one instance of $R^2$ is hydrogen.

In certain embodiments, at least one instance of $R^1$ is hydrogen and at least one instance of $R^2$ is substituted or unsubstituted alkyl, e.g., $-CH_3$.

In certain embodiments, at least one instance of $R^1$ and $R^2$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. Exemplary $C_{1-6}$alkyl groups include, but are not limited to, substituted or unsubstituted methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$).

In certain embodiments, at least one instance of $R^3$ is hydrogen or substituted or unsubstituted aliphatic, e.g., substituted or unsubstituted alkyl, alkenyl, alkynyl, or carbocyclyl. In certain embodiments, at least one instance of $R^3$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. Exemplary $C_{1-6}$alkyl groups include, but are not limited to, substituted or unsubstituted methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$).

In certain embodiments, two instance of $R^3$ when attached to the same nitrogen atom are joined to form a heterocyclic ring.

In certain embodiments, $R^4$ is hydrogen or substituted or unsubstituted aliphatic, e.g., substituted or unsubstituted alkyl, alkenyl, alkynyl, or carbocyclyl. In certain embodiments, $R^4$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. Exemplary $C_{1-6}$alkyl groups include, but are not limited to, substituted or unsubstituted methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$).

In certain embodiments, q1 is 0. In certain embodiments, q1 is 1. In certain embodiments, q1 is 2. In certain embodiments, q1 is 3. In certain embodiments, q1 is 4.

In certain embodiments, $R^q$ is halogen, $-CN$, $-NO_2$, $-N_3$, or optionally substituted alkyl.

In certain embodiments, $$R^a \vphantom{]}{\text{---}}\!\!\left[\!X_{AA}\!\right]_{\!w}\!\!\left[\!G\!\right]_{\!y}\!\!\text{---}\!\xi$$

in Formula (P-I), (I), (P-II), and (II) is one of the following formulae:

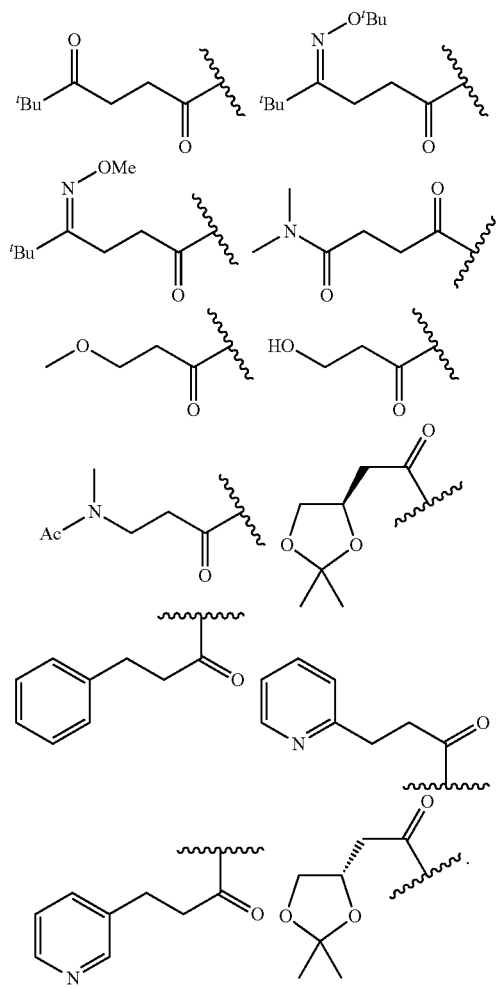

Group XAA and Variables j, y, p, w, z, s and t

As generally defined above, each instance of $X_{AA}$ is, independently, a natural or unnatural amino acid. Various natural and unnatural amino acids are generally described herein, and encompass alpha and beta amino acids moieties joined via peptide bonds.

As generally defined above, and each instance of t, w and z is, independently, an integer between 0 and 100, inclusive.

In certain embodiments z is an integer of 1 to 10, inclusive. In certain embodiments z is an integer of 2 to 10, inclusive. In certain embodiments, z is 1. In certain embodiments, z is 2. In certain embodiments, z is 3. In certain embodiments, z is 4. In certain embodiments, z is 5. In certain embodiments, z is 6. In certain embodiments, z is 7. In certain embodiments, z is 9. In certain embodiments, z is 10.

In certain embodiments w is 0, 1, or 2 and z is an integer between 0 and 100, inclusive. In certain embodiments w is 0, 1, or 2 and z is an integer between 0 and 75, inclusive. In certain embodiments w is 0, 1, or 2 and z is an integer between 0 and 50, inclusive. In certain embodiments w is 0, 1, or 2 and z is an integer between 0 and 25, inclusive. In certain embodiments w is 0, 1, or 2 and z is an integer between 0 and 10, inclusive. In certain embodiments w is 0, 1, or 2 and z is an integer between 0 and 5, inclusive.

In certain embodiments w is 0.

In certain embodiments w is 0, 1, or 2 and t is an integer between 0 and 100, inclusive. In certain embodiments w is 0, 1, or 2 and t is an integer between 0 and 75, inclusive. In certain embodiments w is 0, 1, or 2 and t is an integer between 0 and 50, inclusive. In certain embodiments w is 0, 1, or 2 and t is an integer between 0 and 25, inclusive. In certain embodiments w is 0, 1, or 2 and t is an integer between 0 and 10, inclusive. In certain embodiments w is 0, 1, or 2 and t is an integer between 0 and 5, inclusive.

As generally defined above, y is independently, an integer of 1 to 8, inclusive. In certain embodiments, y is independently, an integer of 1 to 7, inclusive. In certain embodiments, y is independently, an integer of 1 to 6, inclusive. In certain embodiments, y is independently, an integer of 1 to 5, inclusive. In certain embodiments, y is independently, 1, 2, 3, or 4. In certain embodiments, y is 1. In certain embodiments, y is 2. In certain embodiments, y is 3. In certain embodiments, y is 4. In certain embodiments, y is 5. In certain embodiments, y is 6. In certain embodiments, y is 7. In certain embodiments, y is 8.

In certain embodiments, j is 1, p is 2, s is 0 or 1, and y is 1. In certain embodiments, j is 1, p is 2, s is 0 or 1, and y is 2. In certain embodiments, j is 1, p is 2, s is 0 or 1, and y is 3. In certain embodiments, j is 1, p is 2, s is 0 or 1, and y is 4.

The variables y and z indicate how many amino acids, defined by the variable $[X_{AA}]$, there are between amino acids containing terminally unsaturated amino acid side chain(s), as provided in polypeptides of Formulae (P-I), (P-II), (I) and (II). For example, as depicted below for a polypeptide of Formula (P-II), wherein s is 0; i represents one site of an alpha,alpha-disubstituted (terminally unsaturated amino acid side chain) amino acid, variable y provides information as to the position of the amino acid containing a terminally unsaturated side chain on the N-terminal side of i, such as the positions i−3, i−4, i−6, and i−7, and z provides information as to the position of the amino acid containing a terminally unsaturated side chain on the C-terminal side of i, such as the positions i+3, i+4, i+6, and i+7. Table 4 correlates these specific locations of i relative to the variables y and z for formula (P-II-a).

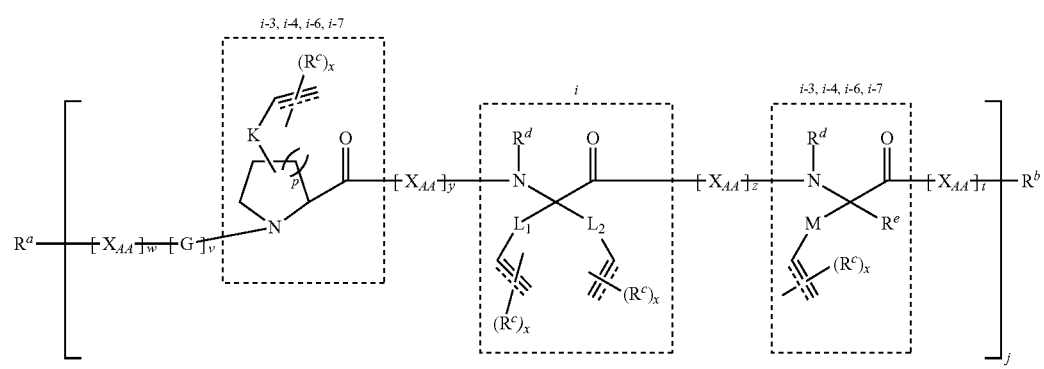

(P-II-a)

As generally defined above, j is, independently, an integer between 1 to 10, inclusive, e.g., j is 1, 2, 3, 4, 5, 6, 7, 8, 9, or 10. In certain embodiments, j is 1. In certain embodiments, j is 2.

As generally defined above, each instance of p is, independently, 1 or 2. In certain embodiments, p is 1. In certain embodiments, p is 2.

In certain embodiments, j is 1 and p is 1. In certain embodiments, j is 1 and p is 2.

In certain embodiments, j is 1, p is 1, and y is 1. In certain embodiments, j is 1, p is 1, and y is 2. In certain embodiments, j is 1, p is 1, and y is 3. In certain embodiments, j is 1, p is 1, and y is 4.

In certain embodiments, j is 1, p is 2, and y is 1. In certain embodiments, j is 1, p is 2, and y is 2. In certain embodiments, j is 1, p is 2, and y is 3. In certain embodiments, j is 1, p is 2, and y is 4.

As generally defined above, s is 0, 1, or 2. In certain embodiments, s is 0. In certain embodiments, s is 1. In certain embodiments, s is 2.

In certain embodiments, j is 1, p is 1, and s is 0 or 1. In certain embodiments, j is 1, p is 2, and s is 0 or 1.

In certain embodiments, j is 1, p is 1, s is 0 or 1, and y is 1. In certain embodiments, j is 1, p is 1, s is 0 or 1, and y is 2. In certain embodiments, j is 1, p is 1, s is 0 or 1, and y is 3. In certain embodiments, j is 1, p is 1, s is 0 or 1, and y is 4.

TABLE 4

|   | i − 7 | i − 6 | i − 4 | i − 3 | i | i + 3 | i + 4 | i + 6 | i + 7 |
|---|---|---|---|---|---|---|---|---|---|
| y | 6 | 5 | 3 | 2 |   |   |   |   |   |
| z |   |   |   |   |   | 2 | 3 | 5 | 6 |

In certain embodiments, each instance of y and z are, independently, 2, 3, 5, or 6.

In certain embodiments, both y and z are 2. In certain embodiments, both y and z are 3. In certain embodiments, both y and z are 5. In certain embodiments, both y and z are 6.

In certain embodiments, y is 2 and z is 3. In certain embodiments, y is 2 and z is 5.

In certain embodiments, y is 2 and z is 6.

In certain embodiments, y is 3 and z is 2. In certain embodiments, y is 3 and z is 5.

In certain embodiments, y is 3 and z is 6.

In certain embodiments, y is 5 and z is 2. In certain embodiments, y is 5 and z is 3.

In certain embodiments, y is 5 and z is 6.

In certain embodiments, y is 6 and z is 2. In certain embodiments, y is 6 and z is 3. In certain embodiments, y is 6 and z is 5.

Additional Embodiments

Various combinations of the above embodiments are contemplated herein.

For example, in certain embodiments of Formula (P-I) and (I), K and L are —CH$_2$—. R$^d$ is —H; R$^e$ is —CH$_2$OH; j is 1; p is 1; v is 0; x is 0; y is 2; and ═══ corresponds to a double bond.

For example, in certain embodiments of Formula (P-I) and (I), K and L are independently —CH$_2$CH$_2$— or —OCH$_2$—; R$^d$ is —H; R$^e$ is —CH$_2$OH; j is 1; p is 1; v is 0; x is 0; y is 2; and, ═══ corresponds to a double bond.

For example, in certain embodiments of Formula (P-I) and (I), K and L are —CH$_2$CH$_2$CH$_2$—; R$^d$ is —H; R$^e$ is —CH$_2$OH; j is 1; p is 1; v is 0; x is 0; y is 2; and, ═══ corresponds to a double bond.

For example, in certain embodiments of Formula (P-I) and (I), K and L are —CH$_2$—; R$^d$ is —H; R$^e$ is —CH$_2$CH$_2$OH; j is 1; p is 1; v is 0; x is 0; y is 2; and, ═══ corresponds to a double bond.

For example, in certain embodiments of Formula (P-I) and (I), K and L are —CH$_2$—; R$^d$ is —H; R$^e$ is —H; j is 1; p is 1; v is 0; x is 0; y is 2; and, ═══ corresponds to a double bond.

For example, in certain embodiments of Formula (P-I) and (I), K and L are —CH$_2$—; R$^d$ is —H; R$^e$ is —CH$_3$; j is 1; p is 1; v is 0; x is 0; y is 2; and, ═══ corresponds to a double bond. In certain embodiments of Formula (P-I) and (I), K is —CH$_2$—; L is —(CH$_2$)$_2$—; R$^d$ is —H; R$^e$ is —CH$_3$; j is 1; p is 1; v is 0; x is 0; y is 2; and, ═══ corresponds to a double bond. In certain embodiments of Formula (P-I) and (I), K is —CH$_2$—; L is —(CH$_2$)$_3$—; R$^d$ is —H; R$^e$ is —CH$_3$; j is 1; p is 1; v is 0; x is 0; y is 2; and, ═══ corresponds to a double bond.

For example, in certain embodiments of Formula (P-I) and (I), K and L are —CH$_2$—; R$^d$ is —H; R$^e$ is —CH$_3$; j is 1; p is 1; v is 0; x is 0; y is 3; and, ═══ corresponds to a double bond. In certain embodiments of Formula (P-I) and (I), K is —CH$_2$—; L is —(CH$_2$)$_2$—; R$^d$ is —H; R$^e$ is —CH$_3$; j is 1; p is 1; v is 0; x is 0; y is 3; and, ═══ corresponds to a double bond. In certain embodiments of Formula (P-I) and (I), K is —CH$_2$—; L is —(CH$_2$)$_3$—; R$^d$ is —H; R$^e$ is —CH$_3$; j is 1; p is 1; v is 0; x is 0; y is 3; and, ═══ corresponds to a double bond.

For example, in certain embodiments of Formula (P-I) and (I), K and L are —CH$_2$—; R$^d$ is —H; R$^e$ is —CH$_3$; j is 1; p is 1; v is 0; x is 0; y is 5; and, ═══ corresponds to a double bond. In certain embodiments of Formula (P-I) and (I), K is —CH$_2$—; L is —(CH$_2$)$_2$—; R$^d$ is —H; R$^e$ is —CH$_3$; j is 1; p is 1; v is 0; x is 0; y is 5; and, ═══ corresponds to a double bond. In certain embodiments of Formula (P-I) and (I), K is —CH$_2$—; L is —(CH$_2$)$_3$—: R$^d$ is —H; R$^e$ is —CH$_3$; j is 1; p is 1; v is 0; x is 0; y is 5; and, ═══ corresponds to a double bond.

For example, in certain embodiments of Formula (P-I) and (I), K and L are —CH$_2$—; R$^d$ is —H; R$^e$ is —CH$_3$; j is 1; p is 1; v is 0; x is 0; y is 6; and, ═══ corresponds to a double bond. In certain embodiments of Formula (P-I) and (I), K is —CH$_2$—; L is —(CH$_2$)$_2$—; R$^d$ is —H; R$^e$ is —CH$_3$; j is 1; p is 1; v is 0; x is 0; y is 6; and, ═══ corresponds to a double bond. In certain embodiments of Formula (P-I) and (I), K is —CH$_2$—; L is —(CH$_2$)$_3$—; R$^d$ is —H; R$^e$ is —CH$_3$; j is 1; p is 1; v is 0; x is 0; y is 6; and, ═══ corresponds to a double bond.

For example, in certain embodiments of Formula (P-I) and (I), K is —CH$_2$O—, wherein O is linked to the heterocyclyl with nitrogen and CH$_2$ is linked to "═══," and L is —CH$_2$—; R$^d$ is —H; R$^e$ is —CH$_3$; j is 1; p is 1; v is 0; x is 0; y is 2; and, ═══ corresponds to a double bond. In certain embodiments of Formula (P-I) and (I), K is —CH$_2$O—, wherein O is linked to the heterocyclyl with nitrogen and CH$_2$ is linked to "═══," and L is —(CH$_2$)$_2$—; R$^d$ is —H; R$^e$ is —CH$_3$; j is 1; p is 1; v is 0; x is 0; y is 2; and, ═══ corresponds to a double bond. In certain embodiments of Formula (P-I) and (I), K is —CH$_2$O—, wherein O is linked to the heterocyclyl with nitrogen and CH$_2$ is linked to "═══," and L is —(CH$_2$)$_3$—; R$^d$ is —H; R$^e$ is —CH$_3$; j is 1; p is 1; v is 0; x is 0; y is 2; and, ═══ corresponds to a double bond.

For example, in certain embodiments of Formula (P-I) and (I), K is —CH$_2$O—, wherein O is linked to the heterocyclyl with nitrogen and CH$_2$ is linked to "═══," and L is —CH$_2$—; R$^d$ is —H; R$^e$ is —CH$_3$; j is 1; p is 1; v is 0; x is 0; y is 3; and, ═══ corresponds to a double bond. In certain embodiments of Formula (P-I) and (I), K is —CH$_2$O—, wherein O is linked to the heterocyclyl with nitrogen and CH$_2$ is linked to "═══," and L is —(CH$_2$)$_2$—; R$^d$ is —H; R$^e$ is —CH$_3$; j is 1; p is 1; v is 0; x is 0; y is 3; and, ═══ corresponds to a double bond. In certain embodiments of Formula (P-I) and (I), K is —CH$_2$O—, wherein O is linked to the heterocyclyl with nitrogen and CH$_2$ is linked to "═══," and L is —(CH$_2$)$_3$—; R$^d$ is —H; R$^e$ is —CH$_3$; j is 1; p is 1; v is 0; x is 0; y is 3; and, ═══ corresponds to a double bond.

For example, in certain embodiments of Formula (P-I) and (I), K is —CH$_2$O—, wherein O is linked to the heterocyclyl with nitrogen and CH$_2$ is linked to "═══," and L is —CH$_2$—; R$^d$ is —H; R$^e$ is —CH$_3$; j is 1; p is 1; v is 0; x is 0; y is 5; and, ═══ corresponds to a double bond. In certain embodiments of Formula (P-I) and (I), K is —CH$_2$O—, wherein O is linked to the heterocyclyl with nitrogen and CH$_2$ is linked to "═══," and L is —(CH$_2$)$_2$—; R$^d$ is —H; R$^e$ is —CH$_3$; j is 1; p is 1; v is 0; x is 0; y is 5; and, ═══ corresponds to a double bond. In certain embodiments of Formula (P-I) and (I), K is —CH$_2$O—, wherein O is linked to the heterocyclyl with nitrogen and CH$_2$ is linked to "═══," and L is —(CH$_2$)$_3$—; R$^d$ is —H; R$^e$ is —CH$_3$; j is 1; p is 1; v is 0; x is 0; y is 5; and, ═══ corresponds to a double bond.

For example, in certain embodiments of Formula (P-I) and (I), K is —CH$_2$O—, wherein O is linked to the heterocyclyl with nitrogen and CH$_2$ is linked to "═══," and L is —CH$_2$—; R$^d$ is —H; R$^e$ is —CH$_3$; j is 1; p is 1; v is 0; x is 0; y is 6; and, ═══ corresponds to a double bond. In certain embodiments of Formula (P-I) and (I), K is —CH$_2$O—, wherein O is linked to the heterocyclyl with nitrogen and CH$_2$ is linked to "═══," and L is —(CH$_2$)$_2$—; R$^d$ is —H; R$^e$ is —CH$_3$; j is 1; p is 1; v is 0; x is 0; y is 6; and, ═══ corresponds to a double bond. In certain embodiments of Formula (P-I) and (I), K is —CH$_2$O—, wherein O is linked to the heterocyclyl with nitrogen and CH$_2$ is linked to "═══," and L is —(CH$_2$)$_3$—; R$^d$ is —H; R$^e$ is —CH$_3$; j is 1; p is 1; v is 0; x is 0; y is 6; and, ═══ corresponds to a double bond.

For example, in certain embodiments of Formula (P-I) and (I), K and L are —CH$_2$—; R$^d$ is —H; R$^e$ is —CH$_3$COOH; j is 1; p is 1; v is 0; x is 0; y is 2; and, ═══ corresponds to a double bond.

For example, in certain embodiments of Formula (P-I) and (I), K and L are —CH$_2$—; R$^d$ is —H; R$^e$ is —CH$_2$CH$_2$COOH; j is 1; p is 1; v is 0; x is 0; y is 2; and, ═══ corresponds to a double bond.

For example, in certain embodiments of Formula (P-I) and (I), K and L are —CH$_2$—; R$^d$ is —H; R$^e$ is —CH$_2$OH; j is 1; p is 2; x is 0; v is 0; y is 2; and, ══ corresponds to a double bond.

For example, in certain embodiments of Formula (P-I) and (I), K and L are —CH$_2$—; R$^d$ is —H; R$^e$ is —CH$_2$OH; j is 1; p is 1; v is 0; x is 2; y is 2; and, ══ corresponds to a double bond.

For example, in certain embodiments of Formula (P-I) and (I), K and L are —CH$_2$—; R$^d$ is —H; R$^e$ is —CH$_2$OH; j is 1; p is 1; v is 1; x is 0; y is 2; [G] is serine; and, ══ corresponds to a double bond.

For example, in certain embodiments of Formula (P-I) and (I), K and L are —CH$_2$—; R$^d$ is —H; R$^e$ is —CH$_2$OH; j is 1; p is 1; v is 1; x is 0; y is 2; [G] is threonine; and, ══ corresponds to a double bond.

For example, in certain embodiments of Formula (P-I) and (I), K and L are —CH$_2$—; R$^d$ is —H; R$^e$ is —CH$_2$OH; j is 1; p is 1; v is 1; x is 0; y is 2; [G] is aspartic acid; and, ══ corresponds to a double bond.

For example, in certain embodiments of Formula (P-I) and (I), K and L are —CH$_2$—; R$^d$ is —H; R$^e$ is —CH$_2$OH; j is 1; p is 1; v is 1; x is 0; y is 2; [G] is glutamic acid; and, ══ corresponds to a double bond.

For example, in certain embodiments of Formula (P-I) and (I), K and L are —CH$_2$—; R$^d$ is —H; R$^e$ is —CH$_2$OH; j is 1; p is 1; v is 1; x is 0; y is 2; [G] is asparagine; and, ══ corresponds to a double bond.

For example, in certain embodiments of Formula (P-I) and (I), K and L are —CH$_2$—; R$^d$ is —H; R$^e$ is —CH$_2$OH; j is 1; p is 1; v is 1; x is 0; y is 2; [G] is;

and, ══ corresponds to a double bond.

For example, in certain embodiments of Formula (P-I) and (I), K and L are —CH$_2$—; R$^d$ is —H; R$^e$ is —CH$_2$OH; j is 1; p is 1; q is 0; v is 0; y is 2; and, ══ corresponds to a double bond.

For example, in certain embodiments of Formula (P-I) and (I), K and L are —CH$_2$—; R$^d$ is —H; R$^e$ is —CH$_2$OH; j is 1; p is 1; q is 0; v is 1; y is 2; [G] is;

and, ══ corresponds to a double bond.

For example, in certain embodiments of Formula (P-II) and (II), L$_1$, L$_2$ and M are —CH$_2$—; R$^d$ is —H; R$^e$ is —H; j is 1; p is 1; s is 0; v is 0; x is 0; y is 2; z is 2; and, ══ corresponds to a double bond. In certain embodiments of Formula (P-II) and (II), L$_1$, L$_2$ are —(CH$_2$)$_3$—; M is —CH$_2$—; R$^d$ is —H; R$^e$ is —CH$_3$; j is 1; p is 1; s is 0; v is 0; x is 0; y is 2; z is 2; and, ══ corresponds to a double bond. In certain embodiments of Formula (P-II) and (II), L$_1$, L$_2$ are —(CH$_2$)$_3$—; M is —(CH$_2$)$_2$—; R$^d$ is —H; R$^e$ is —CH$_3$; j is 1; p is 1; s is 0; v is 0; x is 0; y is 2; z is 2; and, ══ corresponds to a double bond. In certain embodiments of Formula (P-II) and (II), L$_1$, L$_2$ are —(CH$_2$)$_3$—; M is —(CH$_2$)$_3$—; R$^d$ is —H; R$^e$ is —CH$_3$; j is 1; p is 1; s is 0; v is 0; x is 0; y is 2; z is 2; and, ══ corresponds to a double bond. In certain embodiments of Formula (P-II) and (II), L$_1$, L$_2$ are —(CH$_2$)$_3$—; M is —(CH$_2$)$_4$—; R$^d$ is —H; R$^e$ is —CH$_3$; j is 1; p is 1; s is 0; v is 0; x is 0; y is 2; z is 2; and, ══ corresponds to a double bond. In certain embodiments of Formula (P-II) and (II), L$_1$, L$_2$ are —(CH$_2$)$_3$—; M is —(CH$_2$)$_5$—; R$^d$ is —H; R$^e$ is —CH$_3$; j is 1; p is 1; s is 0; v is 0; x is 0; y is 2; z is 2; and, ══ corresponds to a double bond. In certain embodiments of Formula (P-II) and (II), L$_1$, L$_2$ are —(CH$_2$)$_3$—; M is —(CH$_2$)$_6$—; R$^d$ is —H; R$^e$ is —CH$_3$; j is 1; p is 1; s is 0; v is 0; x is 0; y is 2; z is 2; and, ══ corresponds to a double bond.

For example, in certain embodiments of Formula (P-II) and (II), L$_1$, L$_2$ and M are —CH$_2$—; R$^d$ is —H; R$^e$ is —H; j is 1; p is 1; s is 0; v is 0; x is 0; y is 2; z is 3; and, ══ corresponds to a double bond. In certain embodiments of Formula (P-II) and (II), L$_1$, L$_2$ are —(CH$_2$)$_3$—; M is —CH$_2$—; R$^d$ is —H; R$^e$ is —CH$_3$; j is 1; p is 1; s is 0; v is 0; x is 0; y is 2; z is 3; and, ══ corresponds to a double bond. In certain embodiments of Formula (P-II) and (II), L$_1$, L$_2$ are —(CH$_2$)$_3$—; M is —(CH$_2$)$_2$—; R$^d$ is —H; R$^e$ is —CH$_3$; j is 1; p is 1; s is 0; v is 0; x is 0; y is 2; z is 3; and, ══ corresponds to a double bond. In certain embodiments of Formula (P-II) and (II), L$_1$, L$_2$ are —(CH$_2$)$_3$—; M is —(CH$_2$)$_3$—; R$^d$ is —H; R$^e$ is —CH$_3$; j is 1; p is 1; s is 0; v is 0; x is 0; y is 2; z is 3; and, ══ corresponds to a double bond. In certain embodiments of Formula (P-II) and (II), L$_1$, L$_2$ are —(CH$_2$)$_3$—; M is —(CH$_2$)$_4$—; R$^d$ is —H; R$^e$ is —CH$_3$; j is 1; p is 1; s is 0; v is 0; x is 0; y is 2; z is 3; and, ══ corresponds to a double bond. In certain embodiments of Formula (P-II) and (II), L$_1$, L$_2$ are —(CH$_2$)$_3$—; M is —(CH$_2$)$_5$—; R$^d$ is —H; R$^e$ is —CH$_3$; j is 1; p is 1; s is 0; v is 0; x is 0; y is 2; z is 3; and, ══ corresponds to a double bond. In certain embodiments of Formula (P-II) and (II), L$_1$, L$_2$ are —(CH$_2$)$_3$—; M is —(CH$_2$)$_6$—; R$^d$ is —H; R$^e$ is —CH$_3$; j is 1; p is 1; s is 0; v is 0; x is 0; y is 2; z is 3; and, ══ corresponds to a double bond.

For example, in certain embodiments of Formula (P-II) and (II), L$_1$, L$_2$ and M are —CH$_2$—; R$^d$ is —H; R$^e$ is —H; j is 1; p is 1; s is 0; v is 0; x is 0; y is 2; z is 6; and, ══ corresponds to a double bond. In certain embodiments of Formula (P-II) and (II), L$_1$, L$_2$ are —(CH$_2$)$_3$—; M is —CH$_2$—; R$^d$ is —H; R$^e$ is —CH$_3$; j is 1; p is 1; s is 0; v is 0; x is 0; y is 2; z is 6; and, ══ corresponds to a double bond. In certain embodiments of Formula (P-II) and (II), L$_1$, L$_2$ are —(CH$_2$)$_3$—; M is —(CH$_2$)$_2$—; R$^d$ is —H; R$^e$ is —CH$_3$; j is 1; p is 1; s is 0; v is 0; x is 0; y is 2; z is 6; and, ══ corresponds to a double bond. In certain embodiments of Formula (P-II) and (II), L$_1$, L$_2$ are —(CH$_2$)$_3$—; M is —(CH$_2$)$_3$—; R$^d$ is —H; R$^e$ is —CH$_3$; j is 1; p is 1; s is 0; v is 0; x is 0; y is 2; z is 6; and, ══ corresponds to a double bond. In certain embodiments of Formula (P-II) and (II), L$_1$, L$_2$ are —(CH$_2$)$_3$—; M is —(CH$_2$)$_4$—; R$^d$ is —H; R$^e$ is —CH$_3$; j is 1; p is 1; s is 0; v is 0; x is 0; y is 2; z is 2; and, ══ corresponds to a double bond. In certain embodiments of Formula (P-II) and (II), L$_1$, L$_2$ are —(CH$_2$)$_3$—; M is —(CH$_2$)$_5$—; R$^d$ is —H; R$^e$ is —CH$_3$; j is 1; p is 1; s is 0; v is 0; x is 0; y is 2; z is 6; and, ══ corresponds to a double bond. In certain embodiments of Formula (P-II) and (II), L$_1$, L$_2$ are —(CH$_2$)$_3$—; M is —(CH$_2$)$_6$—; R$^d$ is —H; R$^e$ is —CH$_3$; j is 1; p is 1; s is 0; v is 0; x is 0; y is 2; z is 6; and, ══ corresponds to a double bond.

For example, in certain embodiments of Formula (P-II) and (II), $L_1$, $L_2$, K, and M are —$CH_2$—; $R^d$ is —H; $R^e$ is —H; j is 1; p is 1; s is 0; v is 0; x is 0; y is 2; z is 2; and, ===== corresponds to a double bond. In certain embodiments of Formula (P-II) and (II), $L_1$, $L_2$ are —$(CH_2)_3$—; K is —$CH_2$—; M is —$CH_2$—; $R^d$ is —H; $R^e$ is —$CH_3$; j is 1; p is 1; s is 0; v is 0; x is 0; y is 2; z is 2; and, ===== corresponds to a double bond. In certain embodiments of Formula (P-II) and (II), $L_1$, $L_2$ are —$(CH_2)_3$—; K is —$CH_2$—; M is —$(CH_2)_2$—; $R^d$ is —H; $R^e$ is —$CH_3$; j is 1; p is 1; s is 0; v is 0; x is 0; y is 2; z is 2; and, ===== corresponds to a double bond. In certain embodiments of Formula (P-II) and (II), $L_1$, $L_2$ are —$(CH_2)_3$—; K is —$CH_2$—; M is —$(CH_2)_3$—; $R^d$ is —H; $R^e$ is —$CH_3$; j is 1; p is 1; s is 0; v is 0; x is 0; y is 2; z is 2; and, ===== corresponds to a double bond. In certain embodiments of Formula (P-II) and (II), $L_1$, $L_2$ are —$(CH_2)_3$—; K is —$CH_2$—; M is —$(CH_2)_4$—; $R^d$ is —H; $R^e$ is —$CH_3$; j is 1; p is 1; s is 0; v is 0; x is 0; y is 2; z is 2; and, ===== corresponds to a double bond. In certain embodiments of Formula (P-II) and (II), $L_1$, $L_2$ are —$(CH_2)_3$—; K is —$CH_2$—; M is —$(CH_2)_5$—; $R^d$ is —H; $R^e$ is —$CH_3$; j is 1; p is 1; s is 0; v is 0; x is 0; y is 2; z is 2; and, ===== corresponds to a double bond. In certain embodiments of Formula (P-II) and (II), $L_1$, $L_2$ are —$(CH_2)_3$—; K is —$CH_2$—; M is —$(CH_2)_6$—; $R^d$ is —H; $R^e$ is —$CH_3$; j is 1; p is 1; s is 0; v is 0; x is 0; y is 2; z is 2; and, ===== corresponds to a double bond.

For example, in certain embodiments of Formula (P-II) and (II), $L_1$, $L_2$, K, and M are —$CH_2$—; $R^d$ is —H; $R^e$ is —H; j is 1; p is 1; s is 0; v is 0; x is 0; y is 2; z is 3; and, ===== corresponds to a double bond. In certain embodiments of Formula (P-II) and (II), $L_1$, $L_2$ are —$(CH_2)_3$—; K is —$CH_2$—; M is —$CH_2$—; $R^d$ is —H; $R^e$ is —$CH_3$; j is 1; p is 1; s is 0; v is 0; x is 0; y is 2; z is 3; and, ===== corresponds to a double bond. In certain embodiments of Formula (P-II) and (II), $L_1$, $L_2$ are —$(CH_2)_3$—; K is —$CH_2$—; M is —$(CH_2)_2$—; $R^d$ is —H; $R^e$ is —$CH_3$; j is 1; p is 1; s is 0; v is 0; x is 0; y is 2; z is 3; and, ===== corresponds to a double bond. In certain embodiments of Formula (P-II) and (II), $L_1$, $L_2$ are —$(CH_2)_3$—; K is —$CH_2$—; M is —$(CH_2)_3$—; $R^d$ is —H; $R^e$ is —$CH_3$; j is 1; p is 1; s is 0; v is 0; x is 0; y is 2; z is 3; and, ===== corresponds to a double bond. In certain embodiments of Formula (P-II) and (II), $L_1$, $L_2$ are —$(CH_2)_3$—; K is —$CH_2$—; M is —$(CH_2)_4$—; $R^d$ is —H; $R^e$ is —$CH_3$; j is 1; p is 1; s is 0; v is 0; x is 0; y is 2; z is 3; and, ===== corresponds to a double bond. In certain embodiments of Formula (P-II) and (II), $L_1$, $L_2$ are —$(CH_2)_3$—; K is —$CH_2$—; M is —$(CH_2)_5$—; $R^d$ is —H; $R^e$ is —$CH_3$; j is 1; p is 1; s is 0; v is 0; x is 0; y is 2; z is 3; and, ===== corresponds to a double bond. In certain embodiments of Formula (P-II) and (II), $L_1$, $L_2$ are —$(CH_2)_3$—; K is —$CH_2$—; M is —$(CH_2)_6$—; $R^d$ is —H; $R^e$ is —$CH_3$; j is 1; p is 1; s is 0; v is 0; x is 0; y is 2; z is 3; and, ===== corresponds to a double bond.

For example, in certain embodiments of Formula (P-II) and (II), $L_1$, $L_2$, K, and M are —$CH_2$—; $R^d$ is —H; $R^e$ is —H; j is 1; p is 1; s is 0; v is 0; x is 0; y is 2; z is 6; and, ===== corresponds to a double bond. In certain embodiments of Formula (P-II) and (II), $L_1$, $L_2$ are —$(CH_2)_3$—; K is —$CH_2$—; M is —$CH_2$—; $R^d$ is —H; $R^e$ is —$CH_3$; j is 1; p is 1; s is 0; v is 0; x is 0; y is 2; z is 6; and, ===== corresponds to a double bond. In certain embodiments of Formula (P-II) and (II), $L_1$, $L_2$ are —$(CH_2)_3$—; K is —$CH_2$—; M is —$(CH_2)_2$—; $R^d$ is —H; $R^e$ is —$CH_3$; j is 1; p is 1; s is 0; v is 0; x is 0; y is 2; z is 6; and, ===== corresponds to a double bond. In certain embodiments of Formula (P-II) and (II), $L_1$, $L_2$ are —$(CH_2)_3$—; K is —$CH_2$—; M is —$(CH_2)_3$—; $R^d$ is —H; $R^e$ is —$CH_3$; j is 1; p is 1; s is 0; v is 0; x is 0; y is 2; z is 6; and, ===== corresponds to a double bond. In certain embodiments of Formula (P-II) and (II), $L_1$, $L_2$ are —$(CH_2)_3$—; K is —$CH_2$—; M is —$(CH_2)_4$—; $R^d$ is —H; $R^e$ is —$CH_3$; j is 1; p is 1; s is 0; v is 0; x is 0; y is 2; z is 2; and, ===== corresponds to a double bond. In certain embodiments of Formula (P-II) and (II), $L_1$, $L_2$ are —$(CH_2)_3$—; K is —$CH_2$—; M is —$(CH_2)_5$—; $R^d$ is —H; $R^e$ is —$CH_3$; j is 1; p is 1; s is 0; v is 0; x is 0; y is 2; z is 6; and, ===== corresponds to a double bond. In certain embodiments of Formula (P-II) and (II), $L_1$, $L_2$ are —$(CH_2)_3$—; K is —$CH_2$—; M is —$(CH_2)_6$—; $R^d$ is —H; $R^e$ is —$CH_3$; j is 1; p is 1; s is 0; v is 0; x is 0; y is 2; z is 6; and, ===== corresponds to a double bond.

For example, in certain embodiments of Formula (P-II) and (II), $L_1$, $L_2$ and M are —$CH_2CH_2$—; $R^d$ is —H; $R^e$ is —H; j is 1; p is 1; s is 0; v is 0; x is 0; y is 2; z is 2; and, ===== corresponds to a double bond.

For example, in certain embodiments of Formula (P-II) and (II), $L_1$, $L_2$ and M are —$CH_2CH_2CH_2$—; $R^d$ is —H; $R^e$ is —H; j is 1; p is 1; s is 0; v is 0; x is 0; y is 2; z is 2; and, ===== corresponds to a double bond.

For example, in certain embodiments of Formula (P-II) and (II), $L_1$, $L_2$ and M are —$CH_2$—; $R^d$ is —H; $R^e$ is —$CH_3$; j is 1; p is 1; s is 0; v is 0; x is 0; y is 2; z is 2; and, ===== corresponds to a double bond.

For example, in certain embodiments of Formula (P-II) and (II), $L_1$, $L_2$ and M are —$CH_2$—; $R^d$ is —H; $R^e$ is —$CH_2CH_3$; j is 1; p is 1; s is 0; v is 0; x is 0; y is 2; z is 2; and, ===== corresponds to a double bond.

For example, in certain embodiments of Formula (P-II) and (II), $L_1$, $L_2$ and M are —$CH_2$—; $R^d$ is —H; $R^e$ is —H; j is 1; p is 2; s is 0; v is 0; x is 0; y is 2; z is 2; and, ===== corresponds to a double bond.

For example, in certain embodiments of Formula (P-II) and (II), $L_1$, $L_2$ and M are —$CH_2$—; $R^d$ is —H; $R^e$ is —H; j is 1; p is 1; s is 1; v is 0; x is 0; y is 2; z is 2; and, ===== corresponds to a double bond.

For example, in certain embodiments of Formula (P-II) and (II), $L_1$, $L_2$ and M are —$CH_2$—; $R^d$ is —H; $R^e$ is —H; j is 1; p is 1; s is 0; v is 0; x is 2; y is 2; z is 2; and, ===== corresponds to a double bond.

For example, in certain embodiments of Formula (P-II) and II), $L_1$, $L_2$ and M are —$CH_2$—; $R^d$ is —H; $R^e$ is —H; j is 1; p is 1; s is 0; v is 0; x is 0; y is 2; z is 3; and ===== corresponds to a double bond.

For example, in certain embodiments of Formula (P-II) and (II), $L_1$, $L_2$ and M are —$CH_2$—; $R^d$ is —H; $R^e$ is —H; j is 1; p is 1; s is 0; v is 0; x is 0; y is 2; z is 4; and, ===== corresponds to a double bond.

For example, in certain embodiments of Formula (P-II) and (II), $L_1$, $L_2$ and M are —$CH_2$—; $R^d$ is —H; $R^e$ is —H; j is 1; p is 1; s is 0; v is 0; x is 0; y is 2; z is 5; and, ===== corresponds to a double bond.

For example, in certain embodiments of Formula (P-II) and (II), $L_1$, $L_2$ and M are —$CH_2$—; $R^d$ is —H; $R^e$ is —H; j is 1; p is 1; s is 0; v is 1; x is 0; y is 2; z is 2; [G] is serine; and, ===== corresponds to a double bond.

For example, in certain embodiments of Formula (P-II) and (II), $L_1$, $L_2$ and M are —$CH_2$—; $R^d$ is —H; $R^e$ is —H; j is 1; p is 1; s is 0; v is 1; x is 0; y is 2; z is 2; [G] is threonine; and, ===== corresponds to a double bond.

For example, in certain embodiments of Formula (P-II) and (II), $L_1$, $L_2$ and M are —$CH_2$—; $R^d$ is —H; $R^e$ is —H;

j is 1; p is 1; s is 0; v is 1; x is 0; y is 2; z is 2; [G] is aspartic acid; and, ═══ corresponds to a double bond.

For example, in certain embodiments of Formula (P-II) and (II), $L_1$, $L_2$ and M are —$CH_2$—; $R^d$ is —H; $R^e$ is —H; j is 1; p is 1; s is 0; v is 1; x is 0; y is 2; z is 2; [G] is glutamic acid; and, ═══ corresponds to a double bond.

For example, in certain embodiments of Formula (P-II) and (II), $L_1$, $L_2$ and M are —$CH_2$—; $R^d$ is —H; $R^e$ is —H; j is 1; p is 1; s is 0; v is 1; x is 0; y is 2; z is 2; [G] is asparagine; and, ═══ corresponds to a double bond.

For example, in certain embodiments of Formula (P-II) and (II), $L_1$, $L_2$ and M are —$CH_2$—; $R^d$ is —H; $R^e$ is —H; j is 1; p is 1; s is 0; v is 1; x is 0; y is 2; z is 2; [G] is

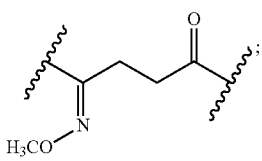

and, ═══ corresponds to a double bond.

For example, in certain embodiments of Formula (P-II) and (II), $L_1$, $L_2$ and M are —$CH_2$—; $R^d$ is —H; $R^e$ is —H; j is 1; p is 1; q is 0; s is 0; v is 0; y is 2; z is 2; and, ═══ corresponds to a double bond.

For example, in certain embodiments of Formula (P-II) and (II), $L_1$, $L_2$ and M are —$CH_2$—; $R^d$ is —H; $R^e$ is —H; j is 1; p is 1; q is 0; s is 0; v is 1; y is 2; z is 2; [G] is

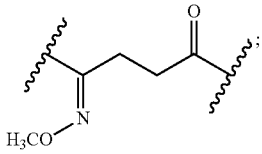 [SMILES: *C(=O)CC/C(*)=N/OC]

and, ═══ corresponds to a double bond.

In any of the above embodiments, wherein [G] is a group of formula:

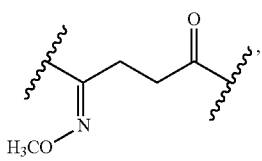

in certain embodiments, w is 0, and $R^a$ is —$C(CH_3)_3$.

In any of the above embodiments, wherein [G] is a group of any one of the following formulae:

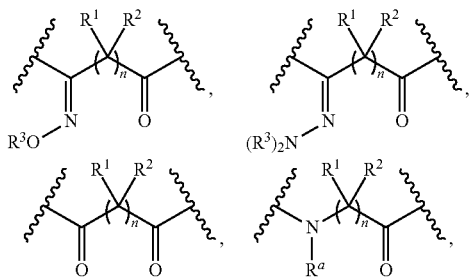

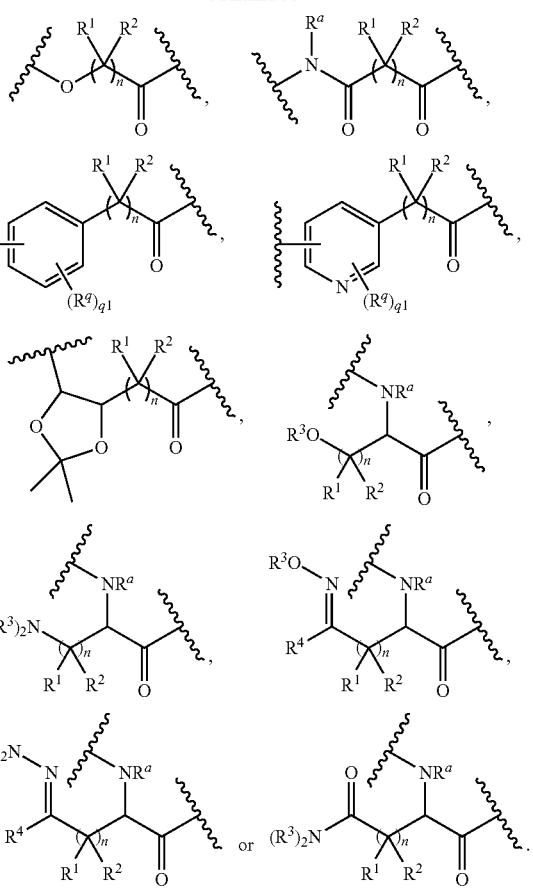

In any of the above embodiments, wherein

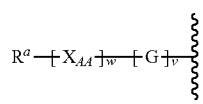

is of any one of the following formulae:

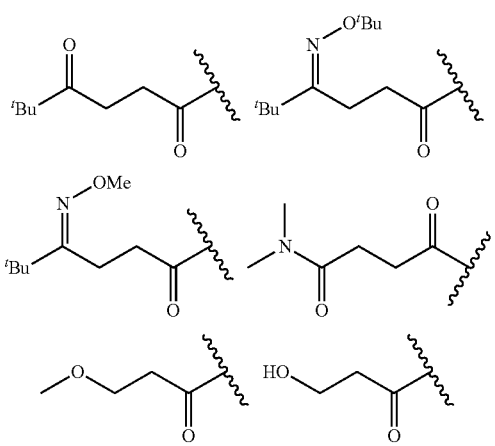

-continued

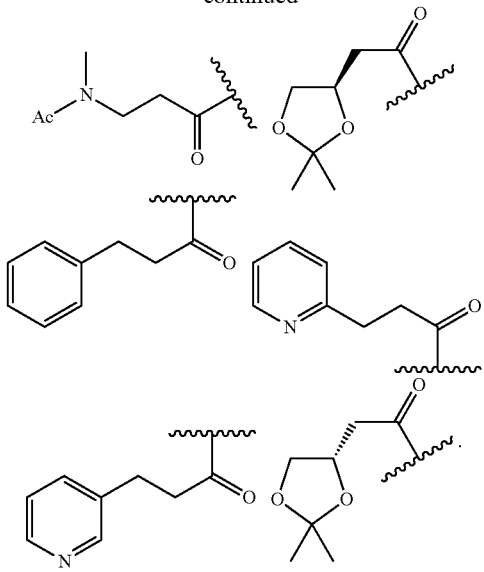

Methods of Use

The present disclosure provides methods of treating a disease, disorder, or condition comprising administering to a subject diagnosed with or having susceptibility to the disease, disorder, or condition, a therapeutically effective amount of a stitched or stapled polypeptide as described herein, or pharmaceutically acceptable salt or stereoisomer thereof. Exemplary diseases, disorders, or conditions which may be treated by administration of a stitched or stapled polypeptide as described herein comprise proliferative, neurological, immunological, endocrinologic, cardiovascular, hematologic, and inflammatory diseases, disorders, or conditions, and conditions characterized by premature or unwanted cell death.

As used herein a proliferative disease, condition, or disorder includes, but is not limited to, cancer, hematopoietic neoplastic disorders, proliferative breast disease, proliferative disorders of the lung, proliferative disorders of the colon, proliferative disorders of the liver, and proliferative disorders of the ovary.

Examples of cancers treatable by the methods disclosed herein include carcinoma, sarcoma, or metastatic disorders, breast cancer, ovarian cancer, colon cancer, lung cancer, fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma, Examples of hematopoietic neoplastic disorders treatable by the above method includes diseases involving hyperplastic/neoplastic cells of hematopoietic origin, e.g., arising from myeloid, lymphoid or erythroid lineages, or precursor cells thereof. In certain embodiments, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Examples of proliferative breast disease treatable by the methods disclosed herein include epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of proliferative disorders of the lung treatable by the methods disclosed herein include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of proliferative disorders of the colon treatable by the methods disclosed herein include, but are not limited to, non-neoplastic polyps, adenomas, familial syndromes, colorectal carcinogenesis, colorectal carcinoma, and carcinoid tumors.

Examples of proliferative disorders of the liver treatable by the methods disclosed herein include, but are not limited to, nodular hyperplasias, adenomas, and malignant tumors, including primary carcinoma of the liver and metastatic tumors.

Examples of proliferative disorders of the ovary treatable by the methods disclosed herein include, but are not limited to, ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors.

The polypeptides described herein can also be used to treat, prevent or diagnose conditions charaterised by overactive cell death or cellular death due to physiologic insult etc. Some examples of conditions characterized by premature or unwanted cell death are or alternatively unwanted or excessive cellular proliferation include, but are not limited to hypocellular/hypoplastic, acellular/aplastic, or hypercellular/hyperplastic conditions. Some examples include hematologic disorders including but not limited to fanconi anemia, aplastic anemia, thalaessemia, congenital neutropenia, myelodysplasia. The polypeptides disclosed herein can be used to decrease apoptosis and can be used to treat disorders associated with an undesirable level of cell death. Thus, the anti-apoptotic of the peptides disclosed herein can be used to treat disorders such as those that lead to cell death associated with viral infection, e.g., associated with infection with human immunodeficiency virus (HIV).

The peptides disclosed herein can be used to treat disorders associated with undesirable cell death. A wide variety of neurological diseases are characterized by the gradual loss of specific sets of neurons, and the anti-apoptotic peptides can be used in the treatment of these disorders. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis.

Some examples of neurologic disorders that can be treated with the polypeptides described herein include but are not limited to Alzheimer's Disease, Down's Syndrome, Dutch Type Hereditary Cerebral Hemorrhage Amyloidosis, Reactive Amyloidosis, Familial Amyloid Nephropathy with Urticaria and Deafness, Muckle-Wells Syndrome, Idiopathic Myeloma; Macroglobulinemia-Associated Myeloma, Familial Amyloid Polyneuropathy, Familial Amyloid Cardiomyopathy, Isolated Cardiac Amyloid, Systemic Senile Amyloidosis, Adult Onset Diabetes, Insulinoma, Isolated Atrial Amyloid, Medullary Carcinoma of the Thyroid, Familial Amyloidosis, Hereditary Cerebral Hemorrhage with Amyloidosis, Familial Amyloidotic Polyneuropathy, Scrapie, Creutzfeldt-Jacob Disease, Gerstmann Straussler-Scheinker Syndrome, Bovine Spongiform Encephalitis, a Prion-mediated disease, Huntington's Disease, Pick's Disease, Amyotrophic Lateral Sclerosis (ALS), Parkinson's Disease, and Lewy Body Disease.

Some examples of endocrinologic disorders that can be treated with the polypeptides described herein include, but are not limited to, diabetes, hypothyroidism, hypopituitarism, hypoparathyroidism, hypogonadism, fertility disorders, etc.

Some examples of immunologic disorders that can be treated with the polypeptides described herein include, but are not limited to, organ transplant rejection, arthritis, lupus, IBD, Crohn's disease, asthma, multiple sclerosis, diabetes, Graft versus host diseases, autoimmune diseases, psoriasis, rheumatoid arthritis, etc.

Examples of cardiovascular disorders that can be treated or prevented with the polypeptides described herein include, but are not limited to, atherosclerosis, myocardial infarction, stroke, thrombosis, aneurism, heart failure, ischemic heart disease, angina pectoris, sudden cardiac death, hypertensive heart disease; non-coronary vessel disease, such as arteriolosclerosis, small vessel disease, nephropathy, hypertriglyceridemia, hypercholesterolernia, hyperlipidemia, xanthomatosis, asthma, hypertension, emphysema and chronic pulmonary disease; or a cardiovascular condition associated with interventional procedures ("procedural vascular trauma"), such as restenosis following angioplasty, placement of a shunt, stent, synthetic or natural excision grafts, indwelling catheter, valve or other implantable devices.

The stapled and stitched polypeptides provides herein can treat the above-described diseases, disorders, or conditions, for instance, by disrupting native protein-protein, protein-ligand, and/or protein-receptor interactions. For example, many biologically important protein/protein interactions, such as p53/MDM2 and Bcl-X1/Bak, are mediated by one protein donating a helix into a cleft of its helix-accepting partner. The interaction of p53 and MDM2 and mutations in the p53 gene have been identified in virtually half of all reported cancer cases (see, Shair *Chem. & Biol.* 1997, 4, 791, the entire contents of which are incorporated herein by reference). As stresses are imposed on a cell, p53 is believed to orchestrate a response that leads to either cell-cycle arrest and DNA repair, or programmed cell death. As well as mutations in the p53 gene that alter the function of the p53 protein directly, p53 can be altered by changes in MDM2. The MDM2 protein has been shown to bind to p53 and disrupt transcriptional activation by associating with the transactivation domain of p53. For example, an 11 amino-acid peptide derived from the transactivation domain of p53 forms an amphipathic alpha-helix of 2.5 turns that inserts into the MDM2 crevice.

Thus, in certain embodiments, a stitched or stapled polypeptide as described herein is an alpha helical polypeptide that is capable of binding tightly to a helix acceptor and disrupting native protein/protein interactions. These structures may then be screened using high throughput techniques to identify optimal small molecule peptides. In certain embodiments, a stitched or stapled polypeptide as described herein is an alpha helical p53 polypeptide capable of binding to the *Xenopus* MDM2 protein. The novel structures that disrupt the MDM2 interaction might be useful for many applications, including, but not limited to, control of soft tissue sarcomas (which overexpresses MDM2 in the presence of wild type p53). These cancers may be held in check with small molecules that could intercept MDM2, thereby preventing suppression of p53. Additionally, small molecules disrupters of MDM2-p53 interactions could be used as adjuvant therapy to help control and modulate the extent of the p53 dependent apoptosis response in conventional chemotherapy.

In certain embodiments, polypeptides disclosed herein are homologous to a known alpha helical peptide. In certain embodiments, the inventive polypeptide is at least 80%, 85%, 90%, or 95% homologous to a known alpha helical peptide.

In addition, polypeptides disclosed herein may be useful in the area of materials science. For example, molecules such as lipids and other polymeric molecules may be attached to the terminal peptide moieties and thus generate potentially important biomaterials.

In addition to the above-mentioned uses, polypeptides disclosed herein may be used for studies in bioinorganic chemistry or in catalysis, either as a ligand for a transition metal capable of mimicking an important biological environment, or by acting in concert with a particular transition metal catalyst to effect a desired chemical reaction.

Pharmaceutical Compositions

The present disclosure provides pharmaceutical compositions comprising a stitched or stapled polypeptide as described herein and, optionally, a pharmaceutically acceptable excipient. Such pharmaceutical compositions may optionally comprise one or more additional biologically-active substances. In accordance with some embodiments, a method of administering a pharmaceutical composition to a subject in need thereof is provided. In some embodiments, pharmaceutical compositions are administered to humans. For the purposes of the present disclosure, the phrase "active ingredient" generally refers to a stitched or stapled polypeptide as described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions as described herein is contemplated include, but are not limited to, humans and/or other primates; mammals, including commercially relevant mammals such as cattle, pigs, horses, sheep, cats, and/or dogs; and/or birds, including commercially relevant birds such as chickens, ducks, geese, and/or turkeys.

The formulations of the pharmaceutical compositions described herein may be prepared by any method known or hereafter developed in the art of pharmacology. In general, such preparatory methods include the step of bringing the active ingredient into association with a carrier and/or one or more other accessory ingredients, and then, if necessary and/or desirable, shaping and/or packaging the product into a desired single- or multi-dose unit.

A pharmaceutical composition may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable carrier, and/or any additional ingredients in a pharmaceutical composition of the disclosure will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, 21$^{st}$ Edition, A. R. Gennaro, (Lippincott, Williams & Wilkins, Baltimore, Md., 2006) discloses various carriers used in formulating pharmaceutical compositions and known techniques for the preparation thereof. Except insofar as any conventional carrier medium is incompatible with a substance or its derivatives, such as by producing any undesirable biological effect or otherwise interacting in a deleterious manner with any other component(s) of the pharmaceutical composition, its use is contemplated to be within the scope of this disclosure.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g.

acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol,); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the polypeptides of the disclosure are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the polypeptides of the disclosure with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and *acacia, c*) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a polypeptide of the disclosure may include ointments, pastes, creams, lotions, gels, powders, solutions, sprays, inhalants and/or patches. Generally, the active component is admixed under sterile conditions with a pharmaceutically acceptable carrier and/or any needed preservatives and/or buffers as may be required. Additionally, the present disclosure contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the disclosure may be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant may be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions as described herein formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the disclosure. Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the additional ingredients described herein. A pharmaceutical composition of the disclosure may be prepared, packaged, and/or sold in a formulation suitable for buccal administration. Such formulations may, for example, be in the form of tablets and/or lozenges made using conventional methods, and may, for example, 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this disclosure.

General considerations in the formulation and/or manufacture of pharmaceutical agents may be found, for example, in *Remington: The Science and Practice of Pharmacy* 21$^{st}$ ed., Lippincott Williams & Wilkins, 2005.

Administration

In some embodiments, a therapeutically effective amount of a pharmaceutical composition as described herein is delivered to a patient and/or organism prior to, simultaneously with, and/or after diagnosis with a disease, disorder, and/or condition. In some embodiments, a therapeutic amount of a pharmaceutical composition as described herein is delivered to a patient and/or organism prior to, simultaneously with, and/or after onset of symptoms of a disease, disorder, and/or condition. In some embodiments, the amount of the stitched or stapled polypeptide as described herein is sufficient to treat, alleviate, ameliorate, relieve, delay onset of, inhibit progression of, reduce severity of, and/or reduce incidence of one or more symptoms or features of the disease, disorder, and/or condition.

The compositions, as disclosed herein, may be administered using any amount and any route of administration effective for treatment. The exact amount required will vary from subject to subject, depending on the species, age, and general condition of the subject, the severity of the infection, the particular composition, its mode of administration, its mode of activity, and the like. The pharmaceutical compositions as described herein are typically formulated in dosage unit form for ease of administration and uniformity of dosage. It will be understood, however, that the total daily usage of the pharmaceutical compositions as described herein will be decided by the attending physician within the scope of sound medical judgment. The specific therapeutically effective dose level for any particular subject or organism will depend upon a variety of factors including the disorder being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The pharmaceutical compositions as described herein may be administered by any route. In some embodiments, the pharmaceutical compositions as described herein are administered variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration), etc. At present the oral and/or nasal spray and/or aerosol route is most commonly used to deliver therapeutic agents directly to the lungs and/or respiratory system. However, the disclosure embraces the delivery of the pharmaceutical compositions as described herein by any appropriate route taking into consideration likely advances in the sciences of drug delivery.

In certain embodiments, pharmaceutical compositions comprising the peptides disclosed herein may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

In some embodiments, the disclosure encompasses "therapeutic cocktails" comprising the polypeptides disclosed herein. In some embodiments, the polypeptide comprises a single species which can bind to multiple targets. In some embodiments, the polypeptides disclosed herein comprise different targeting moiety species, and all of the different targeting moiety species can bind to the same target. In some embodiments, different polypeptides comprise different targeting moiety species, and all of the different targeting moiety species can bind to different targets. In some embodiments, such different targets may be associated with the same cell type. In some embodiments, such different targets may be associated with different cell types.

It will be appreciated that the polypeptides and pharmaceutical compositions as described herein can be employed in combination therapies. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, stitched or stapled polypeptide as described herein may be useful for detecting tumors and may be administered concurrently with another agent useful for detecting tumors), or they may achieve different effects (e.g., control of any adverse effects).

Pharmaceutical compositions as described herein may be administered either alone or in combination with one or more other therapeutic agents. By "in combination with," it is not intended to imply that the agents must be administered at the same time and/or formulated for delivery together, although these methods of delivery are within the scope of the disclosure. The compositions can be administered concurrently with, prior to, or subsequent to, one or more other desired therapeutics or medical procedures. In general, each agent will be administered at a dose and/or on a time schedule determined for that agent. Additionally, the disclosure encompasses the delivery of the a pharmaceutical composition as described herein in combination with agents that may improve their bioavailability, reduce and/or modify their metabolism, inhibit their excretion, and/or modify their distribution within the body.

The particular combination of therapies (therapeutics and/or procedures) to employ in a combination regimen will take into account compatibility of the desired therapeutics and/or procedures and/or the desired therapeutic effect to be achieved. It will be appreciated that the therapies employed may achieve a desired effect for the same disorder (for example, a stitched or stapled polypeptide as described herein may be administered concurrently with another biologically active agent used to treat the same disorder), and/or they may achieve different effects (e.g., control of any adverse effects). In some embodiments, polypeptides of the disclosure are administered with a second biologically active agent that is approved by the U.S. Food and Drug Administration.

In will further be appreciated that biologically active agents utilized in this combination may be administered together in a single composition or administered separately in different compositions.

In general, it is expected that biologically active agents utilized in combination be utilized at levels that do not exceed the levels at which they are utilized individually. In some embodiments, the levels utilized in combination will be lower than those utilized individually.

In some embodiments, a pharmaceutical composition as described herein may be administered in combination with any biologically active agent or therapeutic regimen that is useful to treat, alleviate, ameliorate, relieve, delay onset of, inhibit progression of, reduce severity of, and/or reduce incidence of one or more symptoms or features of cancer. For example, pharmaceutical compositions may be administered in combination with traditional cancer therapies including, but not limited to, surgery, chemotherapy, radiation therapy, hormonal therapy, immunotherapy, complementary or alternative therapy, and any combination of these therapies.

In some embodiments, pharmaceutical compositions are administered in combination with surgery to remove a tumor. Because complete removal of a tumor with minimal or no damage to the rest of a patient's body is typically the goal of cancer treatment, surgery is often performed to physically remove part or all of a tumor. If surgery is unable to completely remove a tumor, additional therapies (e.g. chemotherapy, radiation therapy, hormonal therapy, immunotherapy, complementary or alternative therapy) may be employed.

In some embodiments, pharmaceutical compositions are administered in combination with radiation therapy. Radiation therapy (also known as radiotherapy, X-ray therapy, or irradiation) is the use of ionizing radiation to kill cancer cells and shrink tumors. Radiation therapy may be used to treat almost any type of solid tumor, including cancers of the brain, breast, cervix, larynx, lung, pancreas, prostate, skin, stomach, uterus, or soft tissue sarcomas. Radiation can be used to treat leukemia and lymphoma. Radiation therapy can be administered externally via external beam radiotherapy (EBRT) or internally via brachytherapy. Typically, the effects of radiation therapy are localized and confined to the region being treated. Radiation therapy injures or destroys tumor cells in an area being treated (e.g. a target organ, tissue, and/or cell) by damaging their genetic material, preventing tumor cells from growing and dividing. In general, radiation therapy attempts to damage as many tumor cells as possible while limiting harm to nearby healthy tissue. Hence, it is often administered in multiple doses, allowing healthy tissue to recover between fractions.

In some embodiments, pharmaceutical compositions are administered in combination with immunotherapy. Immunotherapy is the use of immune mechanisms against tumors which can be used in various forms of cancer, such as breast cancer (e.g. trastuzumab/Herceptin®), leukemia (e.g. gemtuzumab ozogamicin/Mylotarg®), and non-Hodgkin's lymphoma (e.g. rituximab/Rituxan®). In some embodiments, immunotherapy agents are monoclonal antibodies directed against proteins that are characteristic to the cells of the cancer in question. In some embodiments, immunotherapy agents are cytokines that modulate the immune system's response. In some embodiments, immunotherapy agents may be vaccines.

In some embodiments, vaccines can be administered to prevent and/or delay the onset of cancer. In some embodiments, cancer vaccines prevent and/or delay the onset of cancer by preventing infection by oncogenic infectious agents. In some embodiments, cancer vaccines prevent and/or delay the onset of cancer by mounting an immune response against cancer-specific epitopes. To give but one example of a cancer vaccine, an experimental vaccine for HPV types 16 and 18 was shown to be 100% successful in preventing infection with these types of HPV and, thus, are able to prevent the majority of cervical cancer cases (Harper et al., 2004, *Lancet*, 364:1757).

In some embodiments, pharmaceutical compositions are administered in combination with complementary and alternative medicine treatments. Some exemplary complementary measures include, but are not limited to, botanical medicine (e.g. use of mistletoe extract combined with traditional chemotherapy for the treatment of solid tumors); acupuncture for managing chemotherapy-associated nausea and vomiting and in controlling pain associated with surgery; prayer; psychological approaches (e.g. "imaging" or meditation) to aid in pain relief or improve mood. Some exemplary alternative measures include, but are not limited to, diet and other lifestyle changes (e.g. plant-based diet, the grape diet, and the cabbage diet).

In some embodiments, pharmaceutical compositions are administered in combination with any of the traditional cancer treatments described herein, which are often associated with unpleasant, uncomfortable, and/or dangerous side effects. For example, chronic pain often results from continued tissue damage due to the cancer itself or due to the treatment (i.e., surgery, radiation, chemotherapy). Alternatively or additionally, such therapies are often associated with hair loss, nausea, vomiting, diarrhea, constipation, anemia, malnutrition, depression of immune system, infection, sepsis, hemorrhage, secondary neoplasms, cardiotoxicity, hepatotoxicity, nephrotoxicity, ototoxicity, etc. Thus, pharmaceutical compositions which are administered in combination with any of the traditional cancer treatments described herein may be also be administered in combination with any therapeutic agent or therapeutic regimen that is useful to treat, alleviate, ameliorate, relieve, delay onset of, inhibit progression of, reduce severity of, and/or reduce incidence of one or more side effects of cancer treatment. To give but a few examples, pain can be treated with opioids and/or analgesics (e.g. morphine, oxycodone, antiemetics, etc.); nausea and vomiting can be treated with $5$-$HT_3$ inhibitors (e.g. dolasetron/Anzemet®, granisetron/Kytril®, ondansetron/Zofran®, palonsetron/Aloxi®) and/or substance P inhibitors (e.g. aprepitant/Emend®); immunosuppression can be treated with a blood transfusion; infection and/or sepsis can be treated with antibiotics (e.g. penicillins, tetracyclines, cephalosporins, sulfonamides, aminoglycosides, etc.); and so forth.

In some embodiments, pharmaceutical compositions may be administered and/or inventive diagnostic methods may be performed in combination with any therapeutic agent or therapeutic regimen that is useful to diagnose one or more symptoms or features of cancer (e.g. detect the presence of and/or locate a tumor). In some embodiments, the stitched or stapled polypeptide as described herein may be used in combination with one or more other diagnostic agents. To give but one example, polypeptides used to detect tumors may be administered in combination with other agents useful in the detection of tumors. For example, the stitched or stapled polypeptide as described hereins may be administered in combination with traditional tissue biopsy followed by immunohistochemical staining and serological tests (e.g. prostate serum antigen test). Alternatively or additionally, the stitched or stapled polypeptide as described hereins may be administered in combination with a contrasting agent for use in computed tomography (CT) scans and/or MRI.

Kits

The disclosure provides a variety of kits comprising one or more of the polypeptides disclosed herein. For example, the disclosure provides a kit comprising a stitched or stapled polypeptide as described herein and instructions for use. A kit may comprise multiple different polypeptides. A kit may comprise any of a number of additional components or reagents in any combination. All of the various combinations are not set forth explicitly but each combination is included in the scope of the disclosure According to certain embodiments of the disclosure, a kit may include, for example, (i) one or more polypeptides and one or more particular biologically active agents to be delivered; (ii) instructions for administering the polypeptide to a subject in need thereof.

Kits typically include instructions which may, for example, comprise protocols and/or describe conditions for production of the polypeptides, administration of the polypeptides to a subject in need thereof, design of the polypeptides, etc. Kits will generally include one or more vessels or containers so that some or all of the individual components and reagents may be separately housed. Kits may also include a means for enclosing individual containers in relatively close confinement for commercial sale, e.g., a plastic box, in which instructions, packaging materials such as styrofoam, etc., may be enclosed. An identifier, e.g., a bar code, radio frequency identification (ID) tag, etc., may be present in or on the kit or in or one or more of the vessels or containers included in the kit. An identifier can be used, e.g., to uniquely identify the kit for purposes of quality control, inventory control, tracking, movement between workstations, etc.

EXAMPLES

These and other aspects of the present invention will be further appreciated upon consideration of the following Examples, which are intended to illustrate certain particular embodiments of the invention but are not intended to limit its scope, as defined by the claims.

Example 1

Pro-Locked Stapled Peptides

Figure 11A:
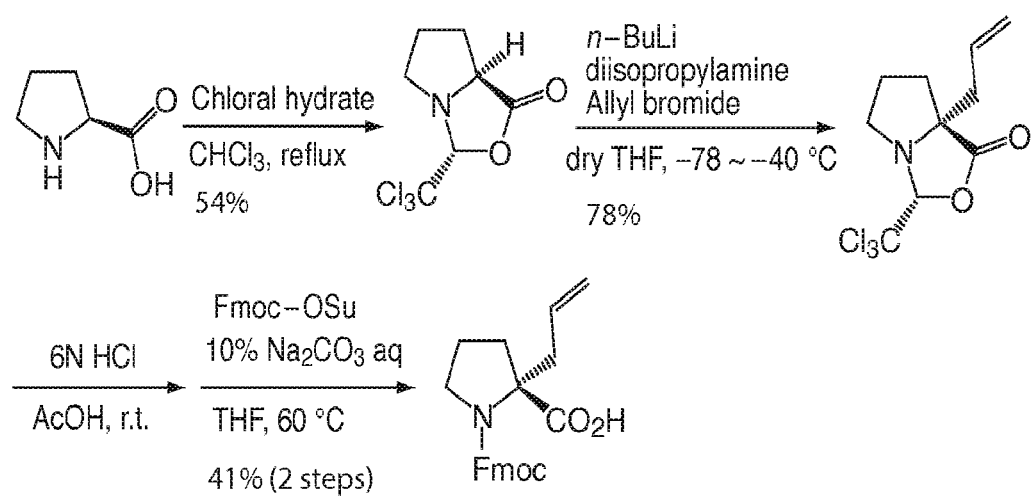
FIG. 11 shows a synthesis scheme for $P_{R3}$.
Figure 11B:
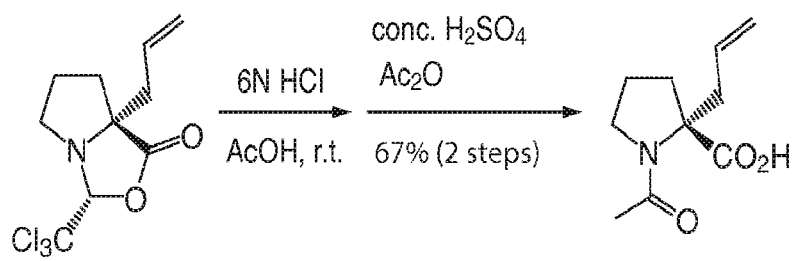

Materials and Methods (R)—N-(Acetyl)-2-(2'-propenyl)proline ("$P_{R3}$"), a novel compound, was synthesized via modification of a reported synthetic route, followed by acetylation (*Synlett,* 1999, 1, 33-36; *Tetrahedron,* 2005, 61, 10018-10035). A scheme for the synthesis of $P_{R3}$ is shown in FIG. 11. (R)—N-[(9H-Fluoren-9-ylmethoxy)carbonyl]-2-(2'-propenyl)proline could be used instead of (R)—N-(Acetyl)-2-(2'-propenyl) proline ("$P_{R3}$").

Figure 12:
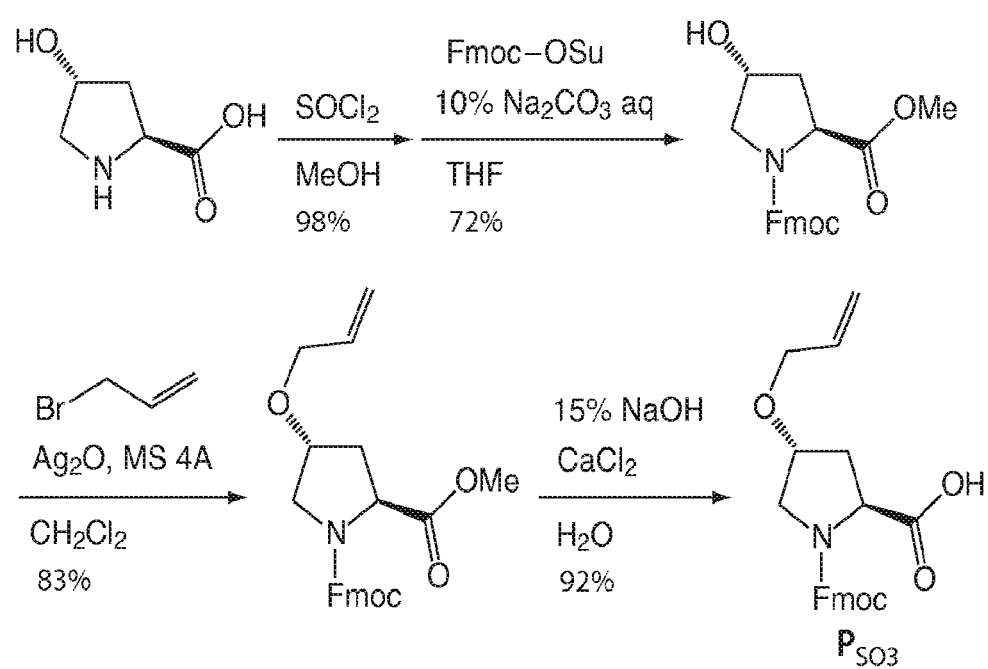
FIG. 12 shows a synthesis scheme for $P_{SO3}$.

The compound $P_{SO3}$ (See FIG. 10) allows for the synthesis of linkers originating from a position other than the alpha-carbon. A scheme for the synthesis of $P_{SO3}$ is shown in FIG. 12. The scheme includes the steps of methylesterification, Fmoc protection, introduction of an allyl group and deprotection of a Fmoc group.

The compound $P_{S3}$ was synthesized from D-proline following the synthetic scheme for preparation of the compound $P_{SO3}$.

The compound $P_{S5}$ was synthesized following the synthetic scheme for preparation of the compound $P_{R3}$ by replacing allyl bromide with 1-iodo-5-pentene.

(S)—N-[(9H-Fluoren-9-ylmethoxy)carbonyl]-2-(2'-propylenyl)alanine was purchased from Okeanos Tech Co.

The GCN4 basic region was used as a test system to investigate the properties of the Pro-locked peptides, because the GCN4 basic region has a canonical nucleating (N-cap) sequence (N-DPAAL-C) at the N-terminus of its DNA-recognition (α-helix. (See FIG. 9)

Generation of Pro-Locked Stapled Peptides

The peptides shown in FIG. 2 were synthesized manually, using solid phase conditions, rink amide MBHA resin (100~200 meshes) (Novabiochem), and Fmoc main-chain protecting group chemistry.

Figure 3:
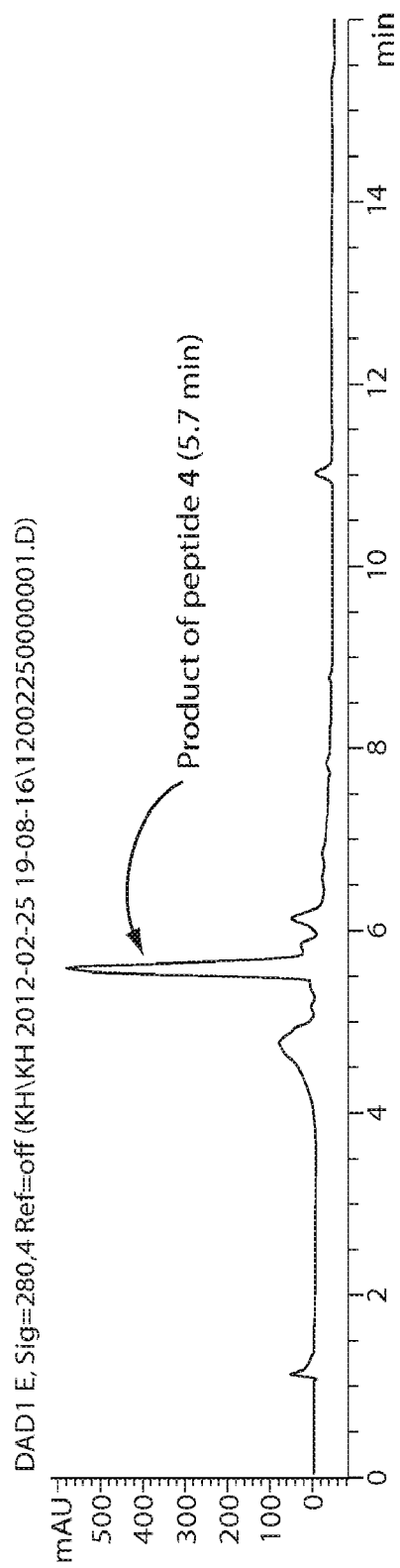
FIG. 3 shows a LC/MS chromatogram of the olefin-metathesis reaction between $P_{R3}$ and $S_3$.

A crosslink was produced through an olefin-metathesis reaction between $P_{R3}$ and $S_3$ (See FIG. 15). The olefin-metathesis reaction between $P_{R3}$ and $S_3$ by Grubbs 1st generation catalyst proceeded completely after 16 h and a single product was observed in LC/MS (FIG. 3 and FIG. 16). The geometry of the generated olefin group in peptide 2 was determined to be Z-isomer by NMR measurement (the coupling constant between two olefinic protons is 11.0 Hz).

Figure 10:
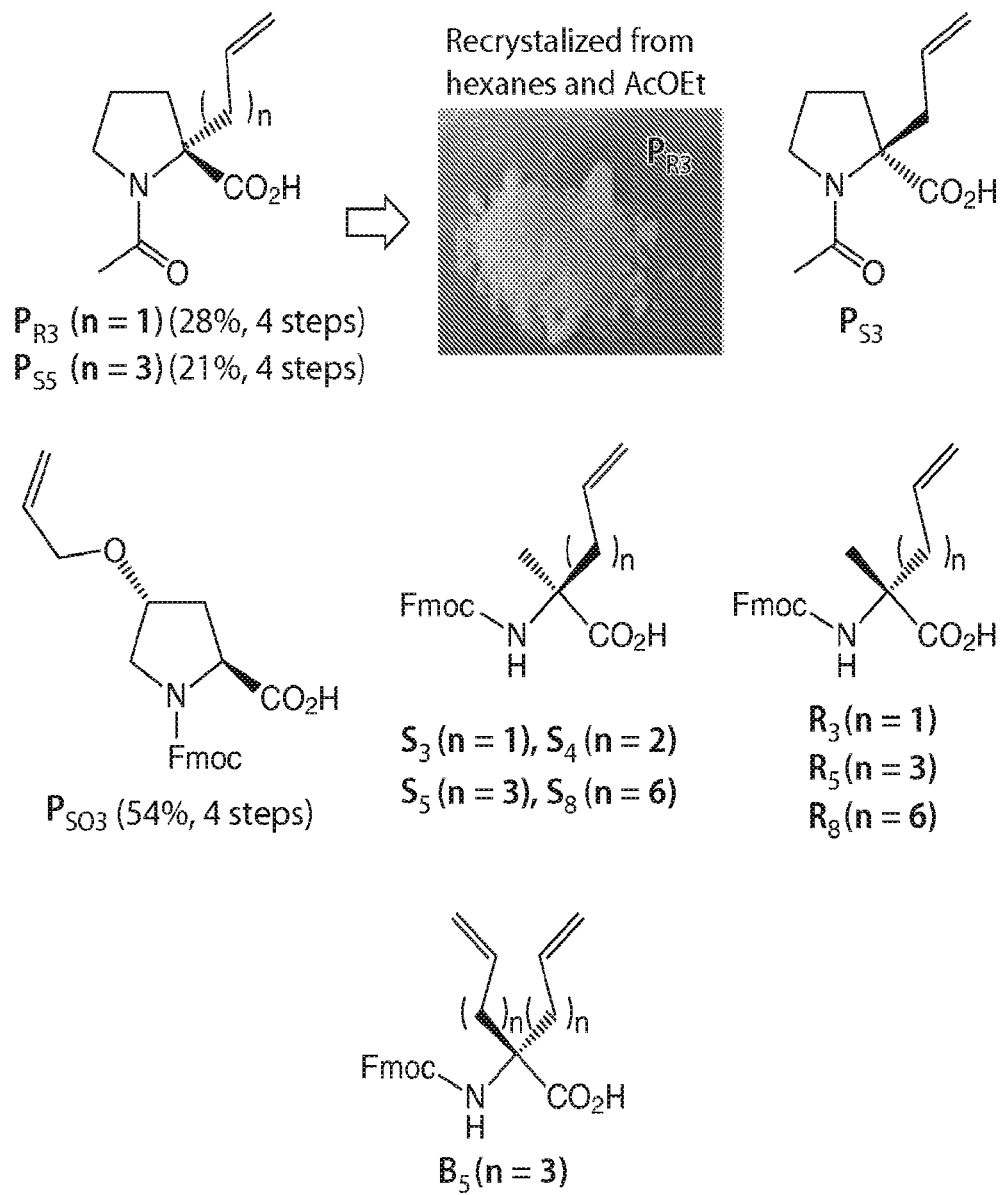
FIG. 10 shows unnatural amino acids used to generate proline-locked stapled peptides.

FIG. 10 provides additional amino acids and amino acid derivatives that were used in the generation of the Pro-locked stapled peptides described herein.

FIGS. 13 and 14 provide additional Pro-locked stapled peptides generated according to the methods provided herein. Non-cross-linked control peptides are provided in FIG. 14.

Helicity and Stability of Pro-Locked Peptides

Figure 4:
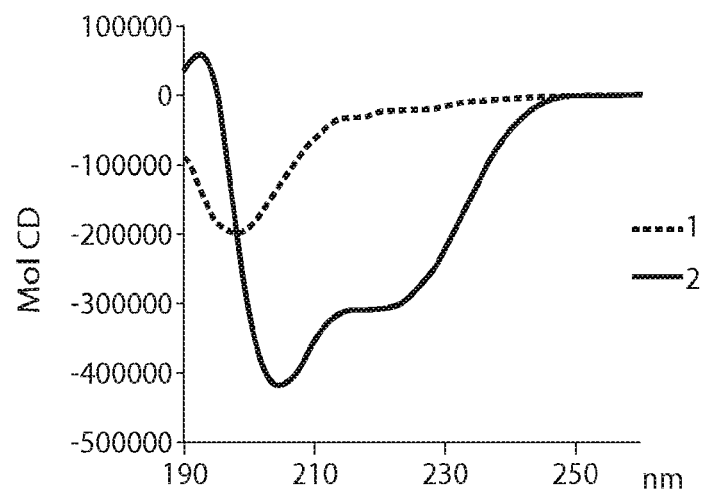
FIG. 4 shows the CD spectra of peptides 1 and 2 at 20° C.

The conformation of peptide 1 and 2 was investigated by CD measurements (FIG. 4). The data show that peptide 1 adopts a random-coil and peptide 2 adopts an (X-helix conformation at 20° C. The % helicity of peptide 2 is 67% at 20° C. The peptide having $S_5$ rather than $S_3$ still adopts an α-helix conformation at 20° C., but the % helicity is reduced to 44%.

Figure 17:
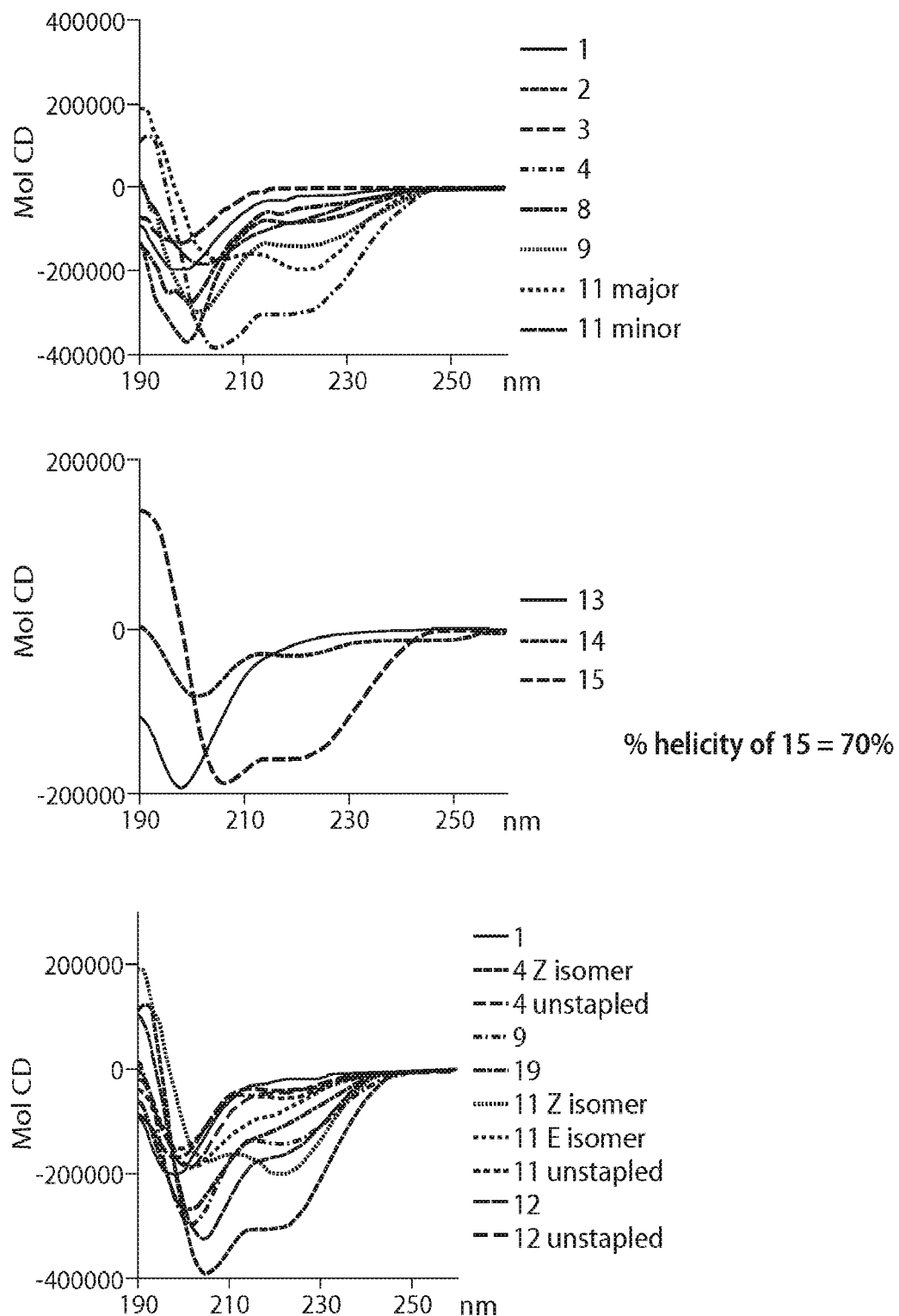
FIG. 17 shows CD spectra of proline-locked stapled peptides.
Figure 18:
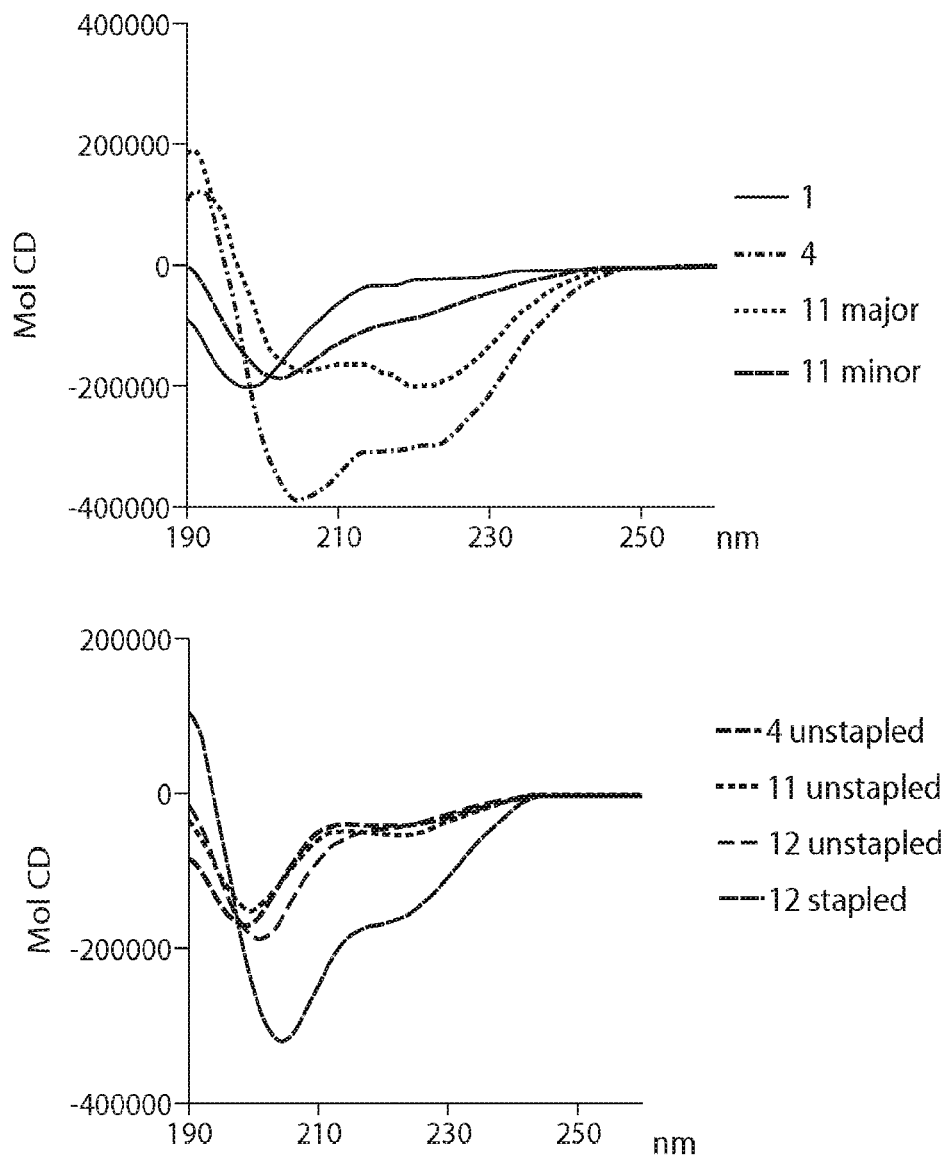
FIG. 18 shows CD spectra of proline-locked stapled peptides.
Figure 20:
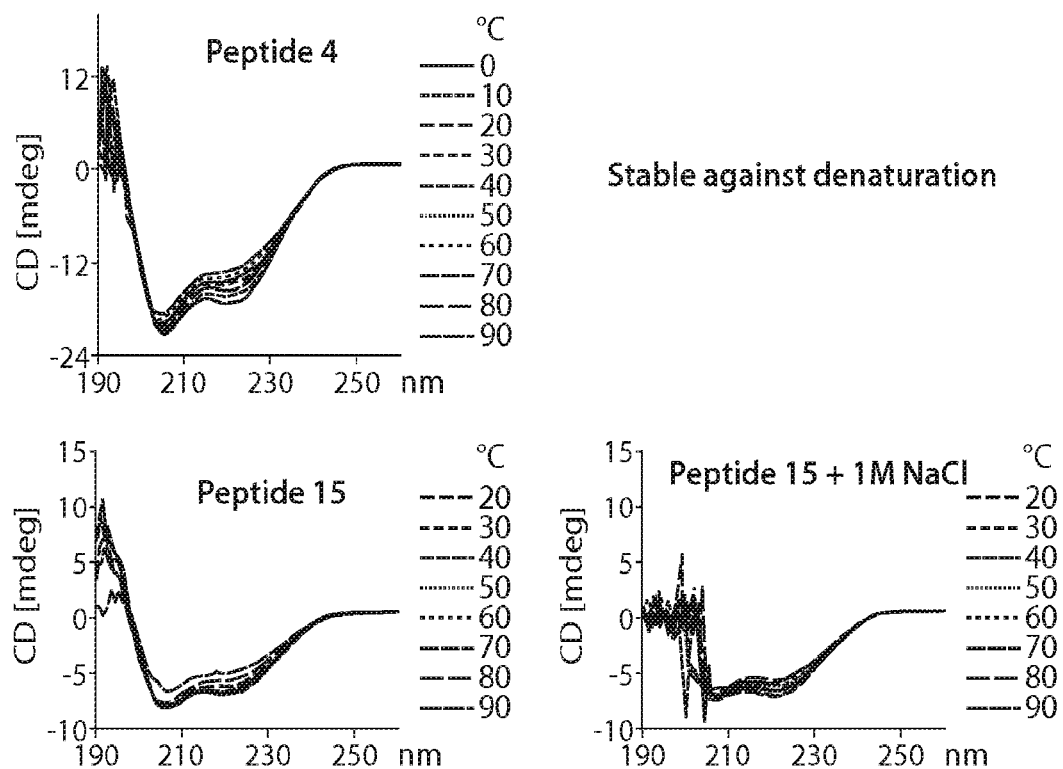
FIG. 20 shows CD spectra of selected proline-locked stapled peptides at various temperatures.
Figure 21:
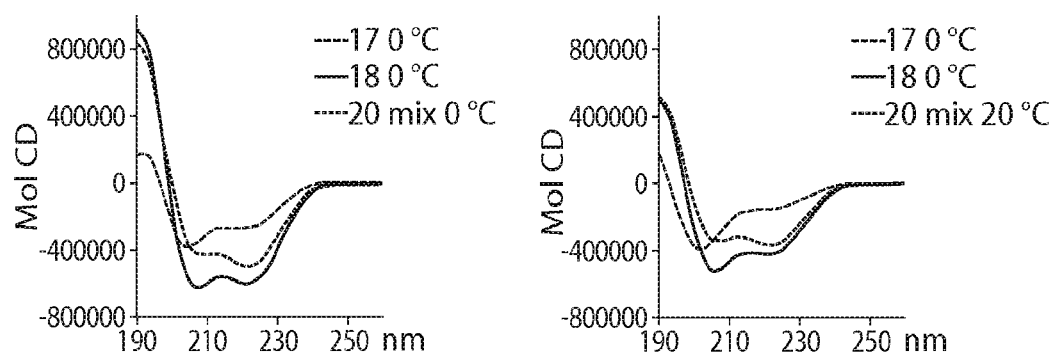
FIG. 21 shows CD spectra of proline-locked stapled peptides based on the full-length GCN basic region.
Figure 22:
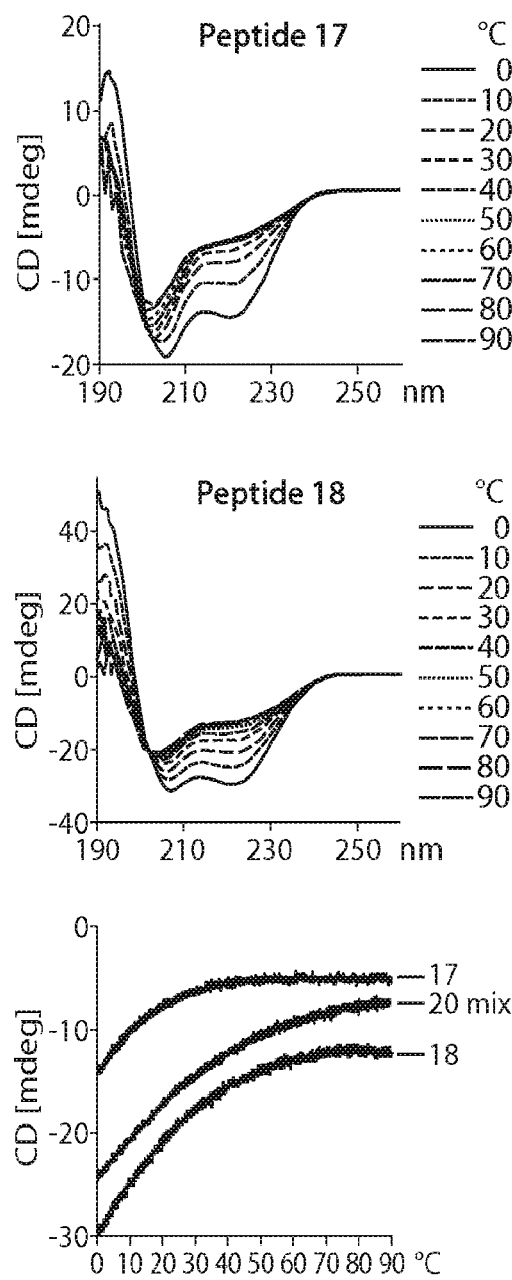
FIG. 22 shows CD spectra of proline-locked stapled peptides at various temperatures. "20 Mix" refers to E and Z isomers mixture of peptide 20.
Figure 23:
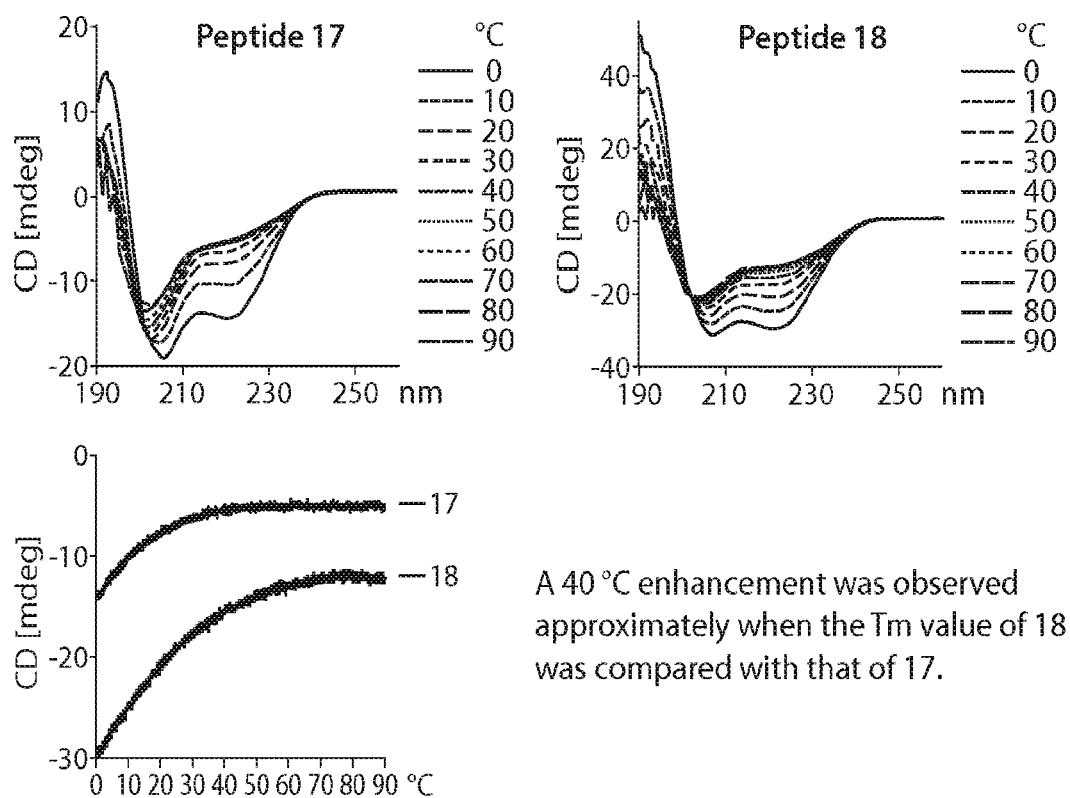
FIG. 23 shows the CD spectra of proline-locked stapled peptides (24 mer).
Figure 26:
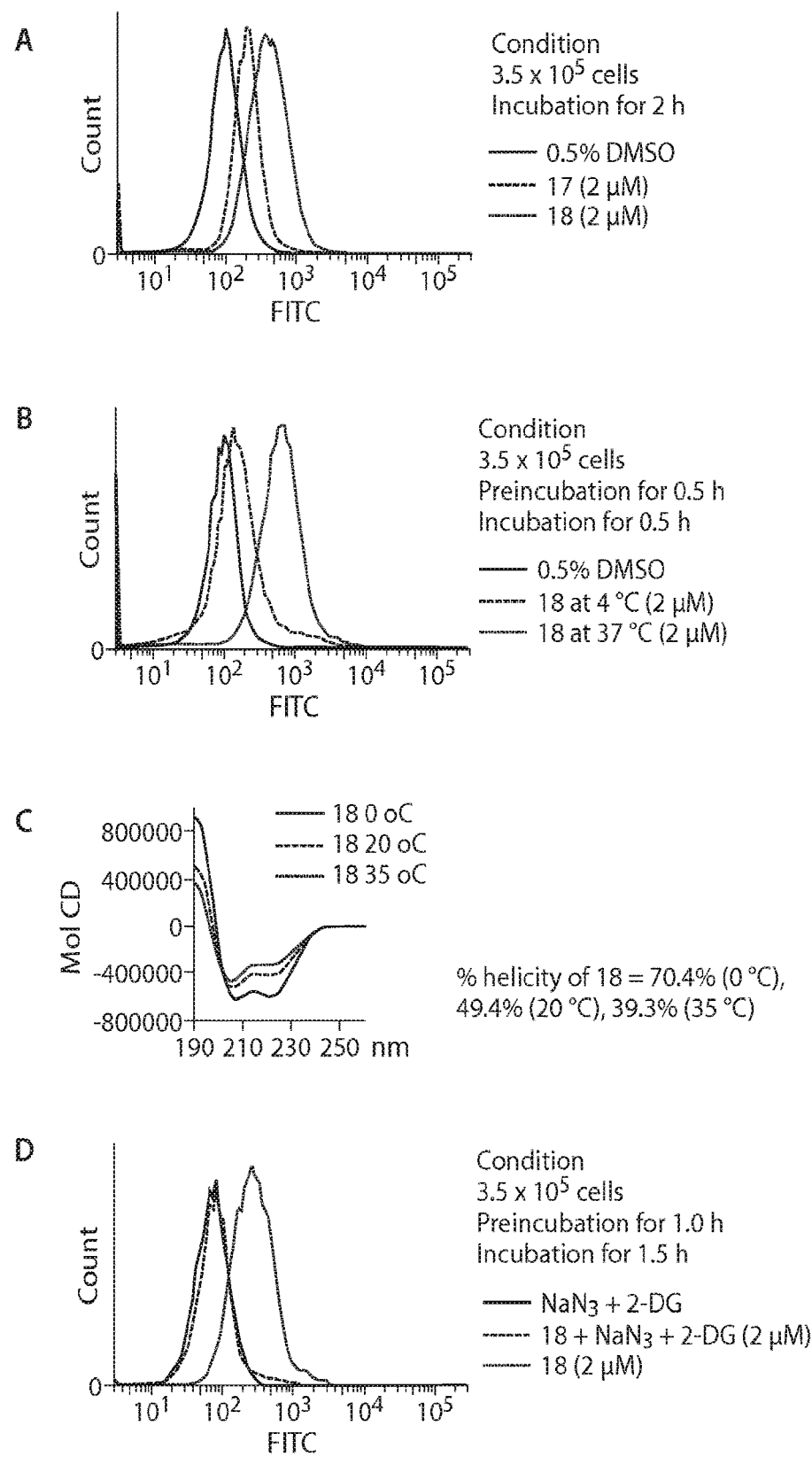
FIG. 26 shows investigation of the endocytosis mechanism of the peptides. The peptides were labeled with FITC. (A) shows flow cytometry of peptide 17 and peptide 18. (B) shows flow cytometry of peptide 18 at different temperatures. (C) shows CD spectra of peptide 18 at different temperatures. (D) shows flow cytometry of peptide 18 in the presence of $NaN_3$+2-deoxy-D-glucose (2-DG), These data indicate that the internalization of peptide 18 is ATP-dependent.
Figure 27:
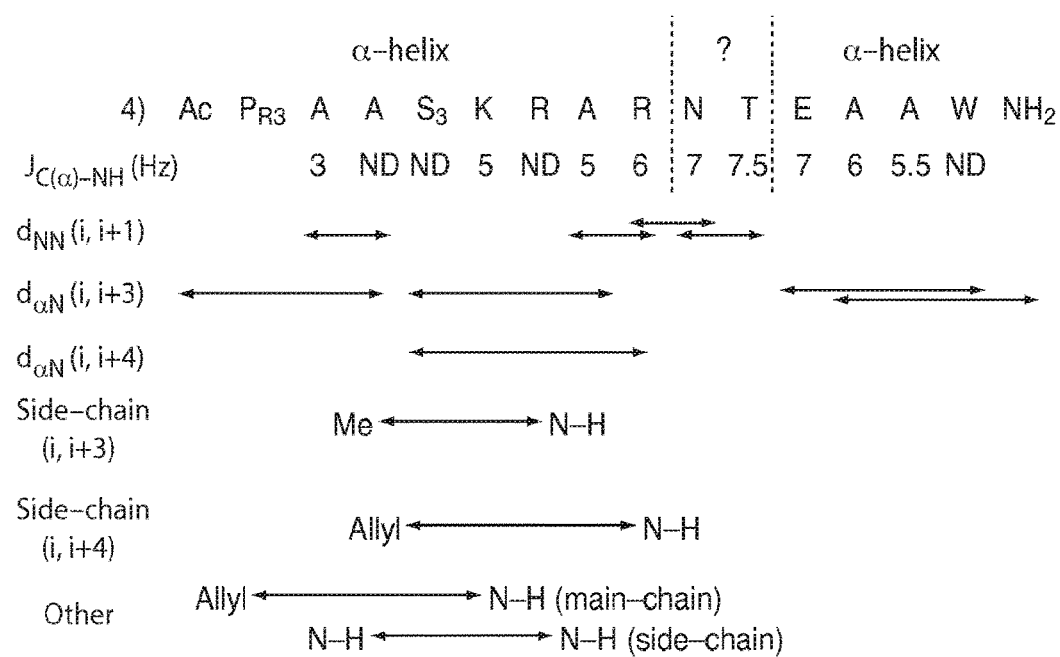
FIG. 27 shows analysis of 1H NMR and NOESY spectra of peptide 4. The crosspeaks indicate alpha-helix conformation of the peptides. dαN(i, i+3) indicates the interaction between an amide N—H at i position and an alpha proton at i+3 position. dαN(i, i+4) indicates the interaction between an amide N—H at i position and an alpha proton at i+4 position. The coupling constant below 4 indicates alpha-helix or 310-helix. The coupling constant below 7 means the existence of a helical structure including random coil. The residues adopt helical structure at N and T because dNN(i, i+1) interaction was observed in these residues. The 13 crosspeaks observed in NOESY spectra of peptide 4 indicate alpha-helix conformation.
Figure 28:
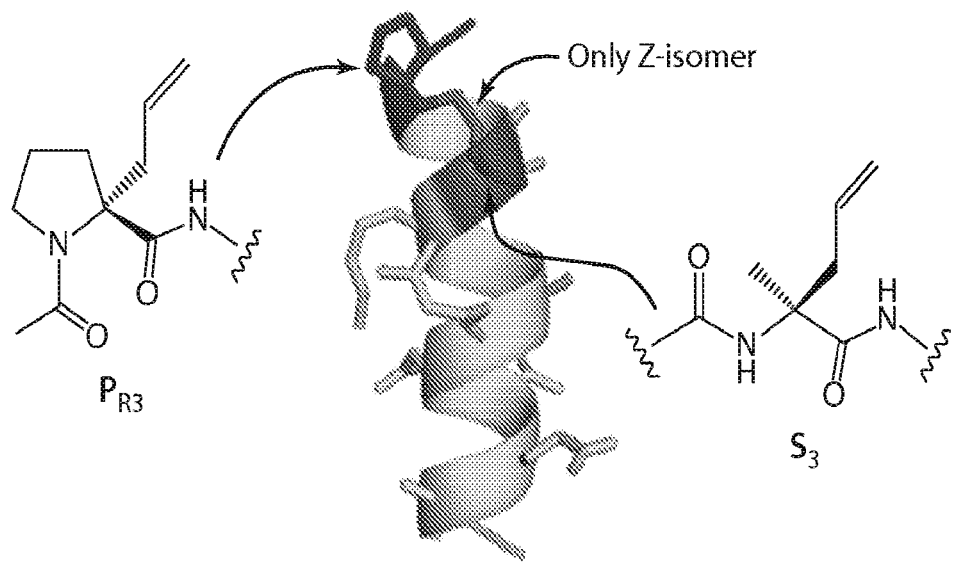
FIG. 28 shows NMR measurements of peptide 4. The coupling constant between two olefinic protons is 11 Hz, which means the olefin in peptide 4 is of the Z conformation. High % NOE value was observed between two olefinic protons (49% and 77%). These values indicate the Z-conformation of the olefin in peptide 4.
Figure 29:
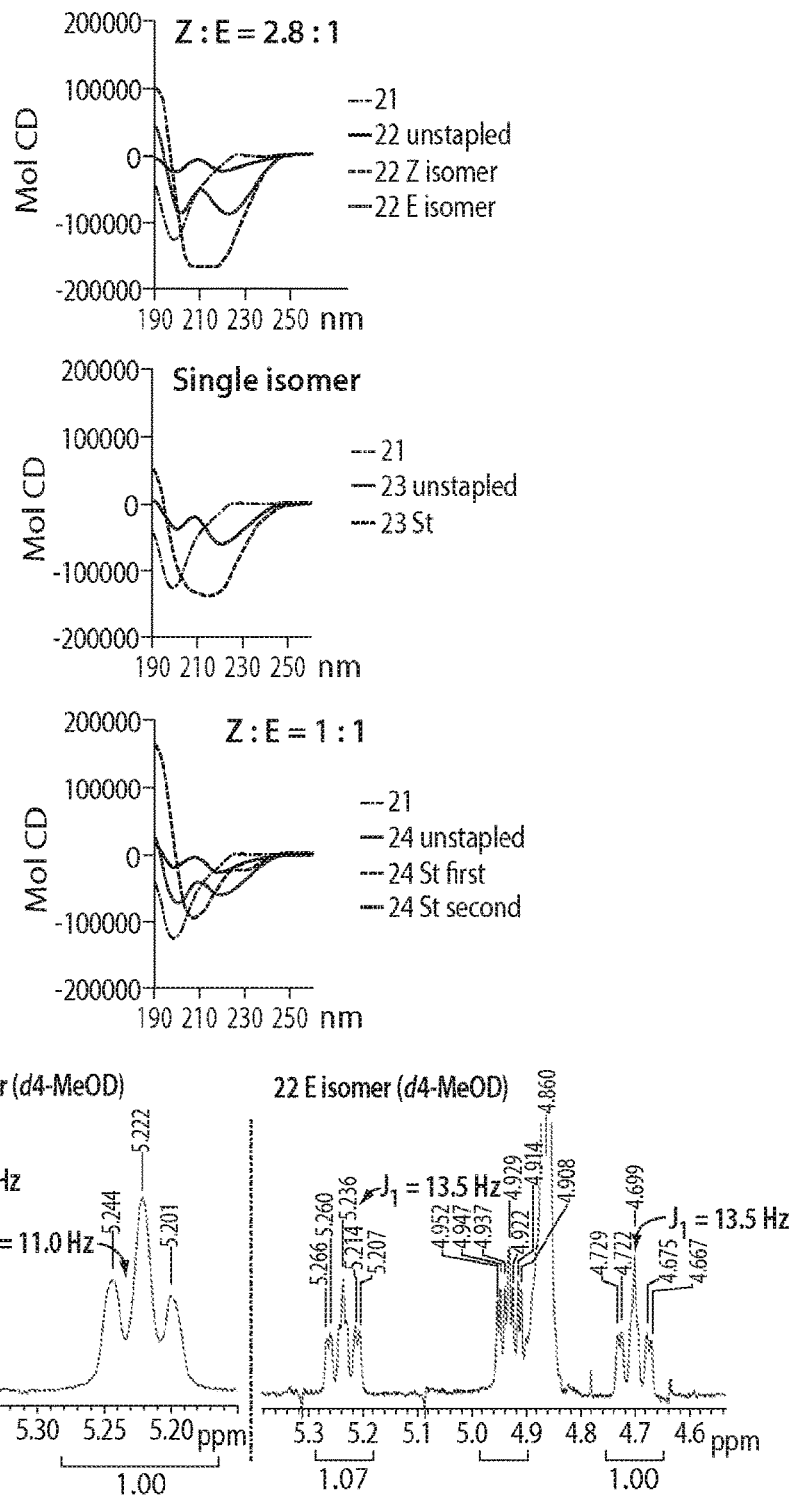
FIG. 29 shows CD spectra and NMR of Pro-locked Stapled peptides (5 mer). (A) shows CD spectra of peptides 21-24. (B) shows NMR of peptide 22 isomers.
Figure 30:
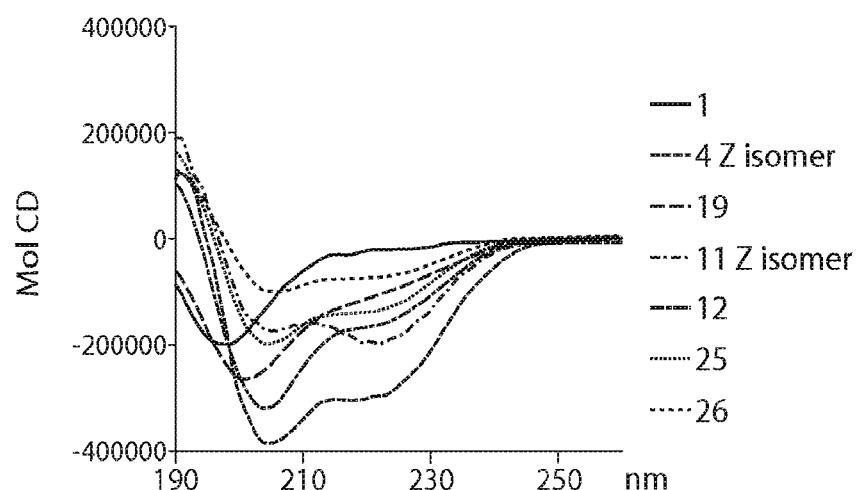
FIG. 30 shows CD spectra of selected stapled peptides (GCN 14 mer).
Figure 32:
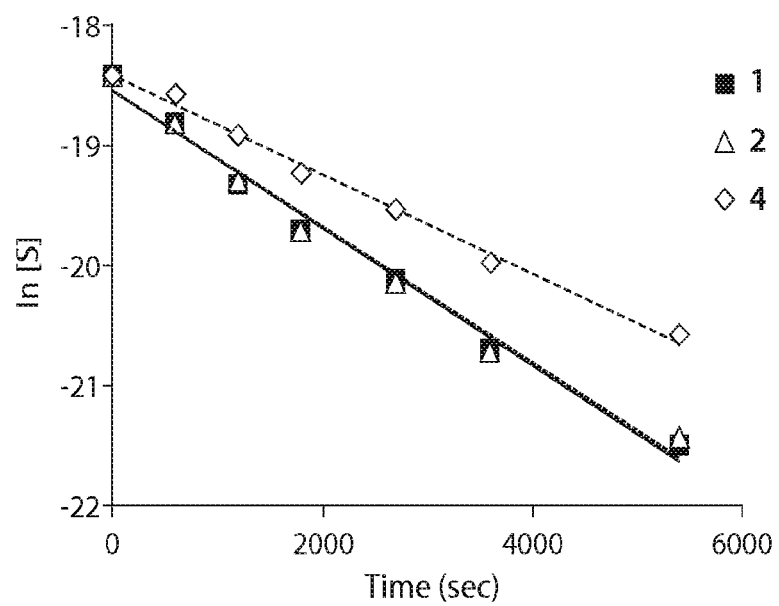
FIG. 32 shows stability of proline stapled peptides against trypsin proteolysis.
Figure 33:
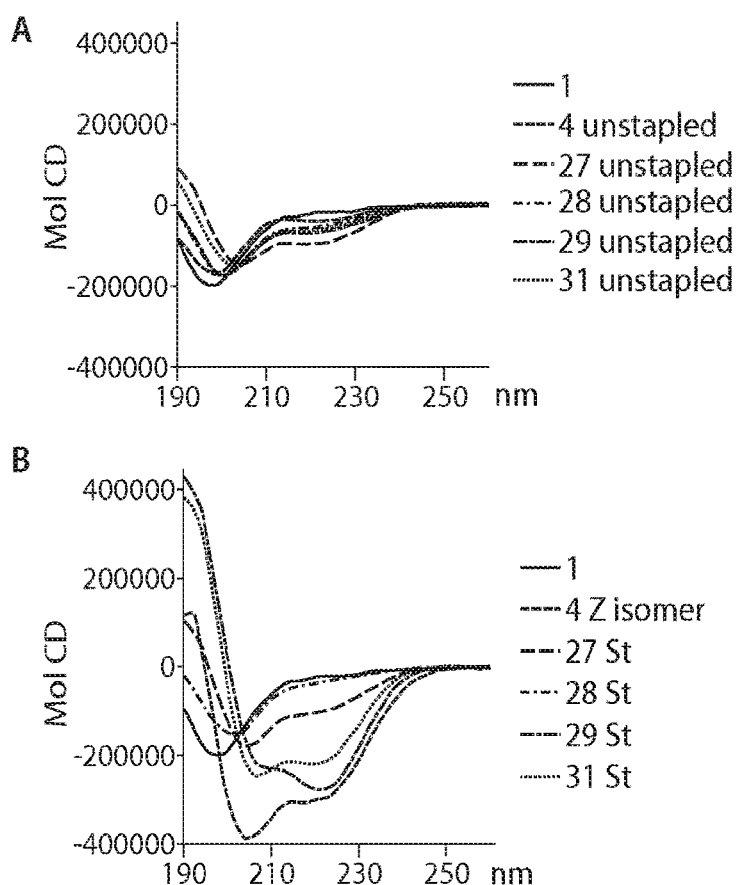
FIG. 33 shows CD spectra of exemplified stapled peptides.
Figure 34:
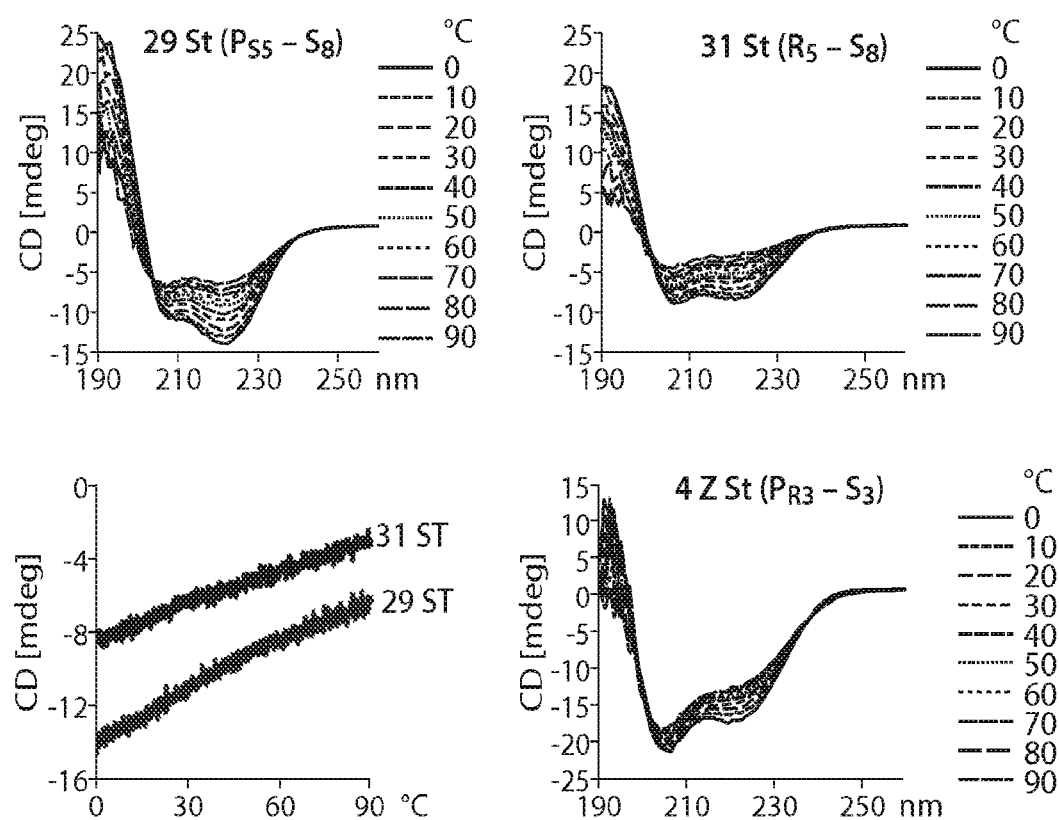
FIG. 34 shows melting curve of exemplified pro-locked stapled peptides (i, i+7).
Figure 35:
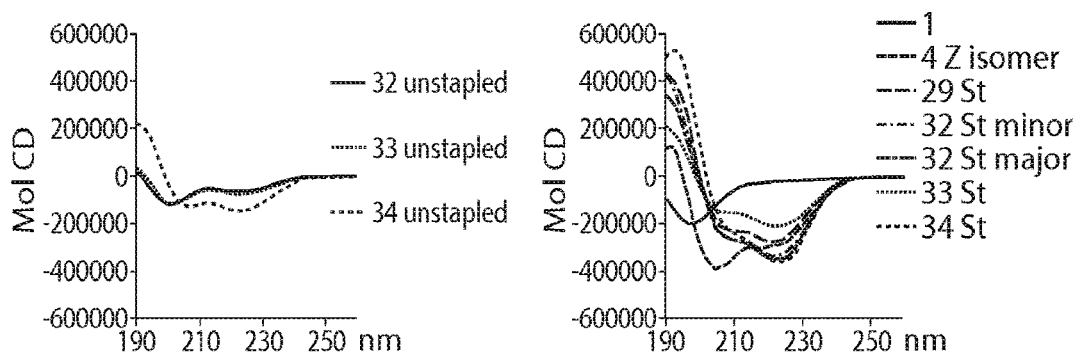
FIG. 35 shows CD spectra of exemplified stapled peptides.

The conformation of additional pro-locked peptides as determined by CD measurements is provided in FIG. 17 and FIG. 18. (Peptide 1 of FIG. 2 corresponds to Peptide "1)" of FIG. 17, while Peptide 2 of FIG. 2 corresponds to Peptide "4)" of FIG. 17).

Figure 5:
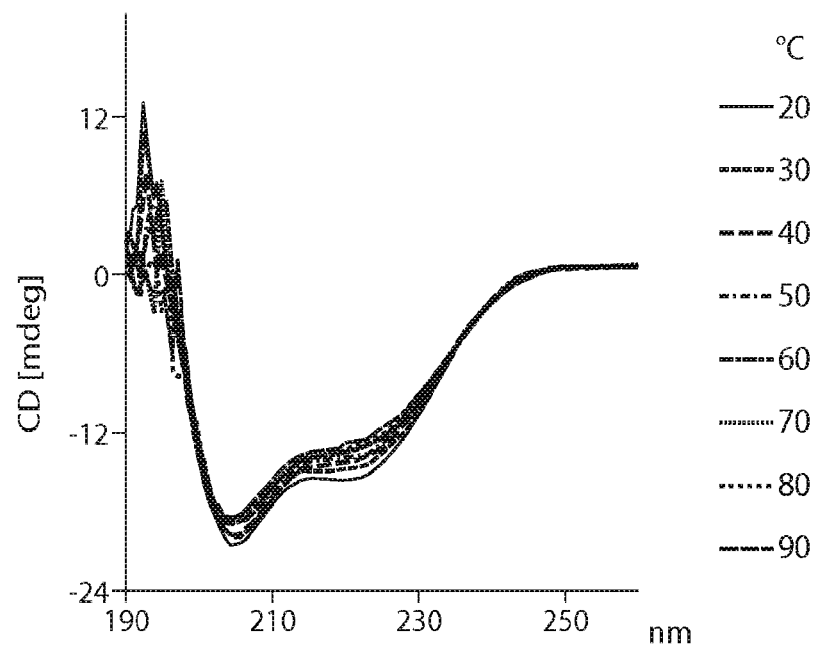
FIG. 5 shows the variable-temperature CD spectra of peptide 2 in 50 mM sodium phosphate solution (pH=8.0).
Figure 6:
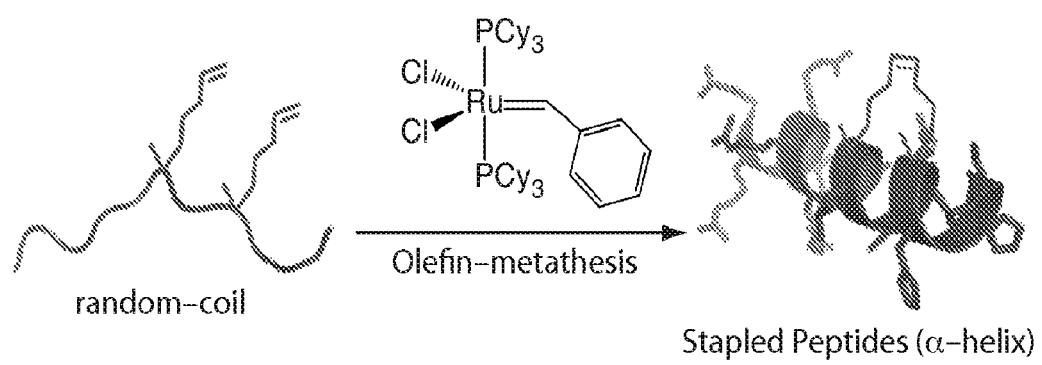
FIG. 6 shows an olefin-metathesis resulting in a stapled peptide.

The stability of the Pro-locked peptide 2 was investigated by variable temperature CD measurement, and it was found that the α-helix conformation was completely maintained in the range from 20° C. to 90° C. in 50 mM sodium phosphate buffer (pH 8.0), alone (FIG. 5) and with 100 mM NaCl, 1 M NaCl, and 10% TFE. These observations indicate that the proline stapled peptides adopt an α-helix conformation with extraordinary stability.

The stability of additional pro-locked peptides as determined by CD measurements is provided in FIGS. 19-23.

Example 2

Caps for Cloaking Exposed N—H Groups in Peptides

Figure 7:
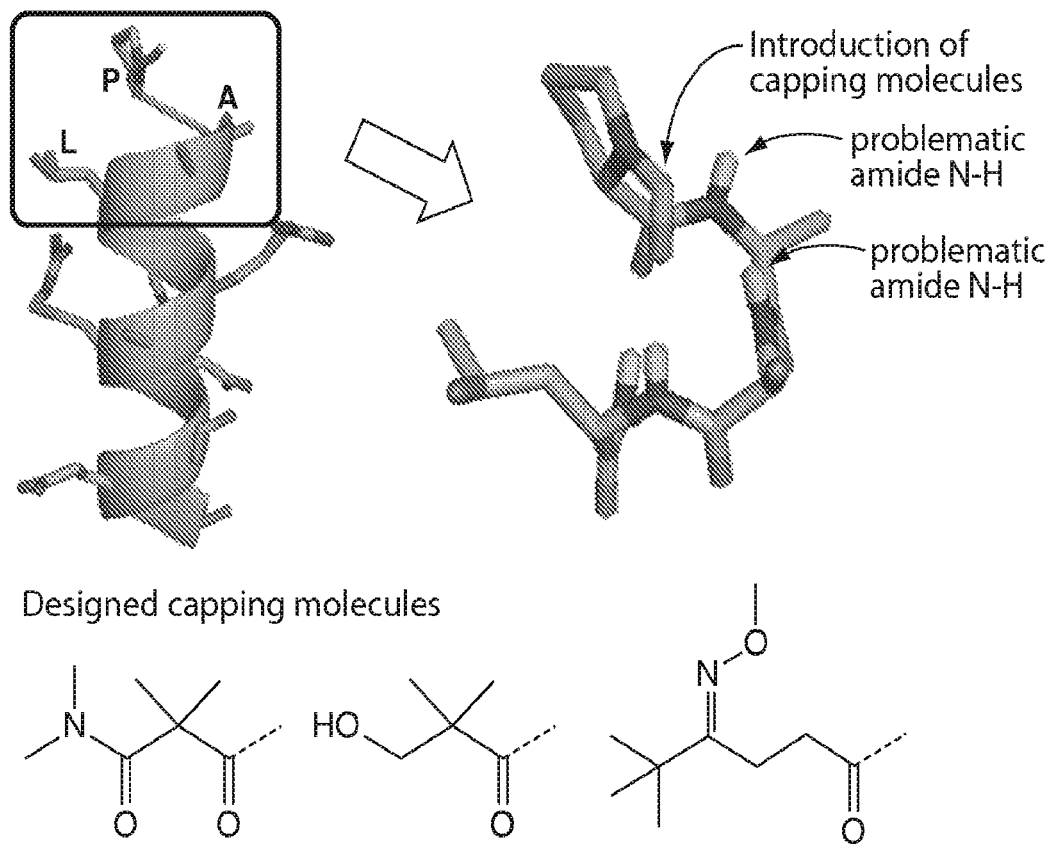
FIG. 7 shows a capping strategy for passive membrane diffusion with a proline-locked stapled peptide.
Figure 8:
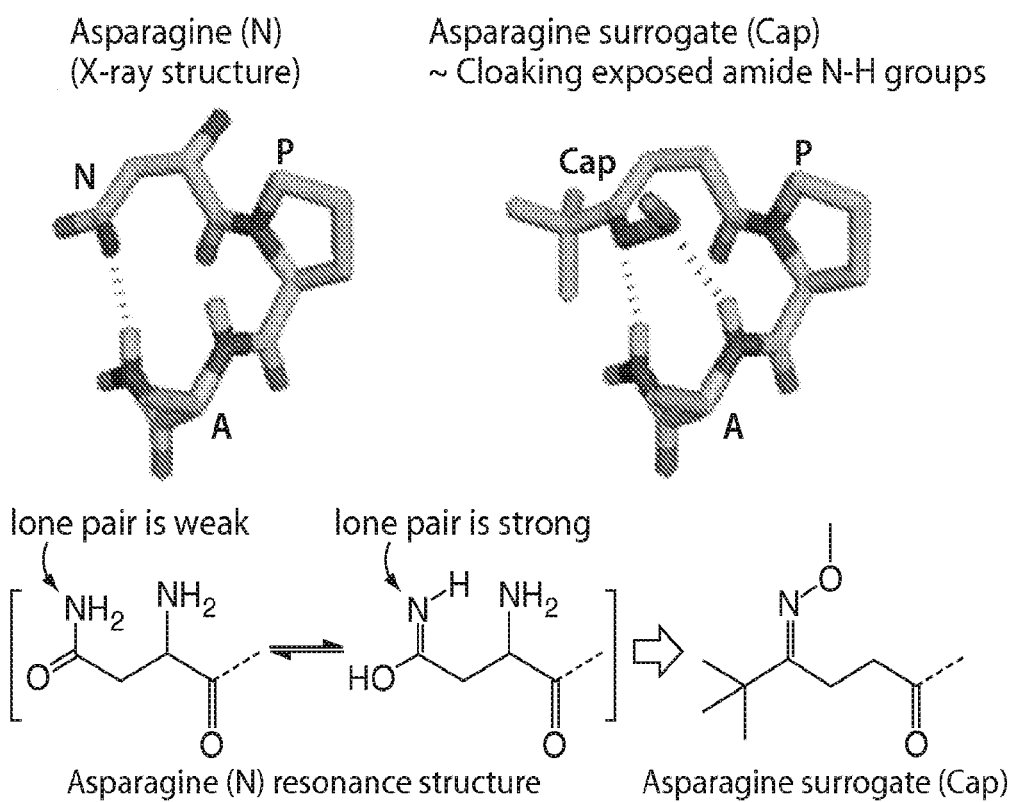
FIG. 8 shows a capping strategy for passive membrane diffusion with an asparagine and an asparagine surrogate.
Figure 36:
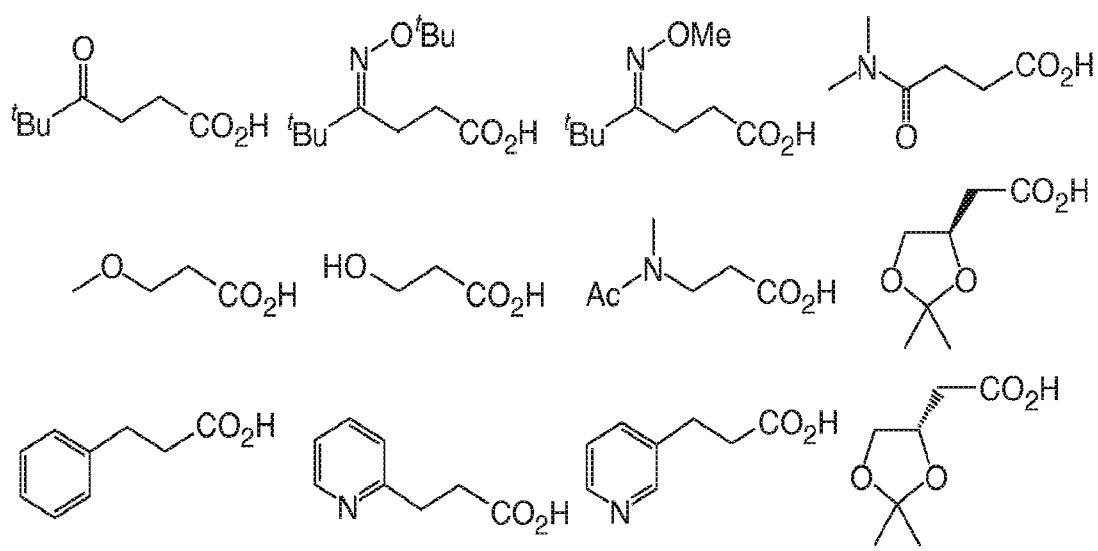
FIG. 36 shows exemplified designed capping molecules.

FIG. 7, FIG. 8, and FIG. 36 provide examples of peptide caps for cloaking exposed amide N—H groups.

Example 3

Improving Passive Membrane Diffusion of Peptides

Cells were grown on chamber slides. FITC-labeled peptides 17 and 18 were added to the cell media at 0.1 microM concentration, and the cells were incubated with the peptide containing cell media. After incubation, the cells were washed and fixed. Cells were stained with DAPI, while the presence of peptide was evaluated using a confocal microscope at a wavelength appropriate for FITC.

FIG. 24 shows cell penetration of Pro-locked stapled peptide 18. Significant cell penetration of a FITC-labeled Pro-locked stapled peptide 18 was shown at 0.1 microM concentration. In contrast, non-locked WT peptide 17 showed no penetration.

Example 4

Trypsin Digestion

Peptides (10 nmole) were dissolved in 120 µl digestion buffer (0.1 M $NH_4HCO_3$, pH=8) and incubated with trypsin agatose for 0, 10, 20, 30, 45, 60, and 90 min. The reactions were quenched by centrifugation. The remaining substrate in the isolated supernatant was quantified by LC/MS-based peak detection at 220 nm.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A polypeptide of Formula (I):

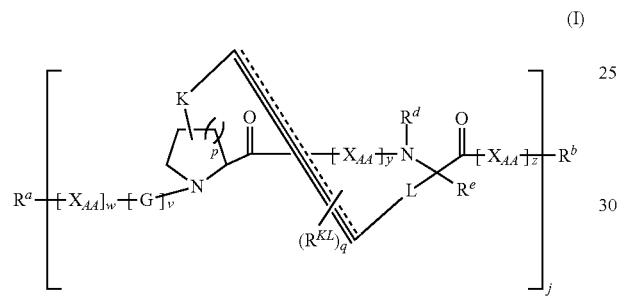

or a salt or stereoisomer thereof;
wherein:

each instance of K and L, is, independently, a bond or a group consisting of one or more combinations of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclene, substituted or unsubstituted carbocyclene, substituted or unsubstituted arylene; substituted or unsubstituted heteroarylene;

$R^a$ is hydrogen; substituted or unsubstituted aliphatic; substituted or unsubstituted heteroaliphatic; substituted or unsubstituted aryl; substituted or unsubstituted heteroaryl; substituted or unsubstituted acyl; a resin; an amino protecting group; a label optionally joined by a linker, wherein the linker is a group consisting of one or more combinations of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted carbocyclene; substituted or unsubstituted heterocyclene; substituted or unsubstituted arylene; or substituted or unsubstituted heteroarylene;

$R^b$ is, $-R^B$, $-OR^B$, $-N(R^B)_2$, or $-SR^B$, wherein each instance of $R^B$ is, independently; hydrogen; substituted or unsubstituted aliphatic; substituted or unsubstituted heteroaliphatic; substituted or unsubstituted aryl; substituted or unsubstituted heteroaryl; substituted or unsubstituted acyl; a resin; a suitable hydroxyl, amino protecting group; or two $R^B$ groups together form a substituted or unsubstituted 5- to 6-membered heterocyclic or heteroaromatic ring;

each instance of $R^{KL}$ is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; azido; cyano; isocyano; halo; or nitro;

each instance of $R^d$ is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; or $R^d$ is an amino protecting group;

each instance of $R^e$ is, independently, a suitable amino acid side chain; hydrogen; substituted or unsubstituted aliphatic; substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; cyano; isocyano; halo; or nitro;

each instance of G is, independently, a natural or unnatural amino acid or a group of the formula:

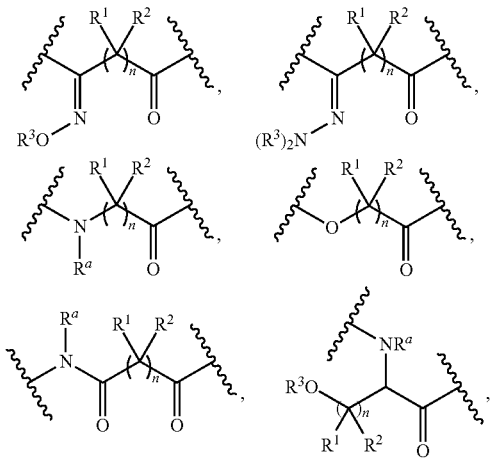

-continued

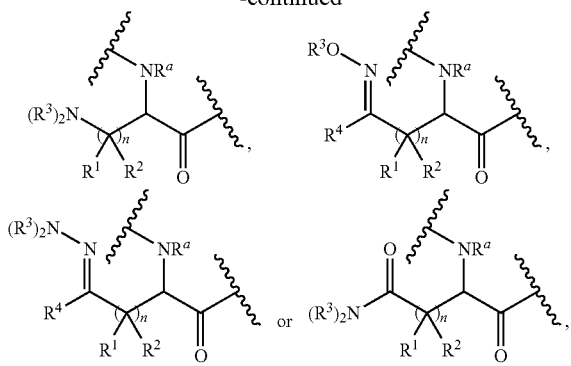

wherein:

n is 1, 2, or 3; and each instance of $R^1$ and $R^2$ is independently hydrogen; substituted or unsubstituted aliphatic;

substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; or halo, or $R^1$ and $R^2$ are joined to form a carbocyclic or heterocyclic ring;

each instance of $R^3$ and $R^4$ is, independently, hydrogen; substituted or unsubstituted aliphatic; substituted or unsubstituted heteroaliphatic; a hydroxyl protecting group when attached to an oxygen atom, or an amino protecting group when attached to a nitrogen atom, or two $R^3$ groups when attached to a nitrogen atom are joined to form a heterocyclic ring;

each instance of $X_{AA}$ is, independently, a natural or unnatural amino acid;

j is, independently, 1, 2, 3, 4, 5, 6, 7, 8, 9, or 10;

p is, independently, 1 or 2;

each instance of q is independently 0, 1, or 2;

v is, independently, 0 or 1;

each instance of w and z is, independently, an integer from 0 to 100;

y is, independently, 1, 2, 3, or 4;

═══ ‒ ‒ ‒ corresponds to a single, double or triple bond.

2. A composition comprising a polypeptide of claim 1, and an excipient.

3. The polypeptide of claim 1 of the formula:

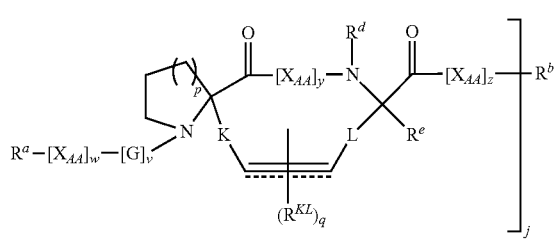

or a salt or stereoisomer thereof.

4. The polypeptide of claim 3 selected from any one of the formula:

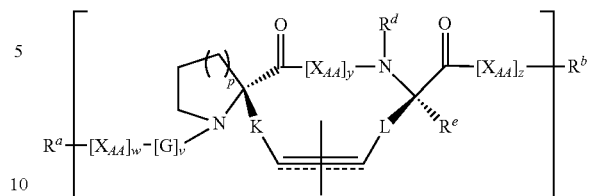

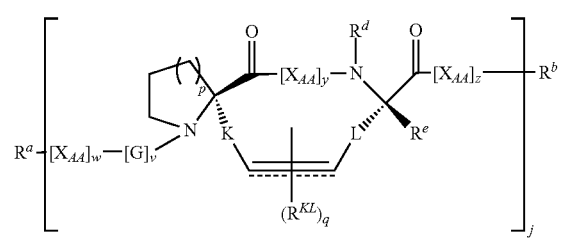

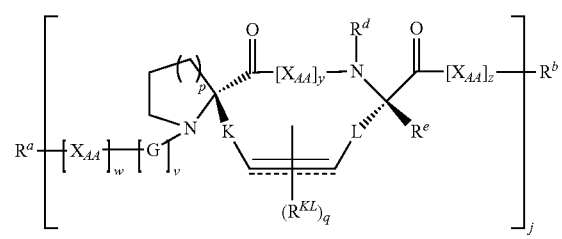

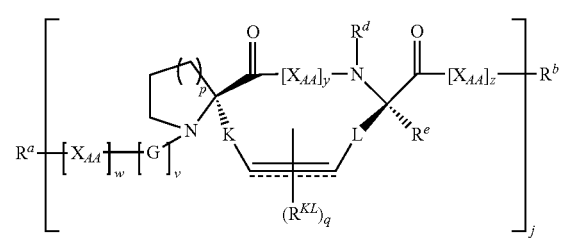

or a salt or stereoisomer thereof.

5. The polypeptide of claim 1 of the formula:

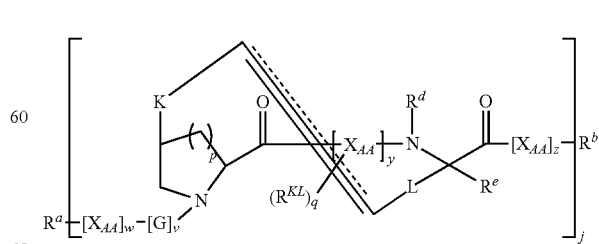

or a salt or stereoisomer thereof.

6. The polypeptide of claim 5 selected from any one of the formula:

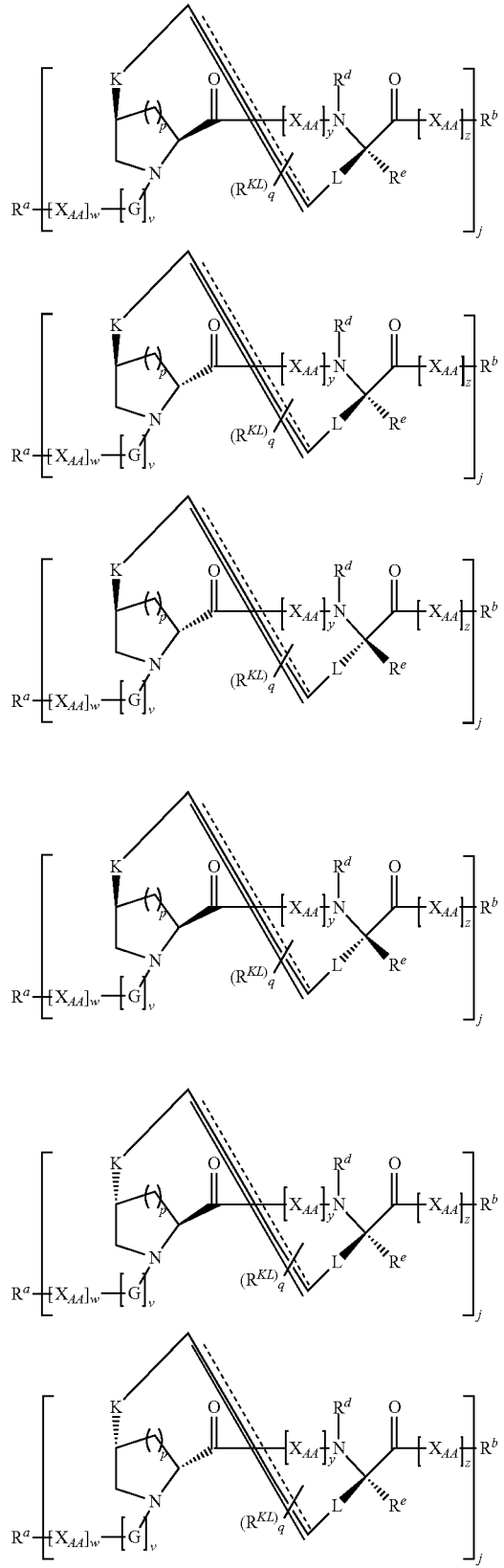

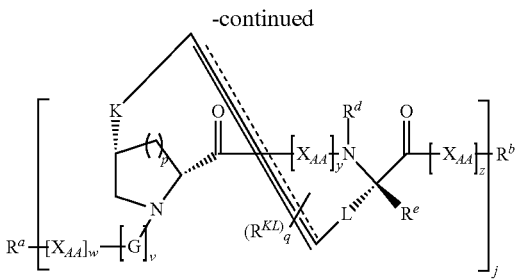

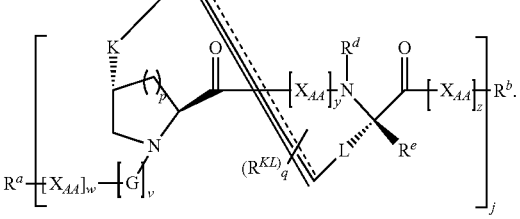

7. The polypeptide of claim 1, wherein p is 1.
8. The polypeptide of claim 1, wherein q is 0.
9. The polypeptide of claim 1, wherein p is 1 and q is 0.
10. The polypeptide of claim 1, wherein each instance of $R^e$ is, independently, hydrogen, $-CH_3$, $-CH_2OH$, $-COOH$, or $-CH_2COOH$.
11. The polypeptide of claim 1, wherein each instance of $R^e$ is $-CH_3$.
12. The polypeptide of claim 1, wherein each $R^d$ is hydrogen.
13. The polypeptide of claim 1, wherein each instance of y is, independently, 1 to 8.
14. The polypeptide of claim 1, wherein each instance of y is 2.
15. The polypeptide of claim 1, wherein $R^a$ is substituted or unsubstituted acyl.
16. The polypeptide of claim 1, wherein $R^a$ is hydrogen.
17. The polypeptide of claim 1, wherein $R^b$ is $-OR^B$.
18. The polypeptide of claim 1, wherein $R^b$ is a $-OH$.
19. The polypeptide of claim 1, wherein each instance of K is, independently, $-CH_2-$, $-(CH_2)_2-$, or $-(CH_2)_3-$.
20. The polypeptide of claim 1, wherein each instance of K is $-CH_2-$.
21. The polypeptide of claim 1, wherein each instance of L is, independently, $-CH_2-$, $-(CH_2)_2-$, or $-(CH_2)_3-$.
22. The polypeptide of claim 1, wherein each instance of L is $-CH_2-$.
23. The polypeptide of claim 1, wherein ═════ ───────── corresponds to a double bond.
24. The polypeptide of claim 1, wherein each instance of $R^e$ is $-CH_3$.
25. The polypeptide of claim 1, wherein:
K and L are $-CH_2-$;
$R^d$ is $-H$;
$R^e$ is $-CH_3$;
j is 1;
p is 1;
q is 0;
y is 2; and
═════ ───────── corresponds to a double bond.

26. The polypeptide of claim 3, wherein:
p is 1;
q is 0;
j is 1;
y is 2;
K is —CH$_2$—, —(CH$_2$)$_2$—, —(CH$_2$)$_3$—, or —O—(CH$_2$)$_{1-3}$—;
L is —(CH$_2$)$_{1-6}$—;
R$^d$ is —H;
and R$^e$ is —CH$_3$; and ═══ ---------- corresponds to a double bond.

27. The polypeptide of claim 1, wherein:
each instance of K and L, is, independently, a bond; substituted or unsubstituted alkylene; or substituted or unsubstituted heteroalkylene;
R$^a$ is hydrogen; substituted or unsubstituted aliphatic; substituted or unsubstituted heteroaliphatic; substituted or unsubstituted aryl; substituted or unsubstituted heteroaryl; substituted or unsubstituted acyl; a resin; an amino protecting group; a label optionally joined by a linker, wherein the linker is a group consisting of one or more combinations of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted carbocyclene; substituted or unsubstituted heterocyclene; substituted or unsubstituted arylene; or substituted or unsubstituted heteroarylene;
R$^b$ is, —R$^B$, —OR$^B$, or —N(R$^B$)$_2$, wherein each instance of R$^B$ is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; a resin; a suitable hydroxyl or amino protecting group; or two R$^B$ groups together form a substituted or unsubstituted 5- to 6-membered heterocyclic or heteroaromatic ring;
each instance of R$^{KL}$ is, independently, hydrogen or substituted or unsubstituted aliphatic; each instance of R$^d$ is, independently, hydrogen; substituted or unsubstituted aliphatic; substituted or unsubstituted heteroaliphatic; substituted or unsubstituted aryl; substituted or unsubstituted heteroaryl; substituted or unsubstituted acyl; or R$^d$ is an amino protecting group;
each instance of R$^e$ is, independently, a suitable amino acid side chain; hydrogen; or substituted or unsubstituted aliphatic;
each instance of G is, independently, a natural or unnatural amino acid or a group of the formula:

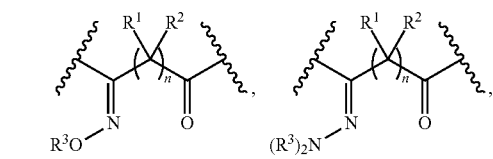

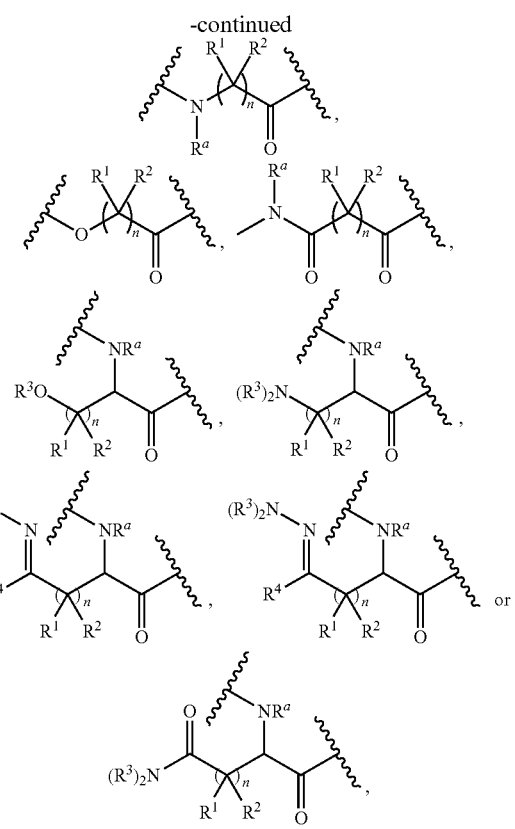

wherein:
n is 1, 2, or 3; and
each instance of R$^1$ and R$^2$ is independently hydrogen; or substituted or unsubstituted aliphatic;
each instance of R$^3$ and R$^4$ is, independently, hydrogen; substituted or unsubstituted aliphatic; a hydroxyl protecting group when attached to an oxygen atom, or an amino protecting group when attached to a nitrogen atom, or two R$^3$ groups when attached to a nitrogen atom are joined to form a heterocyclic ring;
each instance of X$_{AA}$ is, independently, a natural or unnatural amino acid;
j is, independently, 1, 2, 3, 4, 5, 6, 7, 8, 9, or 10;
p is 1 or 2;
each instance of q is independently 0, 1, or 2;
v is, independently, 0 or 1;
each instance of w and z is, independently, an integer from 0 to 100;
y is, independently, 1, 2, 3, or 4;

═══ ---------- corresponds to a single, double or triple bond.

* * * * *

SEQUENCE LISTING

```
<160> NUMBER OF SEQ ID NOS: 38

<210> SEQ ID NO 1
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 1

Pro Ala Ala Leu Lys Arg Ala Arg Asn Thr Glu Ala Ala Trp
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro
<220> FEATURE:
```

```
<221> NAME/KEY: misc_feature
<222> LOCATION: (4)..(4)
<223> OTHER INFORMATION: Xaa is a modified Ser

<400> SEQUENCE: 2

Xaa Ala Ala Xaa Lys Arg Ala Arg Asn Thr Glu Ala Ala Trp
1               5                   10

<210> SEQ ID NO 3
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 3

Met Lys Asp Pro Ala Ala Leu Lys Arg Ala Arg Asn Thr Glu Ala Ala
1               5                   10                  15

Arg Arg Ser Arg Ala Arg Lys Leu Gln Arg
            20                  25

<210> SEQ ID NO 4
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 4

Met Lys Gln Leu Glu Asp Lys Val Glu Glu Leu Leu Ser Lys Asn Tyr
1               5                   10                  15

His Leu Glu Asn Glu Val Ala Arg Leu Lys Lys Leu Val Gly Glu Arg
            20                  25                  30

<210> SEQ ID NO 5
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro

<400> SEQUENCE: 5

Xaa Ala Ala Leu Lys Arg Ala Arg Asn Thr Glu Ala Ala Trp
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro

<400> SEQUENCE: 6

Xaa Ala Ala Leu Lys Arg Ala Arg Asn Thr Glu Ala Ala Trp
1               5                   10

<210> SEQ ID NO 7
<211> LENGTH: 14
<212> TYPE: PRT
```

```
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (4)..(4)
<223> OTHER INFORMATION: Xaa is a modified Arg

<400> SEQUENCE: 7

Xaa Ala Ala Xaa Lys Arg Ala Arg Asn Thr Glu Ala Ala Trp
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (4)..(4)
<223> OTHER INFORMATION: Xaa is a modified Ser

<400> SEQUENCE: 8

Xaa Ala Ala Xaa Lys Arg Ala Arg Asn Thr Glu Ala Ala Trp
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (4)..(4)
<223> OTHER INFORMATION: Xaa is a modified Arg

<400> SEQUENCE: 9

Xaa Ala Ala Xaa Lys Arg Ala Arg Asn Thr Glu Ala Ala Trp
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro

<400> SEQUENCE: 10

Xaa Ala Ala Leu Lys Arg Ala Arg Asn Thr Glu Ala Ala Trp
1               5                   10

<210> SEQ ID NO 11
<211> LENGTH: 14
```

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (4)..(4)
<223> OTHER INFORMATION: Xaa is a modified Ser

<400> SEQUENCE: 11

Xaa Ala Ala Xaa Lys Arg Ala Arg Asn Thr Glu Ala Ala Trp
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (4)..(4)
<223> OTHER INFORMATION: Xaa is a modified Arg

<400> SEQUENCE: 12

Xaa Ala Ala Xaa Lys Arg Ala Arg Asn Thr Glu Ala Ala Trp
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (4)..(4)
<223> OTHER INFORMATION: Xaa is a modified Ser

<400> SEQUENCE: 13

Xaa Ala Ala Xaa Lys Arg Ala Arg Asn Thr Glu Ala Ala Trp
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Arg
<220> FEATURE:
<221> NAME/KEY: misc_feature
<222> LOCATION: (4)..(4)
<223> OTHER INFORMATION: Xaa is a modified Ser

<400> SEQUENCE: 14

Xaa Ala Ala Xaa Lys Arg Ala Arg Asn Thr Glu Ala Ala Trp
```

```
1               5                    10
```

<210> SEQ ID NO 15
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 15

Pro Ala Ala Ala Ala Ala Ala Trp
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro

<400> SEQUENCE: 16

Xaa Ala Ala Ala Ala Ala Ala Trp
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (4)..(4)
<223> OTHER INFORMATION: Xaa is a modified Ser

<400> SEQUENCE: 17

Xaa Ala Ala Xaa Ala Ala Ala Trp
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (4)..(4)
<223> OTHER INFORMATION: Xaa is a modified Ser

<400> SEQUENCE: 18

Xaa Ala Ala Xaa Ala Ala Ala Trp
1               5

<210> SEQ ID NO 19
<211> LENGTH: 14
<212> TYPE: PRT
<213> ORGANISM: Artificial Sequence

```
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (4)..(4)
<223> OTHER INFORMATION: Xaa is a modified Ser

<400> SEQUENCE: 19

Xaa Ala Ala Xaa Lys Arg Ala Arg Asn Thr Glu Ala Ala Trp
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (4)..(4)
<223> OTHER INFORMATION: Xaa is a modified Ser

<400> SEQUENCE: 20

Xaa Ala Ala Xaa Lys Arg Ala Arg Asn Thr Glu Ala Ala Trp
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Arg
<220> FEATURE:
<221> NAME/KEY: misc_feature
<222> LOCATION: (4)..(4)
<223> OTHER INFORMATION: Xaa is a modified Ser

<400> SEQUENCE: 21

Xaa Ala Ala Xaa Lys Arg Ala Arg Asn Thr Glu Ala Ala Trp
1               5                   10

<210> SEQ ID NO 22
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 22

Pro Ala Ala Leu Lys Arg Ala Arg Asn Thr Glu Ala Ala Arg Arg Ser
1               5                   10                  15
Arg Ala Arg Lys Leu Gln Arg Trp
            20

<210> SEQ ID NO 23
<211> LENGTH: 24
<212> TYPE: PRT
<213> ORGANISM: Artificial Sequence
```

```
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (4)..(4)
<223> OTHER INFORMATION: Xaa is a modified Ser

<400> SEQUENCE: 23

Xaa Ala Ala Xaa Lys Arg Ala Arg Asn Thr Glu Ala Ala Arg Arg Ser
1               5                   10                  15

Arg Ala Arg Lys Leu Gln Arg Trp
            20

<210> SEQ ID NO 24
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 24

Pro Ala Ala Leu Trp
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (4)..(4)
<223> OTHER INFORMATION: Xaa is a modified Ser

<400> SEQUENCE: 25

Xaa Ala Ala Xaa Trp
1               5

<210> SEQ ID NO 26
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Ser
<220> FEATURE:
<221> NAME/KEY: misc_feature
<222> LOCATION: (5)..(5)
<223> OTHER INFORMATION: Xaa is a modified Ser

<400> SEQUENCE: 26

Xaa Ala Ala Leu Xaa Arg Ala Arg Asn Thr Glu Ala Ala Trp
1               5                   10

<210> SEQ ID NO 27
<211> LENGTH: 6
<212> TYPE: PRT
<213> ORGANISM: Artificial Sequence
```

<220> FEATURE:
<223> OTHER INFORMATION: Synthetic polypeptide

<400> SEQUENCE: 27

Asn Thr Glu Ala Ala Trp
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (4)..(4)
<223> OTHER INFORMATION: Xaa is a modified Ser

<400> SEQUENCE: 28

Xaa Ala Ala Xaa Lys Arg
1               5

<210> SEQ ID NO 29
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (7)..(7)
<223> OTHER INFORMATION: Xaa is a modified Ser

<400> SEQUENCE: 29

Xaa Ala Ala Leu Lys Arg Xaa Arg Asn Thr Glu Ala Ala Trp
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (7)..(7)
<223> OTHER INFORMATION: Xaa is a modified Arg

<400> SEQUENCE: 30

Xaa Ala Ala Leu Lys Arg Xaa Arg Asn Thr Glu Ala Ala Trp
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic polypeptide
<220> FEATURE:

```
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (8)..(8)
<223> OTHER INFORMATION: Xaa is a modified Ser

<400> SEQUENCE: 31

Xaa Ala Ala Leu Lys Arg Ala Xaa Asn Thr Glu Ala Ala Trp
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (8)..(8)
<223> OTHER INFORMATION: Xaa is a modified Arg

<400> SEQUENCE: 32

Xaa Ala Ala Leu Lys Arg Ala Xaa Asn Thr Glu Ala Ala Trp
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Arg
<220> FEATURE:
<221> NAME/KEY: misc_feature
<222> LOCATION: (8)..(8)
<223> OTHER INFORMATION: Xaa is a modified Ser

<400> SEQUENCE: 33

Xaa Ala Ala Leu Lys Arg Ala Xaa Asn Thr Glu Ala Ala Trp
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (8)..(8)
<223> OTHER INFORMATION: Xaa is a modified Ser

<400> SEQUENCE: 34

Xaa Ala Ala Leu Lys Arg Ala Xaa Asn Thr Glu Ala Ala Trp
1               5                   10

<210> SEQ ID NO 35
<211> LENGTH: 14
```

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (4)..(4)
<223> OTHER INFORMATION: Xaa is synthetic amino acid
<220> FEATURE:
<221> NAME/KEY: misc_feature
<222> LOCATION: (7)..(7)
<223> OTHER INFORMATION: Xaa is a modified Ser

<400> SEQUENCE: 35

Xaa Ala Ala Xaa Lys Arg Xaa Arg Asn Thr Glu Ala Ala Trp
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (4)..(4)
<223> OTHER INFORMATION: Xaa is synthetic amino acid
<220> FEATURE:
<221> NAME/KEY: misc_feature
<222> LOCATION: (8)..(8)
<223> OTHER INFORMATION: Xaa is a modified Arg

<400> SEQUENCE: 36

Xaa Ala Ala Xaa Lys Arg Ala Xaa Asn Thr Glu Ala Ala Trp
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (4)..(4)
<223> OTHER INFORMATION: Xaa is synthetic amino acid
<220> FEATURE:
<221> NAME/KEY: misc_feature
<222> LOCATION: (11)..(11)
<223> OTHER INFORMATION: Xaa is a modified Ser

<400> SEQUENCE: 37

Xaa Ala Ala Xaa Lys Arg Ala Arg Asn Thr Xaa Ala Ala Trp
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Synthetic polypeptide
```

```
<220> FEATURE:
<221> NAME/KEY: misc_feature
<222> LOCATION: (1)..(1)
<223> OTHER INFORMATION: Xaa is a modified Pro
<220> FEATURE:
<221> NAME/KEY: misc_feature
<222> LOCATION: (4)..(4)
<223> OTHER INFORMATION: Xaa is a modified Ser
<220> FEATURE:
<221> NAME/KEY: misc_feature
<222> LOCATION: (12)..(12)
<223> OTHER INFORMATION: Xaa is a modified Arg

<400> SEQUENCE: 38

Xaa Ala Ala Xaa Lys Arg Ala Arg Asn Thr Glu Xaa Ala Trp
1               5                   10
```